(12) United States Patent
Suzuki et al.

(10) Patent No.: US 7,538,123 B2
(45) Date of Patent: May 26, 2009

(54) INDOLE DERIVATIVE HAVING PIPERIDINE RING

(75) Inventors: Yuichi Suzuki, Tsukuba (JP); Koichi Ito, Tsukuba (JP); Atsushi Sasaki, Tsukuba (JP); Koshi Ueno, Tsukuba (JP); Miyuki Sakai, Tsukuba (JP); Hiroki Ishihara, Tsukuba (JP); Atsuhiko Kubota, Tsukuba (JP)

(73) Assignee: Eisai R & D Management Co., Ltd., Tokyo (JP)

( * ) Notice: Subject to any disclaimer, the term of this patent is extended or adjusted under 35 U.S.C. 154(b) by 177 days.

(21) Appl. No.: 11/579,903

(22) PCT Filed: May 11, 2005

(86) PCT No.: PCT/JP2005/008632

§ 371 (c)(1),
(2), (4) Date: Nov. 8, 2006

(87) PCT Pub. No.: WO2005/108389

PCT Pub. Date: Nov. 17, 2005

(65) Prior Publication Data

US 2007/0219179 A1    Sep. 20, 2007

(30) Foreign Application Priority Data

May 12, 2004   (JP) ............... 2004-142437

(51) Int. Cl.
A61K 31/454 (2006.01)
(52) U.S. Cl. .................. 514/323; 514/300; 514/370
(58) Field of Classification Search .................. 514/323
See application file for complete search history.

(56) References Cited

U.S. PATENT DOCUMENTS

| | | | |
|---|---|---|---|
| 5,545,644 A * | 8/1996 | Macor et al. ............... | 514/323 |
| 6,071,920 A | 6/2000 | Leonardi et al. | |
| 6,329,366 B1 | 12/2001 | Fairhurst et al. | |
| 6,448,243 B1 | 9/2002 | Kitazawa et al. | |
| 6,844,338 B2 | 1/2005 | Fairhurst et al. | |
| 2002/0019531 A1 | 2/2002 | Kitazawa et al. | |
| 2002/0086999 A1 | 7/2002 | Kitazawa et al. | |
| 2002/0193383 A1 | 12/2002 | Leonardi et al. | |
| 2003/0130287 A1 | 7/2003 | Ackermann et al. | |
| 2003/0225068 A1 | 12/2003 | Fairhurst et al. | |
| 2004/0024023 A1 | 2/2004 | Bernotas et al. | |
| 2004/0147581 A1 | 7/2004 | Taylor et al. | |
| 2005/0033056 A1 | 2/2005 | Wong | |
| 2005/0256103 A1 | 11/2005 | Suzuki et al. | |
| 2007/0219179 A1 | 9/2007 | Suzuki et al. | |
| 2008/0027039 A1 | 1/2008 | Arakawa et al. | |

FOREIGN PATENT DOCUMENTS

| | | |
|---|---|---|
| EP | 0976732 A1 | 2/2000 |
| JP | 2002-114684 A | 4/2002 |
| JP | 2002-530405 A | 9/2002 |
| JP | 2003-533523 A | 11/2003 |
| WO | WO-98/43956 A1 | 10/1998 |
| WO | WO-99/06384 A1 | 2/1999 |
| WO | WO-03/059351 A1 | 7/2003 |
| WO | WO-2004/009548 A1 | 1/2004 |
| WO | WO-2004/045509 A2 | 6/2004 |
| WO | WO-2004/082584 A2 | 9/2004 |
| WO | WO-2005/108389 A1 | 11/2005 |
| WO | WO-2006/082872 A1 | 8/2006 |
| WO | WO-2006/121104 A1 | 11/2006 |
| WO | WO-2006/121106 A1 | 11/2006 |

OTHER PUBLICATIONS

Peroutka, S. J., Annu. Rev. Neuroscie., vol. 11, pp. 45-60 (1988).
Matsui et al., Neurotransmitter Today, vol. 19, No. 2, pp. 131-146, (1997).
Farde et al., Neuropsychopharmacology, vol. 22, No. 4, pp. 422-429, (2000).
Barros et al., European J. of Pharmacology, vol. 482, pp. 197-203, (2003).

(Continued)

Primary Examiner—Ardin Marschel
Assistant Examiner—Zohreh Vakili
(74) Attorney, Agent, or Firm—Birch, Stewart, Kolasch & Birch, LLP

(57) ABSTRACT

The present invention relates to a compound represented by the following formula, a pharmacologically acceptable salt thereof, or a use thereof as a pharmaceutical:

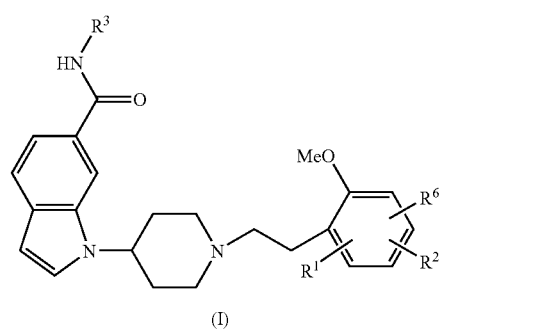

[Formula 1]

wherein $R^1$ and $R^2$ are substituents adjacent to each other, and together with two carbon atoms to each of which they attach, form a 5- to 7-membered non-aromatic carbocyclic group or the like, which may be substituted by 1 to 4 substituents selected from (1) an oxo group, (2) a hydroxyl group, and the like; $R^3$ represents a hydrogen atom or the like; and $R^6$ represents a hydrogen atom or the like. This compound has a superior strength of binding to a 5-HT1A receptor and an antagonism to the receptor, and is useful as an agent for treating or preventing lower urinary tract symptoms, and particularly symptoms regarding urinary storage.

29 Claims, 4 Drawing Sheets

OTHER PUBLICATIONS

Harder et al., Neuropharmacology, vol. 39, pp. 547-552, (2000).
Harder et al., Psychopharmacology, vol. 127, pp. 245-254, (1996).
Ysauno et al., Am. J. Psychiatry, vol. 160, No. 2, pp. 334-340, (2003).
Lecci et al., J. of Pharm. and Exp. Therapeutics, vol. 262, No. 1, pp. 181-189, (1992).
Testa et al., J. of Pharm. and Exp. Therapeutics, vol. 290, No. 3, pp. 1258-1269 (1999).
Anderson et al., Drugs, vol. 63, No. 23, pp. 2595-2611, (2003).
Bourin et al., Biomed & Pharmacother, vol. 50, pp. 7-12, (1996).
Hansenne et al., Psych. Medicine, vol. 32, pp. 935-941, (2002).
Wilson et al., Am. J. Phys. Med. Rehabil., vol. 81, No. 5, pp. 364-372, (2002).
Fletcher et al., TIPS, vol. 14, pp. 441-448, (1993).
Zhou et al., Alcohol. Clin. and Exp. Research, vol. 22, No. 1, pp. 266-269, (1998).
Carey et al., Behavioural Brain Research, vol. 132, pp. 37-46, (2002).
Boers et al., Cephalalgia, vol. 24, pp. 99-109, (2004).
Balducci et al., Psychopharmacology, vol. 167, pp. 28-36, (2003).
Gupta et al., Indian J. Physiol. Pharmacol., vol. 46, No. 4, pp. 463-467, (2002).
Dabire, H., Therapie, vol. 46, pp. 421-429, (1991).
Kruger et al., Neuroreport, vol. 10, No. 12, pp. 2651-2656, (1999).
Suchanek et al., Euro. J. of Pharmacology, vol. 355, pp. 95-101, (1998).
Bibbiani et al., Neurology, vol. 57, pp. 1829-1834, (2001).
Rasmussen et al., J of Pharmacology and Exp. Therapeutics, vol. 294, No. 2, pp. 688-700, (2000).
Gu et al., J. of Pharmacology and Exp. Therapeutics, vol. 310, No. 3, pp. 1266-1272, (2004).
Thor et al., Brain Research, vol. 946, pp. 290-297, (2002).
Aquino et al., "Preparation of Oxazine. . . ." CA 141:89094 (2004).
Kushida et al., "Solid State Characterization. . . ." CA 138:373975 (2002).
Vandenberk et al., "Preparation and Formulation. . . ." Ca 125:221867 (1996).

* cited by examiner

INDOLE DERIVATIVE HAVING PIPERIDINE RING

TECHNICAL FIELD

The present invention relates to a compound having ability to bind to a serotonin 1A receptor, and a use thereof as a pharmaceutical. More specifically, it relates to an agent for treating or preventing lower urinary tract symptoms.

BACKGROUND ART

In the periphery system, serotonin exhibits effects of smooth muscle relaxation, platelet aggregation, and gastrointestinal tract function regulation. On the other hand, in the central nervous system, serotonin functions as a neurotransmitter and is deeply associated with the motor system, perceptive system, physiological functions such as body temperature regulation, sleep, feeding behavior, vomiting, sexual behavior, neuroendocrine system, cognition and memory, or biorhythm, and pathologic conditions such as anxiety, aggression, obsession, mood disorder, hallucination, schizophrenia, autism, or drug dependence (refer to Non-Patent Document 1, Non-Patent Document 2, for example).

Serotonin receptor is classified into 7 families ranging from 5-HT1 to 5-HT7. 5HT1 is composed of 5 subtypes (5-HT1A, 5-HT1B, 5-HT1D, 5-HT1E, and 5-HT1F).

5-HT1A receptor is widely distributed in the central nervous system. In the brain, this receptor is distributed at a high density, particularly in the cerebral limbic system, mainly in the hippocampus, the septum, the amygdaloid complex, and the nuclei raphes. In the spinal cord, it is distributed at a high density in the posterior horn cortex which primary afferent fibers project (I and II laminae), the anterior horn inner portion where motoneurons are localized (VIII-IX laminae), and the intermediolateral nucleus where preganglionic sympathetic cells are present (VII lamina). In the nerve, a serotonin receptor exists as a presynaptic receptor in the cell bodies of the serotonin nerve (5-HT1A somatodendritic autoreceptor), and as a postsynaptic receptor, exists on the nerve in which the serotonin nerve innervates. Such a presynaptic receptor conducts negative feedback regulation to serotonin release.

The action of a 5-HT1A receptor in a living body and diseases in which the receptor is involved have been clarified as a result of the discovery of agonists and antagonists that are selective for the 5-HT1A receptor.

Depression and anxiety disorder are examples of such diseases. It is considered that a presynaptic 5-HT1A receptor is important for treating depression. It is considered that a selective serotonin reuptake inhibitor (SSRI) and a selective serotonin/noradrenalin reuptake inhibitor (SNRI) that are currently used as therapeutic agents. These agents inhibit the uptake of these transmitters in nerve cells, so as to increase the concentration of the transmitters in a synaptic cleft, and that as a result, desensitizes a receptor, thereby exhibiting efficacy. Recently, it has been reported that (−) pindolol (which exhibits affinity for adrenaline β and 5-HT1A receptor and has an antagonistic effect against 5-HT1A receptor) promotes the onset of the pharmacological effects of SSRI, thereby increasing the effective rate thereof in patients with depression. This may be because the release of serotonin at the nerve terminals is increased by the blockage of a presynaptic 5-HT1A receptor, so that the desensitization of the receptor is advanced (refer to Non-Patent Document 3, for example).

The study of Barros M. et al. using marmosets is a report suggesting a possibility of the use of a 5-HT1A receptor antagonist for anxiety disorder. Using, as an index, the fear and anxiety behavior of a marmoset provoked by showing the stuffed specimen of a predaceous animal to the marmoset, the effect of a 5-HT1A receptor antagonist on anxiety was studied. As a result, it was shown that this agent has an anxiolytic effect (refer to Non-Patent Document 4, for example). These results suggested a possibility that the 5-HT1A receptor antagonist is useful as an agent for preventing or treating depression or anxiety disorder.

It has also been strongly suggested that the 5-HT1A receptor is associated with cognition, memory, and learning. An NMDA-type glutamate receptor antagonist, or the fornix transection induce cognitive disorder. Such cognitive disorder was improved by a 5-HT1A receptor antagonist (refer to Non-Patent Document 5 and Non-Patent Document 6, for example). Yasuno F. et al. administered a 5-HT1A receptor antagonist labeled with $^{11}$C ([$^{11}$C]WAY-100635) to a human. Thereafter, they examined the relationship between memory and a portion shared by the 5-HT1A receptor by positron emission tomography (refer to Non-Patent Document 7, for example). As a result, a negative correlation was found between the improvement of remembrance and the affinity of [$^{11}$C]WAY-100635 to bind to a hippocampal postsynaptic 5-HT1A receptor. This result suggests that postsynaptic 5-HT1A receptors distributed over the hippocampus have a negative effect on the memory. These findings suggest a possibility that a 5-HT1A receptor antagonist is effective for cognitive disorder, or memory or learning disorder.

Also, in recent years, the association of a 5-HT1A receptor with urinary reflex has been reported (refer to Non-Patent Document 8, for example).

Various subjective symptoms provoked by urinary dysfunction are generically called lower urinary tract symptoms. Such lower urinary tract symptoms are broadly divided into symptoms regarding urinary storage such as increased urinary frequency, urinary urgency, or urinary incontinence, and voiding symptoms such as difficulty of urination or anuresis. Urinary incontinence is further classified into stress incontinence, urge incontinence, overflow incontinence, reflex urinary incontinence, extraurthral incontinence, or the like. Urinary incontinence having both the symptom of stress incontinence and that of urge incontinence is called mixed urinary incontinence. In the International Continence Society (ICS) that took place in 2001, the following proposal was given: "The overactive bladder is a medical condition referring to the symptoms of frequency and urgency, with or without urge incontinence, when appearing in the absence of local pathologic or metabolic factors that would account for these symptoms." Thus, a pathologic condition determined mainly based on subjective symptoms was defined as overactive bladder.

Examples of a cause of symptoms regarding urine pooling storage may include neuropathic bladder caused by encephalopathy (including cerebrovascular disorder, Parkinson's disease, brain tumor, multiple sclerosis, and the like), senile dementia, myelopathy, or spinal disease, unstable bladder, benign prostatic hyperplasia, prostatic cancer, bladder neurosis, interstitial bladder cystitis, bladder irritation caused by chronic cystitis or chronic prostatitis, cytoplasm, enuresis (including nocturnal enuresis), Nectria, and psychogenic dysuria.

In studies regarding urinary reflex in rats, a 5-HT1A receptor agonist promotes urinary reflex (refer to Non-Patent Document 8, for example), whereas a 5-HT1A receptor antagonist suppresses urinary reflex measured by rhythmical bladder contraction or cystometrogram. In addition, in the case of a 5-HT1A receptor partial agonist, the effect to suppress urinary reflex is reduced depending on the degree of the agonistic action of the agent (refer to Non-Patent Document 9, for example). From these findings, a 5-HT1A receptor antagonist is anticipated as a novel agent for treating symptoms regarding urinary storage based on a novel action mechanism (including increased urinary frequency, urinary urgency, and urinary incontinence, etc.) (refer to Non-Patent Document 10, for example).

Other than the aforementioned diseases, there is a wide range of diseases in which a 5-HT1A receptor would be involved. Examples of such a disease may include neuropsychiatic disorder (e.g. obsessive-compulsive disorder (refer to Non-Patent Document 11, for example), borderline personality disorder (refer to Non-Patent Document 12, for example), post-traumatic stress disorder (refer to Non-Patent Document 13, for example), panic disorder, schizophrenia (refer to Non-Patent Document 14, for example), genital insufficiency (refer to Non-Patent Document 14, for example), alcohol and/or cocaine dependence (refer to Non-Patent Document 15 and Non-Patent Document 16, for example), sleep disorder (refer to Non-Patent Document 14, for example), pain (refer to Non-Patent Document 14, for example), migraine (refer to Non-Patent Document 17, for example), visual attention disorder (refer to Non-Patent Document 18, for example), temperature instability (refer to Non-Patent Document 14, for example), vomiting (refer to Non-Patent Document 19, for example), gastrointestinal disorder (refer to Non-Patent Document 14, for example), eating disorder (refer to Non-Patent Document 14, for example), hypertension (refer to Non-Patent Document 20, for example), neuro-degenerative disease (refer to Non-Patent Document 21 and Non-Patent Document 22, for example) (e.g. cerebral ischemia, Alzheimer's disease, etc.), dyskinesia caused by Parkinson's disease (refer to Non-Patent Document 23, for example), and symptoms associated with withdrawal from nicotine ingestion or smoking (refer to Non-Patent Document 24, for example).

Accordingly, a 5-HT1A receptor antagonist is expected as an agent for preventing or treating such a wide range of diseases. Although studies for developing such a 5-HT1A receptor antagonist have actively been conducted, the agent has not yet been on the market. Thus, the development of a superior 5-HT1A receptor antagonist has been desired.

A large number of reports have previously been made regarding compounds having an antagonistic effect against a 5-HT1A receptor. However, for the use as an agent for treating lower urinary tract symptoms, only a few compounds described in Patent Document 1 and Patent Document 2 have been known.

The compound described in Patent Document 1 is a compound represented by the following formula or a pharmacologically acceptable salt thereof:

[Formula 1]

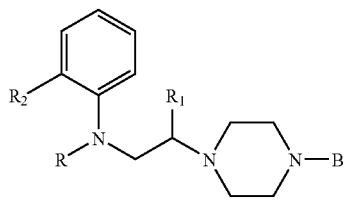

wherein R represents a hydrogen atom or the like; $R^1$ represents a hydrogen atom or the like; $R^2$ represents a halogen atom or the like; and B represents a monocyclic aryl group or the like. The structural characteristics of this compound are that it has an N-phenylaminoalkyl group as a piperazine side chain.

Accordingly, in terms of chemical structure, the compound described in Patent Document 1 completely differs from the compound represented by formula (I) of the present invention characterized in that "it has an unsubstituted or monosubstituted carbamoyl group at position 6 on an indole skeleton, and has a methoxy group on an aryl group of an aryl alkyl side chain extended from a nitrogen atom on a piperidine ring, at an ortho position to the alkyl side chain."

Patent Document 2 is a prior art that is closest to the present invention. This document discloses an agent for treating lower urinary tract symptoms containing a compound represented by the following formula, a salt thereof, or a hydrate thereof:

[Formula 2]

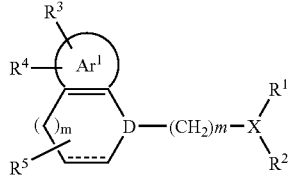

wherein the $Ar^1$ ring represents a benzene ring or the like; D represents a nitrogen atom or the like; $R^3$ and $R^4$ identically or differently represent hydrogen atoms or the like; $R^5$ represents a hydrogen atom or the like; $R^1$ and $R^2$ represent hydrogen atoms or the like, or bind to each other, so as to form a ring containing X; and m represents 0 or an integer between 1 and 6.

The compound described in Patent Document 2 is identical to the compound represented by formula (I) described in Patent Document 3, or the compound described in examples. The structural characteristics of this compound are that "it has an indole or indoline skeleton having a cyclic amine that may be substituted by an arylalkyl group or the like as a side chain structure."

Among the compounds disclosed in Patent Document 3, specific examples of compounds that are close to the compound represented by formula (I) of the present invention may include those represented by the following formula:

[Formula 3]

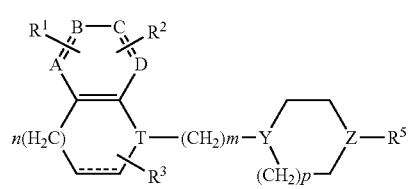

wherein $R^1$ and $R^3$ each represent a hydrogen atom; $R^2$ represents a carbamoyl group; $R^5$ represents an arylalkyl group that may be substituted; n and m represent 0; p represents 2; T and Z each represent a nitrogen atom; and Y represents a methine group. The closest compound is the compound described in Example 337. However, these disclosed compounds are limited to compounds, "which have an indole or indoline skeleton having a cyclic amine that may be substituted by an arylalkyl group or the like as a side chain structure." There are no descriptions suggesting the compound represented by formula (I) of the present invention, "which has an unsubstituted or monosubstituted carbamoyl group at position 6 on an indole skeleton, and has a methoxy group on an aryl group of an aryl alkyl side chain extended from a nitrogen atom on a piperidine ring, at an ortho position to the alkyl side chain."

Accordingly, the compound described in Patent Document 2 differs from the compound represented by formula (I) of the present invention in terms of chemical structure, and thus, it does not have a chemical structure that is specific to the compound of the present invention.

Moreover, Patent Document 2 describes the test methods of a [$^3$H]-8-hydroxy-dipropylaminotetralin binding test (Test example 1), a 5-HT1A receptor antagonist test (Test example 2), and a test regarding an antagonistic effect against a 5-HT1A receptor agonist-induced hypothermia in a rat (Test example 3). However, the document discloses neither test compounds nor specific test results (pharmacological effects). Thus, it is impossible to grasp the entity of the invention based on such descriptions.

Among the compounds described in Patent Document 3 and Patent Document 2, the compound that is closest to the compound represented by formula (I) of the present invention is the compound described in Example 337, which is represented by the following formula

[Formula 4]

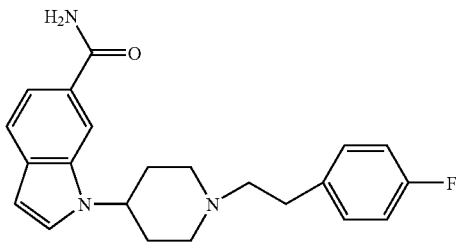

As described later in the results of pharmacological studies, the pharmacological effect of this compound is characterized in that it has affinity for 5-HT1A but its antagonistic effect against the receptor is weak.

On the other hand, the compound of the present invention represented by the following formula (I):

[Formula 5]

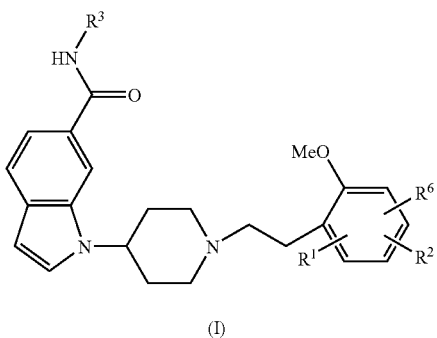

(I)

is characterized in that it has an unsubstituted or monosubstituted carbamoyl group at position 6 on the indole skeleton thereof, and has a methoxy group on an aryl group of an aryl alkyl side chain extended from a nitrogen atom on a piperidine ring, at an ortho position to the alkyl side chain, thereby having an increased antagonism to the 5-HT1A receptor. Therefore, the compound of the present invention has effects that are completely different from those of the compounds described in Patent Document 3 and Patent Document 2.

It is an object of the present invention to provide a compound having affinity for a 5-HT1A receptor and exhibiting an antagonism to the receptor, which is used for therapeutic purposes.

Non-Patent Document 1: Peroutka S. J., 5-Hydroxytryptamine receptor subtypes, Annu Rev Neurosci. 1988; 11: p. 45-60;

Non-Patent Document 2: H. Matsui, and three others, Neurotransmitter Today, 19(2), 1997, p. 131-146;

Non-Patent Document 3: Farde L, and four others, PET-Determination of robalzotan (NAD-299) induced 5-HT(1A) receptor occupancy in the monkey brain, Neuropsychopharmacology, 2000 April; 22(4): p. 422-9;

Non-Patent Document 4: Barros M, and seven others, Anxiolytic-like effects of the selective 5-HT1A receptor antagonist WAY 100635 in non-human primates, Eur J Pharmacol., 2003 Dec. 15; 482(1-3): p. 197-203;

Non-Patent Document 5: Harder J A, Ridley R M. The 5-HT1A antagonist, WAY 100 635, alleviates cognitive impairments induced by dizocilpine (MK-801) in monkeys. Neuropharmacology. 2000 Mar. 15; 39(4): p. 547-52;

Non-Patent Document 6: Harder J A, and four others, The 5-HT1A antagonist, WAY 100635, ameliorates the cognitive impairment induced by fornix transection in the marmoset. Psychopharmacology (Berl). 1996 October; 127(3): 245-54;

Non-Patent Document 7: Yasuno F, and nine others, Inhibitory effect of hippocampal 5-HT1A receptors on human explicit memory, Am J Psychiatry. 2003 February; 160(2): p. 334-40;

Non-Patent Document 8: Lecci A, and three others, Involvement of 5-hydroxytryptamine1A receptors in the modulation of micturition reflexes in the anesthetized rat, J Pharmacol Exp Ther., 1992 July; 262(1): p. 181-9;

Non-Patent Document 9: Testa R, and nine others, Effect of several 5-hydroxytryptamine(1A) receptor ligands on the micturition reflex in rats: comparison with WAY 100635, J Pharmacol Exp Ther., 1999 September; 290(3): p. 1258-69;

Non-Patent Document 10: Andersson K E, Pehrson R, CNS involvement in overactive bladder: pathophysiology and opportunities for pharmacological intervention, Drugs, 2003; 63(23): p. 2595-611;

Non-Patent Document 11: Bourin M, and another, The future of antidepressants, Biomed Pharmacother., 1996; 50(1): p. 7-12;

Non-Patent Document 12: Hansenne M, and seven others, 5-HT1A dysfunction in borderline personality disorder, Psychol Med. 2002 July; 32(5): p. 935-41;

Non-Patent Document 13: Wilson M S, and another, Effects of fluoxetine on the 5-HT1A receptor and recovery of cognitive function after traumatic brain injury in rats, Am J Phys Med Rehabil., 2002 May; 81(5): p. 364-72;

Non-Patent Document 14: Fletcher A, and two others, Silent 5-HT1A receptor antagonists: utility as research tools and therapeutic agents, Trends Pharmacol Sci., 1993 December; 14(12): p. 441-8;

Non-Patent Document 15: Zhou F C, and three others, Additive reduction of alcohol drinking by 5-HT1A antagonist WAY 100635 and serotonin uptake blocker fluoxetine in alcohol-preferring P rats, Alcohol Clin Exp Res., 1998 February; 22(1): p. 266-9;

Non-Patent Document 16: Carey R J, and two others, 5-HT1A agonist/antagonist modification of cocaine stimulant effects: implications for cocaine mechanisms. Behav Brain Res., 2002 Apr. 15; 132(1): p. 37-46;

Non-Patent Document 17: Boers P M, and three others, Naratriptan has a selective inhibitory effect on trigeminovascular neurones at central 5-HT1A and 5-HT(1B/1D) receptors in the cat: implications for migraine therapy, Cephalalgia., 2004 February; 24(2): p. 99-109;

Non-Patent Document 18: Balducci C, and four others, Reversal of visual attention dysfunction after AMPA lesions of the nucleus basalis magnocellularis (NBM) by the cholinesterase inhibitor donepezil and by a 5-HT1A receptor antagonist WAY 100635, Psychopharmacology (Berl)., 2003 April; 167(1): p. 28-36;

Non-Patent Document 19: Gupta Y K, and another, Involvement of 5-HT1A and 5-HT2 receptor in cisplatin induced emesis in dogs, Indian J Physiol Pharmacol., 2002 October; 46(4): p. 463-7;

Non-Patent Document 20: Dabire H, Central 5-hydroxytryptamine (5-HT) receptors in blood pressure regulation, Therapie., 1991 November-December; 46(6): p. 421-9;

Non-Patent Document 21: Kruger H, and two others, Effects of ionotropic glutamate receptor blockade and 5-HT1A receptor activation on spreading depression in rat neocortical slices, Neuroreport., 1999 Aug. 20; 10(12): p. 2651-6;

Non-Patent Document 22: Suchanek B, and two others, The 5-HT1A receptor agonist BAYx3702 prevents staurosporine-induced apoptosis, Eur J Pharmacol., 1998 Aug. 14; 355(1): p. 95-101;

Non-Patent Document 23: Bibbiani F, and two others, Serotonin 5-HT1A agonist improves motor complications in rodent and primate parkinsonian models, Neurology., 2001 Nov. 27; 57(10): p. 1829-34;

Non-Patent Document 24: Kurt Rasmussen, and sixteen others, The Novel 5-Hydroxytryptamine1A Antagonist LY426965: Effects on Nicotine Withdrawal and Interactions with Fluoxetine, J. of Pharmacol. Experimental Therapeutics., 294: 688-700: (2000);

Patent Document 1: International Publication WO99/06384;

Patent Document 2: JP-A-2002-114684;

Patent Document 3: International Publication WO098/43956.

DISCLOSURE OF THE INVENTION

Problems to be Solved by the Invention

As stated above, a compound having ability to bind to a 5-HT1A receptor and also having an antagonistic effect against the receptor can be anticipated as an agent for treating lower urinary tract symptoms based on a novel action mechanism. However, a compound, which has a superior binding affinity to a 5-HT1A receptor and an antagonism to the receptor, and which is able to exhibit superior clinical action to treat or prevent lower urinary tract symptoms, and particularly, symptoms regarding urinary storage has not yet been found.

Means for Solving the Problems

Under such circumstances, the present inventors have conducted intensive studies. As a result, they have found that a compound described below, which shows binding affinity to a 5-HT1A receptor and has an antagonistic effect against receptor, has excellent inhibitory effect on the accentuation of urinary reflex caused by superior brain injury and is useful as an agent for treating or preventing lower urinary tract symptoms, and particularly, increased urinary frequency or urinary incontinence, thereby completing the present invention.

That is to say, the present invention relates to the following features 1) to 34):

1) A compound represented by the following formula (I) or a pharmacologically acceptable salt thereof:

[Formula 6]

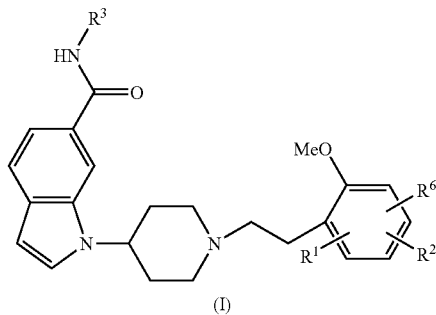

(I)

wherein $R^1$ and $R^2$ are substituents adjacent to each other, and together with two carbon atoms to each of which they attach, form:

(1) a 5- to 7-membered non-aromatic carbocyclic group,
(2) a 5- to 7-membered non-aromatic heterocyclyl group,
(3) a 6-membered aromatic carbocyclic group, or
(4) a 5- or 6-membered aromatic heterocyclyl group, which may be substituted by 1 to 4 substituents selected from the following substituent group B1;

$R^3$ represents a hydrogen atom or methyl group; and $R^6$ represents a substituent selected from the following substituent group A1, Substituent group A1: (1) a hydrogen atom, (2) a halogen atom, (3) a cyano group, (4) a hydroxyl group, (5) a nitro group, (6) a carboxyl group, (7) a C3-C8 cycloalkyl group, (8) a C2-C6 alkenyl group, (9) a C2-C6 alkynyl group, (10) a C1-C6 alkylthio group, (11) a C1-C6 alkoxycarbonyl group, (12) a C1-C6 alkylsulfonyl group, (13) a C1-C6 alkyl group (wherein the above described C1-C6 alkyl group may be substituted by 1 to 3 substituents selected from the group consisting of a halogen atom, a hydroxyl group, and a C1-C6 alkoxy group), (14) a C1-C6 alkoxy group (wherein the above described C1-C6 alkoxy group may be substituted by 1 to 3 halogen atoms), (15) an amino group (wherein the above described amino group may be substituted by a substituent selected from the group consisting of a C1-C6 alkyl group, a formyl group, a C1-C6 alkanoyl group, and a C1-C6 alkylsulfonyl group), and (16) a carbamoyl group (wherein the above described carbamoyl group may be substituted by one or two C1-C6 alkyl groups), Substituent group B1: (1) a hydrogen atom, (2) a halogen atom, (3) a cyano group, (4) a hydroxyl group, (5) a nitro group, (6) an oxo group, (7) a carboxyl group, (8) a C3-C8 cycloalkyl group, (9) a C2-C6 alkenyl group, (10) a C2-C6 alkynyl group, (11) a C1-C6 alkylthio group, (12) a C1-C6 alkoxycarbonyl group, (13) a C1-C6 alkylsulfonyl group, (14) a C1-C6 alkyl group (wherein the above described C1-C6 alkyl group may be substituted by a halogen atom, a hydroxyl group, or a C1-C6 alkoxy group), (15) a C1-C6 alkoxy group (wherein the above described C1-C6 alkoxy group may be substituted by 1 to 3 halogen atoms), (16) an amino group (wherein the above described amino group may be substituted by a substituent selected from the group consisting of a C1-C6 alkyl group, a formyl group, a C1-C6 alkanoyl group, and a C1-C6 alkylsulfonyl group), (17) a carbamoyl group (wherein the above described carbamoyl group may be substituted by one or two C1-C6 alkyl groups), (18) a C1-C6 alkoxyimino group, (19) a C5-C6 cycloalkyl group formed by two C1-C3 alkyl groups attaching to the same carbon atom, and (20) a tetrahydropyranyl group formed by two C1-C3 alkyl groups attaching to the same carbon atom, together with an oxygen atom and the above described carbon atom;

2) The compound according to 1) above or a pharmacologically acceptable salt thereof, wherein $R^1$ and $R^2$ are substituents adjacent to each other, and together with two carbon atoms to each of which they attach, form a group represented by the following formula:

[Formula 7]

1)

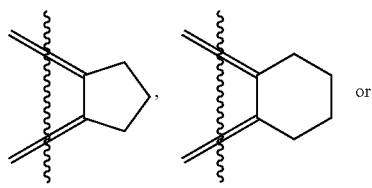

or

2)

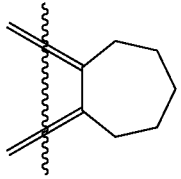

-continued

3)

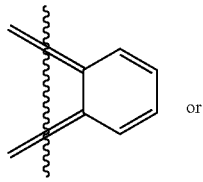

or

4)

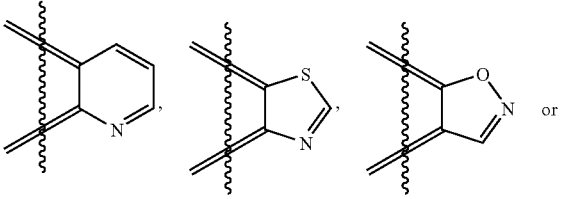

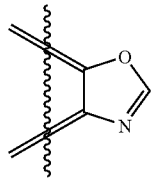

wherein a hydrogen atom on each cyclic group may be substituted by 1 to 4 substituents selected from the following substituent group B1, Substituent group B1: (1) a hydrogen atom, (2) a halogen atom, (3) a cyano group, (4) a hydroxyl group, (5) a nitro group, (6) an oxo group, (7) a carboxyl group, (8) a C3-C8 cycloalkyl group, (9) a C2-C6 alkenyl group, (10) a C2-C6 alkynyl group, (11) a C1-C6 alkylthio group, (12) a C1-C6 alkoxycarbonyl group, (13) a C1-C6 alkylsulfonyl group, (14) a C1-C6 alkyl group (wherein the above described C1-C6 alkyl group may be substituted by a halogen atom, a hydroxyl group, or a C1-C6 alkoxy group), (15) a C1-C6 alkoxy group (wherein the above described C1-C6 alkoxy group may be substituted by 1 to 3 halogen atoms), (16) an amino group (wherein the above described amino group may be substituted by a substituent selected from the group consisting of a C1-C6 alkyl group, a formyl group, a C1-C6 alkanoyl group, and a C1-C6 alkylsulfonyl group), (17) a carbamoyl group (wherein the above described carbamoyl group may be substituted by one or two C1-C6 alkyl groups), (18) a C1-C6 alkoxyimino group, (19) a C5-C6 cycloalkyl group formed by two C1-C3 alkyl groups attaching to the same carbon atom, and (20) a tetrahydropyranyl group formed by two C1-C3 alkyl group attaching to the same carbon atom, together with an oxygen atom and the above described carbon atom;

3) The compound according to 1) above or a pharmacologically acceptable salt thereof, which is represented by formula (I-a-1), formula (I-a-2), formula (I-a-3), or formula (I-a-4):

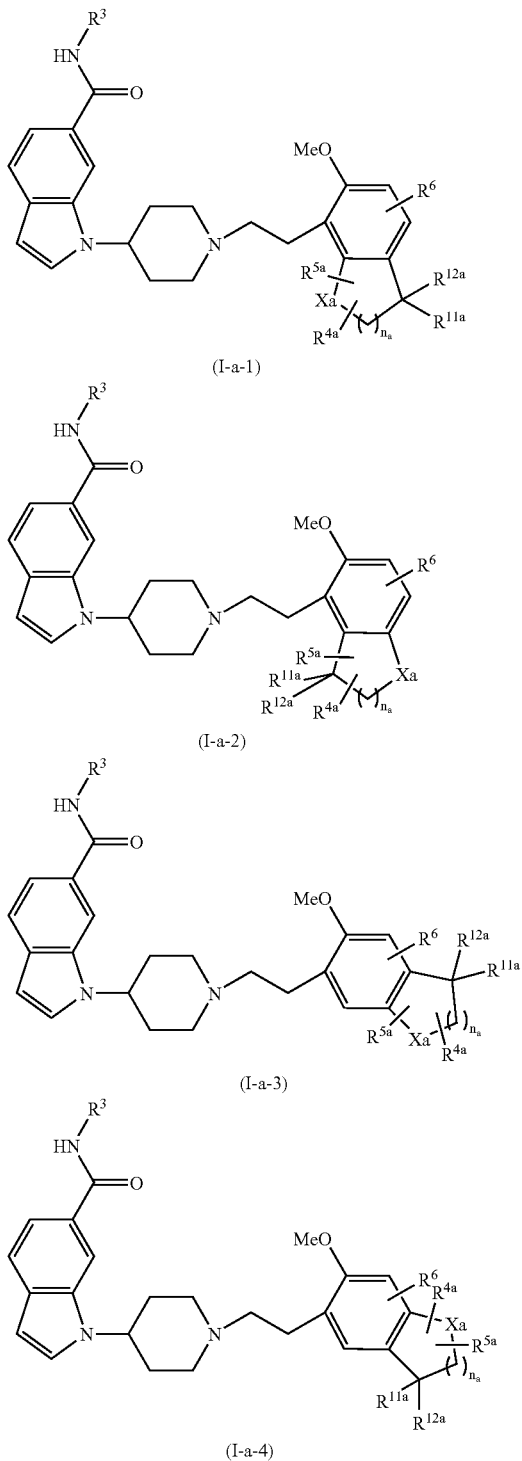

[Formula 8]

(I-a-1)

(I-a-2)

(I-a-3)

(I-a-4)

wherein $R^3$ represents a hydrogen atom or methyl group;
$R^{4a}$ and $R^{5a}$ represent substituents selected from the following substituent group B1; $R^6$ represents a substituent selected from the following substituent group A1; $R^{11a}$ represents a hydroxyl group, $R^{12a}$ represents a hydrogen atom or C1-C6 alkyl group, or $R^{11a}$ and $R^{12a}$ represent a carbonyl group or the formula $C=N-OR^{8c}$ (wherein $R^{8c}$ represents a C1-C6 alkyl group), together with carbon atoms to which $R^{11a}$ and $R^{12a}$ attach;

$X_a$ represents a methylene group wherein the hydrogen atom of the above described methylene group may be substituted by a substituent selected from the following substituent group B1 or oxygen atom; and $n_a$ represents an integer between 1 and 3, Substituent group A1: (1) a hydrogen atom, (2) a halogen atom, (3) a cyano group, (4) a hydroxyl group, (5) a nitro group, (6) a carboxyl group, (7) a C3-C8 cycloalkyl group, (8) a C2-C6 alkenyl group, (9) a C2-C6 alkynyl group, (10) a C1-C6 alkylthio group, (11) a C1-C6 alkoxycarbonyl group, (12) a C1-C6 alkylsulfonyl group, (13) a C1-C6 alkyl group (wherein the above described C1-C6 alkyl group may be substituted by 1 to 3 substituents selected from the group consisting of a halogen atom, a hydroxyl group, and a C1-C6 alkoxy group), (14) a C1-C6 alkoxy group (wherein the above described C1-C6 alkoxy group may be substituted by 1 to 3 halogen atoms), (15) an amino group (wherein the above described amino group may be substituted by a substituent selected from the group consisting of a C1-C6 alkyl group, a formyl group, a C1-C6 alkanoyl group, and a C1-C6 alkylsulfonyl group), and (16) a carbamoyl group (wherein the above described carbamoyl group may be substituted by one or two C1-C6 alkyl groups), Substituent group B1: (1) a hydrogen atom, (2) a halogen atom, (3) a cyano group, (4) a hydroxyl group, (5) a nitro group, (6) an oxo group, (7) a carboxyl group, (8) a C3-C8 cycloalkyl group, (9) a C2-C6 alkenyl group, (10) a C2-C6 alkynyl group, (11) a C1-C6 alkylthio group, (12) a C1-C6 alkoxycarbonyl group, (13) a C1-C6 alkylsulfonyl group, (14) a C1-C6 alkyl group (wherein the above described C1-C6 alkyl group may be substituted by a halogen atom, a hydroxyl group, or a C1-C6 alkoxy group), (15) a C1-C6 alkoxy group (wherein the above described C1-C6 alkoxy group may be substituted by 1 to 3 halogen atoms), (16) an amino group (wherein the above described amino group may be substituted by a substituent selected from the group consisting of a C1-C6 alkyl group, a formyl group, a C1-C6 alkanoyl group, and a C1-C6 alkylsulfonyl group), (17) a carbamoyl group (wherein the above described carbamoyl group may be substituted by one or two C1-C6 alkyl groups), (18) a C1-C6 alkoxyimino group, (19) a C5-C6 cycloalkyl group formed by two C1-C3 alkyl groups attaching to the same carbon atom, and (20) a tetrahydropyranyl group formed by two C1-C3 alkyl group attaching to the same carbon atom, together with an oxygen atom and the above described carbon atom;

4) The compound according to 3) above or a pharmacologically acceptable salt thereof, wherein $R^{11a}$ and $R^{12a}$ form a carbonyl group, together with carbon atoms to which $R^{11a}$ and $R^{12a}$ attach;

5) The compound according to 3) or 4) above or a pharmacologically acceptable salt thereof, wherein $R^{4a}$ and $R^{5a}$ are substituents selected from the following substituent group B2, and $R^6$ represents a substituent selected from the following substituent group A2, Substituent group A2: (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) C1-C6 alkoxy C1-C6 alkyl group, Substituent group B2: (1) a hydrogen atom, (2) a C1-C6 alkyl group, (3) a halogen atom, (4) a hydroxyl group, (5) a C1-C6 alkoxy group, (6) a C1-C6 alkoxy C1-C6 alkyl group, (7) a C5-C6 cycloalkyl group formed by two C1-C3 alkyl groups attaching to the same carbon atom, and (8) a tetrahydropyranyl group formed by two C1-C3 alkyl group attaching to the same carbon atom, together with an oxygen atom and the above described carbon atom;

6) The compound according to any one of 3) to 5) above or a pharmacologically acceptable salt thereof, wherein $R^{4a}$ and $R^{5a}$ represent substituents selected from the following substituent group B5, and $R^6$ represents a substituent selected from the following substituent group A4, Substituent group A4: (1) a hydrogen atom, and (2) a C1-C6 alkoxy group, Substituent group B5: (1) a hydrogen atom, (2) a C1-C6 alkyl group, (3) a C1-C6 alkoxy C1-C6 alkyl group, (4) a C5-C6 cycloalkyl group formed by two C1-C3 alkyl groups attaching to the same carbon atom, and (5) a tetrahydropyranyl group formed by two C1-C3 alkyl group attaching to the same carbon atom, together with an oxygen atom and the above described carbon atom;

7) The compound according to any one of 3) to 6) above or a pharmacologically acceptable salt thereof, wherein $X_a$ represents an oxygen atom;

8) The compound according to 1) above or a pharmacologically acceptable salt thereof, which is represented by formula (I-b-1), formula (I-b-2), formula (I-b-3), or formula (I-b-4):

[Formula 9]

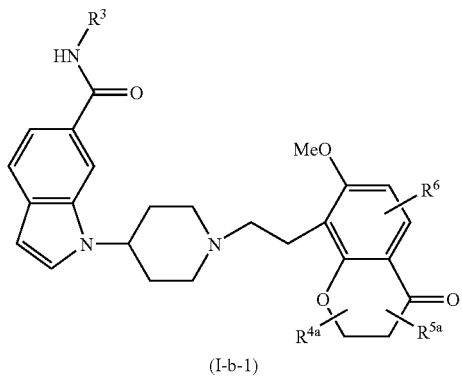
(I-b-1)

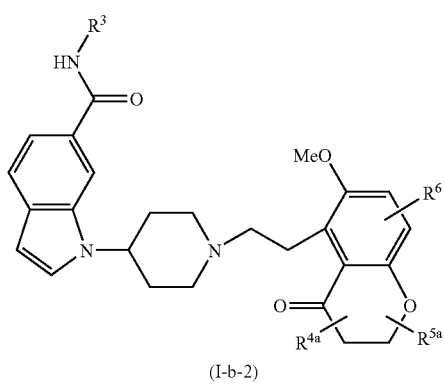
(I-b-2)

-continued
[Formula 10]

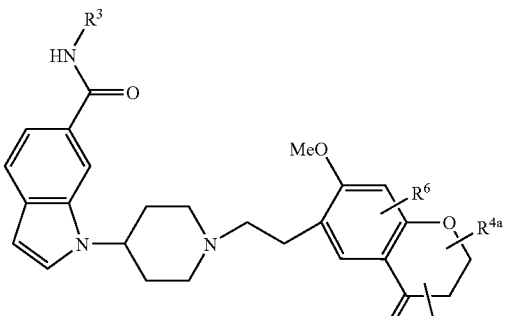
(I-b-3)

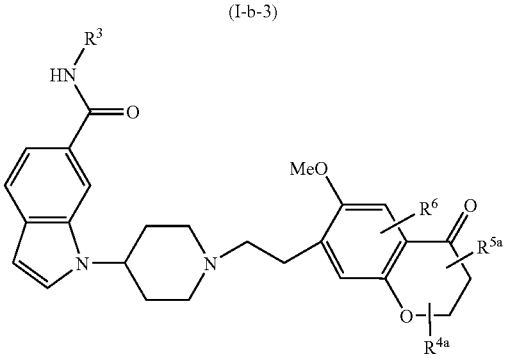
(I-b-4)

wherein $R^{4a}$ and $R^{5a}$ represent substituents selected from the following substituent group B5, and $R^6$ represents a substituent selected from the following substituent group A4, Substituent group A4: (1) a hydrogen atom, and (2) a C1-C6 alkoxy group, Substituent group B5: (1) a hydrogen atom, (2) a C1-C6 alkyl group, (3) a C1-C6 alkoxy C1-C6 alkyl group, (4) a C5-C6 cycloalkyl group formed by two C1-C3 alkyl groups attaching to the same carbon atom, and (5) a tetrahydropyranyl group formed by two C1-C3 alkyl group attaching to the same carbon atom, together with an oxygen atom and the above described carbon atom;

9) The compound according to 3) above or a pharmacologically acceptable salt thereof, wherein $R^{11a}$ represents a hydroxyl group, and $R^{12a}$ represents a hydrogen atom or C1-C6 alkyl group;

10) The compound according to 9) above or a pharmacologically acceptable salt thereof, wherein $R^{4a}$ and $R^{5a}$ are substituents selected from the following substituent group B2, and $R^6$ represents a substituent selected from the following substituent group A2, Substituent group A2: (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) C1-C6 alkoxy C1-C6 alkyl group, Substituent group B2: (1) a hydrogen atom, (2) a C1-C6 alkyl group, (3) a halogen atom, (4) a hydroxyl group, (5) a C1-C6 alkoxy group, (6) a C1-C6 alkoxy C1-C6 alkyl group, (7) a C5-C6 cycloalkyl group formed by two C1-C3 alkyl groups attaching to the same carbon atom, and (8) a tetrahydropyranyl group formed by two C1-C3 alkyl group attaching to the same carbon atom, together with an oxygen atom and the above described carbon atom;

11) The compound according to 9) or 10) above or a pharmacologically acceptable salt thereof, wherein $X_a$ represents an oxygen atom;

12) The compound according to 3) above or a pharmacologically acceptable salt thereof, wherein $R^{11a}$ and $R^{12a}$ together form the formula $=N-OR^{8c}$ (wherein $R^{8c}$ represents a C1-C6 alkyl group);

13) The compound according to 12) above or a pharmacologically acceptable salt thereof, wherein $R^{4a}$ and $R^{5a}$ are substituents selected from the following substituent group B3, and $R^6$ represents a substituent selected from the following substituent group A2, Substituent group A2: (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) C1-C6 alkoxy C1-C6 alkyl group, Substituent group B3: (1) a hydrogen atom, (2) a C1-C6 alkyl group, (3) a halogen atom, (4) a hydroxyl group, (5) a C1-C6 alkoxy group, and (6) a C1-C6 alkoxy C1-C6 alkyl group;

14) The compound according to 12) or 13) above or a pharmacologically acceptable salt thereof, wherein $X_a$ represents an oxygen atom;

15) The compound according to 1) above or a pharmacologically acceptable salt thereof, which is represented by formula (I-c-1) or formula (I-c-2):

[Formula 11]

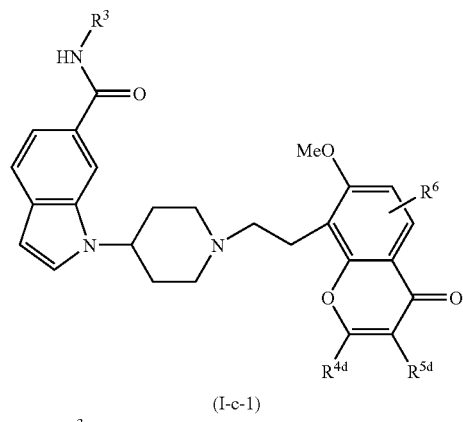

(I-c-1)

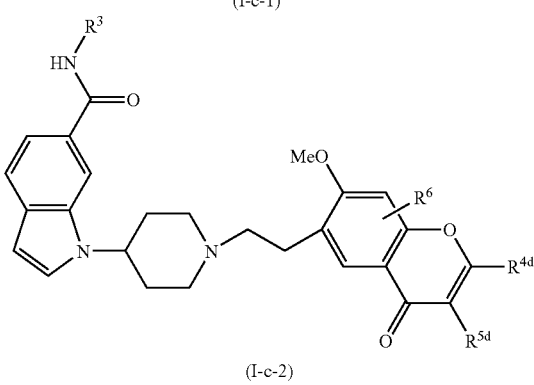

(I-c-2)

wherein $R^3$ represents a hydrogen atom or methyl group; and $R^{4d}$, $R^{5d}$, and $R^6$ represent substituents selected from the following substituent group A1, Substituent group A1: (1) a hydrogen atom, (2) a halogen atom, (3) a cyano group, (4) a hydroxyl group, (5) a nitro group, (6) a carboxyl group, (7) a C3-C8 cycloalkyl group, (8) a C2-C6 alkenyl group, (9) a C2-C6 alkynyl group, (10) a C1-C6 alkylthio group, (11) a C1-C6 alkoxycarbonyl group, (12) a C1-C6 alkylsulfonyl group, (13) a C1-C6 alkyl group (wherein the above described C1-C6 alkyl group may be substituted by 1 to 3 substituents selected from the group consisting of a halogen atom, a hydroxyl group, and a C1-C6 alkoxy group), (14) a C1-C6 alkoxy group (wherein the above described C1-C6 alkoxy group may be substituted by 1 to 3 halogen atoms), (15) an amino group (wherein the above described amino group may be substituted by a substituent selected from the group consisting of a C1-C6 alkyl group, a formyl group, a C1-C6 alkanoyl group, and a C1-C6 alkylsulfonyl group), and (16) a carbamoyl group (wherein the above described carbamoyl group may be substituted by one or two C1-C6 alkyl groups);

16) The compound according to 15) above or a pharmacologically acceptable salt thereof, wherein $R^{4d}$ and $R^{5d}$ are substituents selected from the following substituent group B4, and $R^6$ represents a substituent selected from the following substituent group A2, Substituent group A2: (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) C1-C6 alkoxy C1-C6 alkyl group, Substituent group B4: (1) a hydrogen atom, (2) a C1-C6 alkyl group, (3) C1-C6 alkoxy group and (4) a C1-C6 alkoxy C1-C6 alkyl group;

17) The compound according to 1) above or a pharmacologically acceptable salt thereof, which is represented by formula (I-d-1) or formula (I-d-2):

[Formula 12]

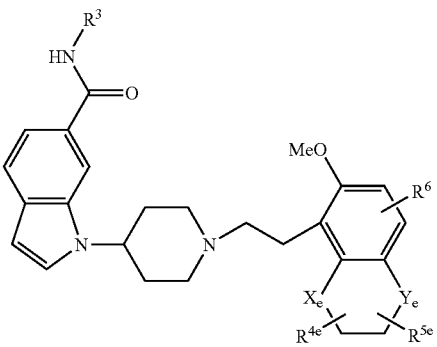

(I-d-1)

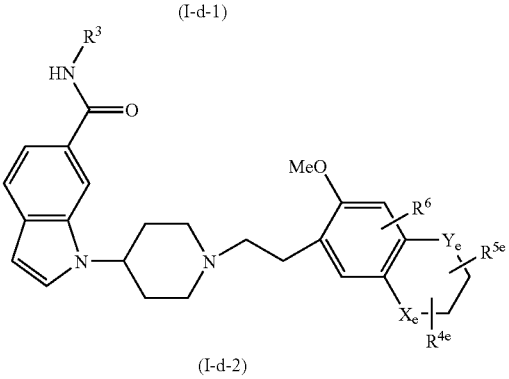

(I-d-2)

wherein R³ represents a hydrogen atom or methyl group;

R⁴ᵉ and R⁵ᵉ represent substituents selected from the following substituent group A1; R⁶ represents a substituent selected from the following substituent group A1; and each of $X_e$ and $Y_e$ represents (1) an oxygen atom, (2) a methylene group, (3) —CONR⁷ᵉ— (wherein R⁷ᵉ represents (1) a hydrogen atom, or (2) a C1-C6 alkyl group), (4) —NR⁷ᵉCO— (wherein R⁷ᵉ has the same above meaning), (5) —NR⁸ᵉ— (wherein R⁸ᵉ represents (1) a C1-C6 alkyl group, or (2) a C1-C6 acyl group), or (6) a single bond, Substituent group A1: (1) a hydrogen atom, (2) a halogen atom, (3) a cyano group, (4) a hydroxyl group, (5) a nitro group, (6) a carboxyl group, (7) a C3-C8 cycloalkyl group, (8) a C2-C6 alkenyl group, (9) a C2-C6 alkynyl group, (10) a C1-C6 alkylthio group, (11) a C1-C6 alkoxycarbonyl group, (12) a C1-C6 alkylsulfonyl group, (13) a C1-C6 alkyl group (wherein the above described C1-C6 alkyl group may be substituted by 1 to 3 substituents selected from the group consisting of a halogen atom, a hydroxyl group, and a C1-C6 alkoxy group), (14) a C1-C6 alkoxy group (wherein the above described C1-C6 alkoxy group may be substituted by 1 to 3 halogen atoms), (15) an amino group (wherein the above described amino group may be substituted by a substituent selected from the group consisting of a C1-C6 alkyl group, a formyl group, a C1-C6 alkanoyl group, and a C1-C6 alkylsulfonyl group), and (16) a carbamoyl group (wherein the above described carbamoyl group may be substituted by one or two C1-C6 alkyl groups);

18) The compound according to 17) above or a pharmacologically acceptable salt thereof, wherein R⁴ᵉ and R⁵ᵉ are substituents selected from the following substituent group B3, and R⁶ represents a substituent selected from the following substituent group A2, Substituent group A2: (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) C1-C6 alkoxy C1-C6 alkyl group, Substituent group B3: (1) a hydrogen atom, (2) a C1-C6 alkyl group, (3) a halogen atom, (4) a hydroxyl group, (5) a C1-C6 alkoxy group, and (6) a C1-C6 alkoxy C1-C6 alkyl group;

19) The compound according to 1) above or a pharmacologically acceptable salt thereof, which is represented by formula (I-e-1) or formula (I-e-2):

[Formula 13]

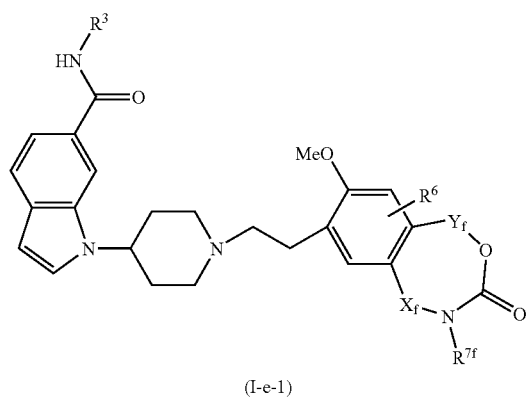

(I-e-1)

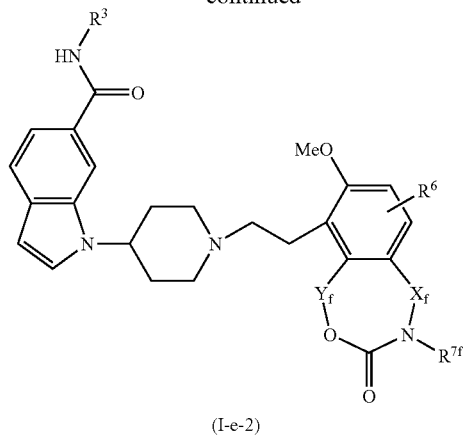

(I-e-2)

wherein R³ represents a hydrogen atom or methyl group;

R⁶ represents a substituent selected from the following substituent group A1; R⁷ᶠ represents (1) hydrogen atom, (2) a C1-C6 alkyl group, (3) a C3-C8 cycloalkyl group, (4) a C2-C6 alkenyl group, (5) a C2-C6 alkynyl group, or (6) a C1-C6 alkoxy C1-C6 alkyl group; and each of $X_f$ and $Y_f$ represents (1) a single bond, (2) a methylene group which may have a substituent selected from the following substituent group A1, or (3) a carbonyl group, Substituent group A1: (1) a hydrogen atom, (2) a halogen atom, (3) a cyano group, (4) a hydroxyl group, (5) a nitro group, (6) a carboxyl group, (7) a C3-C8 cycloalkyl group, (8) a C2-C6 alkenyl group, (9) a C2-C6 alkynyl group, (10) a C1-C6 alkylthio group, (11) a C1-C6 alkoxycarbonyl group, (12) a C1-C6 alkylsulfonyl group, (13) a C1-C6 alkyl group (wherein the above described C1-C6 alkyl group may be substituted by 1 to 3 substituents selected from the group consisting of a halogen atom, a hydroxyl group, and a C1-C6 alkoxy group), (14) a C1-C6 alkoxy group (wherein the above described C1-C6 alkoxy group may be substituted by 1 to 3 halogen atoms), (15) an amino group (wherein the above described amino group may be substituted by a substituent selected from the group consisting of a C1-C6 alkyl group, a formyl group, a C1-C6 alkanoyl group, and a C1-C6 alkylsulfonyl group), and (16) a carbamoyl group (wherein the above described carbamoyl group may be substituted by one or two C1-C6 alkyl groups);

20) The compound according to 19) above or a pharmacologically acceptable salt thereof, wherein R⁶ represents a substituent selected from the following substituent group A2; R⁷ᶠ represents a substituent selected from the following substituent group B4; and each of $X_f$ and $Y_f$ represents (1) a single bond, (2) a methylene group which may have a substituent selected from the following substituent group B4, or (3) a carbonyl group, Substituent group A2: (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) C1-C6 alkoxy C1-C6 alkyl group, Substituent group B4: (1) a hydrogen atom, (2) a C1-C6 alkyl group, (3) C1-C6 alkoxy group and (4) a C1-C6 alkoxy C1-C6 alkyl group;

21) The compound according to 1) above or a pharmacologically acceptable salt thereof, which is represented by formula (I-f-1), formula (I-f-2), formula (I-f-3), formula (I-f-4), formula (I-g-1), formula (I-g-2), formula (I-h-1), formula (I-h-2), formula (I-h-3), or formula (I-h-4):
[Formula 14]
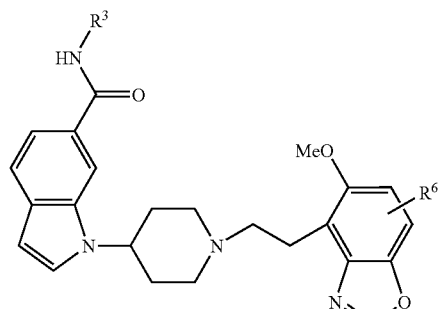
(I-f-1)
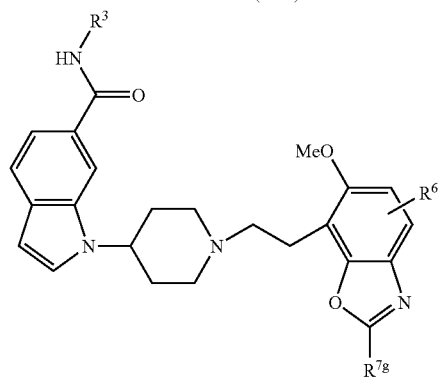
(I-f-2)
[Formula 15]
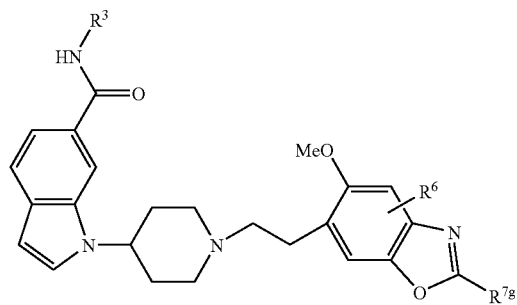
(I-f-3)
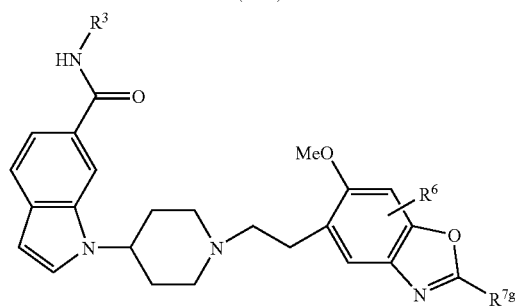
(I-f-4)
[Formula 16]
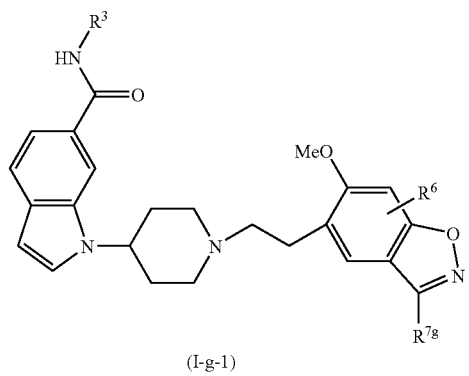
(I-g-1)
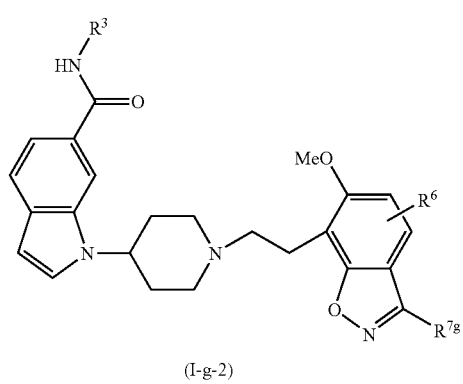
(I-g-2)
[Formula 17]
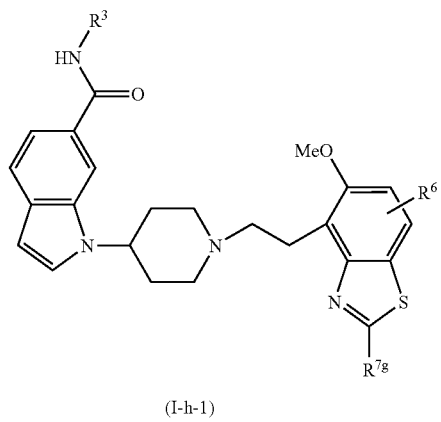
(I-h-1)
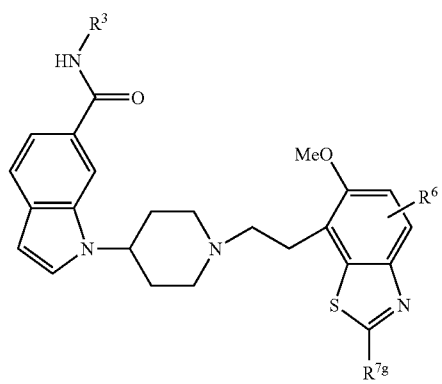
(I-h-2)

-continued

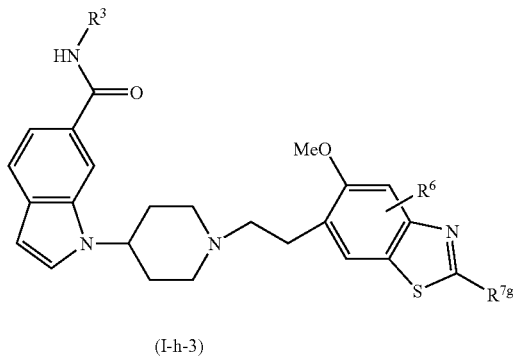

(I-h-3)

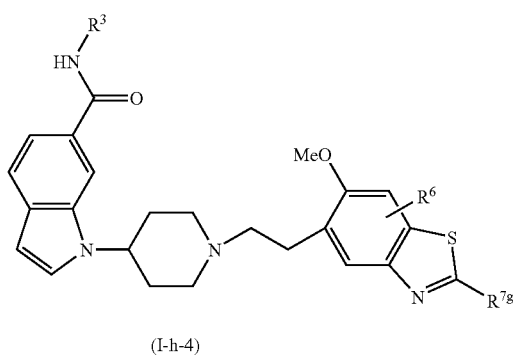

(I-h-4)

wherein R³ represents a hydrogen atom or methyl group;
and R⁶ and R⁷ᵍ represent substituents selected from the following substituent group A1 (excluding a hydroxyl group for R⁷ᵍ), Substituent group A1: (1) a hydrogen atom, (2) a halogen atom, (3) a cyano group, (4) a hydroxyl group, (5) a nitro group, (6) a carboxyl group, (7) a C3-C8 cycloalkyl group, (8) a C2-C6 alkenyl group, (9) a C2-C6 alkynyl group, (10) a C1-C6 alkylthio group, (11) a C1-C6 alkoxycarbonyl group, (12) a C1-C6 alkylsulfonyl group, (13) a C1-C6 alkyl group (wherein the above described C1-C6 alkyl group may be substituted by 1 to 3 substituents selected from the group consisting of a halogen atom, a hydroxyl group, and a C1-C6 alkoxy group), (14) a C1-C6 alkoxy group (wherein the above described C1-C6 alkoxy group may be substituted by 1 to 3 halogen atoms), (15) an amino group (wherein the above described amino group may be substituted by a substituent selected from the group consisting of a C1-C6 alkyl group, a formyl group, a C1-C6 alkanoyl group, and a C1-C6 alkylsulfonyl group), and (16) a carbamoyl group (wherein the above described carbamoyl group may be substituted by one or two C1-C6 alkyl groups);

22) The compound according to 21) above or a pharmacologically acceptable salt thereof, wherein R⁶ represents a substituent selected from the following substituent group A2, and R⁷ᵍ represents a substituent selected from the following substituent group B7, Substituent group A2: (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) C1-C6 alkoxy C1-C6 alkyl group, Substituent group A3: (1) a hydrogen atom, (2) a C1-C6 alkyl group, (3) a halogen atom, (4) a cyano group, and (5) a C1-C6 alkoxy C1-C6 alkyl group;

23) The compound according to 21) or 22) above or a pharmacologically acceptable salt thereof, wherein R⁶ represents a substituent selected from the following substituent group A4, and R⁷ᵍ represents a substituent selected from the following substituent group B6, Substituent group A4: (1) a hydrogen atom, and (2) a C1-C6 alkoxy group, Substituent group B6: (1) a hydrogen atom, and (2) a C1-C6 alkyl group;

24) The compound according to 1) above or a pharmacologically acceptable salt thereof, which is represented by formula (I-i-1) or formula (I-i-2):

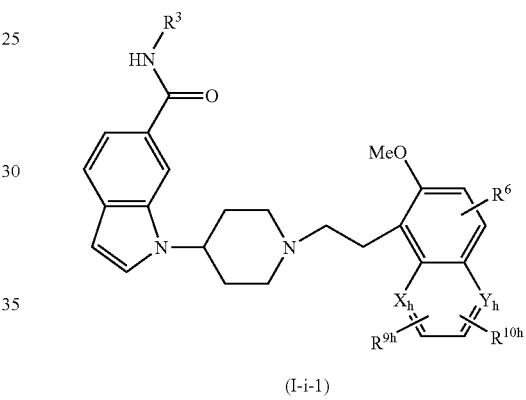

(I-i-1)

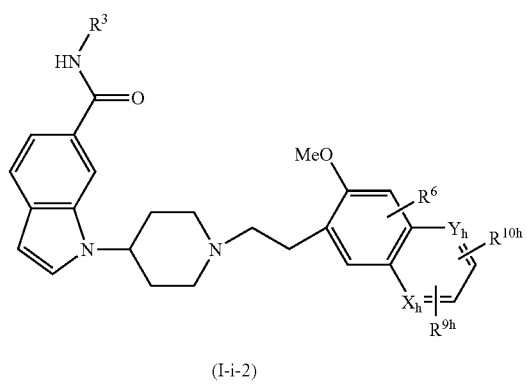

(I-i-2)

wherein R³ represents a hydrogen atom or methyl group;
and R⁶, R⁹ʰ, and R¹⁰ʰ represent substituents selected from the following substituent group A1; and Xₕ and Yₕ represent (1) a methine group or (2) a nitrogen atom, Substituent group A1: (1) a hydrogen atom, (2) a halogen atom, (3) a cyano group, (4) a hydroxyl group, (5) a nitro group, (6) a carboxyl group, (7) a C3-C8 cycloalkyl group, (8) a C2-C6 alkenyl group, (9) a C2-C6 alkynyl group, (10)

a C1-C6 alkylthio group, (11) a C1-C6 alkoxycarbonyl group, (12) a C1-C6 alkylsulfonyl group, (13) a C1-C6 alkyl group (wherein the above described C1-C6 alkyl group may be substituted by 1 to 3 substituents selected from the group consisting of a halogen atom, a hydroxyl group, and a C1-C6 alkoxy group), (14) a C1-C6 alkoxy group (wherein the above described C1-C6 alkoxy group may be substituted by 1 to 3 halogen atoms), (15) an amino group (wherein the above described amino group may be substituted by a substituent selected from the group consisting of a C1-C6 alkyl group, a formyl group, a C1-C6 alkanoyl group, and a C1-C6 alkylsulfonyl group), and (16) a carbamoyl group (wherein the above described carbamoyl group may be substituted by one or two C1-C6 alkyl groups);

25) The compound according to 24) above or a pharmacologically acceptable salt thereof, wherein $R^{9h}$ $R^{10h}$, $R^6$ represent substituents selected from the following substituent group A2; and $X_h$ and $Y_h$ represent (1) a methine group or (2) a nitrogen atom, Substituent group A2: (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) C1-C6 alkoxy C1-C6 alkyl group;

26) The compound according to 8)-25), wherein $R^6$ represents a hydrogen atom;

27) The compound according to 1) above selected from the following group or a pharmacologically acceptable salt thereof:
1) 1-{1-[2-(7-Methoxy-2,2-dimethyl-4-oxochroman-8-yl)ethyl]piperidin-4-yl}-N-methyl-1H-indole-6-carboxamide,
2) 1-{1-[2-(7-Methoxy-2,2-dimethyl-4-oxochroman-8-yl)ethyl]piperidin-4-yl}-1H-indole-6-carboxamide,
3) 1-{1-[2-(7-Methoxy-2,2-dimethyl-4-oxochroman-6-yl)ethyl]piperidin-4-yl}-1H-indole-6-carboxamide,
4) 1-{1-[2-(6-Methoxy-3-oxoindan-5-yl)ethyl]piperidin-4-yl}-1H-indole-6-carboxamide,
5) 1-{1-[2-(6-Methoxy-2-methylbenzoxazol-5-yl)ethyl]piperidin-4-yl}-1H-indole-6-carboxamide,
6) 1-{1-[2-(6-Methoxy-2-methylbenzoxazol-7-yl)ethyl]piperidin-4-yl}-1H-indole-6-carboxamide,
7) 1-{1-[2-(6-Methoxy-3-methylbenzo[d]isoxazol-5-yl)ethyl]piperidin-4-yl}-1H-indole-6-carboxamide,
8) 1-{1-[2-(6-Methoxy-3-methylbenzo[d]isoxazol-7-yl)ethyl]piperidin-4-yl}-1H-indole-6-carboxamide,
9) 1-{1-[2-(5-Methoxy-1-oxoindan-4-yl)ethyl]piperidin-4-yl}-1H-indole-6-carboxamide, and
10) 1-{1-[2-(7-Methoxy-2,3-dihydrobenzo[1,4]dioxin-6-yl)ethyl]piperidin-4-yl}-1H-indole-6-carboxamide;

28) The compound according to 1) above selected from the following group or a pharmacologically acceptable salt thereof:
1) 1-{1-[2-(7-Methoxy-z2,2-dimethyl-4-oxochroman-8-yl)ethyl]piperidin-4-yl}-N-methyl-1H-indole-6-carboxamide,
2) 1-{1-[2-(7-Methoxy-2,2-dimethyl-4-oxochroman-8-yl)ethyl]piperidin-4-yl}-1H-indole-6-carboxamide, and
3) 1-{1-[2-(7-Methoxy-2,2-dimethyl-4-oxochroman-6-yl)ethyl]piperidin-4-yl}-1H-indole-6-carboxamide;

29) A pharmaceutical composition comprising, as an active ingredient, a compound represented by the following formula (I) or a pharmacologically acceptable salt thereof:

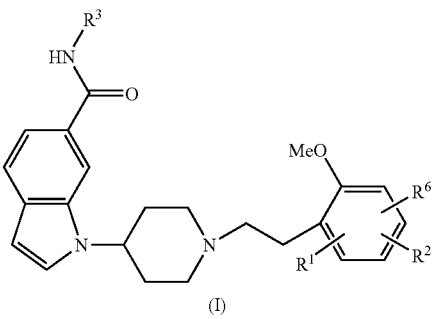

[Formula 20]

(I)

wherein $R^1$ and $R^2$ are substituents adjacent to each other, and together with two carbon atoms to each of which they attach, form:
(1) a 5- to 7-membered non-aromatic carbocyclic group,
(2) a 5- to 7-membered non-aromatic heterocyclyl group,
(3) a 6-membered aromatic carbocyclic group, or
(4) a 5- or 6-membered aromatic heterocyclyl group, which may be substituted by 1 to 4 substituents selected from the following substituent group B1;
$R^3$ represents a hydrogen atom or methyl group; and
$R^6$ represents a substituent selected from the following substituent group A1, Substituent group A1: (1) a hydrogen atom, (2) a halogen atom, (3) a cyano group, (4) a hydroxyl group, (5) a nitro group, (6) a carboxyl group, (7) a C3-C8 cycloalkyl group, (8) a C2-C6 alkenyl group, (9) a C2-C6 alkynyl group, (10) a C1-C6 alkylthio group, (11) a C1-C6 alkoxycarbonyl group, (12) a C1-C6 alkylsulfonyl group, (13) a C1-C6 alkyl group (wherein the above described C1-C6 alkyl group may be substituted by 1 to 3 substituents selected from the group consisting of a halogen atom, a hydroxyl group, and a C1-C6 alkoxy group), (14) a C1-C6 alkoxy group (wherein the above described C1-C6 alkoxy group may be substituted by 1 to 3 halogen atoms), (15) an amino group (wherein the above described amino group may be substituted by a substituent selected from the group consisting of a C1-C6 alkyl group, a formyl group, a C1-C6 alkanoyl group, and a C1-C6 alkylsulfonyl group), and (16) a carbamoyl group (wherein the above described carbamoyl group may be substituted by one or two C1-C6 alkyl groups), Substituent group B1: (1) a hydrogen atom, (2) a halogen atom, (3) a cyano group, (4) a hydroxyl group, (5) a nitro group, (6) an oxo group, (7) a carboxyl group, (8) a C3-C8 cycloalkyl group, (9) a C2-C6 alkenyl group, (10) a C2-C6 alkynyl group, (11) a C1-C6 alkylthio group, (12) a C1-C6 alkoxycarbonyl group, (13) a C1-C6 alkylsulfonyl group, (14) a C1-C6 alkyl group (wherein the above described C1-C6 alkyl group may be substituted by a halogen atom, a hydroxyl group, or a C1-C6 alkoxy group), (15) a C1-C6 alkoxy group (wherein the above described C1-C6 alkoxy group may be substituted by 1 to 3 halogen atoms), (16) an amino group (wherein the above described amino group may be substituted by a substituent selected from the group consisting of a C1-C6 alkyl group, a formyl group, a C1-C6 alkanoyl group, and a C1-C6 alkylsulfonyl group), (17) a carbamoyl group (wherein the above described carbamoyl group may be substituted by one or two C1-C6 alkyl groups), (18) a C1-C6 alkoxyimino group, (19) a C5-C6 cycloalkyl group formed by two C1-C3 alkyl groups attaching to the same carbon atom, and (20) a tetrahydropyranyl group formed by two C1-C3 alkyl group attaching to the same carbon atom, together with an oxygen atom and the above described carbon atom;

30) The pharmaceutical composition according to 28) above characterized in that it is an agent for treating or preventing lower urinary tract symptoms;

31) The pharmaceutical composition according to 30) above characterized in that it is an agent for treating or preventing symptoms regarding urinary storage;

32) The pharmaceutical composition according to 30) or 31) above characterized in that it is an agent for treating or preventing increased urinary frequency or urinary incontinence;

33) The pharmaceutical composition according to 29) above characterized in that it is an agent for treating or preventing cognitive impairment which are associated with Alzheimer's disease or senile dementia; learning or memory disorder, or anxiety disorder, 34) The pharmaceutical composition according to 29) above characterized in that it is an agent for treating or preventing schizophrenia, emotional disorder, alcohol and/or cocaine dependence, symptoms associated with withdrawal from nicotine ingestion or smoking, or visual attention disorder; and 35) The pharmaceutical composition according to 29) above characterized in that it is an agent for treating or preventing sleep disorder, migraine, temperature instability, eating disorder, vomiting, gastrointestinal disorder, or genital insufficiency. The compound represented by formula (I) of the present invention, a pharmacologically acceptable salt thereof, and an agent for treating or preventing lower urinary tract symptoms, which has ability to bind to a serotonin 1A receptor, are all novel inventions that have not been described in any publications.

The meanings of symbols or terms used in the specification of the present application will be explained below, and the present invention will be described in detail.

In addition, it is to be noted that, as a matter of convenience, the structural formula of a compound indicates a fixed isomer in the specification of the present application. However, the present invention includes all of geometrical isomers to occur in the structure of compounds, isomers such as optical isomers on the basis of asymmetric carbon, stereoisomers, tautomers and isomeric mixtures. Thus, the present invention is not limited by the structural formula shown as a matter of convenience in the present specification, but either an isomer or a mixture may be included. Hence, it is likely that a compound has an asymmetric carbon atom in a molecule thereof, and that an optically active substance and racemete exist. In the present invention, there are no limitation regarding such cases, and both cases are included in the scope of the present invention. Moreover, there is the case where a crystal polymorphism exists. This case is also not limited, and it may be either single crystal form or those mixtures likewise, and it may be hydrate besides anhydride.

In the specification of the present application, the term "lower urinary tract symptoms" is used as a generic name for symptoms relating to disorder in urine collection mechanism and disorder in urination mechanism.

In the specification of the present application, the term "urinary dysfunction" is used to mean various types of "disorder/abnormality" impairing normal urination, including (1) "abnormality of the volume of urine" such as polyuria, oliguria, or anuria, (2) "abnormality of the frequency of urination" such as increased urinary frequency or oligakisuria, (3) "difficulty in urination", (4) "anuresis", (5) "urinary incontinence", (6) "abnormality of urination condition" such as enuresis, (7) "abnormality of urinary stream" such as decreased urinary stream, decreased urinary force, interruption, or double voiding, and the like. In addition, the term "urinary dysfunction" also includes diseases specified in the form of subordinate conception, with respect to the "disorders/abnormalities" described in (1) to (7) above that are specified in the form of super-ordinate conception. For example, "urinary dysfunction" naturally includes the following diseases: neuropathic bladder, neurotic increased urinary frequency, unstable bladder, increased urinary frequency associated with a bladder irritation state caused by chronic bladder, increased urinary frequency associated with a bladder irritation state caused by chronic prostatitis, urinary urgency, urge incontinence, reflex urinary incontinence, stress incontinence, overflow incontinence, urinary incontinence associated with a bladder irritation state caused by chronic cystitis, urinary incontinence associated with a bladder irritation state caused by chronic prostatitis, nocturia, psychogenic dysuria, nocturnal enuresis, or the like.

In the specification of the present application, the term "anxiety disorder" is used to mean, for example, generalized anxiety disorder, panic disorder, phobic neurosis (e.g. agoraphobia, anthropophobia, simple phobia), obsessive-compulsive disorder, or the like. The term "emotional disorder" is used herein to mean depression (major depression), manic-depressive psychosis (bipolar disorder), dysthymia (depressive neurosis), or the like.

Each of "a 5- to 7-membered non-aromatic carbocyclic group," "a 5- to 7-membered non-aromatic heterocyclyl group," "a 6-membered aromatic carbocyclic group," and "a 5- or 6-membered aromatic heterocyclyl group" that are contained in the agent of the present invention for treating or preventing lower urinary tract symptoms, represented by the above described formula (I), has the following meaning.

The term "5- to 7-membered non-aromatic carbocyclic group" means a non-aromatic hydrocarbon group containing 5 to 7 carbon atoms. Examples of such a group may include a cyclopentyl group, a cyclohexyl group, and a cycloheptyl group.

The term "5- to 7-membered non-aromatic heterocyclyl group" means a non-aromatic heterocyclyl group containing 1 to 4 heteroatoms. Preferred examples of such a group may include a pyrrolidinyl group, an imidazolidinyl group, a pyrazolidinyl group, a piperidinyl group, a piperazinyl group, a morpholinyl group, a tetrahydropyranyl group, a dioxanyl group, a piperidin-2-oxo yl group, a dihydro-[1,3]oxazin-2-oxo yl group, a [1,4]oxazepan-5-oxo yl group, a dihydro-[1,3]oxazin-2,4-dioxo yl group, a 5,6-dihydro-1H-pyridin-2-oxo yl group, a tetrahydropyran-4-oxo yl group, a 2,3-dihydropyran-4-oxo yl group, a tetrahydropyran-4-hydroxy yl group, an oxepan-4-oxo yl group, a 1,3-oxazolidin-2-oxo yl group and the like.

The term "6-membered aromatic carbocyclic group" means a phenyl group.

A preferred example of the "5- or 6-membered aromatic heterocyclyl group" may be (1) nitrogen containing heteroaromatic groups such as a pyrrolyl group, a pyridyl group, a pyridaziniyl group, a pyrimidinyl group, a pyrazinyl group; (2) sulfur containing heteroaromatic groups such as a thienyl group; (3) oxygen containing heteroaromatic groups such as a furyl group, a oxaspiro[5,4]decanyl group; (4) two or more heteroatoms containing heteroaromatic groups such as a thiazoyl group, an isothiazolyl group, an oxazoyl group, an isoxazolyl group, and those two or more heteroatoms are selected from a nitrogen atom, an oxygen atom, and a sulfur atom.

In formula (I), each of substituent group A1, substituent group A2, substituent group A3, substituent group A4, substituent group B1, substituent group B2, substituent group B3, substituent group B4, substituent group B5, substituent group B6, and substituent group B7, includes the following groups.

Substituent group A1 consists of (1) a hydrogen atom, (2) a halogen atom, (3) a cyano group, (4) a hydroxyl group, (5) a nitro group, (6) a carboxyl group, (7) a C3-C8 cycloalkyl group, (8) a C2-C6 alkenyl group, (9) a C2-C6 alkynyl group, (10) a C1-C6 alkylthio group, (11) a C1-C6 alkoxycarbonyl group, (12) a C1-C6 alkylsulfonyl group, (13) a C1-C6 alkyl group (wherein the above described C1-C6 alkyl group may be substituted by 1 to 3 substituents selected from the group consisting of a halogen atom, a hydroxyl group, and a C1-C6 alkoxy group), (14) a C1-C6 alkoxy group (wherein the above described C1-C6 alkoxy group may be substituted by 1 to 3 halogen atoms), (15) an amino group (wherein the above described amino group may be substituted by a substituent selected from the group consisting of a C1-C6 alkyl group, a formyl group, a C1-C6 alkanoyl group, and a C1-C6 alkylsulfonyl group), (16) a carbamoyl group (wherein the above described carbamoyl group may be substituted by one or two C1-C6 alkyl groups), and (17) a C1-C6 alkoxyimino group.

Substituent group A2 consists of (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) C1-C6 alkoxy C1-C6 alkyl group.

Substituent group A3 consists of (1) a hydrogen atom, (2) a C1-C6 alkyl group, (3) a halogen atom, (4) a cyano group, and (5) a C1-C6 alkoxy C1-C6 alkyl group.

Substituent group A4 consists of (1) a hydrogen atom and (2) a C1-C6 alkoxy group.

Substituent group B1 consists of (1) a hydrogen atom, (2) a halogen atom, (3) a cyano group, (4) a hydroxyl group, (5) a nitro group, (6) an oxo group, (7) a carboxyl group, (8) a C3-C8 cycloalkyl group, (9) a C2-C6 alkenyl group, (10) a C2-C6 alkynyl group, (11) a C1-C6 alkylthio group, (12) a C1-C6 alkoxycarbonyl group, (13) a C1-C6 alkylsulfonyl group, (14) a C1-C6 alkyl group (wherein the above described C1-C6 alkyl group may be substituted by a halogen atom, a hydroxyl group, or a C1-C6 alkoxy group), (15) a C1-C6 alkoxy group (wherein the above described C1-C6 alkoxy group may be substituted by 1 to 3 halogen atoms), (16) an amino group (wherein the above described amino group may be substituted by a substituent selected from the group consisting of a C1-C6 alkyl group, a formyl group, a C1-C6 alkanoyl group, or a C1-C6 alkylsulfonyl group), (17) a carbamoyl group (wherein the above described carbamoyl group may be substituted by one or two C1-C6 alkyl groups), (18) a C1-C6 alkoxyimino group, (19) a C5-C6 cycloalkyl group formed by two C1-C3 alkyl groups attaching to the same carbon atom, and (20) a tetrahydropyranyl group formed by two C1-C3 alkyl group attaching to the same carbon atom, together with an oxygen atom and the above described carbon atom.

When the substituents described in (19) or (20) above are specifically illustrated, they are represented by the following formula, for example:

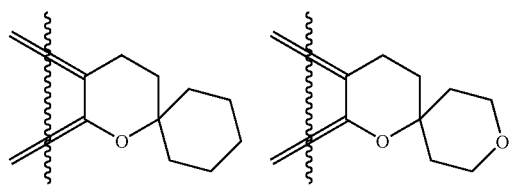

[Formula 21]

Substituent group B2 consists of (1) a hydrogen atom, (2) a C1-C6 alkyl group, (3) a halogen atom, (4) a hydroxyl group, (5) a C1-C6 alkoxy group, (6) a C1-C6 alkoxy C1-C6 alkyl group, (7) a C5-C6 cycloalkyl group formed by two C1-C3 alkyl groups attaching to the same carbon atom, and (8) a tetrahydropyranyl group formed by two C1-C3 alkyl group attaching to the same carbon atom, together with an oxygen atom and the above described carbon atom.

Substituent group B3 consists of (1) a hydrogen atom, (2) a C1-C6 alkyl group, (3) a halogen atom, (4) a hydroxyl group, (5) a C1-C6 alkoxy group, and (6) a C1-C6 alkoxy C1-C6 alkyl group.

Substituent group B4 consists of (1) a hydrogen atom, (2) a C1-C6 alkyl group, (3) a C1-C6 alkoxy group, and (4) a C1-C6 alkoxy C1-C6 alkyl group.

Substituent group B5 consists of (1) a hydrogen atom, (2) a C1-C6 alkyl group, (3) a C1-C6 alkoxy C1-C6 alkyl group, (4) a C5-C6 cycloalkyl group formed by two C1-C3 alkyl groups attaching to the same carbon atom, and (5) a tetrahydropyranyl group formed by two C1-C3 alkyl group attaching to the same carbon atom, together with an oxygen atom and the above described carbon atom.

Substituent group B6 consists of (1) a hydrogen atom and (2) a C1-C6 alkyl group.

Substituent group B7 consists of (1) a hydrogen atom, (2) a C1-C6 alkyl group, (3) a halogen atom, (4) a cyano group, and (5) a C1-C6 alkoxy C1-C6 alkyl group.

The term "halogen atom" means a fluorine atom, chlorine atom, bromine atom, iodine atom. It is preferably a fluorine atom, chlorine atom, or bromine atom.

The term "C1-C6 alkyl group" means an alkyl group containing 1 to 6 carbon atoms. Preferred examples of such a group include linear or branched alkyl groups such as a methyl group, ethyl group, n-propyl group, isopropyl group, n-butyl group, isobutyl group, tert-butyl group, n-pentyl group, isopentyl group, neopentyl group, n-hexyl group, 1-methylpropyl group, 1,2-dimethylpropyl group, 2-ethylpropyl group, 1-methyl-2-ethylpropyl group, 1-ethyl-2-methylpropyl group, 1,1,2-trimethylpropyl group, 1-methylbutyl group, 2-methylbutyl group, 1,1-dimethylbutyl group, 2,2-dimethylbutyl group, 2-ethylbutyl group, 1,3-dimethylbutyl group, 2-methylpentyl group, or 3-methylpentyl group.

The term "C2-C6 alkenyl group" means an alkenyl group containing 2 to 6 carbon atoms. Preferred examples of such a group include linear or branched alkenyl groups such as a vinyl group, allyl group, 1-propenyl group, isopropenyl group, 1-buten-1-yl group, 1-buten-2-yl group, 1-buten-3-yl group, 2-buten-1-yl group, or 2-buten-2-yl group.

The term "C2-C6 alkynyl group" means an alkynyl group containing 2 to 6 carbon atoms. Preferred examples of such a group include linear or branched alkynyl groups such as an ethynyl group, 1-propynyl group, 2-propynyl group, butynyl group, pentynyl group, or hexynyl group.

The term "C3-C8 cycloalkyl group" means a cyclic alkyl group containing 3 to 8 carbon atoms. Preferred examples of such a group include a cyclopropyl group, a cyclobutyl group, a cyclopentyl group, a cyclohexyl group, cycloheptyl group, and cyclooctyl group.

The term "C1-C6 alkoxy group" means an alkyl group containing 1 to 6 carbon atoms, wherein a hydrogen atom is substituted by an oxygen atom. Preferred examples of such a group include a methoxy group, an ethoxy group, a n-propoxy group, an isopropoxy group, a sec-propoxy group, a n-butoxy group, an isobutoxy group, a sec-butoxy group, a tert-butoxy group, a n-pentyloxy group, an isopentyloxy group, a sec-pentyloxy group, a tert-pentyloxy group, a n-hexyloxy group, an isohexyloxy group, a 1,2-dimethylpropoxy group, a 2-ethylpropoxy group, a 1-methyl-2-ethylpropoxy group, a 1-ethyl-2-methylpropoxy group, a 1,1,2-trimethylpropoxy group, a 1,1-dimethylbutoxy group, a 2,2-dimethylbutoxy group, a 2-ethylbutoxy group, a 1,3-dimethylbutoxy group, a 2-methylpentyloxy group, a 3-methylpentyloxy group, a hexyloxy group, and the like.

The term "C1-C6 alkylthio group" means an alkyl group containing 1 to 6 carbon atoms, wherein a hydrogen atom is substituted by a sulfur atom. Preferred examples of such a group include a methylthio group, an ethylthio group, a n-propylthio group, an isopropylthio group, a n-butylthio group, an isobutylthio group, a tert-butylthio group, a n-pentylthio group, an isopentylthio group, a neopentylthio group, a n-hexylthio group, a 1-methylpropylthio group, and the like.

The term "C1-C6 alkoxycarbonyl group" means a group formed by binding a carbonyl group to the aforementioned alkoxy group. Preferred examples of such a group include a methoxycarbonyl group and an ethoxycarbonyl group.

The term "C5-C6 cycloalkyl group formed by two C1-C3 alkyl groups attaching to the same carbon atom" means a cyclopentyl group or cyclohexyl group.

The term "C1-C6 alkanoyl group (C1-C6 alkylcarbonyl group)" means an alkyl group containing 1 to 6 carbon atoms wherein a hydrogen atom is substituted by a carbonyl group. Preferred examples of such a group include an acetyl group, a propionyl group, and a butyryl group, and the like.

The term "C1-C6 alkylsulfonyl group" means an alkyl group containing 1 to 6 carbon atoms wherein a hydrogen atom is substituted by a sulfonyl group. Preferred examples of such a group include a methanesulfonyl group, an ethanesulfonyl group, and the like.

The term "amino group that may be substituted by a C1-C6 alkyl group" means an amino group to which an alkyl group containing 1 to 6 carbon atoms attaches. Preferred examples of such a group include an amino group, a methylamino group, an ethylamino group, a propylamino group, and the like.

Examples of an "amino group that may be substituted by a formyl group" include an amino group and a formylamino group.

The term "amino group that may be substituted by a C1-C6 alkanoyl group" means an amino group to which an alkanoyl group containing 1 to 6 carbon atoms attaches. Preferred examples of such a group include an acetylamino group, a propionylamino group, a butyrylamino group, and the like.

The term "amino group that may be substituted by a C1-C6 alkylsulfonyl group" means an amino group to which an alkylsulfonyl group containing 1 to 6 carbon atoms attaches. Preferred examples of such a group include an amino group, a methanesulfonylamino group, an ethanesulfonylamino group, an n-propanesulfonylamino group, an n-butanesulfonylamino group, an N-methylmethanesulfonylamino group, and the like.

The term "carbamoyl group that may be substituted by one or two C1-C6 alkyl groups" means a carbamoyl group wherein one or two hydrogen atoms may be mono- or di-substituted by C1-C6 alkyl group(s). Preferred examples of such a group include an N-methylcarbamoyl group, an N,N-dimethylcarbamoyl group, an N-ethylcarbamoyl group, an N,N-diethylcarbamoyl group, and the like.

The term "C1-C6 alkoxyimino group" means an imino group wherein a hydrogen atom is substituted by a C1-C6 alkoxy group. Preferred examples of such a group include a methoxyimino group, an ethoxyimino group, and the like.

Next, the compound represented by formula (I) of the present invention will be described.

The compound represented by formula (I) selectively binds to a serotonin 1A receptor and has an antagonism to the receptor. It is used to treat or prevent diseases in which a serotonin 1A receptor is involved, such as lower urinary tract symptoms. Preferred examples of such a compound may include the compound represented by formula (I-a-1), the compound
represented by formula (I-a-2), the compound
represented by formula (I-a-3), the compound
represented by formula (I-a-4), the compound
represented by formula (I-c-1), the compound
represented by formula (I-c-2), the compound
represented by formula (I-d-1), the compound
represented by formula (I-d-2), the compound
represented by formula (I-e-1), the compound
represented by formula (I-e-2), the compound
represented by formula (I-f-1), the compound
represented by formula (I-f-2), the compound
represented by formula (I-f-3), the compound
represented by formula (I-f-4), the compound
represented by formula (I-g-1), the compound
represented by formula (I-g-2), the compound
represented by formula (I-h-1), the compound
represented by formula (I-h-2), the compound
represented by formula (I-h-3), the compound
represented by formula (I-h-4), the compound
represented by formula (I-i-1), and the compound
represented by formula (I-i-2).

Among these compounds, as the compound represented by formula (I-a-1), (I-a-2), (I-a-3), or (I-a-4), a compound wherein, in each formula, $R^{11a}$ and $R^{12a}$ form a carbonyl group, together with carbon atoms to which $R^{11a}$ and $R^{12a}$ attach, $X_a$ represents an oxygen atom, $R^3$ represents a hydrogen atom or methyl group, $R^{4a}$ and $R^{5a}$ represent substituents selected from the group consisting of (1) a hydrogen atom, (2) a C1-C6 alkyl group, (3) a C1-C6 alkoxy C1-C6 alkyl group, (4) a C5-C6 cycloalkyl group formed by two C1-C3 alkyl groups attaching to the same carbon atom, and (5) a tetrahydropyranyl group formed by two C1-C3 alkyl group attaching to the same carbon atom, together with an oxygen atom and the above described carbon atom, $R^6$ represents a substituent selected from the group consisting of (1) a hydrogen atom and (2) a C1-C6 alkoxy group, and Na represents an integer between 1 and 3, or a pharmacologically acceptable salt thereof, is more preferable.

As the compound represented by formula (I-c-1) or (I-c-2), a compound wherein, in each formula, $R^3$ represents a hydrogen atom or methyl group, $R^{4d}$ and $R^{5d}$ are substituents selected from the group consisting of (1) a hydrogen atom, (2) a C1-C6 alkyl group, (3) a C1-C6 alkoxy group, and (4) a C1-C6 alkoxy C1-C6 alkyl group, and R⁶ represents a substituent selected from the group consisting of (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) a C1-C6 alkoxy C1-C6 alkyl group, or a pharmacologically acceptable salt thereof, is more preferable.

As the compound represented by formula (I-d-1) or (I-d-2), a compound wherein, in each formula, $R^3$ represents a hydrogen atom or methyl group, each of $X_e$ and $Y_e$ represents (1) an oxygen atom, (2) a methylene group, (3) —CONR$^{7e}$— (wherein R$^{7e}$ represents (1) a hydrogen atom, or (2) a C1-C6 alkyl group), (4) —NR$^{7e}$CO— (wherein R$^{7e}$ has the same above meaning), (5) —NR$^{8e}$— (wherein R$^{8e}$ represents (1) a C1-C6 alkyl group, or (2) a C1-C6 acyl group), or (6) a single bond, $R^{4e}$ and $R^{5e}$ represent substituents selected from the group consisting of (1) a hydrogen atom, (2) a C1-C6 alkyl group, (3) a halogen atom, (4) a hydroxyl group, (5) a C1-C6 alkoxy group, and (6) a C1-C6 alkoxy C1-C6 alkyl group, and R⁶ represents a substituent selected from the group consisting of (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) a C1-C6 alkoxy C1-C6 alkyl group, or a pharmacologically acceptable salt thereof, is more preferable.

As the compound represented by formula (I-e-1) or (I-e-2), a compound wherein, in each formula, $R^3$ represents a hydrogen atom or methyl group, R⁶ represents a substituent selected from the group consisting of (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) a C1-C6 alkoxy C1-C6 alkyl group, $R^{7f}$ represents a substituent selected from the group consisting of (1) a hydrogen atom, (2) a C1-C6 alkyl group, and (3) a C1-C6 alkoxy C1-C6 alkyl group, and each of $X_f$ and $Y_f$ represents substituents selected from the group consisting of (1) a single bond, (2) a methylene group that may have a substituent selected from the group consisting of a hydrogen atom, a C1-C6 alkyl group, and a C1-C6 alkoxy C1-C6 alkyl group, and (3) a carbonyl group, or a pharmacologically acceptable salt thereof, is more preferable.

As the compound represented by formula (I-f-1), (I-f-2) (I-f-3), (I-f-4), (I-g-1), (I-g-2), (I-h-1), (I-h-2), (I-h-3), or (I-h-4), a compound wherein, in each formula, $R^3$ represents a hydrogen atom or methyl group, R⁶ represents a substituent selected from the group consisting of (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) a C1-C6 alkoxy C1-C6 alkyl group, and $R^{7g}$ represents a substituent selected from the group consisting of (1) a hydrogen atom, (2) a C1-C6 alkyl group, (3) a halogen atom, (4) a cyano group, and (5) C1-C6 alkoxy C1-C6 alkyl group, or a pharmacologically acceptable salt thereof, is more preferable.

As the compound represented by formula (I-i-1) or (I-i-2), a compound wherein, in each formula, $R^3$ represents a hydrogen atom or methyl group, $R^{9h}$, $R^{10h}$, and R⁶ represent substituents selected from the group consisting of (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) a C1-C6 alkoxy C1-C6 alkyl group, and each of $X_h$ and $Y_h$ represents (1) a methine group or (2) a nitrogen atom, or a pharmacologically acceptable salt thereof, is more preferable.

Among these compound groups, the most preferred compounds are as follows. In the case of the compound represented by formula (I-b-1), (I-b-2), (I-b-3), or (I-b-4), a compound wherein, in each formula, $R^3$ represents a hydrogen atom or methyl group, $R^{4a}$ and $R^{5a}$ represent substituents selected from the group consisting of (1) a hydrogen atom, (2) a C1-C6 alkyl group, (3) a C1-C6 alkoxy C1-C6 alkyl group, (4) a C5-C6 cycloalkyl group formed by two C1-C3 alkyl groups attaching to the same carbon atom, and (5) a tetrahydropyranyl group formed by two C1-C3 alkyl group attaching to the same carbon atom, together with an oxygen atom and the above described carbon atom, and R⁶ represents a substituent selected from the group consisting of (1) a hydrogen atom and (2) a C1-C6 alkoxy group or a pharmacologically acceptable salt thereof, is most preferable. In the case of the compound represented by formula (I-f-1), (I-f-2), (I-f-3), (I-f-4), (I-g-1), (I-g-2), (I-h-1), (I-h-2), (I-h-3), or (I-h-4), a compound wherein, in each formula, $R^3$ represents a hydrogen atom or methyl group, R⁶ represents a substituent selected from the group consisting of (1) a hydrogen atom and (2) a C1-C6 alkoxy group, and $R^{7g}$ represents a substituent selected from the group consisting of (1) a hydrogen atom and (2) a C1-C6 alkyl group or a pharmacologically acceptable salt thereof, is most preferable.

In particular, compounds selected from the following group or pharmacologically acceptable salts thereof are preferable:

1) 1-{1-[2-(7-Methoxy-2,2-dimethyl-4-oxochroman-8-yl)ethyl]piperidin-4-yl}-N-methyl-1H-indole-6-carboxamide, 2) 1-{1-[2-(7-Methoxy-2,2-dimethyl-4-oxochroman-8-yl)ethyl]piperidin-4-yl}-1H-indole-6-carboxamide, 3) 1-{1-[2-(7-Methoxy-2,2-dimethyl-4-oxochroman-6-yl)ethyl]piperidin-4-yl}-1H-indole-6-carboxamide, 4) 1-{1-[2-(6-Methoxy-3-oxoindan-5-yl)ethyl]piperidin-4-yl}-1H-indole-6-carboxamide, 5) 1-{1-[2-(6-Methoxy-2-methylbenzoxazol-5-yl)ethyl]piperidin-4-yl}-1H-indole-6-carboxamide, 6) 1-{1-[2-(6-Methoxy-2-methylbenzoxazol-7-yl)ethyl]piperidin-4-yl}-1H-indole-6-carboxamide, 7) 1-{1-[2-(6-Methoxy-3-methylbenzo[d]isoxazol-5-yl)ethyl]piperidin-4-yl}-1H-indole-6-carboxamide,
8) 1-{1-[2-(6-Methoxy-3-methylbenzo[d]isoxazol-7-yl)ethyl]piperidin-4-yl}-1H-indole-6-carboxamide,
9) 1-{1-[2-(5-Methoxy-1-oxoindan-4-yl)ethyl]piperidin-4-yl}-1H-indole-6-carboxamide, and
10) 1-{1-[2-(7-Methoxy-2,3-dihydrobenzo[1,4]dioxin-6-yl)ethyl]piperidin-4-yl}-1H-indole-6-carboxamide.

Among them, for example,
1) 1-{1-[2-(7-Methoxy-2,2-dimethyl-4-oxochroman-8-yl)ethyl]piperidin-4-yl}-N-methyl-1H-indole-6-carboxamide,
2) 1-{1-[2-(7-Methoxy-2,2-dimethyl-4-oxochroman-8-yl)ethyl]piperidin-4-yl}-1H-indole-6-carboxamide, and
3) 1-{1-[2-(7-Methoxy-2,2-dimethyl-4-oxochroman-6-yl)ethyl]piperidin-4-yl}-1H-indole-6-carboxamide.

These compounds or pharmacologically acceptable salts thereof have a good antagonism to a 5-HT1A receptor, and are useful as agents for treating or preventing lower urinary tract symptoms, and particularly, symptoms regarding urinary storage.

Preferred embodiments of the above described compound represented by formula (I) are described above. However, the active ingredients of the pharmaceutical of the present invention are not limited to specific compounds described in the present specification. All of embodiments included in the scope of the compound represented by formula (I) can be selected to the maximum extent possible.

A method for producing the compound represented by formula (I) of the present invention will be described below.

A compound represented by the general formula (I):

[Formula 22]

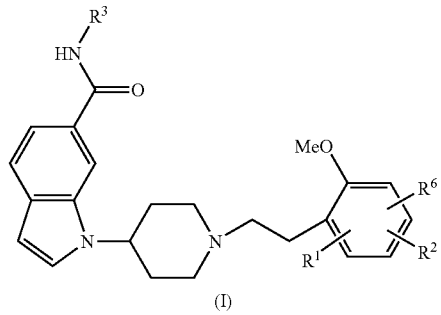

(I)

wherein $R^1$, $R^2$, $R^3$, and $R^6$ have the same meanings as described above, is synthesized by the general production methods 1 to 5 described below, for example. The term "room temperature" described below is used to mean a temperature approximately between 15° C. and 30° C.

[General Production Method 1]

[Formula 23]

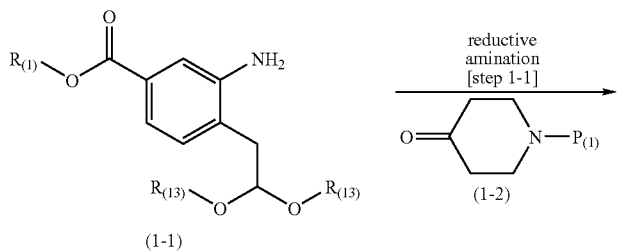

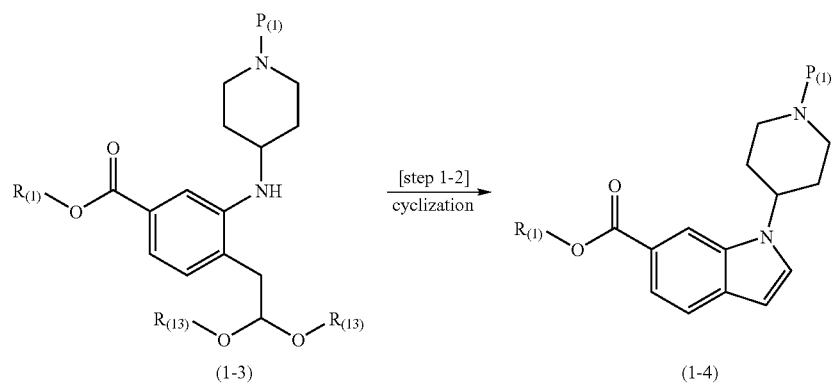

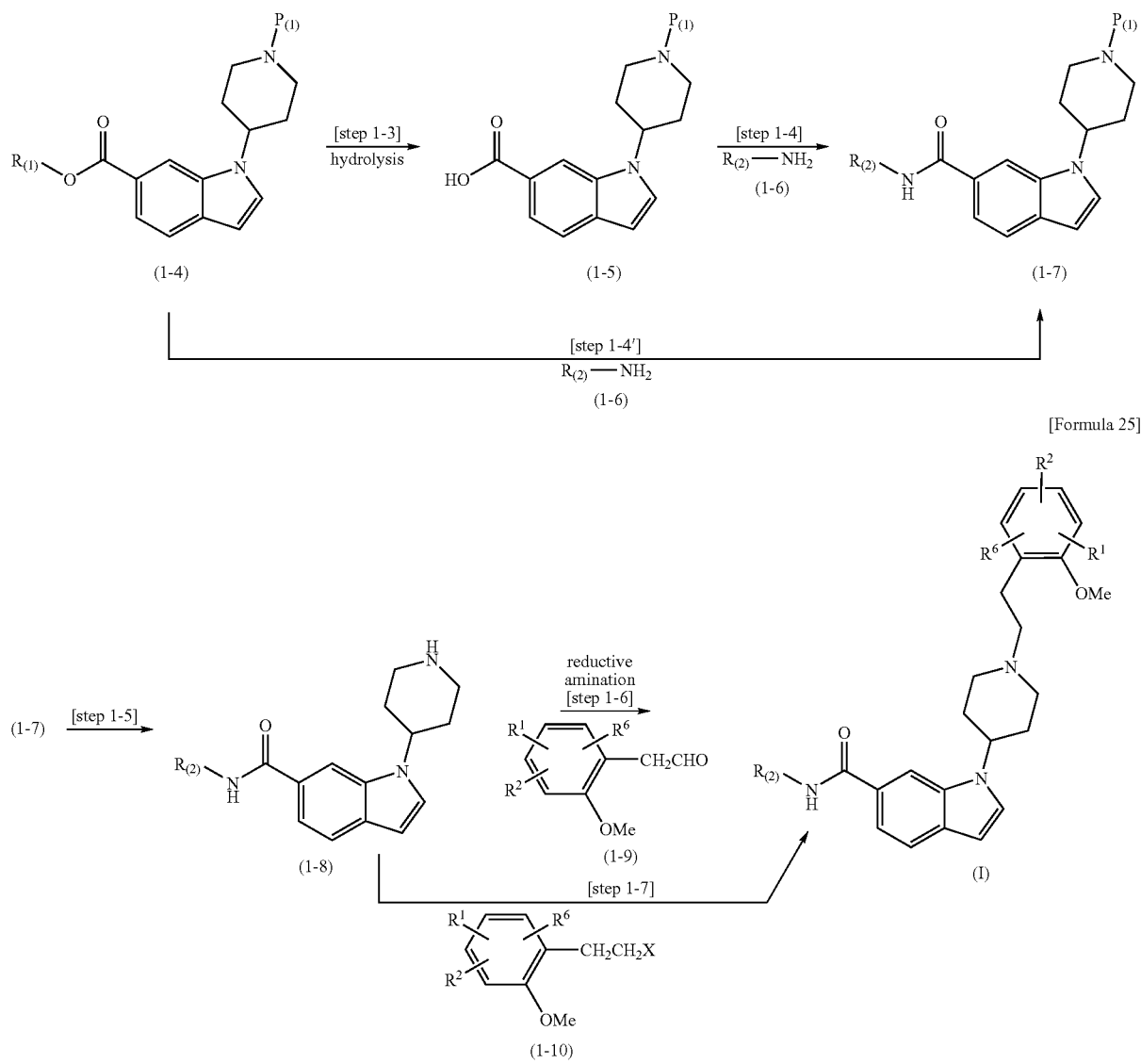

wherein $R_{(1)}$ represents a lower alkyl group such as a methyl group or ethyl group, a lower aralkyl group such as a benzyl group, or the like; $R_{(2)}$ represents a hydrogen atom, a methyl group, or the like; X represents a leaving group including a halogen atom (a chlorine atom, a bromine atom, an iodine atom, etc.), a sulfonyloxy group such as a methanesulfonyloxy group, p-toluenesulfonyloxy group, or trifluoromethanesulfonyloxy group, or the like; $R_{(13)}$ represents a methyl group, an ethyl group, or the like, which are capable of being hydrolyzed; $P_{(1)}$ represents a protecting group for an amino group, which is able to be deprotected, such as a benzyloxycarbonyl group, tert-butyloxycarbonyl group, or the like; and $R^1$, $R^2$, $R^3$, and $R^6$ have the same meanings as described above.

The above described [General Production Method 1] is a method for producing the compound represented by formula (I) of the present invention, which uses compound (1-1) as a raw material and conducts multi-stage steps ranging from [Step 1-1] to [Step 1-7].

Compound (1-1) can also be produced from a commercially available product according to the methods known to persons skilled in the art. Examples of such known methods may include: Coe, J. W.; Vetelino, M. G.; Bradlee, M. J.; Tetrahedron Lett., 37 (34), 6045-6048 (1996), Arai, E.; Tokuyama, H.; Linsell, M. S.; Fukuyama, T.; Tetrahedron Lett., 39 (1), 71-74 (1998), Tishler, A. N., Lanza, T. J.; Tetrahedron Lett., 27 (15), 1653 (1986), and Sakamoto Takao, Kondo Yoshinori, Yamanaka Hiroshi, Chem. Pharm. Bull., Vol. 34, P. 2362 (1986).

With regard to compound (1-2) and compound (1-6), commercially available products may directly be used, or these compounds may also be produced from commercially available products according to methods known to persons skilled in the art. Compound (1-9) and compound (1-10) may be produced from commercially available products according to methods known to persons skilled in the art, or may also be produced by the method described in production examples in the present examples.

[Step 1-1]

This is a step of obtaining compound (1-3) by the reductive amination of compound (1-1) and compound (1-2).

The reaction can be carried out under the same conditions as those commonly used for the reductive amination of a carbonyl compound and an amine compound. The reduction reaction in this step is not particularly limited. Examples of such a reaction may include a reductive amination reaction using a reducing agent such as borane or a boron hydride complex compound, and a catalytic reduction reaction using a metal catalyst under a hydrogen atmosphere.

Examples of a reductive amination reaction using a boron hydride complex compound may be methods described in publications such as W. S. Emerson, Organic Reactions, 4, 174 (1948), C. F. Lane, Synthesis, 135 (1975), J. C. Ctowell and S. J. Pedegimas, Synthesis, 127 (1974), A. F. Abdel-Magid, K. G. Carson, B. D. Harris, C. A. Maryanoff and R. D. Shah, Journal of Organic Chemistry, 61, 3849 (1996).

Examples of a boron hydride complex compound used herein may include sodium borohydride, sodium cyanoborohydride, and sodium triacetoxy borohydride.

When a boron hydride complex compound is used as a reducing agent, a solvent is not particularly limited, as long as it does not inhibit the reaction and dissolves a starting substance to a certain extent. Specific examples of a solvent used herein may include methanol, ethanol, tetrahydrofuran, N,N-dimethylformamide, methylene chloride, and 1,2-dichloroethane. When the present reaction is carried out in the coexistence of acid, preferred results such as the improvement of yield can be obtained. Acid is not particularly limited. Preferred examples of such acid may include mineral acids such as hydrochloric acid, organic acids such as acetic acid, and Lewis acids such as zinc chloride, a boron trifluoride diethyl ether complex, or titanium (IV) tetraisopropoxide.

Compound (1-2) is used at a ratio of 0.8 to 2.5 equivalents, and preferably 1 to 1.5 equivalents, with respect to compound (1-1). A boron hydride complex compound is used at a ratio of 1 to 3 equivalents, and preferably 1 to 1.5 equivalents, with respect to compound (1-1). The reaction time is not particularly limited. It is generally between 0.5 and 48 hours, and preferably between 0.5 and 12 hours.

The reaction temperature is not particularly limited. It is generally between −78° C. and a solvent-reflux temperature, and preferably between a temperature on ice and a room temperature.

When a catalytic reduction reaction is carried out under a hydrogen atmosphere, a solvent used is not particularly limited, as long as it does not inhibit the reaction. Examples of a solvent may include methanol, ethanol, tetrahydrofuran, and 1,4-dioxane. Examples of a metal catalyst used for the reaction may include palladium, platinum oxide, and Raney nickel. The reaction time is not particularly limited. It is generally between 1 and 48 hours, and preferably between 1 and 24 hours.

The reaction conditions are not particularly limited. The reaction can be carried out at a temperature between a room temperature and a solvent-reflux temperature at a pressure between an ordinary pressure and a pressure of 150 atmospheres, and preferably at a temperature between a room temperature and 60° C. at a pressure between an ordinary pressure and a pressure of 5 atmospheres.

[Step 1-2]

This step involves a method of obtaining compound (1-4) by the ring closure of compound (1-3) with acid.

The reaction can be carried out under the same reaction conditions as those described in, for example, Coe, J. W.; Vetelino, M. G.; Bradlee, M. J.; Tetrahedron Lett., 37 (34), 6045-6048 (1996), Arai, E.; Tokuyama, H.; Linsell, M. S.; Fukuyama, T.; Tetrahedron Lett., 39 (1), 71-74 (1998), Tishler, A. N., Lanza, T. J.; Tetrahedron Lett., 27 (15), 1653 (1986), and Sakamoto Takao, Kondo Yoshinori, Yamanaka Hiroshi, Chem. Pharm. Bull., Vol. 34, P. 2362 (1986).

A solvent used in the present reaction is not particularly limited, as long as it does not inhibit the reaction and dissolves a starting substance to a certain extent. Examples of such a solvent may include: water; mixed solvent consisting of water and an organic solvent such as methanol, ethanol, tetrahydrofuran, 1,4-dioxane, benzene, or toluene; and organic solvents such as methanol, ethanol, tetrahydrofuran, 1,4-dioxane, benzene, or toluene. The present reaction can be carried out by allowing appropriate acid at a ratio between 1 equivalent and an excessive amount to acting on the aforementioned compound in the aforementioned solvent. Examples of acid used herein may include acetic acid, hydrogen chloride, hydrochloric acid, hydrobromic acid, sulfuric acid, nitric acid, trifluoroacetic acid, p-toluenesulfonic acid, p-toluenesulfonic acid-pyridinium salt, and camphorsulfonic acid.

The reaction time is not particularly limited. It is generally between 1 and 24 hours, and preferably between 1 and 4 hours.

The reaction temperature is generally between a temperature on ice and a solvent-reflux temperature. It is to be noted that [Step 1-1] and [Step 1-2] can also be carried out by one-pot reaction without isolating compound (1-3).

[Step 1-3]

This is a step of obtaining compound (1-5) by alkaline hydrolysis of compound (1-4).

The reaction can be carried out under the same reaction conditions as those described in, for example, Matassa, V. G.; Brown, F. J.; Bernstein, P. R.; Shapiro, H. S.; Maduskuie, T. P. J.; Cronk, L. A.; Vacek, E. P.; Yee, Y. K.; Snyder, D. W.; Krell, R. D.; Lerman, C. L.; Maloney, J. J.; J. Med. Chem., 33 (9), 2621-2629 (1990).

Specifically, for example, a base such as sodium hydroxide is added to a solution containing compound (1-4). The mixture is then stirred for several hours to 1 day. Thereafter, the resultant mixture is treated with acid such as citric acid, so as to obtain compound (1-5).

A solvent used in the present reaction is not particularly limited, as long as it does not inhibit the reaction and dissolves a starting substance to a certain extent. Examples of such a solvent may include methanol, ethanol, 2-propanol, tetrahydrofuran, and 1,4-dioxane. A base used herein is not particularly limited. Preferred examples of such a base may include sodium hydroxide, potassium hydroxide, and lithium hydroxide. The amount of a base used is between 1 equivalent and an excessive amount, and preferably between 1 and 20 equivalents, with respect to compound (1-4).

The reaction time is not particularly limited. It is generally between 1 and 24 hours, and preferably between 1 and 6 hours.

The reaction temperature is not particularly limited. It is generally between a room temperature and a solvent-reflux temperature.

When an ester is a benzyl ester or allyl ester, carboxylic acid can be obtained under the same conditions as those generally used for the deprotection of a protecting group for a carboxylic acid compound (which are conditions described in publications such as T. W. Green and P. G. M. Wuts, "Protective groups in Organic Chemistry, Second Edition", John Wiley & Sons (1991), pp. 248-251).

[Step 1-4]

This is a step of obtaining compound (1-7) by condensing compound (1-5) and compound (1-6) with a condensing agent.

The condensation reaction of compound (1-5) and (1-6) with a condensing agent can be carried out under the same conditions as commonly used conditions described in the following publications. Such known methods include Rosowsky, A.; Forsch, R. A.; Moran, R. G.; Freisheim, J. H.; J. Med. Chem., 34 (1), 227-234 (1991), Brzostwska, M.; Brossi, A.; Flippen-Anderson, J. L.; Heterocycles, 32 (10), 1969-1972 (1991), Romero, D. L.; Morge, R. A.; Biles, C.; Berrios-Pena, N.; May, P. D.; Palmer, J. R.; Johnson, P. D.; Smith, H. W.; Busso, M.; Tan, C.-K.; Voorman, R. L.; Reusser, F.; Althaus, I. W.; Downey, K. M.; So, A. G.; Resnick, L.; Tarpley, W. G., Aristoff, P. A.; J. Med. Chem., 37 (7), 999-1014 (1994).

Compound (1-6) may be either a free form or a salt.

A solvent used in the present reaction is not particularly limited, as long as it does not inhibit the reaction. Examples of such a solvent may include tetrahydrofuran, 1,4-dioxane, ethyl acetate, methyl acetate, methylene chloride, chloroform, N,N-dimethylformamide, toluene, and xylene. Examples of a condensing agent may include CDI (N,N'-carbonyldiimidazole), Bop (1H-1,2,3-benzotriazol-1-yloxy (tri(dimethylamino))phosphonium hexafluorophosphate), WSC (1-ethyl-3-(3-dimethylaminopropyl)carbodiimide hydrochloride), DCC (N,N-dicyclohexylcarbodiimide), and diethylphosphoryl cyanide. Compound (1-6) is used at a ratio between 1 equivalent and an excessive amount with respect to compound (1-5). In addition, an organic base such as triethylamine may also be added at a ratio between 1 equivalent and an excessive amount, as necessary.

The reaction time is not particularly limited. It is generally between 0.5 and 48 hours, and preferably between 0.5 and 24 hours.

The reaction temperature is not particularly limited, and is different depending on a raw material used, a solvent used, and the like. It is preferably between a temperature on ice and a solvent-reflux temperature.

Moreover, compound (1-7) can also be produced from compound (1-5) and compound (1-6) according to alternative methods described in (1) and (2) below.

Alternative Method (1)

Compound (1-5) is converted into a mixed acid anhydride. Then, the mixed acid anhydride is allowed to react with compound (1-6), so as to obtain compound (1-7). Such a mixed acid anhydride can be synthesized by means known to persons skilled in the art. For example, compound (1-5) is allowed to react with a chloroformic ester such as ethyl chloroformate in the presence of a base such as triethylamine. Such a chloroformic ester and a base are used at a ratio between 1 and 2 equivalents with respect to compound (1-5). The reaction temperature is between −30° C. and a room temperature, and preferably between −20° C. and a room temperature.

A step of condensing a mixed acid anhydride and compound (1-6) is carried out, for example, by allowing the mixed acid anhydride to react with compound (1-6) in a solvent such as methylene chloride, tetrahydrofuran, or N,N-dimethylformamide. Compound (1-6) is used at a ratio between 1 equivalent and an excessive amount with respect to the mixed acid anhydride.

The reaction time is not particularly limited. It is generally between 0.5 and 48 hours, and preferably between 0.5 and 12 hours.

The reaction temperature is between −20° C. and 50° C., and preferably between −20° C. and a room temperature.

Alternative Method (2)

Compound (1-5) is converted into an activated ester. Then, the activated ester is allowed to react with compound (1-6), so as to obtain compound (1-7). A step of obtaining such an activated ester can be carried out by allowing compound (1-5) to react with an activated ester-synthesizing reagent in a solvent such as 1,4-dioxane, tetrahydrofuran, or N,N-dimethylformamide, in the presence of a condensing agent such as DCC. N-hydroxysuccinimide is an example of such an activated ester-synthesizing reagent. Such an activated ester-synthesizing reagent and a condensing agent are used at a ratio between 1 and 1.5 equivalents with respect to compound (1-5). The reaction time is not particularly limited. It is generally between 0.5 and 48 hours, and preferably between 0.5 and 24 hours.

The reaction temperature is between −20° C. and 50° C., and preferably between −20° C. and a room temperature.

A step of condensing an activated ester and compound (1-6) is carried out by allowing the activated ester to react with compound (1-6) in a solvent such as methylene chloride, tetrahydrofuran, or N,N-dimethylformamide. Compound (1-6) is used at a ratio between 1 equivalent and an excessive amount with respect to the activated ester.

The reaction time is not particularly limited. It is generally between 0.5 and 48 hours, and preferably between 0.5 and 24 hours.

The reaction temperature is between −20° C. and 50° C., and preferably between −20° C. and a room temperature.

[Step 1-4']

This is a step of obtaining compound (1-7) by condensing compound (1-4) and compound (1-6).

This condensation reaction can be carried out under the same conditions as those commonly used for the condensation reaction of an ester compound and an amine compound. Known methods include Dodd, J. H.; Guan, J.; Schwender, C. F.; Synth. Commun., 23 (7), 1003-1008 (1993), Sim, T. B.; Yoon, N. M.; and Synlett, (10), 827-828 (1994). An amine compound (1-6) used may be either a free form or a salt.

A solvent used in the present reaction is not particularly limited, as long as it does not inhibit the reaction. Examples of such a solvent may include methanol, ethanol, 1-propanol, 2-propanol, 1-butanol, tetrahydrofuran, 1,4-dioxane, toluene, xylene, and acetic acid. In addition, it is also possible to use an amine compound (1-6) as a solvent. Compound (1-6) is used at a ratio between 1 equivalent and an excessive amount with respect to compound (1-4).

The reaction time is not particularly limited. It is generally between 1 and 48 hours, and preferably between 1 and 24 hours.

The reaction temperature is not particularly limited, and is different depending on a raw material used, a solvent used, and the like. It is preferably between a room temperature and a solvent-reflux temperature.

Moreover, in the present reaction, acids such as p-toluenesulfonic acid or camphorsulfonic acid, Lewis acids such as trimethylaluminum, or bases such as sodium hydride may be added to the reaction, thereby obtaining good results such as the reduction of the reaction time or the improvement of yield. Furthermore, a well-closed heat-resisting container such as an autoclave may be used to heat a reaction mixture to a high temperature between 100° C. and 250° C., thereby obtaining good results such as the reduction of the reaction time.

[Step 1-5]

This is a step of obtaining compound (1-8) by deprotecting a protecting group for the secondary amine of compound (1-7).

The deprotection reaction can be carried out under the same conditions as those commonly used for the deprotection of a protecting group for an amino compound. Such conditions are described in publications such as T. W. Green and P. G. M. Wuts, "Protective groups in Organic Chemistry, Second Edition", John Wiley & Sons (1991), pp. 309-405. When the amino group of compound (1-7) is protected by a benzyloxycarbonyl group, for example, the protecting group is deprotected by hydrogenolysis of compound (1-7) using palladium on carbon as a catalyst in a solvent such as alcohol, so as to obtain compound (1-8).

[Step 1-6]

This is a step of obtaining a compound represented by general formula (I) by the reductive amination of compound (1-8) and compound (1-9).

In this step, compound (1-8) and compound (1-9) are used as raw materials, and the method described in the aforementioned production method ([Step 1-1]) is applied, so as to synthesize the compound represented by general formula (I). In addition, a commercially available product may directly be used as compound(1-9), or the above compound may also be produced from a commercially available product by a method known to persons skilled in the art. Moreover, it can also be produced by production examples in the present examples, or the method described in the [General production method A, B, C, D, or E] section. Furthermore, the used compound (1-8) may be either a free form or a salt.

[Step 1-7]

This is a step of obtaining a compound represented by general formula (I) by the nucleophilic substitution reaction of compound (1-8) and compound (1-10).

This nucleophilic substitution reaction can be carried out under the same conditions as those commonly used for the reaction of a secondary amine with a halogen compound (for example, conditions described in Hirai, Y.; Terada, T.; Okaji, Y.; Yamazaki, T.; Tetrahedron Lett., 31 (33), 4755-4758 (1990), etc.). In addition, a commercially available product may directly be used as compound (1-10), or the above compound may also be produced from a commercially available product by a method known to persons skilled in the art. Moreover, it can also be produced by production examples in the present examples, or the method described in the [General Production Method E] section. Furthermore, the used compound (1-8) may be either a free form or a salt.

A solvent used in the reaction is not particularly limited, as long as it does not inhibit the reaction and dissolves a starting substance to a certain extent. Preferred examples of such a solvent may include methanol, ethanol, propanol, tetrahydrofuran, benzene, toluene, xylene, acetonitrile, methylene chloride, chloroform, N,N-dimethylformamide, and dimethyl sulfoxide. Compound (1-10) is used at a ratio between 1 and 10 equivalents, and preferably between 1 and 5 equivalents, with respect to compound (1-8).

The reaction time is not particularly limited. It is generally between 1 and 72 hours, and preferably between 1 and 48 hours.

The reaction temperature is generally between a room temperature and a solvent-reflux temperature, and preferably between a room temperature and 100° C.

Moreover, addition of a base may provide good results such as the improvement of yield. A base used is not particularly limited, as long as it does not inhibit the reaction. Preferred examples of such a base may include sodium carbonate, potassium carbonate, sodium hydroxide, potassium hydroxide, diazabicycloundecen, sodium hydride, potassium hydride, sodium methoxide, potassium methoxide, potassium tert-butoxide, triethylamine, and diisopropylethylamine.

The compound represented by general formula (I) can also be produced by the following [General Production Method 1'].

[General Production Method 1']

[Formula 26]

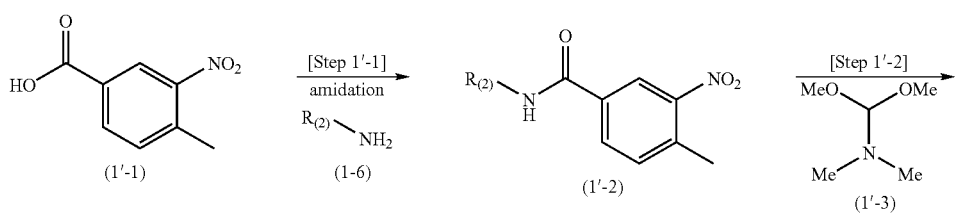

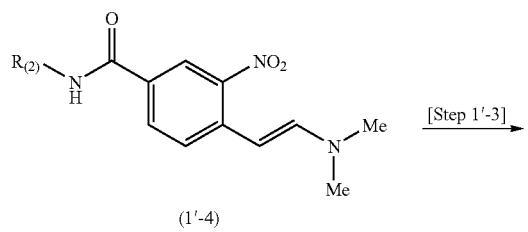

-continued
[Formula 27]
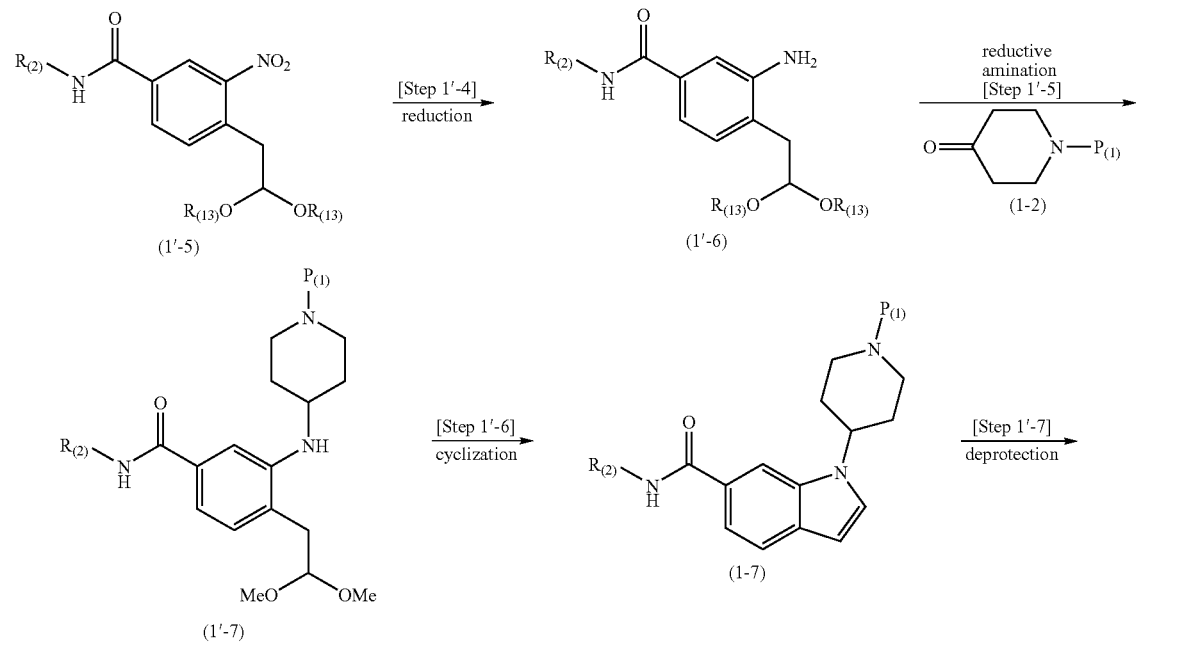
[Formula 29]
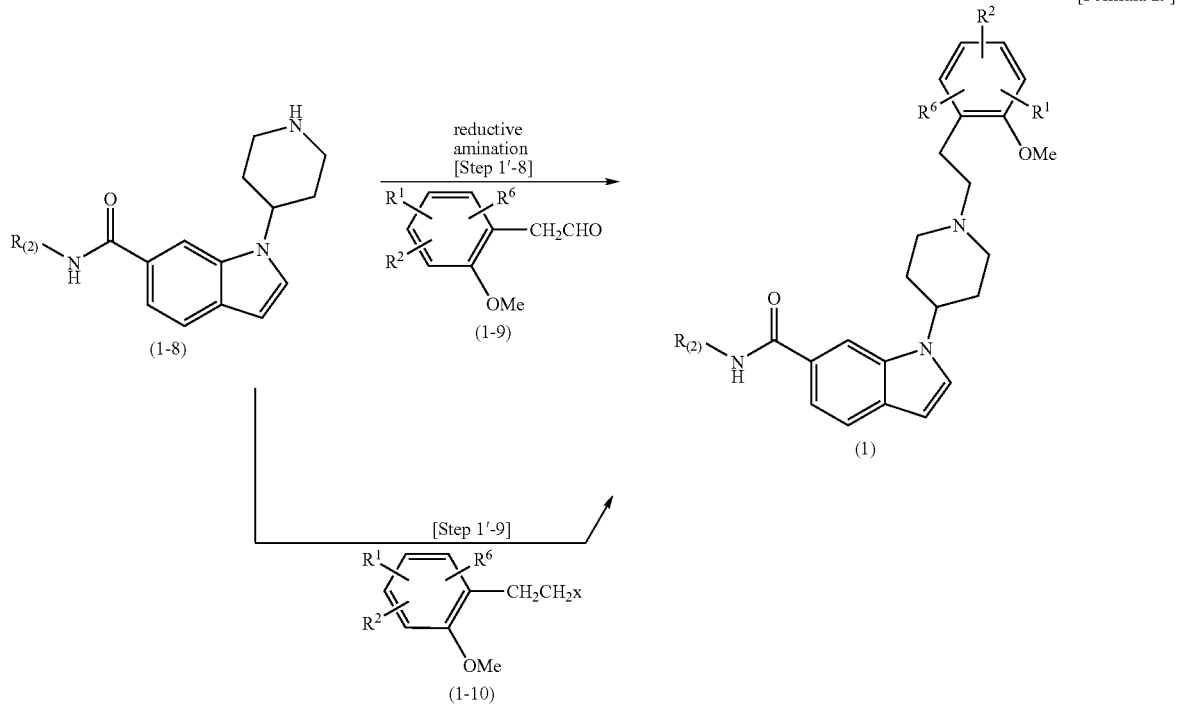

wherein $R_{(2)}$, $R^1$, $R^2$, $R^6$, and $P_{(1)}$ have the same meanings as described above; and X represents a leaving group, such as a halogen atom (a chlorine atom, bromine atom, iodine atom, or the like) or a sulfonyloxy group such as a methanesulfonyloxy group, p-toluenesulfonyloxy group, or trifluoromethanesulfonyloxy group.

The above described [General Production Method 1'] is a method for producing the compound represented by general formula (I) of the present invention, which comprises multi-stage steps ranging from [Step 1'-1] to [Step 1'-9].

A commercially available product may directly be used as compound (1'-1), or the compound may be produced from a commercially available product according to a method known to persons skilled in the art. In addition, commercially available products may directly be used as compound (1-2) and compound (1-6), or these compounds may be produced from commercially available products according to methods known to persons skilled in the art.

[Step 1'-1]

This is a step of synthesizing compound (1'-2) by using compound (1'-1) and compound (1-6) as raw materials and applying the method described in the aforementioned production method ([Step 1-4]).

[Step 1'-2] to [Step 1'-4]

This is a step of producing compound (1'-6) from compound (1'-2) by the combined use of various reactions that have been known to persons skilled in the art.

Examples of such a known method may include:
Coe, J. W.; Vetelino, M. G.; Bradlee, M. J.; Tetrahedron Lett., 37 (34), 6045-6048 (1996), Arai, E.; Tokuyama, H.; Linsell, M. S.; Fukuyama, T.; Tetrahedron Lett., 39 (1), 71-74 (1998), Tishler, A. N., Lanza, T. J.; Tetrahedron Lett., 27 (15), 1653 (1986), and Sakamoto Takao, Kondo Yoshinori, Yamanaka Hiroshi, Chem. Pharm. Bull., Vol. 34, P. 2362 (1986).

Specifically, compound (1'-6) can be produced by performing steps ranging from [Step 1'-2] to [Step 1'-4]. Needless to say, the method for producing compound (1'-6) is not limited to these steps. Compound (1'-6) can also be produced by methods described in the aforementioned publications.

[Step 1'-2]

This is a step of obtaining compound (1'-4) from compound (1'-2) and compound (1'-3).

A method for producing an enamine derivative of compound (1'-4) from a nitrotoluene derivative of compound (1'-2) is a synthesis method known to persons skilled in the art. The reaction can be carried out under the same conditions as those described in, for example, Coe, J. W.; Vetelino, M. G.; Bradlee, M. J.; Tetrahedron Lett., 37 (34), 6045-6048 (1996).

[Step 1'-3]

This is a step of obtaining compound (1'-5) from compound (1'-4).

A method for producing an acetal derivative of compound (1'-5) from an enamine derivative of compound (1'-4) is a synthesis method known to persons skilled in the art. The reaction can be carried out under the same conditions as those described in Coe, J. W.; Vetelino, M. G.; Bradlee, M. J.; Tetrahedron Lett., 37 (34), 6045-6048 (1996); etc.

[Step 1'-4]

This is a step of obtaining compound (1'-6) from compound (1'-5).

A method for synthesizing an aniline compound of compound (1'-6) by reducing a nitro compound of compound (1'-5) is a synthesis method known to persons skilled in the art. An example of such a method may be a reduction by catalytic hydrogenation using a precious metal catalyst such as Raney nickel, palladium, ruthenium, or rhodium. In this case, means for using palladium or palladium hydroxide is preferable. Otherwise, a reduction reaction using iron under neutral conditions where ammonium chloride is used, is also preferable.

[Step 1'-5]

This is a step of synthesizing compound (1'-7) by using compound (1'-6) and compound (1-2) as raw materials and applying the method described in the above production method ([Step 1-1]).

[Step 1'-6]

This is a step of synthesizing compound (1-7) by using compound (1'-7) as a raw material and applying the method described in the above production method ([Step 1-2]).

[Step 1'-7]

This is a step of synthesizing compound (1-8) by using compound (1-7) as a raw material and applying the method described in the above production method ([Step 1-5]).

[Step 1'-8]

This is a step of synthesizing the compound represented by general formula (I) by using compound (1-8) and compound (1-9) as raw materials and applying the method described in the above production method ([Step 1-6]).

[Step 1'-9]

This is a step of synthesizing the compound represented by general formula (I) by using compound (1-8) and compound (1-10) as raw materials and applying the method described in the above production method ([Step 1-7]).

[General Production Method 2]

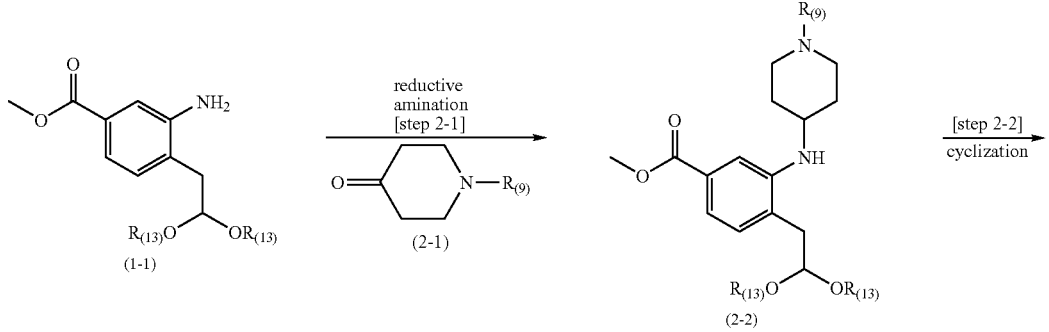

[Formula 30]

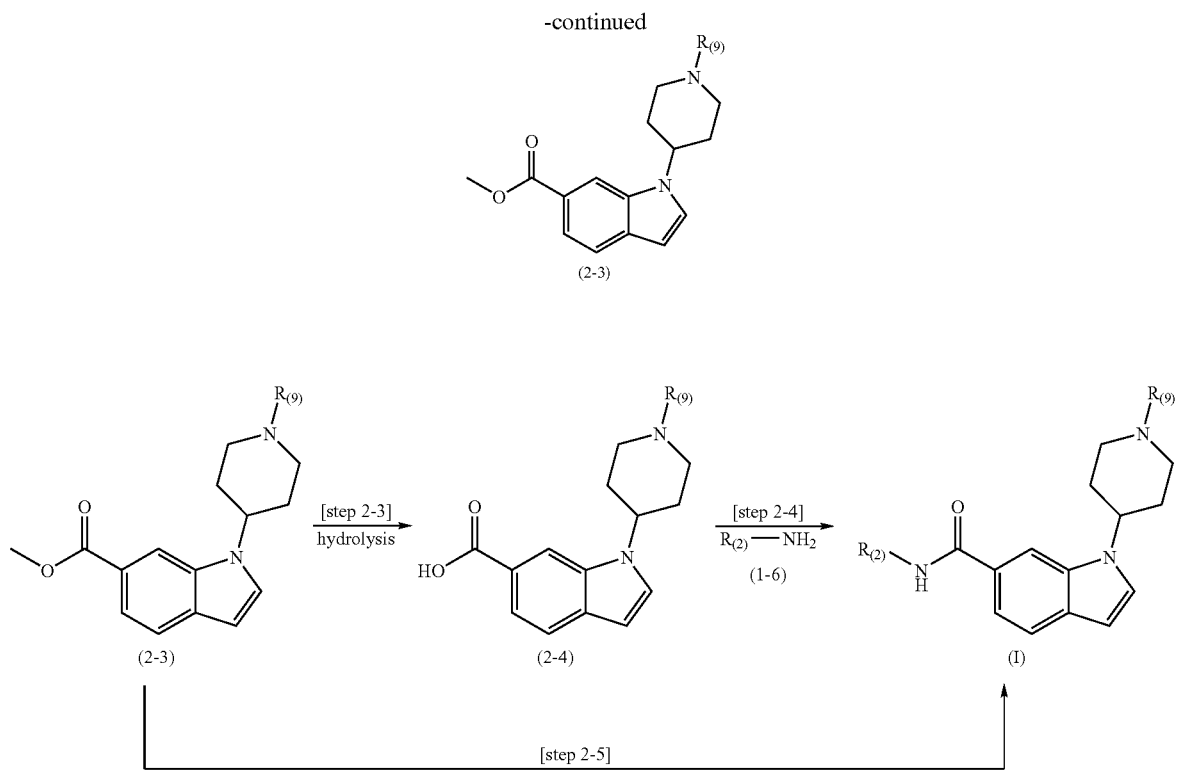

wherein $R_{(2)}$ has the same meaning as described above; and $R_{(9)}$ represents $C_6H(R^1)(R^2)(R^6)(OMe)$—$(CH_2)_2$—.

Compound (1-1) can be produced from a commercially available product according to a method known to persons skilled in the art. Examples of such a method may include: Coe, J. W.; Vetelino, M. G.; Bradlee, M. J.; Tetrahedron Lett., 37 (34), 6045-6048 (1996), Arai, E.; Tokuyama, H.; Linsell, M. S.; Fukuyama, T.; Tetrahedron Lett., 39 (1), 71-74 (1998), Tishler, A. N., Lanza, T. J.; Tetrahedron Lett., 27 (15), 1653 (1986), and Sakamoto Takao, Kondo Yoshinori, Yamanaka Hiroshi, Chem. Pharm. Bull., Vol. 34, P. 2362 (1986).

In addition, a commercially available product may directly be used as compound (2-1), or the above compound may also be produced from a commercially available product by a method known to persons skilled in the art. Moreover, it can also be produced by the method described in the [General Production Method F] section.

[Step 2-1]

This is a step of synthesizing compound (2-2) by conducting the reductive amination reaction of compound (1-1) and compound (2-1) according to the method described in the above production method ([Step 1-1]).

[Step 2-2]

This is a step of synthesizing compound (2-3) by using compound (2-2) as a raw material and applying the method described in the above production method ([Step 1-2]).

[Step 2-3]

This is a step of synthesizing compound (2-4) by using compound (2-3) as a raw material and applying the method described in the above production method ([Step 1-3]).

[Step 2-4]

This is a step of synthesizing the compound represented by general formula (I) by using compound (2-4) as a raw material and applying the method described in the above production method ([Step 1-4]). A commercially available product may directly be used as compound (1-6), or the above compound may also be produced from a commercially available product according to a method known to persons skilled in the art.

[Step 2-5]

This is a step of synthesizing the compound represented by general formula (I) by using compound (2-3) as a raw material and applying the method described in the above production method ([Step 1-4']).

The compound represented by general formula (I) can also be produced by the following [General Production Method 2'].

[General Production Method 2']

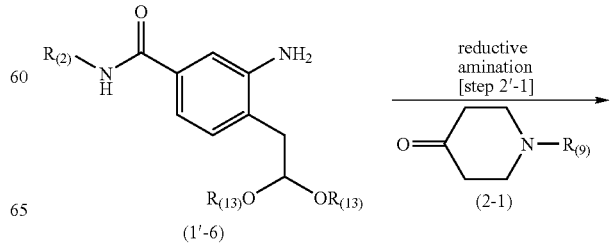

-continued

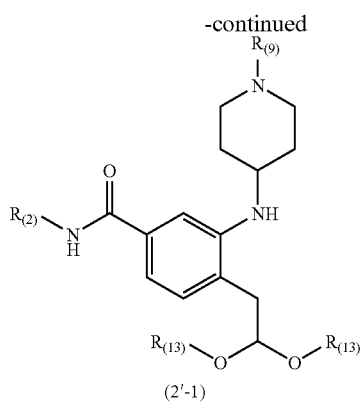
(2'-1)

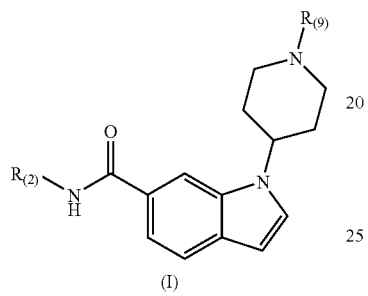
(I)

wherein R$_{(2)}$, R$_{(9)}$, and R$_{(13)}$ have the same meanings as described above.

This is a step of producing the compound represented by general formula (I) of the present invention, which uses compound (1'-6) as a raw material and performs [Step 2'-1] and [Step 2'-2]. Compound (1'-6) can be produced from a commercially available product according to a method known to persons skilled in the art. Compound (2-1) can be produced from a commercially available product according to a method known to persons skilled in the art. Further, it can also be produced by the method described in [General Production Method F] that will be described later.

[Step 2'-1]

This is a step of synthesizing compound (2'-1) by using compound (1'-6) and compound (2-1) as raw materials and applying the method described in the above production method (Step 1-1).

[Step 2'-2]

This is a step of synthesizing the compound represented by general formula (I) by using compound (2'-1) as a raw material and applying the method described in the above production method ([Step 1-2]).

[General Production Method 3]

[Formula 32]

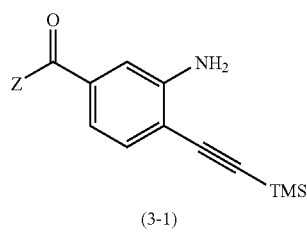
(3-1)

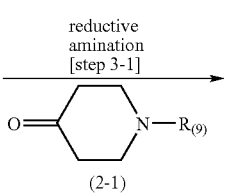
(2-1)

-continued

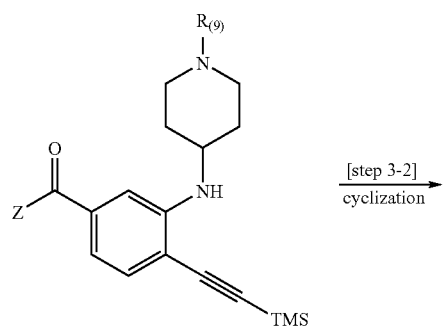
(3-2)

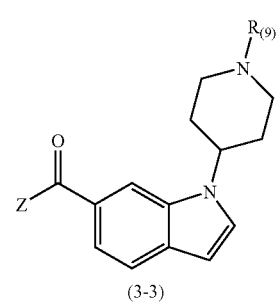
(3-3)

[Formula 33]

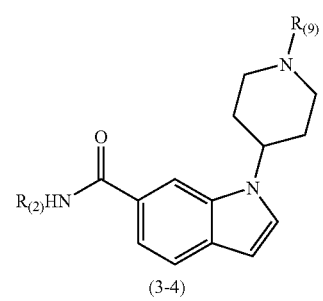

wherein R$_{(2)}$ and R$_{(9)}$ have the same meanings as described above; Z represents OR$_{(1)}$ (wherein R$_{(1)}$ has the same meaning as described above) or R$_{(2)}$HN.

[Step 3-1]

Compound (3-2) can be synthesized by using compound (3-1) and compound (2-1) as raw materials and applying the method described in the above production method ([Step 1-1]).

[Step 3-2]

This is a step of obtaining compound (3-3) by the cyclization of compound (3-2). A method for synthesizing indole by the cyclization of an acetylene compound (3-2) has been known to persons skilled in the art. The reaction can be carried out under the same conditions as those described in, for example, Fujiwara Junya, Fukutani Yoshimi, Sano Hiromi, Maruoka Keiji, Yamamoto Hisashi, J. Am. Chem. Soc., Vol. 105, P. 7177 (1983); and Ezquerra, J.; Pedregal, C.; Lamas, C.; Barluenga, J.; Perez, M.; Garcia-Martin, M. A.; Gonzalez, J. M.; J. Org. Chem., 61 (17), 5804-5812 (1996).

[Step 3-3]

This is a step of synthesizing compound (3-4) by using compound (3-3) and applying the method described in the above production method ([Step 2-3]). In a case where compound (3-3) has already had an appropriate substituent, however, this step can be omitted.

[Step 3-4]

This is a step of synthesizing the compound represented by general formula (I) by using compound (3-4) as a raw material and applying the method described in the above production method ([Step 1-4]). In a case where compound (3-3) has already had an appropriate substituent, however, this step can be omitted. Compound (3-1) used in a general production method can be synthesized by [General Production Method G].

[General Production Method 4]

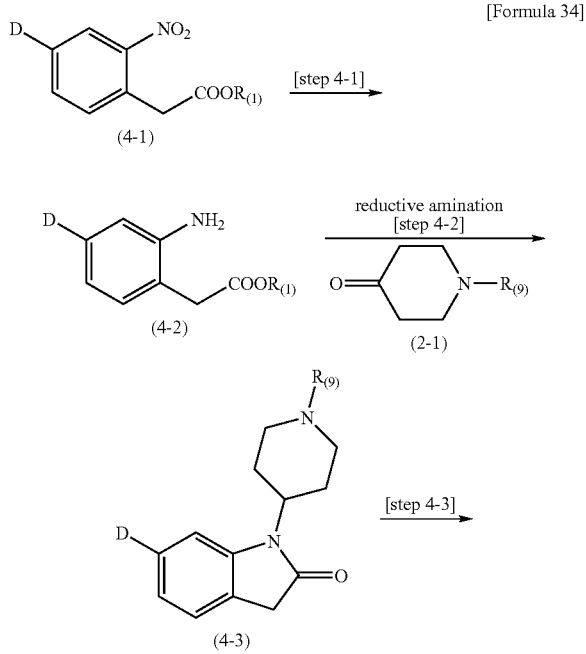

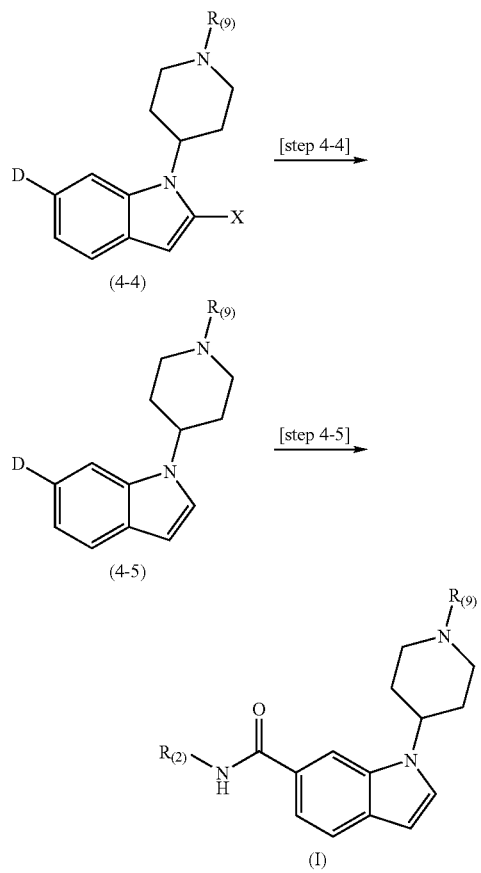

wherein $R_{(1)}$, $R_{(2)}$, $R_{(9)}$, and X have the same meanings as described above; and D represents a carboxyl group or a group capable of being modified to a carboxyl group.

Compound (4-1) can be produced by a method known to persons skilled in the art. The compound can be synthesized under the same conditions as those described in, for example, Quallich, G. J.; Morrissey, P. M.; Synthesis, (1), 51-53 (1993), Urban, F. J.; Breitenbach, R.; Gonyaw, D.; Synth. Commun., 26 (8), 1629-1638 (1996), Zhu, J.; Beugelmans, R.; Bourdent, S.; Chastanet, J.; Roussi, G.; J. Org. Chem., 60 (20), 6389-6396 (1995).

[Step 4-1]

This is a step of obtaining an amino compound (4-2) by subjecting a nitro compound (4-1) to a reduction reaction.

The reduction of a nitro group is a reaction known to persons skilled in the art. An example of such a reduction may be catalytic hydrogenation using a precious metal catalyst such as Raney nickel, palladium, palladium hydroxide, ruthenium, rhodium, or platinum. Another example may be means for using iron, tin, or zinc under neutral or acidic conditions.

[Step 4-2]

This is a step of synthesizing compound (4-3) by using compound (4-2) as a raw material and applying the method described in the above production method ([Step 1-1]).

[Step 4-3]

This is a step of obtaining compound (4-4) by the halogenation of compound (4-3).

The reaction can be carried out under the same conditions as those described in, for example, Chan, F.; Magnus, P.; Mciver, E. G.; Tetrahedron Lett., 41 (6), 835-838 (2000)., Owa, T.; Okauchi, T.; Yoshimatsu, K.; Sugi, N.; Ozawa, Y.; Nagasu, T.; Koyanagi, N.; Okabe, T.; Kitoh, K.; Yoshino, H.; Bioorg. Med. Chem. Lett., 10 (11), 1223-1226 (2000)., Kubo. A., Nakai. T., Synthesis, 365 (1980).

Specifically, for example, a solution containing compound (4-3) is heated together with phosphorus oxychloride or the like, so as to obtain compound (4-4).

A solvent used in the reaction is not particularly limited, as long as it does not inhibit the reaction and dissolves a starting substance to a certain extent. Preferred examples of such a solvent may include acetonitrile and toluene. In addition, phosphorus oxychloride may also be used as a solvent. Such phosphorus oxychloride is used at a ratio between 1 equivalent and an excessive amount with respect to a raw material.

The reaction temperature is generally between a temperature on ice and a solvent-reflux temperature, and more preferably between a room temperature and a solvent-reflux temperature.

The reaction time is not particularly limited. It is generally between 0.2 and 48 hours, and preferably between 0.2 and 24 hours.

Moreover, there may be cases where good results such as the improvement of yield can be obtained by addition of a base. A base used herein is not particularly limited, as long as it does not inhibit the reaction. Preferred examples of such a base may include triethylamine, pyridine, and diisopropylethylamine.

[Step 4-4]

This is a step of obtaining compound (4-5) by the dehalogenation reaction of compound (4-4).

This reaction can be carried out under the same conditions as those used for the known dehalogenation reaction of an aromatic ring. The reaction can be carried out under the same conditions as those described in, for example, Candiani, I.; Debernardinis, S.; Cabri, W.; Marchi, M.; Bedeschi, A.; Penco, S.; Synlett, (4), 269-270 (1993)., Tanaka, A.; Ito, K.; Nishino, S.; Motoyama, Y.; Takasugi, H.; Chem. Pharm. Bull., 42 (3), 560-569 (1994).

Specifically, compound (4-5) can be obtained by the hydrogenation of a solution containing compound (4-4) in the presence of a metal catalyst.

A solvent used in a catalytic reduction reaction in a hydrogen atmosphere is not particularly limited, as long as it does not inhibit the reaction. Examples of such a solvent may include methanol, ethanol, tetrahydrofuran, and 1,4-dioxane. Examples of a metal catalyst used in the reaction may include palladium, platinum oxide, and Raney nickel. The reaction conditions are not particularly limited. The reaction can be carried out at a temperature between a room temperature and a solvent-reflux temperature at a pressure between an ordinary pressure and a pressure of 150 atmospheres, and preferably at a temperature between a room temperature and 60° C. at a pressure between an ordinary pressure and a pressure of 5 atmospheres. The reaction time is not particularly limited. It is generally between 0.5 and 48 hours, and preferably between 0.5 and 24 hours.

[Step 4-5]

This is a step of obtaining the compound represented by general formula (I) by the conversion of a substituent D in compound (4-5).

Conversion of compound (4-5) into the compound represented by general formula (I) can be conducted by a general method known to persons skilled in the art. When the substituent D is an alkoxycarbonyl group for example, the compound represented by general formula (I) can be synthesized by applying the methods described in [Step 1-3] and [Step 1-4] or [Step 1-4'].

[General Production Method 5]

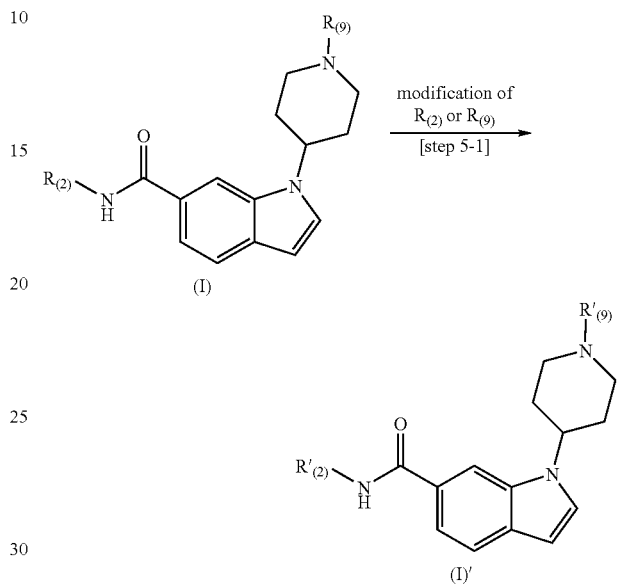

wherein $R_{(2)}$ and $R_{(9)}$ have the same meanings as described above; and $R'_{(2)}$ and $R'_{(9)}$ represent $R_{(2)}$ and $R_{(9)}$, respectively, which are appropriately modified.

[General Production Method 5] is a method for producing a compound represented by general formula (I)' from the compound represented by general formula (I) as a raw material. (The compound represented by general formula (I)' is included in the compound represented by general formula (I).)

The compound represented by general formula (I) can be produced by the above described [General Production Method 1] or the like.

[Step 5-1]

This is a step of obtaining the compound. represented by general formula (I)' by modification of $R_{(2)}$ or $R_{(9)}$ in the compound represented by general formula (I).

Modification of $R_{(2)}$ and $R_{(9)}$ can be carried out by performing various reactions known to persons skilled in the art, or by the combined use of various reactions. In addition, the compound represented by general formula (I)' can also be produced by methods described in production examples in the present examples.

Next, a method for producing main raw material compounds used in the invention of the present application will be described. First, compound (1-9) used in [General Production Method 1] and [General Production Method 1'] will be described. Compound [1-9] can be produced by [General Production Method A] to [General Production Method E] and [General Production Method H]. The final compounds produced by these production methods may sometimes be indicated by different formulas to explain each step. However, all these compounds correspond to compound (1-9).

[General Production Method A] (Synthesis Method of Compound (1-9))
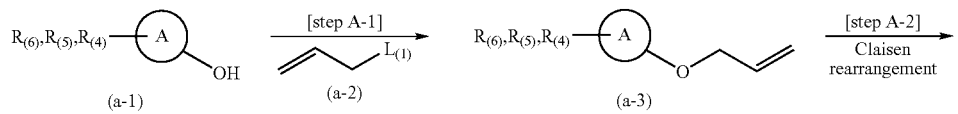
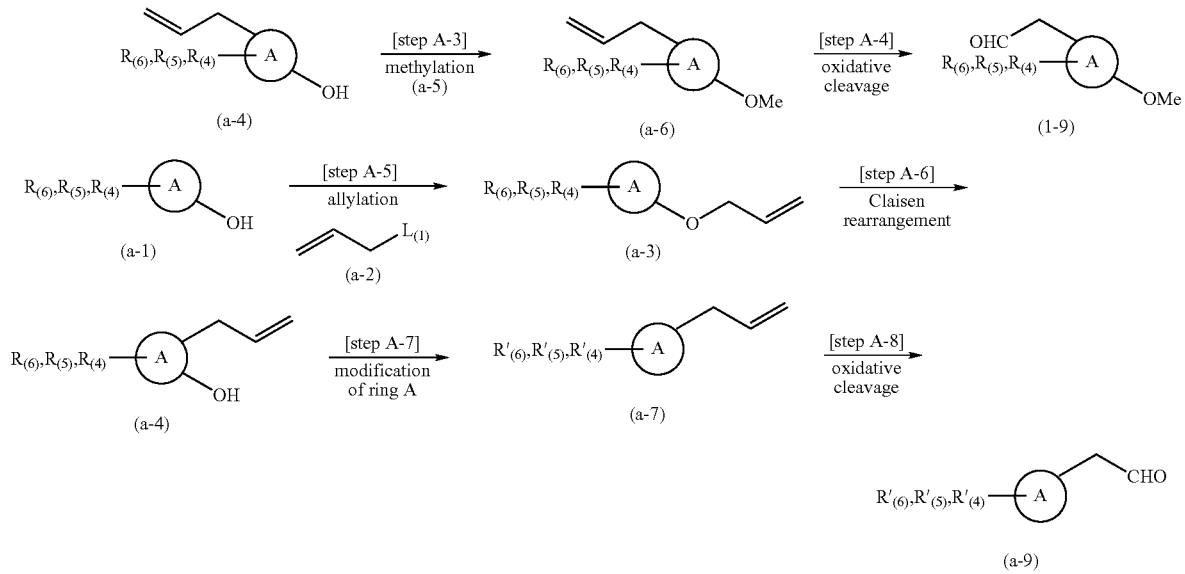
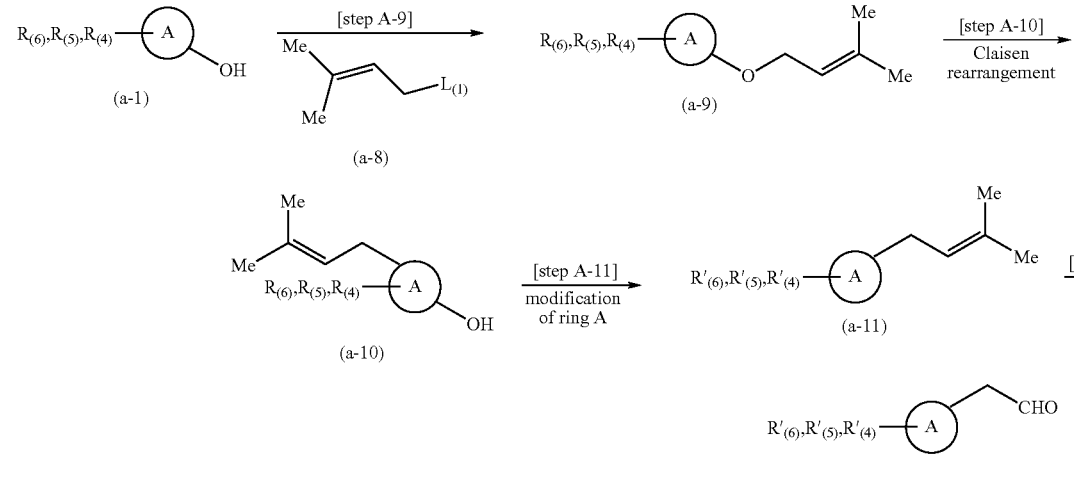
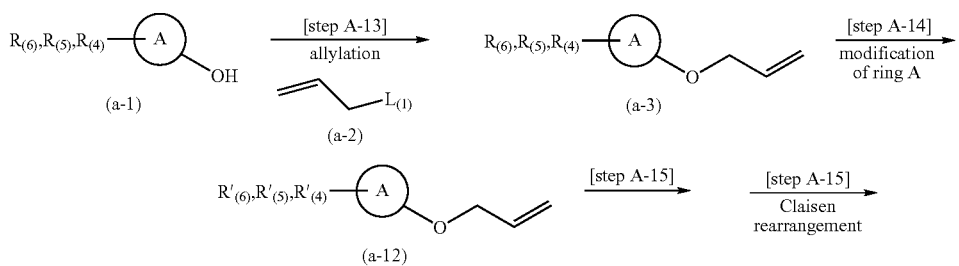

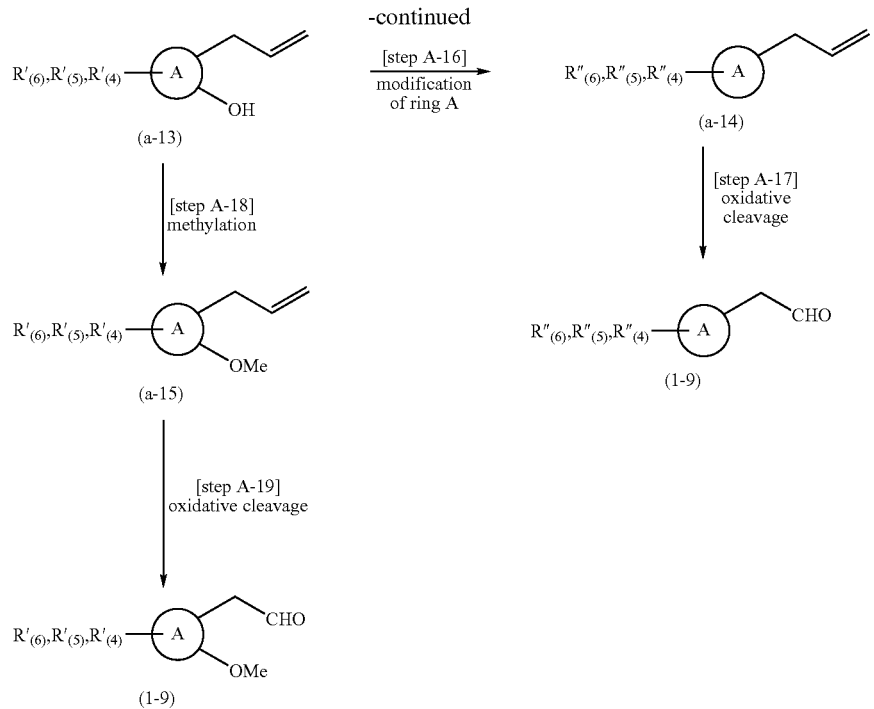

wherein ring A represents (1) a bicyclic group formed by condensation of a benzene ring and a 5- to 7-membered non-aromatic carbocyclic group, (2) a bicyclic group formed by condensation of a benzene ring and a 5- to 7-membered non-aromatic heterocyclyl group, (3) a bicyclic group formed by condensation of a benzene ring and a 6-membered aromatic carbocyclic group, (4) a bicyclic group formed by condensation of a benzene ring and a 5- or 6-membered aromatic heterocyclyl group, or a benzene ring capable of being converted into (1) to (4) above; each of $R_{(4)}$, $R_{(5)}$, and $R_{(6)}$ represents a substituent necessary for synthetic modification as appropriate, such as a C1-C6 alkanoyl group, a hydroxymethyl group that may be protected by a TBDMS group or the like, or a C1-C6 alkoxy group that may be substituted by a C1-C6 alkoxycarbonyl group, as well as a substituent selected from the following substituent group B1, and $R'_{(4)}$, $R''_{(4)}$, $R'_{(5)}$, $R''_{(5)}$, $R'_{(6)}$, $R''_{(6)}$ represent those formed by appropriately modifying $R_{(4)}$, $R_{(5)}$, and $R_{(6)}$, wherein each of $R_{(4)}$, $R_{(5)}$, $R_{(6)}$, $R'_{(4)}$, $R'_{(5)}$, $R'_{(6)}$, $R''_{(4)}$, $R''_{(5)}$, and $R''_{(6)}$ represents a substituent existing on ring A; and $L_{(1)}$ is a leaving group and represents a halogen atom (a chlorine atom, bromine atom, or iodine atom) or a sulfonyloxy group such as a methanesulfonyloxy group, p-toluenesulfonyloxy group, or trifluoromethanesulfonyloxy group, Substituent group B1: (1) a hydrogen atom, (2) a halogen atom, (3) a cyano group, (4) a hydroxyl group, (5) a nitro group, (6) an oxo group, (7) a carboxyl group, (8) a C3-C8 cycloalkyl group, (9) a C2-C6 alkenyl group, (10) a C2-C6 alkynyl group, (11) a C1-C6 alkylthio group, (12) a C1-C6 alkoxycarbonyl group, (13) a C1-C6 alkylsulfonyl group, (14) a C1-C6 alkyl group (wherein the above described C1-C6 alkyl group may be substituted by a halogen atom, a hydroxyl group, or a C1-C6 alkoxy group), (15) a C1-C6 alkoxy group (wherein the above described C1-C6 alkoxy group may be substituted by 1 to 3 halogen atoms), (16) an amino group (wherein the above described amino group may be substituted by a substituent selected from the group consisting of a C1-C6 alkyl group, a formyl group, a C1-C6 alkanoyl group, and a C1-C6 alkylsulfonyl group), (17) a carbamoyl group (wherein the above described carbamoyl group may be substituted by one or two C1-C6 alkyl groups), (18) a C1-C6 alkoxyimino group, (19) a C5-C6 cycloalkyl group formed by two C1-C3 alkyl groups attaching to a single carbon atom, and (20) a tetrahydropyranyl group formed by two C1-C3 alkyl groups attaching to a single carbon atom, together with an oxygen atom and the above described carbon atom.

A commercially available product may directly be used as compound (a-1), or the above compound may also be produced from a commercially available product by a method known to persons skilled in the art. Moreover, it can also be produced by production examples in the present examples.

[Step A-1]

This is a step of obtaining compound (a-3) by the allylation reaction of compound (a-1) with compound (a-2).

This reaction can be carried out under the same conditions as those used in the allylation reaction of allyl halide with a phenol derivative (including a heterocyclic ring) (which are conditions described in, for example, Nichols, D. E.; Snyder, S. E.; Oberlender, R.; Johnson, M. P.; Huang, X.; J. Med. Chem., 34 (1), 276-281 (1991), Sato, H.; Dan, T.; Onuma, E.; Tanaka, H.; Aoki, B.; Koga, H.; Chem. Pharm. Bull., 39 (7), 1760-1772 (1991)).

Specifically, a base is allowed to react with a solution containing compound (a-1) to obtain phenoxide, and the phenoxide compound is then allowed to react with compound (a-2), so as to obtain compound (a-3).

This reaction can be carried out by allowing an appropriate base to react with the above compound at a ratio between 1 equivalent and an excessive amount to the compound, in an organic solvent such as acetone, 2-butanone, acetonitrile, N,N-dimethylformamide, dimethyl sulfoxide, benzene or toluene, or a mixed solvent thereof. Examples of a base used herein may include sodium carbonate, potassium carbonate, sodium hydroxide, potassium hydroxide, diazabicycloundecen, sodium hydride, potassium hydride, sodium methoxide, potassium methoxide, and potassium tert-butoxide. Compound (a-2) is used at a ratio between 1 and 3 equivalents, and preferably between 1 and 1.7 equivalents, with respect to compound (a-1).

The reaction time is not particularly limited. It is generally between 1 and 48 hours, and preferably between 1 and 24 hours.

The reaction temperature is generally between a temperature on ice and a solvent-reflux temperature.

There may be cases where preferred results such as the improvement of yield or the reduction of the reaction time can be obtained by the coexistence of an ammonium salt such as tetra-n-butylammonium chloride, tetra-n-butylammonium bromide, or tetra-n-butylammonium iodide.

[Step A-2]

This is a step of obtaining compound (a-4) by subjecting compound (a-3) to a Claisen rearrangement reaction.

This reaction can be carried out under the same conditions as those described in, for example, Nichols, D. E.; Snyder, S. E.; Oberlender, R.; Johnson, M. P.; Huang, X.; J. Med. Chem., 34 (1), 276-281 (1991), Sato, H.; Dan, T.; Onuma, E.; Tanaka, H.; Aoki, B.; Koga, H.; Chem. Pharm. Bull., 39 (7), 1760-1772 (1991).

Specifically, for example, a solution containing compound (a-3) is heated, so as to obtain compound (a-4).

This reaction can be carried out in the absence of solvent, or in a solvent such as N,N-dimethylaniline, N,N-diethylaniline, N-methylpyrrolidone, or dichlorobenzene.

The reaction temperature is generally between 100° C. and a solvent-reflux temperature, and more preferably between 160° C. and 210° C.

This reaction is preferably carried out in a nitrogen or argon atmosphere. There may be cases where preferred results such as the reduction of the reaction time or the improvement of yield can be obtained by performing this reaction using a microwave reactor.

In addition, there may be cases where a positional isomer is synthesized in this reaction (Claisen rearrangement), although it depends on the type of a raw material. When an allyloxy group is defined at position 1, compounds formed by transferring an allyl group to position 2, 4, or 6, are also included in the scope of present invention.

[Step A-3]

This is a step of obtaining compound (a-6) by the methylation reaction of compound (a-4) with compound (a-5).

This reaction can be carried out under the same conditions as those used in the alkylation (methylation) reaction of a phenol derivative (including a heterocyclic ring) with a methyl halide or dimethyl sulfate (which are conditions described in, for example, Chilin, A.; Rodighiero, P.; Pastorini, G.; Guitto, A.; J. Org. Chem., 56 (3), 980-983 (1991), Dike, S. Y.; Merchant, J. R.; Sapre, N. Y.; Tetrahedron, 47 (26), 4775-4786 (1991)).

Specifically, a base is allowed to react with a solution containing compound (a-4) to obtain phenoxide, and the phenoxide compound is then allowed to react with compound (a-5), so as to obtain compound (a-6).

This reaction can be carried out by allowing an appropriate base to react with the above compound at a ratio between 1 equivalent and an excessive amount to the compound, in an organic solvent such as acetone, 2-butanone, acetonitrile, N,N-dimethylformamide, dimethyl sulfoxide, benzene or toluene, or a mixed solvent thereof. Examples of a base used herein may include sodium carbonate, potassium carbonate, sodium hydroxide, potassium hydroxide, diazabicycloundecen, sodium hydride, potassium hydride, sodium methoxide, potassium methoxide, and potassium tert-butoxide.

Examples of a methylating reagent may include methyl iodide, methyl bromide, methyl chloride, and dimethyl sulfate.

Compound (a-5) is used at a ratio between 1 and 5 equivalents, and preferably between 1 and 3 equivalents, with respect to compound (a-4). The reaction time is not particularly limited. It is generally between 0.5 and 48 hours, and preferably between 0.5 and 24 hours.

The reaction temperature is generally between a temperature on ice and a solvent-reflux temperature.

There may be cases where preferred results such as the improvement of yield or the reduction of the reaction time can be obtained by the coexistence of an ammonium salt such as tetra-n-butylammonium chloride, tetra-n-butylammonium bromide, or tetra-n-butylammonium iodide.

In addition, compound (a-6) can be produced from compound (a-4) by the following alternative method.

Alternative Method

For example, to a solution containing compound (a-4), diazomethane, trimethylsilyldiazomethane, or the like is added at a ratio between 1 equivalent and an excessive amount, so as to carry out a reaction, thereby obtaining compound (a-6). Examples of a reaction solvent may include ether and methanol. The reaction temperature is generally between a temperature on ice and a room temperature. This method has been known to persons skilled in the art. The reaction can be carried out under the same conditions as those described in, for example, White, J. D.; Butlin, R. J.; Hahn, H.-G.; Johnson, A. T.; J. Am. Chem. Soc., 112 (23), 8595-8596 (1990).

[Step A-4]

This is a step of obtaining compound (1-9) by the oxidative cleavage of olefin in the allyl part of compound (a-6).

The reaction can be carried out under the same conditions as those generally used in an oxidative cleavage reaction of obtaining aldehyde from olefin. An oxidative cleavage reaction used in the present reaction is not particularly limited. An oxidative cleavage reaction involving ozone oxidation, the use of osmium tetroxide (wherein an oxidizing agent may be used in combination), the use of $K_2OsO_4$ (wherein an oxidizing agent is used in combination), the use of chromic acid, or electrode oxidation, may be an example of such an oxidative cleavage reaction.

An oxidizing agent is used at a ratio between a catalytic amount (0.01 equivalent) and an excessive amount with respect to compound (a-6). An oxidizing agent that is used in combination is used at a ratio between 1 equivalent and an excessive amount with respect to the above oxidizing agent.

Examples of an oxidative cleavage reaction involving ozone oxidation may include methods described in, for example, Jagadeesh, S. G.; Krupadanam, G. L. D.; Srimannarayana, G.; Synth. Commun., 31 (10), 1547-1557 (2001), Cannon, J. G.; Roufos, I.; J. Heterocycl. Chem., 27 (7), 2093-2095 (1990).

In an oxidative cleavage reaction involving the ozone oxidation of olefin, specifically, for example, oxygen current containing several percentage of ozone (prepared with an ozone generator) is applied to a solution containing compound (a-6), and then, the generated ozonide (hydroperoxide, when methanol is used as a solvent) is treated with a reducing agent without being isolated, so as to obtain compound (1-9).

A solvent used in the present reaction is not particularly limited, as long as it does not inhibit the reaction and dissolves a starting substance to a certain extent. Preferred examples may include methylene chloride, ethyl acetate, and methanol. The reaction temperature is generally between −100° C. and a room temperature, and more preferably between −78° C. and a room temperature. The reaction time is not particularly limited. It is generally between 0.5 and 48 hours, and preferably between 0.5 and 24 hours.

In the treatment with a reducing agent, a reducing agent used under the reaction conditions that are commonly used in the aforementioned oxidative cleavage reaction can be used. Specific examples of such a reducing agent may include zinc-acetic acid, triphenylphosphine, triethyl phosphite, catalytic hydrogenation, and dimethyl sulfide.

In addition, the method described in Lai, G.; Anderson, W. K.; Tetrahedron Lett., 34 (43), 6849-6852 (1993) is an example of an oxidative cleavage reaction using osmium tetroxide (wherein an oxidizing agent may be used in combination), $K_2OsO_4$ (wherein an oxidizing agent is used in combination), AD-mix-α(β), or the like.

The oxidative cleavage reaction of olefin using osmium tetroxide or the like can be carried out under the same conditions as commonly used reaction conditions (for example, conditions described in the aforementioned publications).

An oxidizing agent used in combination is not particularly limited. An example of such an oxidizing agent may be sodium periodate.

A solvent used herein may be a mixed solvent consisting of water and an organic solvent such as ether, tetrahydrofuran, 1,4-dioxane, or acetone. The reaction temperature is generally between a temperature on ice and a room temperature.

An oxidative cleavage reaction using osmium tetroxide can also be carried out by two-step reaction, wherein olefin is oxidized with osmium tetroxide (that may be used together with an oxidizing agent) into 1,2-diol, and then aldehyde is obtained from the 1,2-diol using an oxidizing agent such as lead tetraacetate or sodium periodate.

Such two-step reaction can be carried out under the same conditions as commonly used reaction conditions (for example, conditions described in Masquelin, T.; Hengartner, U.; Streith, J.; Synthesis, 7, 780-786 (1995), Banfield, S. C.; England, D. B.; Kerr, M. A.; Org. lett., 3 (21), 3325-3327 (2001)).

Examples of an oxidizing agent used when olefin is converted into 1,2-diol may include N-methylmorpholine N-oxide, and $K_3Fe(CN)_6$. A solvent used herein is a mixed solvent consisting of water and an organic solvent such as acetonitrile, acetone, tert-butanol, or tetrahydrofuran. The reaction temperature is generally between a temperature on ice and a room temperature. The reaction time is not particularly limited. It is generally between 0.2 and 48 hours, and preferably between 0.2 and 24 hours.

In addition, examples of an oxidizing agent used when 1,2-diol is converted into aldehyde may include lead tetraacetate and sodium periodate. Examples of a solvent used herein may include organic solvents such as benzene, toluene, methylene chloride, ether, tetrahydrofuran, 1,4-dioxane, or acetone, and mixed solvents consisting of water and these organic solvents. The reaction temperature is generally between a temperature on ice and a room temperature. The reaction time is not particularly limited. It is generally between 5 minutes and 48 hours, and preferably between 5 minutes and 24 hours.

[Step A-5]

This is a step of synthesizing compound (a-3) by using compound (a-1) as a raw material and applying the method described in the above production method ([Step A-1]).

[Step A-6]

This is a step of synthesizing compound (a-4) by using compound (a-3) as a raw material and applying the method described in the above production method ([Step A-2]).

[Step A-7]

This is a step of obtaining compound (a-7) by modifying (converting) ring A of compound (a-4) as appropriate. Modification (conversion) of ring A of compound (a-4) of the present invention can be carried out by performing various reactions known to persons skilled in the art, or by the combined use of various reactions. The above compound can also be produced by the method described in production examples in the present examples. The term "modification (conversion) of ring A" includes the modification (conversion) of a substituent ($R_{(4)}$, $R_{(5)}$, or $R_{(6)}$).

Specific examples of various reactions known to persons skilled in the art may include: an oxidation of converting alcohol into a carbonyl compound such as aldehyde or ketone; an oxidation of converting an aldehyde compound into carboxylic acid; a reduction of converting ester, carboxylic acid, or nitrile into aldehyde or alcohol; a nitration reaction of an aromatic ring; a halogenation of an aromatic ring; a reduction from a nitro group into an amino group; a reduction of a carbon-carbon double bond or a triple bond due to hydrogenation in the presence of a transition metal catalyst; an esterification of carboxylic acid; hydrolysis of an ester into carboxylic acid; synthesis of an aldehyde compound by hydrolysis of an enol ether compound; a conversion of hydrolyzing nitrile into an amide compound or carboxylic acid; a reduction of an amide compound into an amino compound; a hydroboration; an oximation of a carbonyl compound such as aldehyde or ketone; a nitrilation of an oxime group; an N-alkylation using a reductive amination; a method of synthesizing amides using an acylation of an amino group; a sulfonamidation of an amino group; an amidation by the condensation of a carboxylic acid compound and an amino compound; an amidation reaction by the condensation of an ester compound and an amino compound; an amidation by the condensation of acid chloride and an amino compound; a condensation between an amino group and a hydroxyl group, which uses N,N'-carbonyldiimidazole, phosgene, or triphosgene; a condensation between amide and a hydroxyl group, which uses N,N'-carbonyldiimidazole, phosgene, or triphosgene; a reaction of converting a hydroxyl group into fluorine using a DAST (dimethylaminosulfur trifluoride) reagent or the like; an O-alkylation of alcohol or phenols; an N-alkylation of an amide group; an N-alkylation of an urethane compound; an alkylation of a carbonyl group into α-position by a reaction with alkyl halide following the treatment of a carbonyl compound with a base such as LDA (lithium diisopropyl amide); a demethylation reaction from an anisole derivative into a phenol derivative; a reaction of converting a hydroxyl group into a leaving group, such as mesylation or bromination of a hydroxyl group; a nucleophilic substitution reaction between a compound having a leaving group such as a bromo group and an amine compound; a nucleophilic substitution reaction between a compound having a leaving group such as a bromo group and sodium cyanide; a nucleophilic reaction of a carbonyl group with a Grignard reagent or alkyl or phenyl lithium; Wittig reaction; Horner-Emmons reaction; Mitsunobu reaction; Beckmann rearrangement; synthesis of benzoxazole by Beckmann rearrangement; Curtius rearrangement; Baeyer-Villiger reaction; Dieckmann condensation; a coupling reaction using a transition metal (for example, Suzuki coupling reaction, Ulmann-type coupling reaction, Sonogashira reaction), the coupling reaction of S. L. Buchwald et al. between an amino compound and halogenated aryl compounds, Stille coupling reaction, etc.); a reaction of synthesizing isoxazole by a 1,3-dipole addition; a reaction of synthesizing oxazole using an aldehyde compound and a TOSMIC reagent (tosylmethyl isocyanide); metallation due to halogen-metal exchange; a formylation or amidation due to the reaction between a metallated (lithiated) compound (lithiation, etc.) and a formylating agent such as N,N-dimethylformamide or an amidating agent such as dimethylcarbamoyl chloride; a reaction of converting a pyridine compound into a quaternary compound using methyl iodide or benzyl bromide; a reduction reaction of a quaternary pyridine compound into piperidine due to hydrogenation in the presence of a transition metal catalyst; a method of synthesizing a ketone compound due to the decarboxylation of a 1,3-ketoester compound; and protection and deprotection of various functional groups described in the publication, T. W. Green and P. G. M. Wuts, "Protective groups in Organic Chemistry, Second Edition", John Wiley & Sons (1991). However, examples are not limited to these reactions.

[Step A-8]

This is a step of synthesizing compound (1-9) by using compound (a-7) as a raw material and applying the above production method ([Step A-4]).

[Step A-9]

This is a step of synthesizing compound (a-9) by using compound (a-1) and compound (a-8) as raw materials and applying the above production method ([Step A-1]) based on the methods described in the publications such as Molina, P., Alajarin, M.; Vidal, A.; Fenau-Dupomt, J.; Declerq, J. P.; J. Org. Chem., 56 (12), 4008-4016 (1991), Mann, A.; Muller, C.; Tyrrell, E.; J. Chem. Soc., Perkin Trans. I, (8), 1427-1438 (1998).

[Step A-10]

This is a step of synthesizing compound (a-10) by using compound (a-9) as a raw material and applying the above production method ([Step A-2]).

This production method may provide preferred results, when the Claisen rearrangement of a 3-methyl-2-butenyl group is conducted in a para-position selective manner to 3-methyl-2-butenyloxy group.

[Step A-11]

This is a step of synthesizing compound (a-11) by appropriately modifying ring A, using compound (a-10) as a raw material and applying the above production method ([Step A-7]).

[Step A-12]

This is a step of synthesizing compound (1-9) by using compound (a-11) as a raw material and applying the above production method ([Step A-4]).

[Step A-13]

This is a step of synthesizing compound (a-3) by using compound (a-1) as a raw material and applying the above production method ([Step A-1]).

[Step A-14]

This is a step of synthesizing compound (a-12) by appropriately modifying ring A, using compound (a-3) as a raw material and applying the above production method ([Step A-7]).

[Step A-15]

This is a step of synthesizing compound (a-13) by using compound (a-12) as a raw material and applying the above production method ([Step A-2]).

[Step A-16]

This is a step of synthesizing compound (a-14) by appropriately modifying ring A, using compound (a-13) as a raw material and applying the above production method ([Step A-7]).

[Step A-17]

This is a step of synthesizing compound (1-9) by using compound (a-14) as a raw material and applying the above production method ([Step A-4]).

[Step A-18]

This is a step of synthesizing compound (a-15) by using compound (a-13) as a raw material and applying the above production method ([Step A-3]).

[Step A-19]

This is a step of synthesizing compound (1-9) by using compound (a-15) as a raw material and applying the above production method ([Step A-4]).

[General Production Method B] (Synthesis Method of Compound (1-9))

[Formula 42]

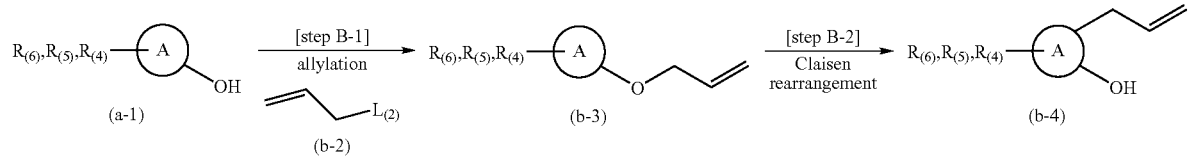

-continued

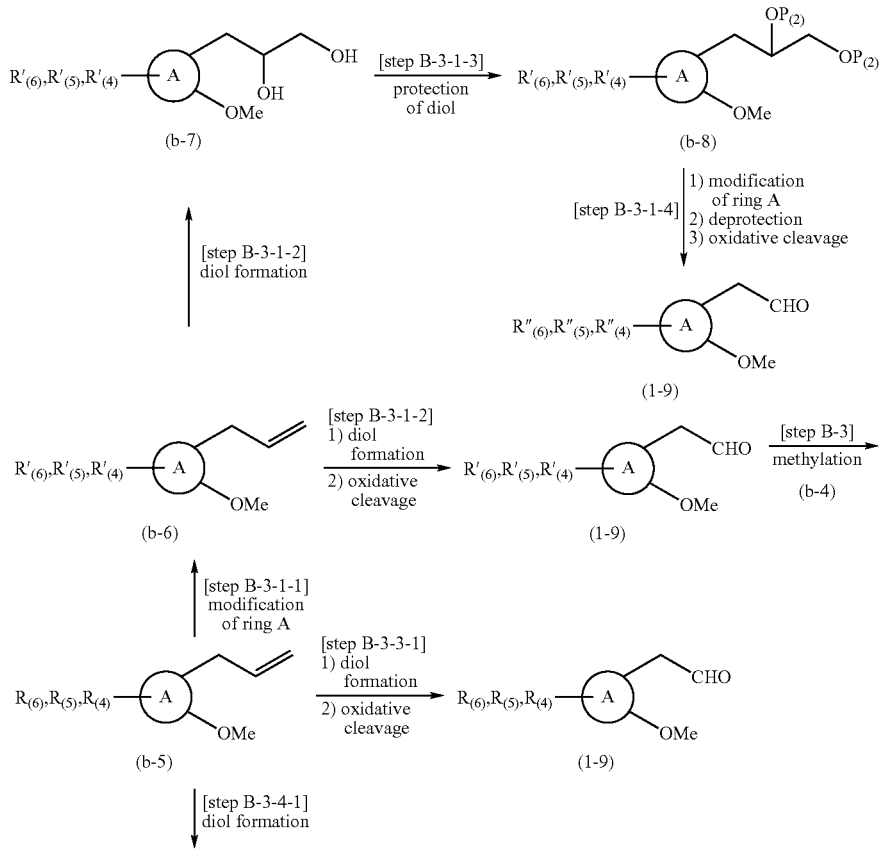

[Formula 43]

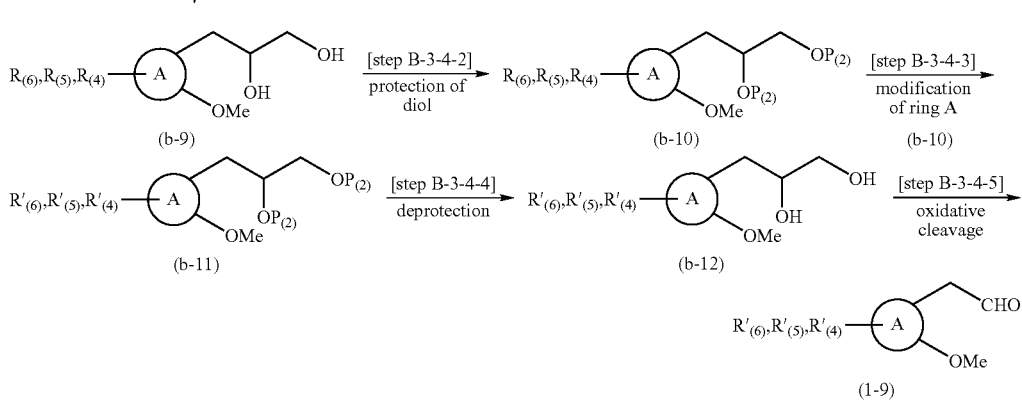

[Formula 44]

wherein each of ring A, $R_{(4)}$, $R_{(5)}$, $R_{(6)}$, $R'_{(4)}$, $R'_{(5)}$, $R'_{(6)}$, $R''_{(4)}$, $R''_{(5)}$, and $R''_{(6)}$ has the same meaning as described above; $P_{(2)}$ represents a protecting group for a hydroxyl group, which is —CH(Me)$_2$ or the like formed by a methyl group, an ethyl group, or $P_{(2)}$ attaching to a carbon atom adjacent thereto; $L_{(2)}$ represents a leaving group, which is a halogen atom (chlorine atom, bromine atom, iodine atom), or a sulfonyloxy group such as a methanesulfonyloxy group, p-toluenesulfonyloxy group, or trifluoromethanesulfonyloxy group.

A commercially available product may directly be used as compound (a-1), or the above compound may also be produced from a commercially available product by a method known to persons skilled in the art. Moreover, it can also be produced by production examples in the present examples.

A commercially available product may directly be used as compound (b-2), or the above compound may also be produced from a commercially available product by a method known to persons skilled in the art.

[Step B-1]

This is a step of synthesizing compound (b-3) by using compound (a-1) as a raw material and applying the above production method ([Step A-1]).

[Step B-2]

This is a step of synthesizing compound (b-4) by using compound (b-3) as a raw material and applying the above production method ([Step A-2]).

[Step B-3]

This is a step of synthesizing compound (b-5) by using compound (b-4) as a raw material and applying the above production method ([Step A-3]).

[Step B-3-1-1]

This is a step of synthesizing compound (b-6) by appropriately modifying ring A, using compound (b-5) as a raw material and applying the above production method ([Step A-7]).

[Step B-3-1-2]

This is a step of synthesizing compound (b-7) by using compound (b-6) as a raw material and applying the above production method ([Step A-4]).

[Step B-3-1-3]

This is a step of obtaining compound (b-8) by protecting 1,2-diol of compound (b-7).

The reaction can be carried out under the same conditions as those commonly used for the protection of 1,2-diol (for example, conditions described in publications such as T. W. Green and P. G. M. Wuts, "Protective groups in Organic Chemistry, Second Edition", John Wiley & Sons (1991), pp. 118-142).

For example, a protecting group (acetonide) can be introduced into 1,2-diol under conditions in which 2,2-dimethoxypropane, pyridium p-toluenesulfonate at a catalytic amount, and the like, are allowed to react with the above compound in an acetone solvent.

[Step B-3-1-4]

This is a step of obtaining compound (1-9) by using compound (b-8) as a raw material and applying the above production method ([Step A-7]). By this method, ring A is modified (converted) as appropriate, the protecting group of 1,2-diol is deprotected, and oxidative cleavage is conducted, thereby obtaining the compound of interest.

The reaction can be carried out under the same conditions as those commonly used in the deprotection of 1,2-diol (for example, conditions described in publications such as T. W. Green and P.G. M. Wuts, "Protective groups in Organic Chemistry, Second Edition", John Wiley & Sons (1991), pp. 118-142).

For example, 1,2-diol can be obtained by deprotecting the protecting group (acetonide) of 1,2-diol under conditions in which a 4N hydrogen chloride-ethyl acetate solution is allowed to act on the compound in an ethyl acetate solvent.

Oxidative cleavage can be carried out using the method described in the above production method ([Step A-4]).

[Step B-3-2-1]

This is a step of synthesizing compound (1-9) by using compound (b-6) as a raw material and applying the above production method ([Step A-4]).

[Step B-3-3-1]

This is a step of synthesizing compound (1-9) by using compound (b-5) as a raw material and applying the above production method ([Step A-4]).

[Step B-3-4-1]

This is a step of synthesizing compound (b-9) by using compound (b-5) as a raw material and applying the above production method ([Step A-4]).

[Step B-3-4-2]

This is a step of synthesizing compound (b-10) by using compound (b-9) as a raw material and applying the above production method ([Step B-3-1-3]).

[Step B-3-4-3]

This is a step of synthesizing compound (b-11) by appropriately modifying ring A, using compound (b-10) as a raw material and applying the above production method ([Step A-7]).

[Step B-3-4-4]

This is a step of synthesizing compound (b-12) by using compound (b-11) as a raw material and applying the above production method ([Step B-3-1-4]).

[Step B-3-4-5]

This is a step of synthesizing compound (1-9) by using compound (b-12) as a raw material and applying the above production method ([Step A-4]).

[General Production Method C] (Synthesis Method of Compound (1-9))

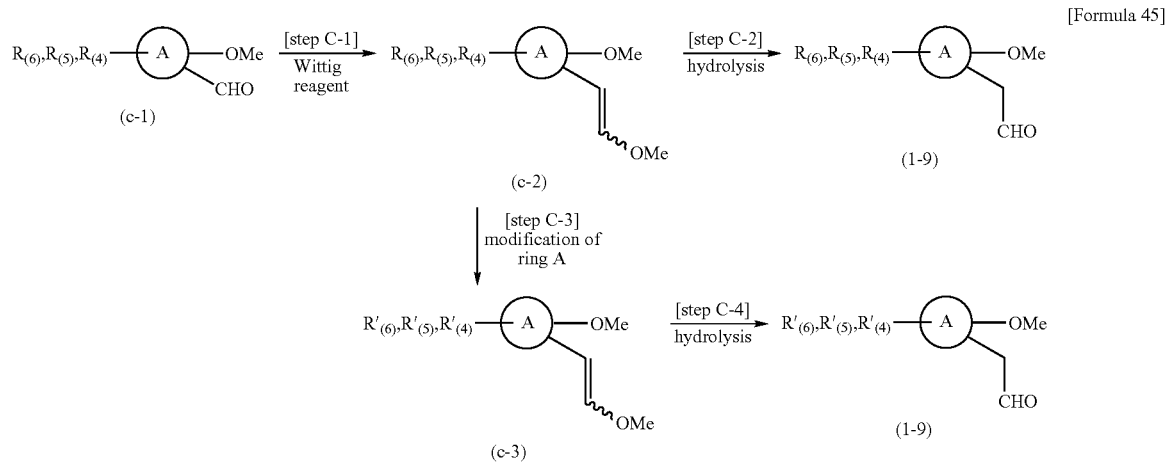

[Formula 45]

wherein each of ring A, $R_{(4)}$, $R_{(5)}$, $R_{(6)}$, $R'_{(4)}$, $R'_{(5)}$, and $R'_{(6)}$ has the same meaning as described above.

A commercially available product may directly be used as compound (c-1), or the above compound may also be produced from a commercially available product by a method known to persons skilled in the art. Moreover, it can also be produced using production examples in the present examples, or the method described in [General Production Method C'] or the like.

[Step C-1]

This is a step of obtaining compound (c-2), which has one more carbon atom by Wittig reaction.

The reaction can be carried out under same conditions as those commonly used for aldehyde and a Wittig reagent (Wittig reaction) (methoxymethyltriphenylphosphonium chloride) (for example, conditions described in Gibson, S. E.; Guillo, N.; Middleton, R. J,; Thuilliez, A.; Tozer, M. J.; J. Chem. Soc., Perkin Trans. I, 4, 447-455 (1997)).

Specifically, for example, a Wittig reagent (methoxymethyltriphenylphosphonium chloride) is allowed to react with a base, and it is then allowed to react with compound (c-1), so as to obtain compound (c-2).

The present reaction can be carried out by allowing a base to act on a Wittig reagent at a ratio between 0.8 and 1 equivalent with respect to the reagent in an organic solvent such as ether, tetrahydrofuran, 1,4-dioxane, 1,2-dimethoxyethane, benzene, or toluene. Examples of a base used herein may include sodium hydride, potassium hydride, sodium methoxide, potassium methoxide, potassium tert-butoxide, n-butyllithium, and LDA (lithium diisopropylamide).

The reaction time is not particularly limited. It is generally between 5 minutes and 24 hours, and preferably between 5 minutes and 12 hours.

The reaction temperature is generally between −78° C. and a room temperature, and more preferably between a temperature on ice and a room temperature.

[Step C-2]

This is a step of obtaining compound (1-9) by allowing compound (c-2) to react with acid.

The reaction can be carried out under the same conditions as those described in, for example, Gibson, S. E.; Guillo, N.; Middleton, R. J.; Thuilliez, A.; Tozer, M. J.; J. Chem. Soc., Perkin Trans. I, 4, 447-455 (1997).

Specifically, for example, compound (c-2) is dissolved in 5N hydrochloric acid or the like followed by heating, so as to obtain compound (1-9).

The reaction can be carried out by allowing acid to react with the above compound at a ratio between 1 equivalent and an excessive amount to the compound, in a mixed solvent consisting of water and an organic solvent such as methanol, ethanol, tetrahydrofuran, or 1,4-dioxane, or in an organic solvent such as methanol, ethanol, tetrahydrofuran, 1,4-dioxane, ethyl acetate, methylene chloride, or acetonitrile. Preferred examples of acid used herein may include hydrogen chloride, hydrochloric acid, hydrobromic acid, sulfuric acid, nitric acid, trifluoroacetic acid, and formic acid. In addition, it is also possible to convert the compound into aldehyde with trimethylsilyl iodide (which may be generated from trimethylsilyl chloride and sodium iodide in the reaction system).

The reaction time is not particularly limited. It is generally between 0.5 and 24 hours, and preferably between 0.5 and 12 hours.

The reaction temperature is generally between a temperature on ice and a solvent-reflux temperature.

[Step C-3]

This is a step of synthesizing compound (c-3) by appropriately modifying ring A, using compound (c-2) as a raw material and applying the above production method ([Step A-7]).

[Step C-4]

This is a step of synthesizing compound (1-9) by using compound (c-3) as a raw material and applying the above production method ([Step C-2]).

Compound (c-1) can also be produced by [General Production Method C'] or [General Production Method C''], for example.

[General Production Method C'] (Synthesis Method of Compound (c-1))

[Formula 46]

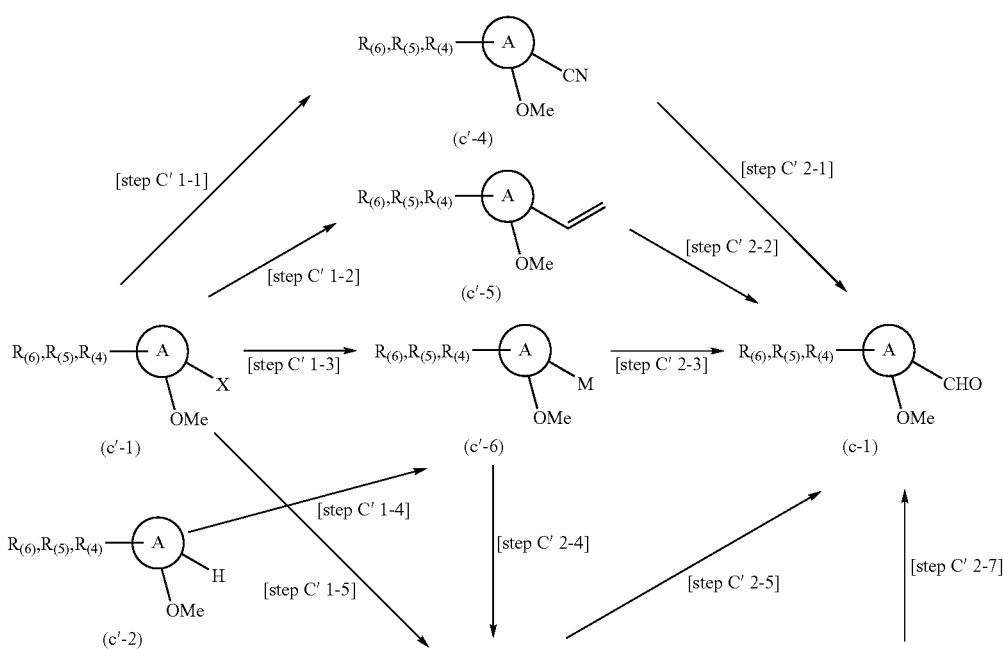

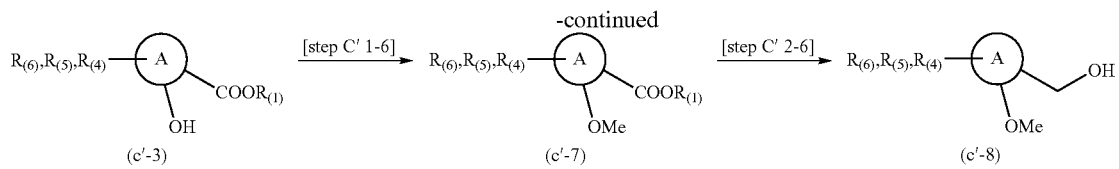

wherein each of ring A, $R_{(1)}$, $R_{(4)}$, $R_{(5)}$, and $R_{(6)}$ has the same meaning as described above; X represents a halogen atom such as a chlorine atom or bromine atom, a trifluoromethanesulfonyloxy group, or the like; and M represents a metal atom such as lithium or magnesium.

A commercially available product may directly be used as compound (c'-1), compound (c'-2), or compound (c'-3). These compounds may also be produced from commercially available products by methods known to persons skilled in the art. Moreover, they can also be produced by production examples in the present examples.

[Step C' 1-1]

This is a step of producing a cyano compound (c'-4) by allowing compound (c'-1) to react with a metal cyanide compound in the presence or absence of an organometallic catalyst.

A substitution reaction of a metal cyanide with a halogenated aryl (including a heterocyclic ring) compound is a method known to persons skilled in the art. This reaction is carried out under the same conditions as those described in, for example, Bouyssou, P.; Legoff, C.; Chenault, J.; J. Heterocycl. Chem.; 29 (4), 895-898 (1992), Agarwal, A.; Jalluri, R. K.; Blanton, C. D. J.; Taylor, E. W.; Synth. Commun., 23 (8), 1101-1110 (1993), Tschaen, D. M.; Desmond, R.; King, A. O.; Fortin, M. C.; Pipik, B.; King, S.; Verhoeven, T. R.; Synth. Commun. 24 (6), 887-890 (1994), Tschaen, D. M.; Abramson, L.; Cai, D.; Desmond, R.; Dolling, U.-H.; Frey, L.; Karady, S.; Shi, Y, Y.-J.; Verhoeven, T. R.; J. Org. Chem., 60 (14), 4324-4330 (1995).

[Step C' 1-2]

This is a step of producing compound (c'-5) by allowing compound (c'-1) to react with an organometallic compound in the presence of an organometallic catalyst.

This reaction can be carried out under the same conditions as those commonly used in the coupling reaction of a halogenated aryl (including a heterocyclic ring) compound or the like with an organometallic compound in the presence of an organometallic catalyst. For example, a reaction using a tin reagent as such an organometallic compound is described in publications such as Martorell, G.; Garcia-Raso, A.; Saa, J. M.; Tetrahedron Lett., 31 (16), 2357-2360 (1990), Kiely, J. S.; Laborde, E.; Lesheski, L. E.; Bucsh, R. A.; J. Heterocycl. Chem., 28 (6), 1581-1585 (1991). A reaction using a boron compound as such an organometallic compound is described in publications such as Kerins, F.; O'Shea, D. F.; J. Org. Chem., 67 (14), 4968-4971 (2002). A reaction using a magnesium reagent as such an organometallic compound is described in publications such as Park, M.; Buck, J. R.; Rizzo, C. J.; Tetrahedron, 54 (42), 12707-12714 (1998). A reaction using a zinc reagent as such an organometallic compound is described in publications such as Mohanakrishnan, A. K.; Cushman, M.; Synlett, 7, 1097-1099 (1999).

An organometallic catalyst used in the present reaction is not particularly limited. Preferred examples of such an organometallic catalyst may include tetrakis(triphenylphosphine) palladium(0), dichlorobis(triphenylphosphine)palladium (II), bis(tert-butylphosphine)palladium(0), (1,1'-bis (diphenylphosphino)ferrocene)palladium(II) dichloride, palladium(II) acetate, and (1,3-bis(diphenylphosphino)propane)nickel(II). Such an organometallic catalyst is used at a ratio between approximately 0.001 and 0.1 equivalent with respect to a raw material.

An organometallic compound is not particularly limited. Preferred examples of such an organometallic compound may include organotin reagents such as vinyl tri-n-butyl tin, and organoboron compounds such as 2,4,6-trivinyl cyclotriboroxane. Such an organometallic compound is used at a ratio between 1 and 5 equivalents with respect to a raw material.

A solvent used in the present reaction is not particularly limited, as long as it does not inhibit the reaction. Preferred examples of such a solvent may include benzene, toluene, xylene, N,N-dimethylformamide, 1-methyl-2-pyrrolidone, tetrahydrofuran, 1,4-dioxane, acetonitrile, and propionitrile. The reaction temperature is not particularly limited. It is generally between a temperature on ice and a solvent-reflux temperature, and preferably between a room temperature and a solvent-reflux temperature. The reaction time is not particularly limited. It is generally between 1 and 48 hours, and preferably between 1 and 24 hours.

There may be cases where good results such as the improvement of yield can be obtained by performing the present reaction in the coexistence of a base. Such a base is not particularly limited. Preferred examples of a base may include sodium carbonate, potassium carbonate, cesium carbonate, potassium phosphate, and trimethylethyleneamine.

[Step C' 1-3]

This is a step of obtaining an aryl metallic compound (c'-6) by performing the halogen metal exchange of a halogenated aryl compound (including a heterocyclic compound).

Such a halogen metal exchange can be carried out by a method known to persons skilled in the art. Specifically, for example, compound (c'-1) is subjected to a halogen metal exchange using a commercially available organometallic reagent, and preferably, an alkyllithium reagent such as n-, sec-, or tert-butyllithium, and a Grignard reagent such as isopropylmagnesium bromide, or metal magnesium, so as to prepare the corresponding aryl (including a heterocyclic ring) lithium reagent, or aryl (including a heterocyclic ring) magnesium reagent.

A solvent used in the present step differs depending on a starting material or a reagent used. Such a solvent is not particularly limited, as long as it does not inhibit the reaction, dissolves a starting substance to a certain extent, and is constantly inactive during the reaction. Preferred examples of such a solvent may include diethyl ether, tetrahydrofuran, benzene, and toluene. The reaction time is not particularly limited. It is generally between 0.1 and 48 hours, and preferably between 0.1 and 2 hours. The reaction temperature differs depending on a starting material or a reagent used. In order to reduce the generation of by-products to the minimum, it is preferable to maintain the temperature to be low, such as a temperature of −78° C.

In addition, there may be cases where good results such as the improvement of yield or the reduction of the reaction time can be obtained by adding TMEDA (tetramethylethylenediamine), HMPA (hexamethylphosphoroamide), or the like, as an additive.

[Step C' 1-4]

This is a step of obtaining an aryl metallic compound (c'-6) by the metallation reaction of an aryl (including a heterocyclic compound) compound (c'-2).

The metallation reaction of an aryl compound (including a heterocyclic compound) can be carried out by a method known to persons skilled in the art. Specifically, for example, a commercially available organic metal reagent, and preferably, an alkyllithium reagent such as n-, sec-, or tert-butyllithium, is allowed to act on compound (c'-2), so as to prepare the corresponding aryl (including a heterocyclic ring) lithium reagent (c'-6).

Such a reaction can be carried out under the same conditions as those described in, for example, Jacob, P. III; Shulgin, A. T.; Synth. Commun., 11 (12), 957 (1981) or the like.

A solvent used in the present step differs depending on a starting material or a reagent used. Such a solvent is not particularly limited, as long as it does not inhibit the reaction, dissolves a starting substance to a certain extent, and is constantly inactive during the reaction. Preferred examples of such a solvent may include diethyl ether, tetrahydrofuran, benzene, and toluene. The reaction temperature differs depending on a starting material or a reagent used. In order to reduce the generation of by-products to the minimum, it is preferable to maintain the temperature to be low, such as a temperature of −78° C. The reaction time is not particularly limited. It is generally between 0.1 and 48 hours, and preferably between 0.1 and 24 hours.

In addition, there may be cases where good results such as the improvement of yield or the reduction of the reaction time can be obtained by adding TMEDA (tetramethylethylenediamine), HMPA (hexamethylphosphoroamide), or the like, as an additive.

[Step C' 1-5]

This is a step of obtaining an ester or carboxylic acid compound (c'-7) by subjecting halogenated aryl (including a heterocyclic compound) or an aryl triflate compound (including a heterocyclic compound) (C'-1) to a carbon monoxide insertion reaction.

When a carbon monoxide insertion reaction is carried out using a transition metal catalyst, and preferably, a commercially available palladium complex such as palladium(II) acetate, in the coexistence of alcohol, such as preferably methanol, ethanol, or tert-butanol, under common conditions that have been known to persons skilled in the art, a halogen atom can be converted into a desired carboxylate group. Subsequently, alkaline hydrolysis or acid hydrolysis is carried out under common conditions known to persons skilled in the art, so as to obtain the corresponding carboxylic acid compound.

[Step C' 1-6]

This is a step of synthesizing compound (c'-7) by using compound (c'-3) as a raw material and applying the method described in the above production method ([Step A-3]).

[Step C' 2-1]

This is a step of obtaining compound (c-1) by subjecting compound (c'-4) to a reduction reaction.

As a reduction reaction of converting a cyano group into a formyl group, a reduction reaction of using metal hydride such as diisobutyl aluminum hydride in an inactive solvent such as tetrahydrofuran, has been known to persons skilled in the art. In addition, the above compound can also be produced by a reduction reaction of using Raney nickel described in T. Sohda et al. (Chem. Pharm. Bull., 39 (6), 1440-1445 (1991)) or O.G. Backeberg et al. (J. Chem. Soc., 3961-3963 (1962)) (which is means for heating the compound in a formic acid-water mixed solvent, or means for allowing the compound to react with sodium hypophosphite in a pyridine-acetic acid-water mixed solvent at a temperature between a room temperature and 40° C.). The reaction time is not particularly limited. It is generally between 0.5 and 48 hours, and preferably between 0.5 and 24 hours.

[Step C' 2-2]

This is a step of synthesizing compound (c-1) by using compound (c'-5) as a raw material and applying the above production method ([Step A-4]).

[Step C' 2-3]

This is a step of obtaining an aldehyde compound (c-1) from the aryl metallic compound (c'-6) prepared in the above described [Step C' 1-3] or [Step C' 1-4].

The aryl metallic compound (c'-6) prepared in the above described [Step C' 1-3] or [Step C' 1-4] is allowed to react with a commercially available formylating agent, and preferably, with a reagent such as N,N-dimethylformamide, N-formylmorpholine, or ethyl formate, so as to produce the corresponding aldehyde compound (c-1). This formylation reaction has been known to persons skilled in the art.

[Step C' 2-4]

This is a step of obtaining an ester or carboxylic acid compound (c'-7) from the aryl metal compound (c'-6) prepared in the above described [Step C' 1-3] or [Step C' 1-4].

The aryl metallic compound (c'-6) prepared in the above described [Step C' 1-3] or [Step C' 1-4] is allowed to react with a commercially available esterifying agent, and preferably, with a reagent such as diethyl carbonate or carbon dioxide, so as to convert the above compound into the corresponding ester or carboxylic acid compound (c'-7). This reaction of converting the compound into an ester or carboxylic acid has been known to persons skilled in the art.

[Step C' 2-5]

This is a step of obtaining compound (c-1) by subjecting compound (c'-7) to a reduction reaction. The reaction can be carried out under the same conditions as those commonly used in the reduction reaction from an ester compound to an aldehyde compound (for example, conditions described in E. Winterfeldt; Synthesis, 617 (1975)).

Preferred reducing agents used in the reaction include diisobutyl aluminum hydride, sodium bis(2-methoxyethoxy) aluminum hydride, and bis(N-methylpiperazino)aluminum hydride.

A solvent used in the reaction is not particularly limited, as long as it does not inhibit the reaction and dissolves a starting substance to a certain extent. Preferred examples of such a solvent may include tetrahydrofuran, toluene, and methylene chloride.

The reaction time is not particularly limited. It is generally between 0.5 and 48 hours, and preferably between 0.5 and 24 hours.

The reaction temperature is not particularly limited. It is generally between −78° C. and a room temperature, and preferably between −78° C. and a temperature on ice.

[Step C' 2-6]

This is a step of obtaining an alcohol compound (c'-8) by subjecting an ester compound (c'-7) to a reduction reaction.

The alcohol compound (c'-8) can be obtained from an ester or carboxylic acid compound (c'-7) according to a method known to persons skilled in the art.

In the case of an ester, examples of a reducing agent used in the reaction may include lithium aluminum hydride, lithium borohydride, and diisobutyl aluminum hydride. The reaction temperature is not particularly limited. It is generally between −78° C. and a solvent-reflux temperature, and preferably between −78° C. and a room temperature. A solvent used in the reaction is not particularly limited, as long as it does not inhibit the reaction and dissolves a starting substance to a certain extent. Preferred examples of such a solvent may include tetrahydrofuran, ether, toluene, and methylene chloride.

In the case of carboxylic acid, examples of a reducing agent used in the reaction may include lithium aluminum hydride, a borane-tetrahydrofuran complex, and a borane-dimethylsulfide complex. The reaction temperature is not particularly limited. It is generally between −78° C. and a solvent-reflux temperature, and preferably between a temperature on ice and a solvent-reflux temperature. A solvent used in the reaction is not particularly limited, as long as it does not inhibit the reaction and dissolves a starting substance to a certain extent. Preferred examples of such a solvent may include tetrahydrofuran and ether. The reaction time is not particularly limited. It is generally between 0.5 and 48 hours, and preferably between 0.5 and 24 hours.

[Step C' 2-7]

This is a step of obtaining an aldehyde compound (c-1) by subjecting an alcohol compound (c'-8) to an oxidation reaction. An aldehyde compound can be obtained from an alcohol compound according to a method known to persons skilled in the art.

Examples of a known oxidation method used in the present reaction may include Swern oxidation, Corey-Kim oxidation, Moffatt oxidation, PCC oxidation, PDC oxidation, Dess-Martin oxidation, $SO_3$-pyridine oxidation, and manganese dioxide oxidation.

A solvent used in the reaction is not particularly limited, as long as it does not inhibit the reaction and dissolves a starting substance to a certain extent. Preferred examples of such a solvent may include dimethyl sulfoxide, tetrahydrofuran, toluene, methylene chloride, and chloroform.

The reaction temperature is not particularly limited. It is generally between −78° C. and a solvent-reflux temperature, and preferably between −78° C. and a room temperature. The reaction time is not particularly limited. It is generally between 0.5 and 48 hours, and preferably between 0.5 and 24 hours.

[General Production Method C"] (Synthesis Method of Compound (c-1))

[Formula 47]

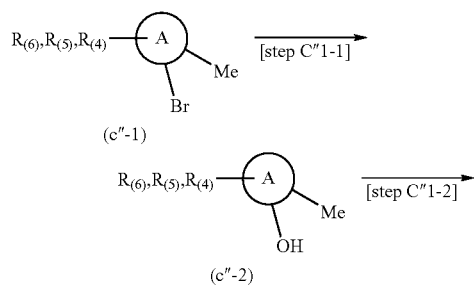

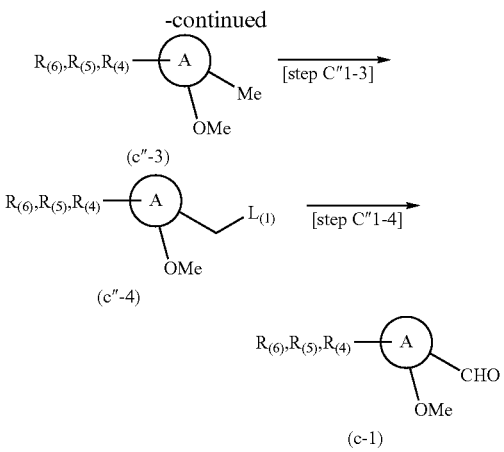

wherein each of ring A, $R_{(4)}$, $R_{(5)}$, and $R_{(6)}$ has the same meaning as described above; and $L_{(1)}$ represents a halogen atom such as a chlorine atom or bromine atom.

A commercially available product may directly be used as compound (c"-1), or the above compound may also be produced from a commercially available product by a method known to persons skilled in the art. Moreover, it can also be produced by production examples in the present examples.

[Step C" 1-1]

This is a step of obtaining compound (c"-2) via the successive treatment, in which the halogen metal exchange of compound (c"-1) is performed and the resultant metal compound is treated with trialkyl borate such as trimethyl borate to give a boronic acid derivative, which is treated with an oxidizing reagent such as peracetic acid or N-methylmorpholine N-oxide to produce compound (c"-2).

Such a reaction via boronic acid is a synthesis method that has been known to persons skilled in the art. The reaction can be carried out under the same conditions as those described in, for example, Gotteland, J.-P.; Halazy, S.; Synlett, 9, 931-932 (1995).

[Step C" 1-2]

This is a step of synthesizing compound (c"-3) by using compound (c"-2) as a raw material and applying the above production method ([Step A-3]).

[Step C" 1-3]

This is a step of obtaining compound (c"-4) by the halogenation reaction of compound (c"-3).

This halogenation reaction is a synthesis method that has been known to persons skilled in the art. The reaction can be carried out under the same conditions as those described in, for example, Gray, M. A.; Konopski, L.; Langlois, Y.; Synth. Commun., 24 (10), 1367-1379 (1994).

[Step C" 1-4]

This is a step of obtaining compound (c-1) from compound (c"-4).

The method of producing compound (c-1) is a synthesis method that has been known to persons skilled in the art. The reaction can be carried out under the same conditions as those described in, for example, Valenti, P.; Chiarini, A.; Gasperi, F.; Budriesi, R.; Arzneim.-Forsch., 40 (2), 122-125 (1990); Ventelon, L.; Moreaux, L.; Mertz, J.; Blanchard-Desce, M.; Chem. Commun. (Cambridge), 20, 2055-2056 (1999).

[General Production Method D] (Synthesis Method of Compound (1-9))

[Formula 48]

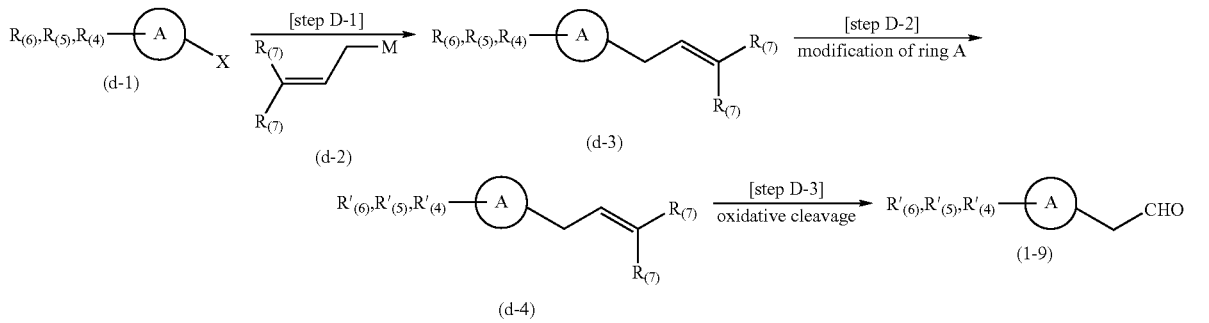

[Formula 49]

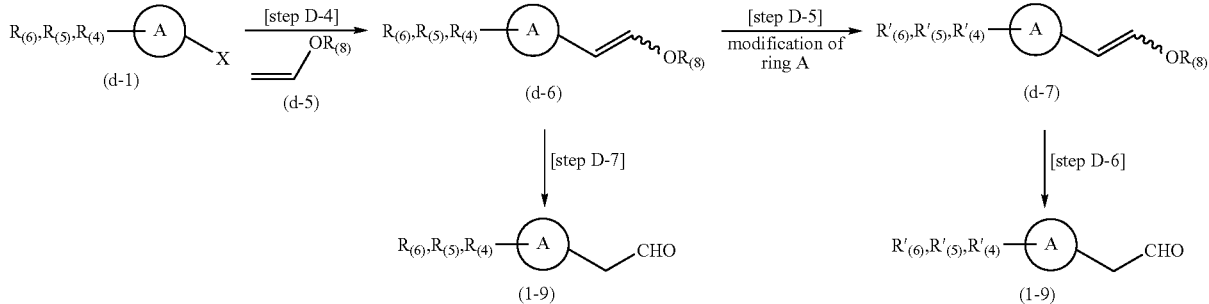

wherein each of ring A, $R_{(4)}$, $R_{(5)}$, $R_{(6)}$, $R'_{(4)}$, $R'_{(5)}$, $R'_{(6)}$, X, and M has the same meaning as described above; $R_{(7)}$ represents a hydrogen atom or a lower alkyl group such as a methyl group or ethyl group; and $R_{(8)}$ represents a lower alkyl group such as a methyl group or ethyl group.

Commercially available products may directly be used as compound (d-1), compound (d-2), and compound (d-5). Otherwise, these compounds may also be produced from commercially available products by methods known to persons skilled in the art. Moreover, these compounds may also be produced by production examples in the present examples.

[Step D-1]

This is a step of producing compound (d-3) by allowing compound (d-1) to react with an organometallic compound (d-2) in the presence of an organometallic catalyst.

This reaction can be carried out under the same conditions as those commonly used in the coupling reaction of a halogenated heteroaryl compound or the like with an organometallic compound in the presence of an organometallic catalyst.

For example, a reaction of using an organic tin reagent as an organic metal compound is described in publications such as Mckittrick, B.; Failli, A.; Steffan, R. J.; Soll, R. M.; Hughes, P.; Schmid, J.; Asselin, A. A.; Shaw, C. C.; Noureldin, R.; Gavin, G.; J. Heterocycl. Chem., 27 (7), 2151-2163 (1990). A reaction of using an organic zinc reagent as an organometallic compound is described in publications such as Campbell James B. (JR), Firor Judy Wawerchak, Davenport Timothy W., Synth. Commun., 19, 2265-2272 (1989).

An organometallic catalyst used in the present reaction is not particularly limited. Preferred examples of such an organic metal catalyst may include tetrakis(triphenylphosphine) palladium(O), dichlorobis(triphenylphosphine) palladium(II), (1,1'-bis(diphenylphosphino)ferrocene) palladium (II) dichloride, bis(tert-butylphosphine) palladium(O), palladium(II) acetate, and (1,3-bis(diphenylphosphino)-propane) nickel(II). Such an organometallic catalyst is used at a ratio between approximately 0.001 and 0.1 equivalent with respect to a raw material.

An organometallic compound is not particularly limited. Preferred examples of such an organometallic compound may include organic tin reagents such as aryl tri-n-butyl tin or tributyl(3-methyl-2-butenyl)tin, and organic boron reagents such as aryl boronic acid or 2-aryl-4,4,5,5-tetramethyl-1,3-dioxaborolane. Such an organic metal compound is used at a ratio between 1 and 5 equivalents with respect to a raw material.

A solvent used in the present reaction is not particularly limited, as long as it does not inhibit the reaction. Preferred examples of such a solvent may include benzene, toluene, xylene, N,N-dimethylformamide, 1-methyl-2-pyrrolidone, tetrahydrofuran, 1,4-dioxane, acetonitrile, and propionitrile. The reaction temperature is not particularly limited. It is generally between a temperature on ice and a solvent-reflux temperature, and preferably between a room temperature and a solvent-reflux temperature. The reaction time is not particularly limited. It is generally between 0.5 and 48 hours, and preferably between 0.5 and 24 hours.

There may be cases where good results such as the improvement of yield can be obtained by performing the present reaction in the coexistence of a base. Such a base is not particularly limited. Preferred examples of a base may include sodium carbonate, potassium carbonate, cesium carbonate, potassium phosphate, and triethylamine.

[Step D-2]

This is a step of synthesizing compound (d-4) by appropriately modifying ring A, using compound (d-3) as a raw material and applying the above production method ([Step A-7]).

[Step D-3]

This is a step of synthesizing compound (1-9) by using compound (d-4) as a raw material and applying the above production method ([Step A-4]).

[Step D-4]

This is a step of producing compound (d-6) by allowing compound (d-1) to react with compound (d-5) in the presence of an organometallic catalyst.

This reaction can be carried out under the same conditions as those commonly used in the coupling reaction of a halogenated heteroaryl compound or the like with a vinyl ether compound or the like in the presence of an organometallic catalyst.

For example, the reaction can be carried out under the same conditions as those described in, for example, Andersson, C,-M.; Larsson, J.; Hallberg, A.; J. Org. Chem., 55 (22), 5257-5761 (1990).

An organometallic catalyst used in the present reaction is not particularly limited. Preferred examples of such an organic metal catalyst may include tetrakis(triphenylphosphine) palladium(0), dichlorobis(triphenylphosphine) palladium(II), (1,1'-bis(diphenylphosphino)ferrocene) palladium (II) dichloride, palladium(II) acetate, and (1,3-bis(diphenylphosphino)propane) nickel(II). Such an organic metal catalyst is used at a ratio between approximately 0.001 and 0.1 equivalent with respect to a raw material.

A solvent used in the present reaction is not particularly limited, as long as it does not inhibit the reaction. Preferred examples of such a solvent may include benzene, toluene, xylene, N,N-dimethylformamide, 1-methyl-2-pyrrolidone, tetrahydrofuran, 1,4-dioxane, acetonitrile, and propionitrile. The reaction temperature is not particularly limited. It is generally between a temperature on ice and a solvent-reflux temperature, and preferably between a room temperature and a solvent-reflux temperature. The reaction time is not particularly limited. It is generally between 0.5 and 48 hours, and preferably between 0.5 and 24 hours.

There may be cases where good results such as the improvement of yield can be obtained by performing the present reaction in the coexistence of a base. Such a base is not particularly limited. Preferred examples of a base may include sodium carbonate, potassium carbonate, cesium carbonate, potassium phosphate, and triethylamine.

There may also be cases where preferred results such as the improvement of yield or the reduction of the reaction time can be obtained by the coexistence of an ammonium salt such as tetra-n-butylammonium chloride, tetra-n-butylammonium bromide, or tetra-n-butylammonium iodide.

[Step D-5]

This is a step of synthesizing compound (d-7) by appropriately modifying ring A, using compound (d-6) as a raw material and applying the above production method ([Step A-7]).

[Step D-6]

This is a step of synthesizing compound (1-9) by using compound (d-7) as a raw material and applying the above production method ([Step C-2]).

[Step D-7]

This is a step of synthesizing compound (1-9) by using compound (d-6) as a raw material and applying the above production method ([Step C-2]).

[General Production Method E] (Synthesis Method of Compound (1-9) and Compound (1-10))

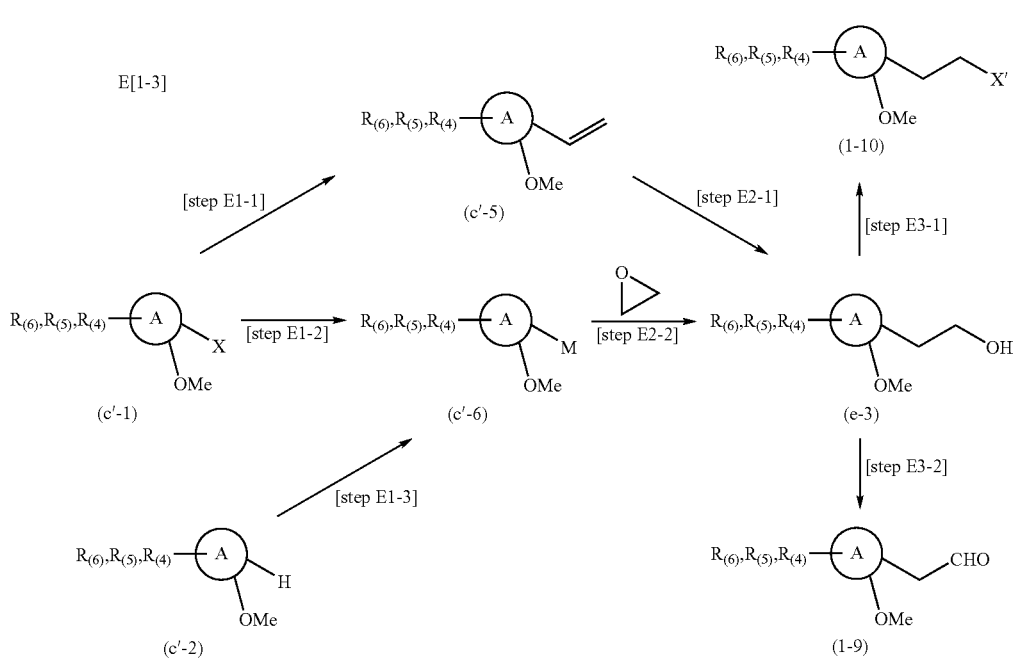

[Formula 50]

wherein each of ring A, $R_{(4)}$, $R_{(5)}$, $R_{(6)}$, X, and M represents the same meaning as described above; X' represents a leaving group that is, for example, a halogen atom (a chlorine atom, bromine atom, iodine atom, etc.) or a sulfonyloxy group such as a methanesulfonyloxy group, p-toluenesulfonyloxy group, or trifluoromethanesulfonyloxy group.

Commercially available products may directly be used as compound (c'-1) and compound (c'-2). The above compounds may also be produced from commercially available products by methods known to persons skilled in the art. Moreover, these compounds can also be produced by production examples in the present examples.

[Step E1-1]

This is a step of synthesizing compound (c'-5) by using compound (c'-1) as a raw material and applying the above production method ([Step C'1-2]).

[Step E1-2]

This is a step of synthesizing compound (c'-6) by using compound (c'-1) as a raw material and applying the above production method ([Step C'1-3]).

[Step E1-3]

This is a step of synthesizing compound (c'-6) by using compound (c'-2) as a raw material and applying the above production method ([Step C'1-4]).

[Step E2-1]

This is a step of obtaining compound (e-3) by hydroboration of compound (c'-5).

Hydroboration of olefin is carried out by a common method that has been known to persons skilled in the art, so as to obtain an alcohol compound.

[Step E2-2]

This is a step of obtaining compound (e-3) by allowing a metallated aryl compound (including a heterocyclic ring) (C'-6) to react with ethylene oxide.

A metallated aryl compound (including a heterocyclic ring) is allowed to react with ethylene oxide according to a general method known to persons skilled in the art, so as to obtain an alcohol compound.

[Step E3-1]

This is a step of obtaining compound (1-10) by converting a hydroxyl group of compound (e-3) into a leaving group.

Examples of a leaving group may include halogen atoms (a chlorine atom, bromine atom, iodine atom, etc.) and sulfonyloxy groups such as a methanesulfonyloxy group, p-toluenesulfonyloxy group, or trifluoromethanesulfonyloxy group.

This reaction can be carried out under the same conditions as those commonly used in a reaction of converting a hydroxyl group into the above leaving groups (conditions described in, for example, R. K. Crossland and K. L. Servis, J. Org. Chem., 35, 3195 (1970)).

When such a leaving group is a halogen atom for example, compound (1-10) can be produced by allowing compound (e-3) to react with thionyl chloride, thionyl bromide, phosphorus tribromide, tetrahalogenomethane-triphenylphosphine, or the like. A solvent used in the reaction is not particularly limited, as long as it does not inhibit the reaction and dissolves a starting substance to a certain extent. Preferred examples of such a solvent may include benzene, toluene, xylene, methylene chloride, and chloroform.

The reaction temperature is generally between −78° C. and a solvent-reflux temperature, and preferably between a temperature on ice and a solvent-reflux temperature.

The reaction time is not particularly limited. It is generally between 5 minutes and 48 hours, and preferably between 5 minutes and 12 hours.

When such a leaving group is a sulfonyloxy group for example, compound (1-10) can be produced by allowing compound (e-3) to react with methanesulfonyl chloride, p-toluenesulfonyl chloride, trifluoromethanesulfonic anhydride, or the like.

A solvent used in the reaction is not particularly limited, as long as it does not inhibit the reaction and dissolves a starting substance to a certain extent. Preferred examples of such a solvent may include tetrahydrofuran, toluene, xylene, methylene chloride, chloroform, and N,N-dimethylformamide.

The reaction temperature is generally between −78° C. and a solvent-reflux temperature, and preferably between −78° C. and a room temperature. There may be cases where good results such as the improvement of yield can be obtained by addition of a base. A base used herein is not particularly limited, as long as it does not inhibit the reaction. Preferred examples of such a base may include sodium carbonate, potassium carbonate, triethylamine, pyridine, and diisopropylethylamine.

[Step E3-2]

This is a step of obtaining compound (1-9) by subjecting compound (e-3) to an oxidation reaction. An aldehyde compound can be obtained from an alcohol compound according to a method known to persons skilled in the art.

Examples of a known oxidation method used in the present reaction may include Swern oxidation, Corey-Kim oxidation, Moffatt oxidation, PCC oxidation, PDC oxidation, Dess-Martin oxidation, $SO_3$-pyridine oxidation, and TEMPO oxidation.

A solvent used in the reaction is not particularly limited, as long as it does not inhibit the reaction and dissolves a starting substance to a certain extent. Examples of such a solvent may include dimethyl sulfoxide, tetrahydrofuran, toluene, methylene chloride, and chloroform.

The reaction temperature is not particularly limited. It is generally between −78° C. and a solvent-reflux temperature, and preferably between −78° C. and a room temperature. The reaction time is not particularly limited. It is generally between 5 minutes and 48 hours, and preferably between 5 minutes and 24 hours.

[General Production Method F] (Synthesis Method of Compound (2-1))

[General Production Method F] is a method for producing compound (2-1) that is used in [General Production Method 2'].

[Formula 51]

[Formula 52]

83

-continued

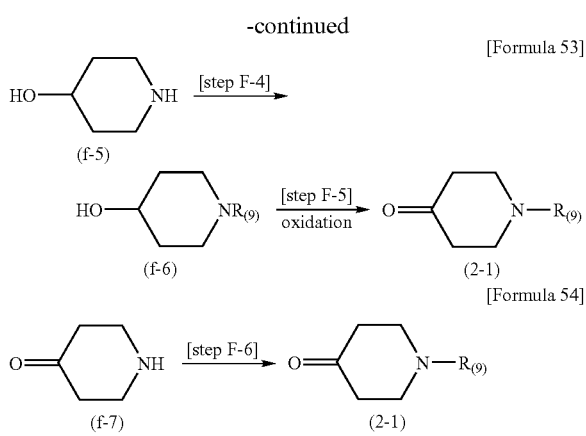

[Formula 53]

[Formula 54]

wherein R(9) has the same meaning as described above; and R(14) represents a lower alkyl group such as a methyl group or ethyl group, or an aralkyl group such as a benzyl group.

[Step F-1]

This is a step of obtaining compound (2-1) by allowing compound (f-1) to react with a primary amine (f-10).

This reaction has been known to persons skilled in the art. It can be carried out under the same conditions as those described in, for example, Tschaen, D. M.; Abramson, L.; Cai, D.; Desmond, R.; Dolling, U.-H.; Frey, L.; Karady, S.; Shi, Y.-J.; Verhoeven, T. R.; J. Org. Chem., 60 (14), 4324-4330 (1995).

[Step F-2]

This is a step of synthesizing compound (f-4) by using compound (f-3) as a raw material and applying the above production method ([Step 1-6]) or ([Step 1-7]).

[Step F-3]

This is a step of obtaining compound (2-1) by hydrolysis of compound (f-4). This reaction can be carried out under the same conditions as those commonly used in the hydrolysis of a ketal compound (for example, conditions described in publications such as T. W. Green and P. G. M. Wuts, "Protective groups in Organic Chemistry, Second Edition", John Wiley & Sons (1991), pp. 175-223).

The reaction is carried out in the presence of acid. Examples of acid used herein may include hydrochloric acid, p-toluenesulfonic acid, trifluorosulfonic acid, and camphorsulfonic acid. A solvent used in the reaction is not particularly limited, as long as it does not inhibit the reaction and dissolves a starting substance to a certain extent. Preferred examples of a solvent used herein may include solvents such as methanol, ethanol, acetone or tetrahydrofuran, or mixed solvents consisting of water and methanol, ethanol, acetone, tetrahydrofuran, or the like.

[Step F-4]

This is a step of synthesizing compound (f-6) by using compound (f-5) as a raw material and applying the above production method ([Step 1-6]) or ([Step 1-7]).

[Step F-5]

This is a step of synthesizing compound (2-1) by using compound (f-6) as a raw material and applying the above production method ([Step E3-2]).

84

[Step F-6]

This is a step of synthesizing compound (2-1) by using compound (f-7) as a raw material and applying the above production method ([Step 1-6]) or ([Step 1-7]).

[General Production Method G] (Synthesis Method of Compound (3-1))

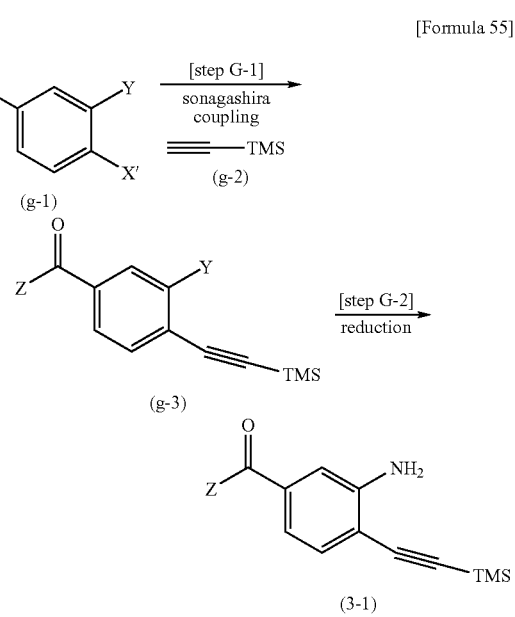

[Formula 55]

wherein X' and Z have the same meanings as described above; and Y represents a nitro group or amino group.

A commercially available product may directly be used as compound (g-1), or the above compound may also be produced from a commercially available product by a method known to persons skilled in the art. Moreover, it can also be produced by production examples in the present examples.

[Step G-1]

This is a step of obtaining compound (g-3) by the Sonogashira reaction of compound (g-1) with trimethylsilylacetylene (g-2). Sonogashira reaction is a synthesis method known to persons skilled in the art. It can be carried out under the same conditions as those described in, for example, Erdelyi, M.; Gogoll, A.; J. Org. Chem., 66 (12), 4165-4169 (2001), Ezquerra, J.; Pedregal, C.; Lamas, C.; Barluenga, .J.; Perez, M.; Garcia-Martin, M. A.; Gonzalez, J. M.; J. Org. Chem., 61 (17), 5804-5812 (1996).

[Step G-2]

This is a step of obtaining compound (3-1) by subjecting compound (g-3) to a reduction reaction.

The reduction of a nitro group is a reaction known to persons skilled in the art. As a reduction reaction performed in the presence of acetylene, a method of reducing a nitro group into an amino group using tin or zinc under acidic conditions is preferable. Moreover, a reduction with iron, which uses ammonium chloride under neutral conditions, is also applied. The reaction can be carried out under the same conditions as those described in, for example, Izumi, T.; Yokota, T.; J. Heterocycl. Chem., 29 (5), 1085-1090 (1992)., Hartman, W. W.; Dickey, J. B.; Stampfli, J. G.; Org. Synth., II, 175 (1943) (when Y is an amino group, however, this step does not need to be carried out).

[Concerning Preparation of Compound (g-1)]

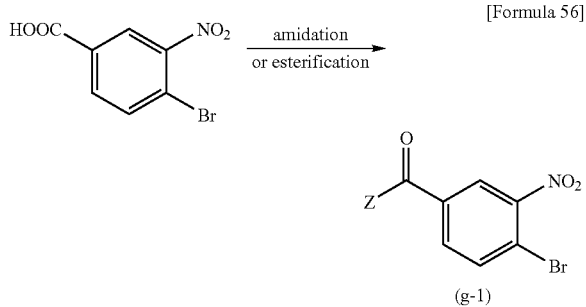

wherein Z has the same meaning as described above.

As described above, a commercially available product can directly be used as compound (g-1), or the above compound may also be produced from a commercially available product according to a method known to persons skilled in the art. Specifically, various ester compounds or an amide compound as compound (g-1) can be synthesized from 4-bromo-3-nitrobenzoic acid according to general methods known to persons skilled in the art.

[General Production Method H] (Synthesis Method of Compound (1-9))

This is a method for synthesizing compound (1-9), which differs from General production method E.

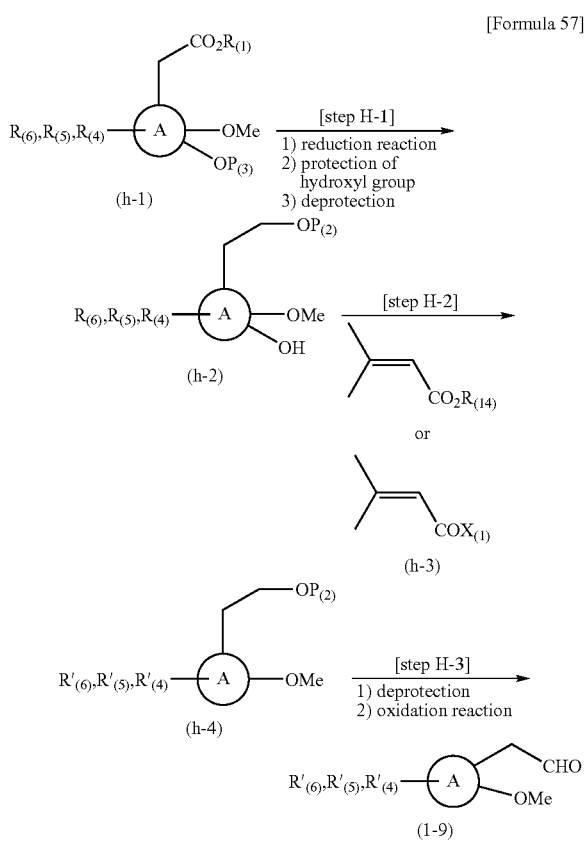

wherein each of ring A, $R_{(1)}$, $R_{(4)}$, $R_{(5)}$, $R_{(6)}$, $R'_{(4)}$, $R'_{(5)}$, and $R'_{(6)}$ has the same meaning as described above; $R_{(14)}$ represents a hydrogen atom, a lower alkyl group such as a methyl group or ethyl group, or a lower aralkyl group such as a benzyl group; $X_{(1)}$ represents a halogen atom such as a fluorine atom, chlorine atom, bromine atom, or iodine atom; $P_{(2)}$ represents a protecting group for an alcoholic hydroxyl group, such as an acyl group or benzoyl group; and $P_{(3)}$ represents a protecting group for a phenolic hydroxyl group, such as a methoxymethyl group, 1-ethoxyethyl group, or tetrahydropyranyl group.

[Step H-1]

A commercially available product may directly be used as compound (h-1), or the above compound may also be produced from a commercially available product according to a method know to persons skilled in the art, such as the method described in J. Velkov; Z. Mincheva; J. Bary; G. Boireau; C. Fujier; Synthetic Communications, 27 (3), 375-378 (1997).

This is a step of obtaining compound (h-2) by subjecting compound (h-1) to a reduction reaction, protecting an alcoholic hydroxyl group, and then deprotecting the protecting group of a phenolic hydroxyl group.

The reduction reaction of an ester group can be carried out under the same conditions as commonly used conditions described in, for example, the 4$^{th}$ edition Jikken Kagaku Koza 26, pp. 159 to 266.

Examples of a reducing agent used in the reaction may include lithium aluminum hydride, lithium borohydride, diisobutyl aluminum hydride, and sodium bis(2-methoxyethoxy)aluminum hydride. The reaction temperature is not particularly limited. It is generally between −78° C. and a solvent-reflux temperature, and preferably between −78° C. and a room temperature. A solvent used in the reaction is not particularly limited, as long as it does not inhibit the reaction and dissolves a starting substance to a certain extent. Preferred examples of such a solvent may include tetrahydrofuran, ether, dimethoxyethane, cyclopentyl methyl ether, toluene, and methylene chloride.

Such a reducing agent is used at a ratio between 1 and 3 equivalents, and preferably between 1 and 1.5 equivalents, with respect to compound (h-1).

Introduction of a protecting group into an alcoholic hydroxyl group can be carried out under the same conditions as commonly used conditions described in publications such as T. W. Green and P. G. M. Wuts, "Protective groups in Organic Chemistry, Second Edition", John Wiley & Sons, Inc.

In the present reaction, when an alcoholic hydroxyl group is protected by a benzoyl group for example, benzoyl chloride is allowed to react with the above alcohol form in the presence of a base such as triethylamine in a solvent such as toluene, xylene, ethyl acetate or ether solvent such as dimethoxyethane or cyclopentyl methyl ether, so as to obtain a product of interest. Benzoyl chloride can be used at a ratio between 1 equivalent and an excessive amount with respect to the compound alcohol form. Triethylamine can be used at a ratio between 1 equivalent and an excessive amount with respect to the compound alcohol form. There may be cases where preferred results such as the improvement of yield or the reduction of the reaction time are obtained by the coexistence of N,N,N,N-tetramethylethylenediamine, diisopropylethylamine, N,N-dimethylaniline, or the like, in the present invention.

The reaction time is not particularly limited. It is generally between 0.5 and 48 hours, and preferably between 0.5 and 4 hours. The reaction temperature is between 0° C. and 100° C., and preferably between 0° C. and a room temperature.

Deprotection of a protecting group for a phenolic hydroxyl group can be carried out under the same conditions as those described in publications such as T. W. Green and P. G. M. Wuts, "Protective groups in Organic Chemistry, Second Edition", John Wiley & Sons, Inc.

In the present reaction, when a phenolic hydroxyl group is protected by a methoxymethyl group, 1-ethoxyethyl group, or the like, the hydroxyl group is allowed to react with hydrochloric acid in a mixed solvent consisting of toluene, dimethoxyethane, and tetrahydrofuran, so as to obtain compound (h-2). The amount of hydrochloric acid used is between 1 equivalent and an excessive amount with respect to a starting substance. The reaction time is not particularly limited. It is generally between 0.5 and 48 hours, and preferably between 1 and 4 hours. The reaction temperature is between 0° C. and 100° C., and preferably between 0° C. and a room temperature.

[Step H-2]

This is a step of obtaining compound (h-4) by allowing a phenolic compound to react with 3,3-dimethylacryloyl acid or a 3,3-dimethylacryloyl acid derivative such as 3,3-dimethylaclyloyl chloride.

The reaction can be carried out under the same conditions as those described in publications such as T. Timar et al., "Synthesis of 2,2-Dimethyl-4-Chromanones", J. Heterocyclic Chem., 37, 1389 (2000), J. C. Jaszberenyi et al., "On the Synthesis of Substituted 2,2-Dimethyl-4-Chromanones and Related Compound" Tetrahedron Letters, 30 (20), 2791-2794, (1992), J. C. Jaszberenyi et al., Heterocycles, 38 (9), 2099, (1994). Other than these methods, compound (h-4) can also be obtained by allowing compound (h-2) to react with 3,3-dimethylacryloyl acid in the presence of methanesulfonic acid. 3,3-dimethylacryloyl acid is used at a ratio between 1 equivalent and an excessive amount with respect to compound (h-2). The reaction time is not particularly limited. It is generally between 0.5 and 48 hours, and preferably between 1 and 4 hours.

The reaction temperature is between a room temperature and 100° C., and preferably between 40° C. and 60° C.

[Step H-3]

This is a step of obtaining compound (1-9) by deprotecting an alcoholic hydroxyl group of compound (h-4) and then oxidizing the obtained alcohol compound.

The reaction can be carried out under the same conditions as those commonly used for deprotection of a protecting group for an alcoholic hydroxyl group described in publications such as T. W. Green and P. G. M. Wuts, "Protective groups in Organic Chemistry, Second Edition", John Wiley & Sons, Inc. For example, an alcoholic hydroxyl group protected by a benzoate ester group or the like in compound (h-4) is allowed to react with 2N-NaOH or the like in an organic solvent such as tetrahydrofuran, methanol or ethanol, or in a mixed solvent thereof, so as to obtain a product of interest. 2N-NaOH is used at a ratio between 1 equivalent and an excessive amount with respect to compound (h-4). The reaction time is not particularly limited. It is generally between 0.5 and 48 hours, and preferably between 1 and 5 hours.

The reaction temperature is between 0° C. and 100° C., and preferably between a room temperature and 50° C.

The following reaction involves a step of obtaining compound (1-9) by subjecting the thus obtained compound having an alcoholic hydroxyl group to an oxidation reaction.

An aldehyde compound can be obtained from an alcohol compound according to a method known to persons skilled in the art.

Examples of a known oxidation method used in the present reaction may include Swern oxidation, Corey-Kim oxidation, Moffatt oxidation, PCC oxidation, PDC oxidation, Dess-Martin oxidation, $SO_3$-pyridine oxidation, and TEMPO oxidation.

A solvent used in the reaction is not particularly limited, as long as it does not inhibit the reaction and dissolves a starting substance to a certain extent. Examples of such a solvent may include dimethyl sulfoxide, tetrahydrofuran, toluene, methylene chloride, chloroform, ethyl acetate, water, and a mixed solvent thereof.

An oxidizing agent is used at a ratio between a catalytic amount and an excessive amount with respect to an alcohol form.

The reaction temperature is not particularly limited. It is generally between −78° C. and a solvent-reflux temperature, and preferably between −5° C. and a room temperature. The reaction time is not particularly limited. It is generally between 3 and 10 hours, and preferably between 3 and 5 hours.

In the case of TEMPO oxidation for example, it can be carried out according to the method described in *Jikken Kagaku Koza* 23, *Yuki Gosei V, Sanka Hanno* Maruzen Co., Ltd., pp. 485-513.

A solvent used in the reaction is not particularly limited, as long as it does not inhibit the reaction and dissolves a starting substance to a certain extent. Examples of such a solvent may include dimethyl sulfoxide, tetrahydrofuran, toluene, methylene chloride, chloroform, ethyl acetate, water, and a mixed solvent thereof.

An oxidizing agent, for example, sodium hypochlorite contained in a sodium bicarbonate aqueous solution, is used at a ratio between a catalytic amount and an excessive amount with respect to an alcohol form in the presence of 2,2,6,6-tetramethylpiperidinooxy-sodium bromide.

The reaction temperature is not particularly limited. It is generally between −20° C. and a room temperature, and preferably between −5° C. and a room temperature. The reaction time is not particularly limited. It is generally between 3 and 10 hours, and preferably between 3 and 5 hours.

In the case of Swern oxidation for example, it can be carried out according to the method described in *Jikken Kagaku Koza* 23, *Yuki Gosei V, Sanka Hanno*, Maruzen Co., Ltd., pp. 369-403.

A solvent used in the reaction is not particularly limited, as long as it does not inhibit the reaction and dissolves a starting substance to a certain extent. Examples of such a solvent may include dimethyl sulfoxide, tetrahydrofuran, toluene, methylene chloride, chloroform, ethyl acetate, and a mixed solvent thereof.

As an oxidizing agent acting as an activator of dimethyl sulfoxide, oxalyl chloride, trifluoroacetic anhydride, acetic anhydride, cyclohexylimide, diphosphorus pentoxide, or the like is used at a ratio between a two-times molar amount and an excessive amount with respect to an alcohol form.

As a base, triethylamine, N,N-diisopropylethylamine, pyridine, or the like is used at a ratio between a two-times molar amount and an excessive amount with respect to an alcohol form.

The reaction temperature is not particularly limited. It is generally between −70° C. and a room temperature. The reaction time is generally between 3 and 10 hours, and preferably between 3 and 5 hours.

An aldehyde compound (1-9) can simply be purified by converting it into a sodium bisulfite adduct according to the method described in D. P. Kjell et al., "A Novel, Nonaqueous Method for Regeneration of Aldehydes from Bisulfite Adducts" J. Organic. Chemistry. 64, 5722-5724 (1999). In addition, aldehyde can also easily be regenerated. A sodium bisulfite adduct can be obtained by allowing an aldehyde form (1-9) to react with a sodium bisulfite aqueous solution for example, in an organic solvent such as ethanol, ethyl acetate or methanol, or in a mixed solvent thereof. Such sodium bisulfite is used at a ratio between 1 equivalent and an excessive amount with respect to compound (1-9). The reaction temperature is not particularly limited. It is generally between 10° C. and 40° C., and preferably a room temperature. The reaction time is generally between 1 and 48 hours, and preferably between 12 and 24 hours.

The thus obtained sodium bisulfite adduct is treated with a base such as potassium carbonate, sodium carbonate, sodium hydroxide, or potassium hydroxide, in an organic solvent such as ethanol, ethyl acetate, or methanol, or in a mixed solvent thereof, so as to obtain an aldehyde form (1-9). A base is used at a ratio between 1 equivalent and an excessive amount with respect to the sodium bisulfite adduct. The reaction temperature is not particularly limited. It is generally between 10° C. and 40° C., and preferably a room temperature. The reaction time is generally between 1 and 24 hours, and preferably between 1 and 2 hours.

Compound (1-9) can be used to produce the compound represented by formula (I), with or without purification.

EFFECTS OF THE INVENTION

In order to demonstrate the usefulness of the compound represented by general formula (I) of the present invention, the present inventors have conducted the following tests.

The test examples and reference examples indicated below are provided for illustrative purposes only. Thus, the agent of the present invention for treating or preventing lower urinary tract symptoms is not limited to these examples in any case. Persons skilled in the art can realize the present invention to the maximum, not only by using the test examples and reference examples indicated below, but also by adding various modifications to the scope of claims in the specification of the present application. Such modifications are included in the scope of claims in the specification of the present application.

TEST EXAMPLE 1

Test Regarding Affinity for Serotonin 1A Receptor (1) The affinity of a test substance for a 5-HT1A receptor was examined by an inhibition experiment, in which the inhibitory effect of the test substance against the binding of [$^3$H]-4-(2'-methoxy)phenyl-1-(2'-(N-2''-pyridinyl)-p-fluorobenzamido)ethyl-piperazine (MPPF) that selectively binds to the 5-HT1A receptor in a swine hippocampal membrane fraction was examined. The 5-HT1A receptor that is a G-protein binding receptor becomes a G-protein binding state with addition of $MgCl_2$. In contrast, it becomes a G-protein non-binding state with addition of guanylylimido diphosphate (Gpp(NH)p). Generally, it has been known that a G-protein receptor agonist exhibits strong affinity for a receptor that is in a G-protein binding state, depending on the level of intrinsic activity thereof. Thus, both the affinity of a test substance to the receptor that was in a state of not binding to the G-protein and the affinity of the test substance to the receptor that was in a state of binding to the G-protein were obtained. Then, the obtained values were compared to each other, so as to estimate the level of the intrinsic activity of the test substance. Theoretically, when the value (L/H) obtained by dividing the affinity of a test substance to the receptor that is in a low affinity state (IC50 value) by the affinity of a test substance to the receptor that is in a high affinity state (IC50 value) is 1 or less, the intrinsic activity thereof is zero. The greater this value, the higher the intrinsic activity that can be obtained. Actually, it was judged that a test substance had no intrinsic activity when it had an L/H value of 1 or smaller, and that the test substance had intrinsic activity when it had an L/H value of 2 or greater.

Swine hippocampus was homogenized in a 50 mM Tris-Hcl buffer (pH 7.4; hereinafter referred to as buffer A) that had been cooled on ice. The suspension was centrifuged at 40,000×g for 15 minutes. The obtained pellet was suspended in buffer solution A, and the thus obtained solution was then centrifuged at 40,000×g for 15 minutes. The same operation was repeated 2 or 3 times. The finally obtained pellet was suspended in a buffer solution A in an amount 10 times the wet weight of the swine hippocampus, so as to obtain a membrane fraction. The obtained membrane fraction was stored at −80° C. until use.

A mixture (0.5 ml) used for incubation comprised an appropriate amount of the membrane fraction, a test substance with a desired concentration, $MgCl_2$ (final concentration: 10 mM) or Gpp(NH)p (final concentration: 1 mm ), [$^3$H]MPPF (final concentration: 0.5 nM), dimethyl sulfoxide (final concentration: 1% (v/v)), and a 50 mM Tris-Hcl buffer (pH 7.4). The reaction was initiated with addition of the membrane fraction, and the mixture was incubated at 37° C. for 30 minutes. After completion of the incubation, the mixture was subjected to vacuum filtration with a glass filter, using Cell Harvester. The filter was washed with buffer solution A that had been cooled on ice. Thereafter, radioactivity binding to the receptor was measured with a liquid scintillation counter. Non-specific binding was defined as binding detected in the presence of 10 μM WAY-100,635. The following Table 1 shows data regarding affinity that are indicated by IC50 values obtained from an inhibition curve.

(2) Results

The compound of the present invention, a salt thereof, a hydrate thereof exhibited superior receptor binding action. It is to be noted that compound A indicates the compound described in Example 337 of WO98/43956.

TABLE 1

| Test substance Compound No. | Low affinity IC50 (nM) | High affinity IC50 (nM) | L/H ratio |
|---|---|---|---|
| Compound A | 0.5 | 0.1 | 3.7 |
| 1 | 0.26 | 0.16 | 1.6 |
| 2 | 0.35 | 0.27 | 1.3 |
| 3 | 0.34 | 0.46 | 0.7 |
| 4 | 0.15 | 0.17 | 0.9 |
| 5 | 0.45 | 0.57 | 0.8 |
| 6 | 0.2 | 0.2 | 1 |
| 7 | 0.3 | 0.41 | 0.7 |
| 8 | 0.23 | 0.22 | 1 |
| 9 | 0.13 | 0.17 | 0.8 |
| 15 | 0.61 | 0.72 | 0.8 |
| 19 | 0.69 | 1.1 | 0.6 |
| 20 | 0.16 | 0.2 | 0.8 |
| 22 | 0.1 | 0.13 | 0.8 |
| 24 | 0.17 | 0.22 | 0.8 |
| 25 | 0.16 | 0.18 | 0.9 |
| 26 | 0.2 | 0.16 | 1.3 |
| 27 | 0.26 | 0.23 | 1.1 |
| 28 | 0.19 | 0.14 | 1.4 |
| 30 | 0.19 | 0.2 | 1 |

TABLE 2

| Test substance Compound No. | Low affinity IC50 (nM) | High affinity IC50 (nM) | L/H ratio |
| --- | --- | --- | --- |
| Compound A | 0.5 | 0.1 | 3.7 |
| 31 | 0.15 | 0.16 | 0.9 |
| 32 | 0.25 | 0.26 | 1 |
| 33 | 0.12 | 0.17 | 0.7 |
| 34 | 0.2 | 0.26 | 0.8 |
| 35 | 0.23 | 0.27 | 0.9 |
| 36 | 0.14 | 0.26 | 0.5 |
| 37 | 0.39 | 0.55 | 0.7 |
| 38 | 0.13 | 0.2 | 0.7 |
| 44 | 0.47 | 0.4 | 1.2 |
| 45 | 0.69 | 0.58 | 1.2 |
| 46 | 0.33 | 0.24 | 1.4 |
| 47 | 0.23 | 0.23 | 1 |
| 48 | 1.1 | 1.2 | 0.9 |
| 49 | 0.27 | 0.22 | 1.2 |
| 51 | 0.17 | 0.18 | 0.9 |
| 52 | 0.2 | 0.22 | 0.9 |
| 53 | 0.46 | 0.31 | 1.5 |
| 54 | 0.13 | 0.18 | 0.7 |
| 57 | 0.24 | 0.18 | 1.3 |
| 58 | 0.39 | 0.33 | 1.2 |
| 59 | 0.12 | 0.19 | 0.6 |
| 60 | 0.24 | 0.28 | 0.9 |

TABLE 3

| Test substance Compound No. | Low affinity IC50 (nM) | High affinity IC50 (nM) | L/H ratio |
| --- | --- | --- | --- |
| Compound A | 0.5 | 0.1 | 3.7 |
| 11 | 0.1 | 0.22 | 0.4 |
| 12 | 0.16 | 0.17 | 0.9 |
| 13 | 0.22 | 0.32 | 0.7 |
| 14 | 0.34 | 0.46 | 0.7 |
| 16 | 0.17 | 0.18 | 0.9 |
| 29 | 0.3 | 0.34 | 0.9 |
| 39 | 0.09 | 0.13 | 0.7 |
| 40 | 0.17 | 0.18 | 0.9 |
| 41 | 0.14 | 0.2 | 0.7 |
| 43 | 0.15 | 0.22 | 0.7 |
| 50 | 0.21 | 0.21 | 1 |
| 56 | 0.04 | 0.07 | 0.5 |

TEST EXAMPLE 2

Antagonistic Effect on a Serotonin 1A Receptor Agonist-induced Hypothermia in Mouse (1) A thermistor probe was inserted at a depth of approximately 2 cm into the rectum of CD-1 (ICR) male mice (25-45 g), so as to measure the body temperature thereof. Body temperature is decreased by subcutaneous administration of serotonin 1A receptor agonist (8-hydroxy-dipropylaminotetralin) 0.5 mg/kg. Since a serotonin 1A antagonist inhibits such action, the antagonistic effect of a test substance to a serotonin 1A receptor was evaluated using the inhibitory effect of the hypothermia as an index. The test results are shown in Table 3 indicated below. A test substance was administered 15 minutes before the administration of the serotonin 1A agonist. A serotonin 1A partial agonist alone decreases the body temperature, depending on the degree of the agonistic action thereof. In addition, it has a weak antagonistic effect on 8-hydroxy-dipropylaminotetralin-induced hypothermia.

(2) Results

The compound of the present invention, a salt thereof, or a hydrate thereof exhibited a superior pharmacological effect.

TABLE 4

| Test substance Compound No. | ED50 (mg/kg, sc) |
| --- | --- |
| Compound A | >1 |
| 1 | 0.3 |
| 2 | 0.4 |
| 3 | 0.18 |
| 4 | 0.1 |
| 5 | 0.24 |
| 6 | 0.35 |
| 7 | 0.38 |
| 8 | 0.07 |
| 9 | 0.3 |
| 20 | 0.03 |
| 22 | 0.1 |
| 24 | 0.3 |
| 25 | 0.1 |
| 26 | 0.25 |
| 27 | 0.42 |
| 28 | 0.02 |
| 30 | 0.62 |
| 31 | 0.04 |
| 32 | 0.04 |
| 33 | 0.12 |
| 34 | 0.37 |
| 35 | 0.2 |
| 36 | 0.2 |
| 38 | 0.19 |
| 44 | 0.41 |
| 45 | 0.26 |
| 46 | 0.3 |
| 47 | 0.21 |
| 48 | 0.06 |
| 49 | 0.28 |
| 51 | 0.66 |
| 52 | 0.5 |
| 53 | 0.3 |
| 54 | 0.84 |
| 57 | 0.1 |
| 58 | 0.53 |
| 59 | 0.3 |
| 60 | 0.52 |

TEST EXAMPLE 3

Inhibitory Action Against the Accentuated Urinary Reflex Action of Rat Due to Destruction of the Superior Colliculus Thereof (1) In the present test, Sprague-Dawley female rats (200-350 g) were used. The rats were subjected to median incision of the abdomen under anesthesia. Thereafter, a hole with a minor diameter was made on the head portion of the bladder, and a catheter used for measurement of an intravesical pressure was placed therein. A catheter used for administration of a test substance was placed in the femoral vein. These catheters were fixed at the occipital region of the rat through the subcutis. One day later, the urinary reflex of the rats was measured with a cystometrogram. Thereafter, the rats were fixed on a brain stereotaxis apparatus under anesthesia, and then subjected to median incision of the scalp. Thereafter, a hole was created with a dental drill at the cranium in the upper portion of the superior colliculus in accordance with the coordinate of a brain diagram. A microelectrode (diameter: 0.7 mm; length: 1.5 mm) of a legion generator was then inserted into the superior colliculus through the hole. Thereafter, electric current was applied (65° C., 4 minutes), so as to damage the brain tissues. After completion of the operation, when the rat awakened from anesthesia, cystometrogram was conducted again to confirm the enhanced state of urinary reflex. A test substance was administered through the catheter placed in the femoral vein, and the action of the test substance to the urinary reflex was evaluated. In addition, the effects of several test substances were compared using the maximal reaction (Emax). The results are shown in Table 4.

(2) Results

The compound of the present invention, a salt thereof, or a hydrate thereof exhibited superior pharmacological effects.

TABLE 5

| Test substance No. | Dose (mg/kg, iv) | Bladder capacity Emax (%) |
|---|---|---|
| Compound A | 0.01 | −36 |
| 3 | 0.03 | 62 |
| 4 | 0.03 | 107 |
| 20 | 0.3 | 94 |

TEST EXAMPLE 4

Effect of Controlling Memory Disorder Induced by 8-OH-DPAT in Rats (1) A Sprague-Dawley male rats (130-200 g) were bred in an individual cage and used in the present test. For appetite stimulation, the body weight of the rats was reduced to approximately 80% of the original weight by fasting. Thereafter, an increase in the body weight was continuously suppressed by restricted feeding. As a maze test, an elevated 8-arm radial maze (central platform diagonal length: 34 cm, arm length: 60 cm; arm width: 12 cm) was used. In order to allow the rats to remember the positions of baits placed on the arms, the rats were left on the platform of the maze in which baits had been placed on the tips of the 4 predetermined arms. Thereafter, the rats were left on the maze for a certain period of time or until it ate all the baits. This training was carried out 1 to 3 times a day. The rats that had sufficiently learned were subjected to the following experiment. A solvent or test substance was subcutaneously administered to the rats. Twenty minutes later, 0.5 mg/kg 8-OH-DPAT was subcutaneously administered thereto. Further, 20 minutes later, the same maze test as that in the training was carried out. A reference memory error was defined as an action to enter arms on which no baits had been placed, and a working memory error was defined as an action to enter again arms on which baits had previously been placed. Thus, the actions of the rat were recorded. In addition, the time required for the rat to take all the four baits was also recorded. When the rat did not take all the four baits within a certain period of time, the test was terminated at that time, and the required time was defined as an elapsed time. (Reference: Yoshihiro Hiraga, "Effects of scopolamine upon delayed radial-arm maze performance in rats" Folia pharmacol. Japon. 97, 351-359 (1991)). The results are shown in Table 4.

(2) Results

The compound of the present invention, a salt thereof, or a hydrate thereof exhibited superior pharmacological effect.

TABLE 6

| | Number of working memory errors | Number of reference memory errors | Elapsed time (second) | N |
|---|---|---|---|---|
| Solvent (1 mL/kg, s.c.) | 7.13 ± 1.01 | 2.63 ± 0.63 | 371 ± 44.8 | 8 |
| Test compound No. 20 (0.3 mg/kg, s.c.) | 0.25 ± 0.16 | 1.50 ± 0.57 | 52 ± 9.9 | 8 |

Mean ± S.E.

TEST EXAMPLE 5

Evaluation of Antianxiety Effect by Mouse Light/dark Box Test (1) The method of Belzung C., Misslin R., and Vogel E. (Reference: Behavioural effects of the benzodiazepine receptor partial agonist RO16-6028 in mice, Psychopharmacology, 97, 388-391, 1989) was modified. The present mouse light/dark box test was carried out according to such a modified method. As a test device used in this test, a lidded black acryl box (dark box, 15×10×20 cm) was connected to a lidless white acryl box (light box, 15×20×20 cm) using a black acryl tunnel (10×7×4.5 cm), so as to prepare a light/dark box in which a mouse can freely move between the dark box and the light box. In this test device, in order to observe the behavior of the mouse, the anterior surface (20×20 cm) and back surface (20×20 cm) of the light box were made from transparent acryl. The illumination was set to provide in an illuminance of 150 Lux on the floor of the light box. Thereafter, each of male C57BL mice (20-35 g) was placed in the dark box, and the test was started. In this test, a test substance was subcutaneously administered to the test animal 30 minutes before the initiation of the test.

The behavior of the mice was observed for 5 minutes after the initiation of the test. A state where the 4 legs of the mouse were contacted with on the floor of the light box was defined as stay at a light place, and the time when the mouse stayed at a light place was measured. The obtained time was used as an index of antianxiety action. The results are shown in Table 5.

(2) Results

The compound of the present invention, a salt thereof, or a hydrate thereof exhibited superior pharmacological effect.

TABLE 7

| Test substance Compound No. 20 (mg/kg, sc) | Time of stay at light place (second) | N |
|---|---|---|
| solvent | 39 ± 5.5 | 7 |
| 0.03 | 46 ± 9.4 | 7 |
| 0.1 | 67 ± 19 | 7 |

From the above results, it was found that the compound represented by formula (I) of the present invention that is a novel compound exhibits superior action and effects as a pharmaceutical and is useful as a novel agent for treating or preventing lower urinary tract symptoms, learning or memory disorder or anxiety disorder. That is to say, the agent for treating and preventing lower urinary tract symptoms, learning or memory disorder or anxiety disorder of the present invention is a pharmaceutical, which contains, as an active ingredient, a compound having affinity for a 5-HT1A receptor selectively and also having antagonistic effect to the above receptors in the central nerve system, a salt thereof, or a hydrate thereof. It exerts particularly remarkable effects of treating or preventing symptoms regarding urinary storage, such as frequent urination, urinary urgency, or urinary incontinence.

The term "salt" is used to mean a pharmacologically acceptable salt. Such a salt is not particularly limited, as long as it forms a pharmacologically acceptable salt of the compound represented by general formula (I) contained in a therapeutic or preventive agent for lower urinary tract symptoms. Preferred examples of such a salt may include halogenated hydroacid salts (e.g., hydrofluoride, hydrochloride, hydrobromate, and hydroiodide), inorganic acid salts (e.g., sulfate, nitrate, perchlorate, phosphate, carbonate, and bicarbonate), organic carboxylates (e.g., acetate, oxalate, maleate, tartrate, fumarate, and citrate), organic sulfonates (e.g., methanesulfonate, trifluoromethanesulfonate, ethanesulfonate, benzenesulfonate, toluenesulfonate, and camphorsulfonate), amino acid salts (e.g., aspartate and glutamate), quaternary amine salts, alkali metal salts (e.g., sodium salt and potassium salt), and alkali-earth metal salts (e.g., magnesium salt and calcium salt).

The therapeutic or preventive agent for lower urinary tract symptoms of the present invention can be formulated by common methods. Preferred dosage forms include a tablet, a powder, a parvule, a granule, a coated tablet, a capsule, a syrup, a troche, an inhalant, a suppository, an injection, an ointment, an eye drop, an eye ointment, a nasal drop, an ear drop, a poultice, and a lotion. For formulation, commonly used additives may be used. Examples of such an additive may include an excipient, a binder, a lubricant, a coloring agent, flavor, as well as, a stabilizer, an emulsifier, an adsorption enhancer, a surfactant, a pH regulator, an antiseptic, and antioxidant, as necessary. The above described agent can be formulated by mixing ingredients that are commonly used as raw materials for pharmaceutical formulations according to common methods. Examples of such ingredients may include: animal or vegetable oils such as soybean oil, tallow, or synthetic glyceride; hydrocarbons such as liquid paraffin, squalane, or solid paraffin; ester oils such as octyldodecyl myristate or isopropyl myristate; higher alcohols such as cetostearyl alcohol or behenyl alcohol; silicone resins; silicone oils, surfactants such as polyoxyethylene fatty acid ester, sorbitan fatty acid ester, glycerin fatty acid ester, polyoxyethylene sorbitan fatty acid ester, polyoxyethylene hydrogenated castor oil, or a polyoxyethylene-polyoxypropylene block copolymer; water soluble polymers such as hydroxyethyl cellulose, polyacrylic acid, a carboxyvinyl polymer, polyethylene glycol, polyvinylpyrrolidone, or methyl cellulose; lower alcohols such as ethanol or isopropanol; polyvalent alcohols such as glycerin, propylene glycol, dipropylene glycol, or sorbitol; sugars such as glucose or sucrose; inorganic powders such as silicic acid anhydride, magnesium aluminum silicate, or aluminum silicate; and purified water. Examples of an excipient may include lactose, corn starch, saccharose, glucose, mannitol, sorbit, crystalline cellulose, and silicon dioxide. Examples of a binder may include polyvinyl alcohol, polyvinyl ether, methylcellulose, ethylcellulose, gum Arabic, Tragacanth, gelatin, shellac, hydroxypropylmethylcellulose, hydroxypropylcellulose, polyvinylpyrrolidone, a polypropylene glycol-polyoxyethylene block polymer, and meglumine. Examples of a disintegrant may include starch, agar, gelatin powder, crystalline cellulose, calcium carbonate, sodium bicarbonate, calcium citrate, dextrin, pectin, and carboxymethylcellulose calcium. Examples of a lubricant may include magnesium stearate, talc, polyethylene glycol, silica, and hydrogenated vegetable oil. As a coloring agent, products that are allowed for addition to pharmaceuticals are used. Examples of flavor used herein may include cocoa powder, menthol, aromatic powder, peppermint oil, borneol, and cinnamon powder.

In the case of an oral formulation, for example, a compound as an active ingredient, a salt thereof, or a hydrate thereof is mixed with an excipient. In addition, a binder, a disintegrant, a lubricant, a coloring agent, flavor, or the like is added thereto, as necessary. Thereafter, the thus obtained mixture is formulated into a powder, a fine granule, a granule, a tablet, a coated tablet, a capsule, or the like, according to common methods. In the case of a tablet or granule, these formulations are naturally appropriately coated with sugar or other materials, as necessary. In the case of a syrup or a formulation used for injection, a pH regulator, a resolvent, an isotonizing agent are added, and as necessary, a solubilizer, a stabilizer, and the like are also added. Thereafter, the obtained mixture is formulated according to common methods. In the case of an external preparation, the production method thereof is not limited, and the external preparation can be produced by common methods. Various materials that are commonly used for pharmaceuticals, quasi drugs, cosmetics, or the like, can be used herein as base materials. Examples of such a material may include animal and vegetable oils, mineral oils, ester oils, waxes, higher alcohols, fatty acids, silicone oils, surfactants, phospholipids, alcohols, polyvalent alcohols, water soluble polymers, clay minerals, and purified water. In addition, a pH regulator, an antioxidant, a chelating agent, antiseptic and antifungal agents, a coloring agent, a perfume, or the like may also be added, as necessary. Moreover, components having differentiation-inducing action, such as a blood flow-promoting agent, an antibacterial agent, an antiphlogistic, a cell activator, vitamins, amino acid, a moisturizer, or keratolytic drug may also be added, as necessary. The dosage of the therapeutic or preventive agent of the present invention is different depending on the degree of symptoms, age, sex, body weight, dosage form, the type of salts, specific type of disease, or the like. In general, the pharmaceutical is orally administered once or divided over several administrations per day, at a dosage approximately between 30 µg and 10 g, preferably between 100 µg and 5 g, and more preferably between 100 µg and 100 mg to adults. When the pharmaceutical is administered by injection, it is administered once or divided over several administrations per day, at a dosage approximately between 30 µg and 1 g, preferably between 100 µg and 500 mg, and more preferably between 100 µg and 30 mg to adults.

BEST MODE FOR CARRYING OUT THE INVENTION

The present invention will be described more in detail in the reference examples and examples indicated below. The examples are provided for illustrative purposes only, and are not intended to limit the scope of the invention. The therapeutic or preventive agent for lower urinary tract symptoms of the present invention is a pharmaceutical, which contains, as an active ingredient, a compound having affinity for a 5-HT1A receptor selectively and also having antagonistic effect to the above receptor in the central nerve system, a salt thereof, or a hydrate thereof. Persons skilled in the art can realize the present invention to the maximum, not only by using the reference examples and examples indicated below, but also by adding various modifications to the scope of claims in the specification of the present application. Such modifications are included in the scope of claims in the specification of the present application.

EXAMPLES

Production Example 1

Synthesis of 1-(piperidin-4-yl)-1H-indole-6-carboxamide

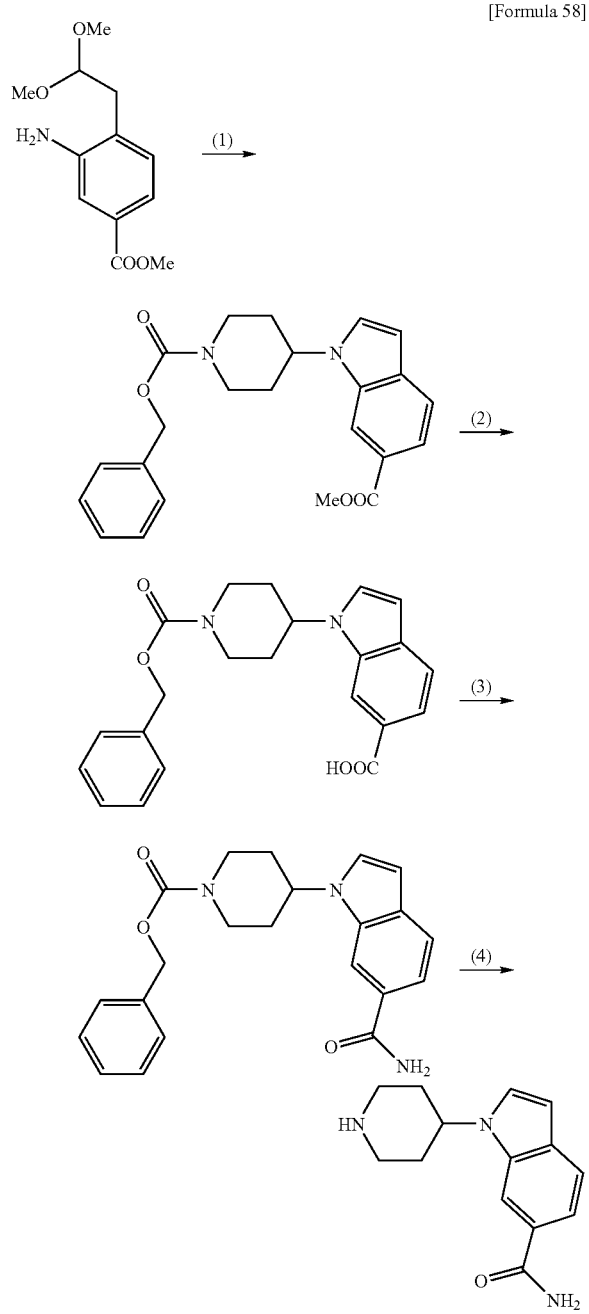

(1) Synthesis of methyl 1-(1-benzyloxycarbonylpiperidin-4-yl)-1H-indole-6-carboxylate 44.3 g of methyl 3-amino-4-(2,2-dimethoxyethyl)benzoate synthesized according to the publication (Tetrahedron Letters, Vol. 37, No. 34, pp. 6045-6048) and 64.9 g of benzyl 4-oxo-1-piperidinecarboxylate were dissolved in 485 ml of acetic acid, followed by stirring at room temperature. Approximately 20 minutes later, 58.9 g of sodium triacetoxyborohydride was added to the reaction solution. Then, the reaction solution was further stirred for 2 hours. Thereafter, 485 ml of water was added to the reaction solution, and the obtained mixture was heated to a temperature between 100° C. and 115° C. Approximately 3 hours later, the reaction solution was cooled, and then concentrated under a reduced pressure. Thereafter, water and ethyl acetate were added thereto, so as to separate an organic layer. The obtained organic layer was washed with a saturated sodium bicarbonate aqueous solution and a saturated sodium chloride solution, and dried over anhydrous magnesium sulfate. After removing the drying agent by filtration, the organic layer was concentrated under a reduced pressure, and the residue was then purified by NH silica gel column chromatography (hexane/ethyl acetate). The obtained solid was suspended in a mixed solvent consisting of hexane and t-butylmethyl ether, followed by filtration, so as to obtain 64.6 g of the subject compound.

$^1$H-NMR (CDCl$_3$) δ 1.80-2.05 (m, 2H), 2.05-2.23 (m, 2H), 2.92-3.15 (m, 2H), 3.96 (s, 3H), 4.30-4.60 (m, 3H), 5.18 (s, 2H), 6.58 (dd, J=0.4, 2.8 Hz, 1H), 7.30-7.45 (m, 6H), 7.64 (dd, J=0.4, 8.4 Hz, 1H), 7.80 (dd, J=1.6, 8.4 Hz, 1H), 8.14 (s, 1H).

(2) Synthesis of 1-(1-benzyloxycarbonylpiperidin-4-yl)-1H-indole-6-carboxylic acid 90.0 g of methyl 1-(1-benzyloxycarbonylpiperidin-4-yl)-1H-indole-6-carboxylate was dissolved in a mixed solution consisting of 760 ml of methanol and 200 ml of tetrahydrofuran. Thereafter, 92 ml of a 5 N sodium hydroxide aqueous solution was added to the reaction solution, and the mixture was then heated to a temperature between 60° C. and 70° C. After completion of the reaction, the reaction solution was cooled, and 65.0 g of ammonium chloride was added thereto, followed by concentration under a reduced pressure. A 5% KHSO$_4$ aqueous solution was added to the residue, so as to adjust pH to be 5 to 6, followed by extraction with ethyl acetate. The organic layer was washed with water and a saturated sodium chloride solution, and then dried over anhydrous magnesium sulfate. After removing the drying agent by filtration, the organic layer was concentrated under a reduced pressure. Thereafter, the residue was solidified, and then collected from a mixed solvent consisting of hexane and t-butylmethyl ether by filtration, so as to obtain 75.6 g of the subject compound.

$^1$H-NMR (CDCl$_3$) δ 1.80-2.04 (m, 2H), 2.06-2.21 (m, 2H), 2.94-3.16 (m, 2H), 4.30-4.58 (m, 3H), 5.19 (s, 2H), 6.60 (dd, J=0.8, 3.6 Hz, 1H), 7.30-7.44 (m, 6H), 7.68 (dd, J=0.8, 8.4 Hz, 1H), 7.88 (dd, J=1.6, 8.4 Hz, 1H), 8.22 (s, 1H).

(3) Synthesis of benzyl 4-(6-carbamoyl-1H-indol-1-yl)piperidin-1-carboxylate 75.0 g of 1-(1-benzyloxycarbonylpiperidin-4-yl)-1H-indole-6-carboxylic acid was dissolved in 620 ml of tetrahydrofuran. Thereafter, 38.6 g of 1,1'-carbonylbis-1H-imidazole was added thereto. The reaction solution was stirred at room temperature for 1.5 hours, and 134 ml of a 28% ammonium water was then added thereto. After completion of the reaction, the reaction solution was concentrated under a reduced pressure, and then extracted with ethyl acetate. The obtained organic layer was washed with a saturated sodium chloride solution and a saturated ammonium chloride aqueous solution. Tetrahydrofuran was added to the separated organic layer, and a partially solidified subject compound was dissolved therein, followed by drying over anhydrous magnesium sulfate. After removing the drying agent by filtration, the organic layer was concentrated under a reduced pressure. The solidified subject compound was collected by filtration. The thus collected subject compound was suspended in tetrahydrofuran, and the mixture was heated, followed by filtration. The thus collected subject compound was then suspended in a mixed solvent consisting of tetrahydrofuran and methanol, and the obtained mixture was heated, followed by filtration. The generated filtrates were gathered and concentrated, and thus, the subject compound was obtained in the same above manner. The total amount of the subject compounds was 64.8 g.

$^1$H-NMR (CDCl$_3$) δ 1.93 (brs, 2H), 2.04-2.18 (m, 2H), 3.02 (brs, 2H), 4.26-4.60 (m, 3H), 5.18 (s, 2H), 6.58 (dd, J=0.8, 3.2 Hz, 1H), 7.28-7.44 (m, 7H), 7.65 (dd, J=0.4, 8.4 Hz, 1H), 8.10 (s, 1H).

(4) Synthesis of 1-(piperidin-4-yl)-1H-indole-6-carboxamide 43 g of benzyl 4-(6-carbamoyl-1H-indol-1-yl)piperidin-1-carboxylate was suspended in a mixed solution consisting of 400 ml of methanol and 600 ml of tetrahydrofuran. Thereafter, 3.3 g of 10% palladium carbon was added thereto. This suspension was substituted by hydrogen, and it was then stirred at room temperature. After completion of the reaction, 10% palladium carbon was filtered off from the reaction solution, and the reaction solution was then concentrated under a reduced pressure. Tetrahydrofuran was added to the residue, and the obtained mixture was concentrated again under a reduced pressure. Tetrahydrofuran was added to the generated residue, followed by stirring, so as to solidify the subject compound. Thereafter, tetrahydrofuran and ether were added thereto, followed by cooling on ice. The solidified subject compound was collected by filtration. The generated filtrate was concentrated, and thus, the subject compound was obtained in the same above manner. The total amount of the subject compounds was 25.2 g.

$^1$H-NMR (CDCl$_3$) δ 1.88-2.02 (m, 2H), 2.06-2.16 (m, 2H), 2.80-2.92 (m, 2H), 3.22-3.32 (m, 2H), 4.46 (tt, J=4.0, 12.0 Hz, 1H), 6.58 (dd, J=0.8, 3.2 Hz, 1H), 7.36-7.44 (m, 2H), 7.65 (d, J=8.4 Hz, 1H), 8.11 (s, 1H).

Production Example 2

Synthesis of N-methyl-1-(piperidin-4-yl)-1H-indole-6-carboxamide

[Formula 59]

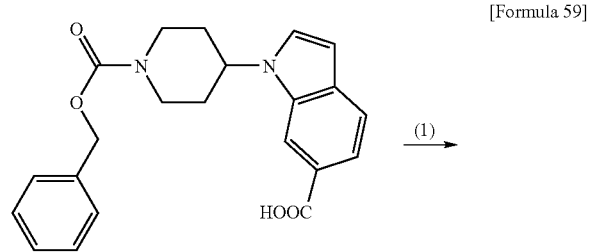

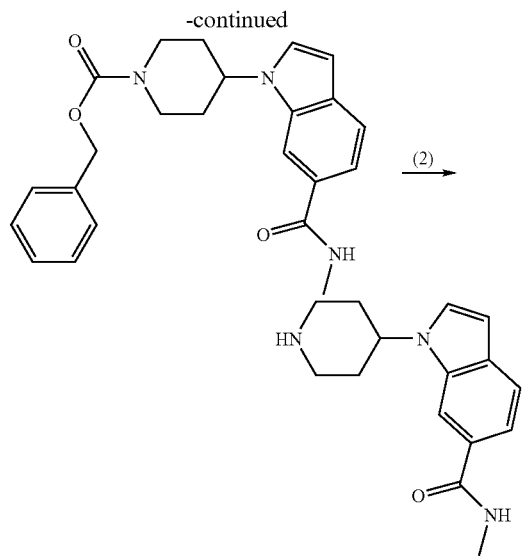

(1) Synthesis of N-methyl-1-(1-benzyloxycarbonylpiperidin-4-yl)-1H-indole-6-carboxamide 2.00 g of 1-(1-benzyloxycarbonylpiperidin-4-yl)-1H-indole-6-carboxylic acid was dissolved in 20 ml of tetrahydrofuran, and 1.03 g of 1,1'-carbonylbis-1H-imidazole was then added thereto. The obtained mixture was stirred at room temperature for 1.5 hours, and 4.11 ml of a 40% methylamine aqueous solution was added thereto. After completion of the reaction, the reaction solution was extracted with ethyl acetate. The organic layer was washed with a saturated sodium bicarbonate aqueous solution, a saturated ammonium chloride aqueous solution, and a saturated sodium chloride solution. Thereafter, the organic layer was dried over anhydrous magnesium sulfate. After removing the drying agent by filtration, the organic layer was concentrated under a reduced pressure, and the residue was then purified by NH silica gel column chromatography (ethyl acetate) and silica gel column chromatography (hexane/ethyl acetate), so as to obtain 1.77 g of the subject compound.

$^1$H-NMR (CDCl$_3$) δ 1.80-2.00 (m, 2H), 2.03-2.17 (m, 2H), 2.90-3.10 (m, 2H), 3.06 (d, J=4.8 Hz, 3H), 4.30-4.58 (m, 3H), 5.16 (s, 2H), 6.21 (brs, 1H), 6.55 (dd, J=0.8, 3.2 Hz, 1H), 7.27 (d, J=3.6 Hz, 1H), 7.28-7.40 (m, 6H), 7.61 (dd, J=0.8, 8.0 Hz, 1H), 8.03 (s, 1H).

(2) Synthesis of N-methyl-1-(piperidin-4-yl)-1H-indole-6-carboxamide 1.77 g of N-methyl-1-(1-benzyloxycarbonylpiperidin-4-yl)-1H-indole-6-carboxamide was dissolved in 30 ml of methanol. Then, 200 mg of 10% palladium carbon was added to the obtained solution. The reaction atmosphere was replaced by hydrogen, and it was then stirred at room temperature. After completion of the reaction, 10% palladium carbon was filtered off from the reaction solution, and the reaction solution was then concentrated under a reduced pressure. The residue was purified by NH silica gel column chromatography (ethyl acetate/methanol), followed by solidification from a mixed solution consisting of ethyl acetate, t-butylmethyl ether, and methanol, so as to obtain 973 mg of the subject compound.

$^1$H-NMR (CDCl$_3$) δ 1.86-1.99 (m, 2H), 2.06-2.14 (m, 2H), 2.84 (dt, J=2.4, 12.4 Hz, 2H), 3.06 (d, J=4.8 Hz, 3H), 3.22-3.30 (m, 2H), 4.44 (tt, J=4.0, 12.0 Hz, 1H), 6.24 (brs, 1H), 6.54 (dd, J=0.8, 3.2 Hz, 1H), 7.32-7.36 (m, 2H), 7.61 (dd, J=0.4, 8.4 Hz, 1H), 8.04 (s, 1H).

Production Example 3

Synthesis of 3-amino-4-(2,2-dimethoxyethyl)benzamide

[Formula 60]

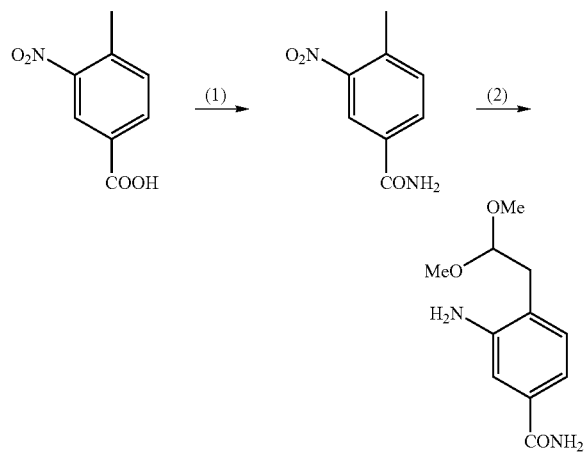

(1) Synthesis of 3-nitro-4-methylbenzamide 20.0 g of 3-nitro-4-methylbenzoic acid was dissolved in 400 ml of tetrahydrofuran. Thereafter, 21.5 g of 1,1'-carbonyldiimidazole and 0.1 ml of dimethylformamide were added thereto. The obtained mixture was stirred for 45 minutes. Thereafter, 20 ml of 28% ammonia water was added thereto, followed by stirring at room temperature for 24 hours. After completion of the reaction, the reaction solution was concentrated under a reduced pressure, and the residue was separated into 600 ml of ethyl acetate and 200 ml of water. The organic layer was separated, and then washed with 200 ml of 2 N hydrochloric acid, 100 ml of water, 100 ml of a saturated sodium bicarbonate aqueous solution, and 100 ml of a saturated sodium chloride solution. It was then dried over anhydrous magnesium sulfate. After removing the drying agent by filtration, the filtrate was concentrated under a reduced pressure, so as to obtain 19.5 of the subject compound.

$^1$H-NMR (CDCl$_3$) δ 2.67 (s, 3H), 7.47 (d, J=7.6 Hz 1H), 7.98 (dd, J=2.0 Hz, 1H), 8.40 (d, J=2.0 Hz, 1H).

(2) Synthesis of 3-amino-4-(2,2-dimethoxyethyl)benzamide 19.5 g of 3-nitro-4-methylbenzamide and 30 g of dimethylformamide dimethyl acetal were dissolved in 200 ml of dimethylformamide. The obtained mixture was stirred at 140° C. for 20 hours. The mixture was then concentrated under a reduced pressure. Thereafter, 360 ml of methanol and 25 g of chlorotrimethylsilane were added to the residue. The obtained solution was heated to reflux for 16 hours. The reaction solution was cooled and then concentrated under a reduced pressure. Water and ethyl acetate were added thereto, so as to divide an organic layer. The organic layer was separated, and then washed with a saturated sodium bicarbonate aqueous solution and a saturated sodium chloride solution. It was then dried over anhydrous magnesium sulfate. The mixture was filtered through 100 g of a silica gel layer, and then washed with ethyl acetate. Thereafter, the filtrate was concentrated under a reduced pressure. 0.9 g of 10% palladium carbon was added to 150 ml of a methanol solution containing the obtained crude product, and the mixture was intensively stirred in a hydrogen atmosphere. After completion of the reaction, the catalyst was removed by filtration, and the filtrate was concentrated under a reduced pressure. The obtained residue was purified by NH silica gel column chromatography (hexane/ethyl acetate), so as to obtain 11.5 g of the subject compound.

$^1$H-NMR (CDCl$_3$) δ 2.90 (d, J=5.2 Hz, 2H), 3.38 (s, 6H), 4.16-4.24 (br, 2H), 4.99 (t, J=5.2 Hz, 3H), 5.52-5.67 (br, 1H), 5.93-6.10 (br, 1H), 7.07 (dd, J=1.6, 7.6 Hz, 1H), 7.10 (d, J=7.6 Hz, 1H), 7.18 (d, J=1.6 Hz, 1H).

Example 1

Synthesis of 1-{1-[2-(6-methoxy-3-methylbenz[d]isoxazol-7-yl)ethyl]piperidin-4-yl}-1H-indole-6-carboxamide

[Formula 61]

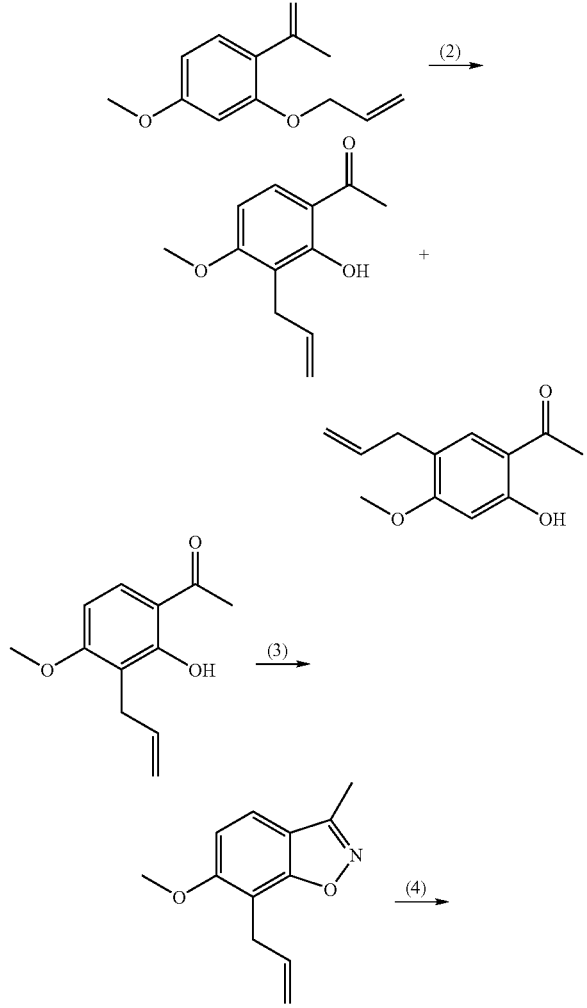

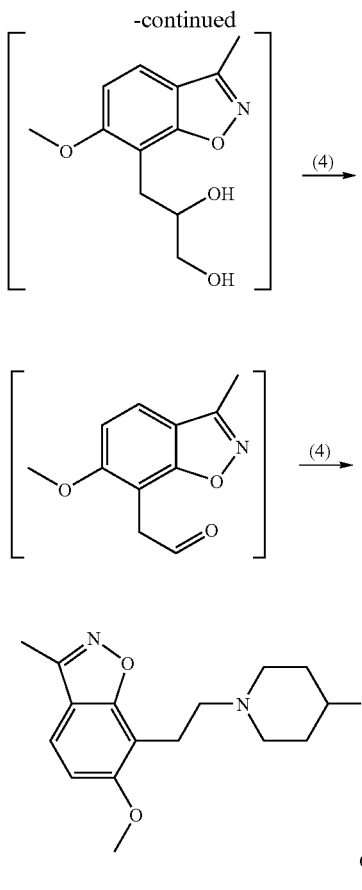

(1) 2'-Allyloxy-4'-methoxyacetophenone 5.00 g of 2'-hydroxy-4'-methoxyacetophenone was dissolved in 40 ml of N,N-dimethylformamide at room temperature. Thereafter, 4.16 g of potassium carbonate and 2.80 ml of allyl bromide were successively added to the reaction solution. After the disappearance of materials had been confirmed, water and ethyl acetate were added to the reaction solution, so as to separate an organic layer. The obtained organic layer was washed with water and a saturated sodium chloride aqueous solution, and then dried over anhydrous magnesium sulfate. After removing the drying agent by filtration, the organic layer was concentrated under a reduced pressure, and the residue was then purified by silica gel column chromatography (hexane/ethyl acetate), so as to obtain 5.60 g of the subject compound.

$^1$H-NMR (CDCl$_3$) δ (ppm): 2.61 (s, 3H), 3.84 (s, 3H), 4.60-4.65 (m, 2H), 5.30-5.37 (m, 1H), 5.41-5.49 (m, 1H), 6.01-6.18 (m, 1H), 6.44 (d, J=2.4 Hz, 1H), 6.53 (dd, J=2.4, 8.8 Hz, 1H), 7.84 (d, J=8.8 Hz, 1H).

(2) 3'-Allyl-2'-hydroxy-4'-methoxyacetophenone and 5'-allyl-2'-hydroxy-4'-methoxyacetophenone 5.60 g of 2'-allyloxy-4'-methoxyacetophenone was dissolved in 10 ml of N,N-diethylaniline. The reaction solution was heated to reflux under nitrogen atmosphere. Approximately 6 hours later, the reaction solution was stood to cool, and then, water and ethyl acetate were added thereto, so as to separate an organic layer. The obtained organic layer was washed with 5 N hydrochloric acid and a saturated sodium chloride aqueous solution, and then dried over anhydrous magnesium sulfate. After removing the drying agent by filtration, the organic layer was concentrated under a reduced pressure, and the residue was then purified by silica gel column chromatography (hexane/ethyl acetate), so as to obtain 3.37 g of 3'-allyl-2'-hydroxy-4'-methoxyacetophenone and 1.07 g of 5'-allyl-2'-hydroxy-4'-methoxyacetophenone.

3'-allyl-2'-hydroxy-4'-methoxyacetophenone $^1$H-NMR (CDCl$_3$) δ (ppm): 2.57 (s, 3H), 3.35-3.50 (m, 2H), 3.89 (s, 3H), 4.90-5.05 (m, 2H), 5.85-6.05 (m, 1H), 6.48 (d, J=8.8 Hz, 1H), 7.64 (d, J=8.8 Hz, 1H), 12.8 (s, 1H).

5'-Allyl-2'-hydroxy-4'-methoxyacetophenone $^1$H-NMR (CDCl$_3$) δ (ppm): 2.55 (s, 3H), 3.24-3.32 (m, 2H), 3.86 (s, 3H), 5.01-5.10 (m, 2H), 5.90-6.04 (m, 1H), 6.41 (s, 1H), 7.42 (s, 1H), 12.7(s, 1H).

(3) 7-Allyl-6-methoxy-3-methylbenzo[d]isoxazole 3.37 g of 3'-allyl-2'-hydroxy-4'-methoxyacetophenone was dissolved in 55 ml of ethanol. Thereafter, 2.61 g of hydroxylamine hydrochloride, 3.21 g of sodium acetate, and 13 ml of water were uccessively added to the reaction solution. The reaction solution was heated to reflux for approximately 3.5 hours. Thereafter, 1.30 g of hydroxylamine hydrochloride and 1.6 g of sodium acetate were dissolved in 6 ml of water, and the obtained solution was added to the reaction solution. The thus obtained reaction solution was further heated to reflux. After the disappearance of materials had been confirmed, water and ethyl acetate were added thereto, so as to separate an organic layer. The obtained organic layer was washed with water and a saturated sodium chloride aqueous solution, and then dried over anhydrous magnesium sulfate. After removing the drying agent by filtration, the organic layer was concentrated under a reduced pressure, so as to obtain 3.48 g of a crude oxime derivative. The obtained oxime derivative and 6.95 g of triphenylphosphine were dissolved in 150 ml of tetrahydrofuran (THF), and the obtained solution was cooled on ice. Thereafter, 5.22 ml of diisopropyl azodicarboxylate dissolved in 75 ml of THF was added dropwise thereto. After completion of the dropping, the reaction solution was warmed to a room temperature, it was then stirred for approximately 15 hours. The reaction solution was concentrated under a reduced pressure, and the residue was then purified by silica gel column chromatography (hexane/ethyl acetate), so as to obtain 1.30 g of the subject compound.

$^1$H-NMR (CDCl$_3$) δ (ppm): 2.53 (s, 3H), 3.62-3.68 (m, 2H), 3.93 (s, 3H), 4.97-5.13 (m, 2H), 5.92-6.10 (m, 1H), 6.95 (d, J=8.8 Hz, 1H), 7.42 (d, J=8.8 Hz, 1H).

(4) 1-{1-[2-(6-methoxy-3-methylbenz[d]isoxazol-7-yl)ethyl]piperidin-4-yl}-1H-indole-6-carboxamide 1.00 g of AD-mix-α (manufactured by Aldrich; hereinafter, the same can be said for the same terms found in the present specification) was dissolved in 5 ml of t-butanol and 5 ml of water. Thereafter, 180 mg of 7-allyl-6-methoxy-3-methylbenzo[d]isoxazole dissolved in 2 ml of t-butanol was added thereto. The reaction solution was stirred at room temperature. After the disappearance of materials had been confirmed, 1.20 g of sodium sulfite was added to the reaction solution, and the obtained mixture was stirred for approximately 3 hours. Water and ethyl acetate were added to the reaction solution, so as to separate an organic layer. The obtained organic layer was washed with a saturated sodium chloride aqueous solution and then dried over anhydrous magnesium sulfate. After removing the drying agent by filtration, the organic layer was concentrated under a reduced pressure, so as to obtain 176 mg of a crude diol derivative. 176 mg of the obtained diol derivative was dissolved in 9 ml of tetrahydrofuran and 3 ml of water, and then, 261 mg of sodium metaperiodate was added thereto. The obtained mixture was vigorously stirred. After the disappearance of materials had been confirmed, water and ethyl acetate were added to the reaction solution, so as to separate an organic layer. The obtained organic layer was washed with a saturated sodium chloride aqueous solution and then dried over anhydrous magnesium sulfate. After removing the drying agent by filtration, the organic layer was concentrated under a reduced pressure, so as to obtain 121 mg of a crude aldehyde derivative.

121 mg of the above aldehyde derivative dissolved in 2 ml of dichloromethane and 57 μl of acetic acid were successively added to 4 ml of dichloromethane containing 122 mg of 1-(piperidin-4-yl)-1H-indole-6-carboxamide. The reaction solution was then stirred for 5 minutes. Thereafter, 159 mg of sodium triacetoxyborohydride was added to the reaction solution, and the mixture was then stirred at room temperature for 8 hours. Thereafter, 5 N HaOH, a saturated sodium chloride aqueous solution, and chloroform were added to the reaction solution, so as to separate an organic layer. The obtained organic layer was washed with a saturated sodium chloride aqueous solution and then dried over anhydrous magnesium sulfate. After removing the drying agent by filtration, the organic layer was concentrated under a reduced pressure, and the residue was purified by NH silica gel column chromatography (ethyl acetate), so as to obtain 100 mg of the subject compound.

$^1$H-NMR (CDCl$_3$) δ (ppm): 2.06-2.16 (m, 4H), 2.28-2.39 (m, 2H), 2.54 (s, 3H), 2.70-2.78 (m, 2H), 3.11-3.19 (m, 2H), 3.23-3.31 (m, 2H), 3.95 (s, 3H), 4.34-4.46 (m, 1H), 6.56 (d, J=3.2 Hz, 1H), 6.95 (d, J=8.4 Hz, 1H), 7.38-7.45 (m, 3H), 7.64 (d, J=8.4 Hz, 1H), 8.09 (s, 1H).

Example 2

Synthesis of 1-{1-[2-(6-methoxy-3-methylbenzo[d]isoxazol-5-yl)ethyl]piperidin-4-yl}-1H-indole-6-carboxamide

[Formula 62]

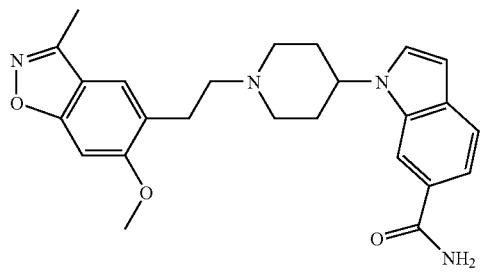

The subject compound was synthesized using 5'-allyl-2'-hydroxy-4'-methoxyacetophenone as a raw material according to the methods described in Example 1, (3)-(4).

$^1$H-NMR (CDCl$_3$) δ (ppm): 2.08-2.18 (m, 4H), 2.26-2.36 (m, 2H), 2.54 (s, 3H), 2.62-2.70 (m, 2H), 2.90-2.99 (m, 2H), 3.18-3.28 (m, 2H), 3.93 (s, 3H), 4.36-4.48 (m, 1H), 6.58 (d, J=3.2 Hz, 1H), 6.97 (s, 1H), 7.35 (s, 1H), 7.38-7.44 (m, 2H), 7.65 (d, J=8.4 Hz, 1H), 8.13 (s, 1H).

Example 3

Synthesis of 1-{1-[2-(6-methoxy-2-methylbenzoxazol-7-yl)ethyl]piperidin-4-yl}-1H-indole-6-carboxamide

[Formula 63]

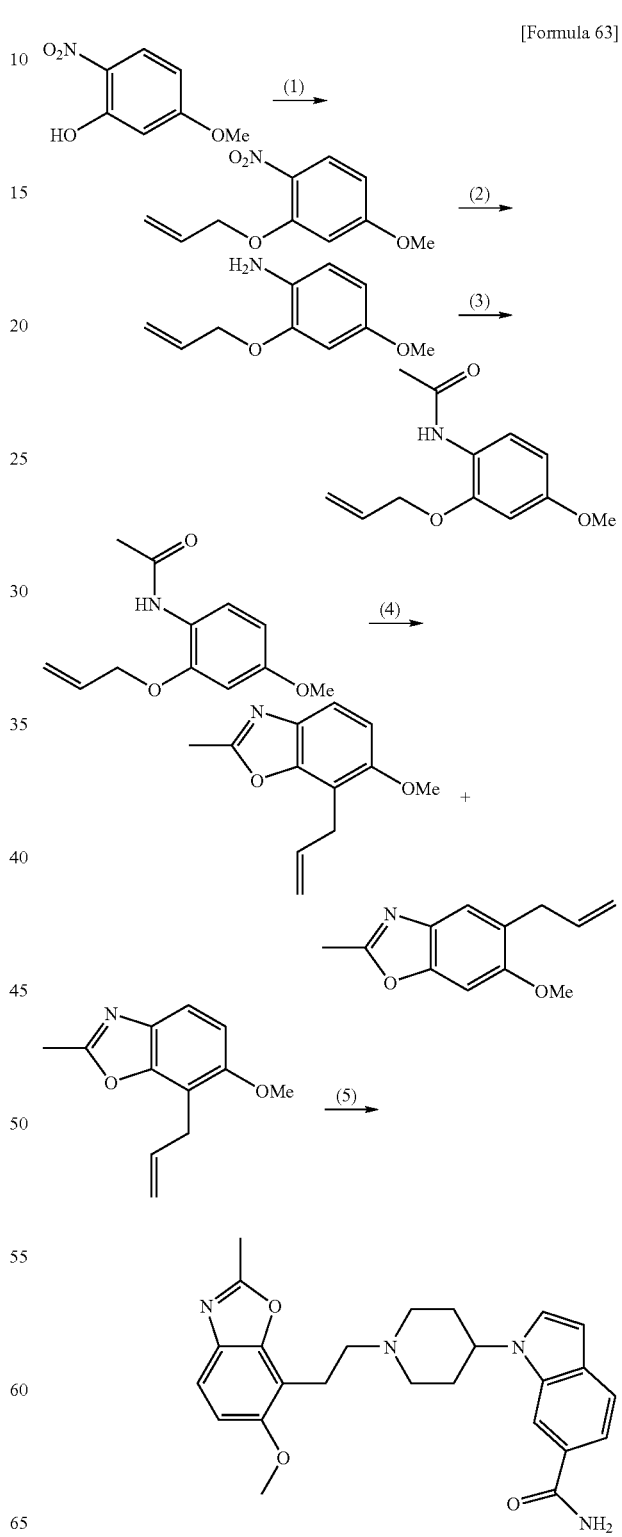

(1) 2-Allyloxy-4-methoxynitrobenzene 1.88 g of 5-methoxy-2-nitrophenol was dissolved in 20 ml of N,N-dimethylformamide. Thereafter, 1.53 g of potassium carbonate and 1.03 ml of allyl bromide were successively added to the reaction solution. After the disappearance of materials had been confirmed, water and ethyl acetate were added to the reaction solution, so as to separate an organic layer. The obtained organic layer was washed with water and a saturated sodium chloride solution, and then dried over anhydrous magnesium sulfate. After removing the drying agent by filtration, the organic layer was concentrated under a reduced pressure, and the residue was then purified by silica gel column chromatography (hexane/ethyl acetate), so as to obtain 2.09 g of the subject compound.

$^1$H-NMR (CDCl$_3$) δ (ppm): 3.87 (s, 3H), 4.62-4.70 (m, 2H), 5.30-5.38 (m, 1H), 5.50-5.58 (m, 1H), 6.00-6.12 (m, 1H), 6.48-6.56 (m, 2H), 8.00 (d, J=9.6 Hz, 1H).

(2) 2-Allyloxy-4-methoxyaniline 2.09 g of 2-allyloxy-4-methoxynitrobenzene was dissolved in 20 ml of ethanol, 5 ml of THF, and 4 ml of water. Thereafter, 4.27 g of ammonium chloride and 2.23 g of iron were added to the reaction solution, and the obtained mixture was stirred while heating at 80° C. for 4 hours. Thereafter, 2 g of ammonium chloride, 1 g of iron, and 0.25 ml of 5 N HCl were added to the reaction solution, and the obtained mixture was further stirred while heating for approximately 2 hours. The reaction solution was stood to cool and then filtered through celite. A saturated sodium bicarbonate aqueous solution and ethyl acetate were added thereto, so as to separate an organic layer. The obtained organic layer was washed with a saturated sodium chloride solution and then dried over anhydrous magnesium sulfate. After removing the drying agent by filtration, the organic layer was concentrated under a reduced pressure, and the residue was then purified by NH silica gel column chromatography (hexane/ethyl acetate), so as to obtain 1.09 g of the subject compound.

$^1$H-NMR (CDCl$_3$) δ (ppm): 3.74 (s, 3H), 4.52-4.58 (m, 2H), 5.25-5.32 (m, 1H), 5.37-5.46 (m, 1H), 6.01-6.12 (m, 1H), 6.36 (dd, J=2.4, 8.4 Hz, 1H), 6.46 (d, J=2.4 Hz, 1H), 6.66 (d, J=8.4 Hz, 1H).

(3) 2'-Allyloxy-4'-methoxyacetanilide 3 mg of 4-(dimethylamino)pyridine and 1 ml of acetic anhydride were successively added to 2 ml of pyridine containing 1.09 g of 2-allyloxy-4-methoxyaniline, and the reaction solution was then stirred at room temperature. After the disappearance of the raw material had been confirmed, 5 N HCl and ethyl acetate were added to the reaction solution, so as to separate an organic layer. The obtained organic layer was washed with a saturated sodium chloride solution and then dried over anhydrous magnesium sulfate. After removing the drying agent by filtration, the organic layer was concentrated under a reduced pressure. The residue was then solidified from t-butyl methyl ether-hexane, so as to obtain 1.04 g of the subject compound.

$^1$H-NMR (CDCl$_3$) δ (ppm): 2.18 (s, 3H), 3.78 (s, 3H), 4.54-4.62 (m, 2H), 5.30-5.45 (m, 2H), 6.00-6.12 (m, 1H), 6.45-6.52 (m, 2H), 7.54 (brd-s, 1H), 8.22 (d, J=9.6 Hz, 1H).

(4) 7-Allyl-6-methoxy-2-methylbenzoxazole 1.04 g of 2'-allyloxy-4'-methoxyacetanilide was dissolved in 20 ml of 1-methyl-2-pyrrolidone. The reaction solution was then stirred while heating at 190° C. under nitrogen atmosphere. Eight hours later, the reaction solution was stood to cool. Thereafter, water and ethyl acetate were added to the reaction solution, so as to separate an organic layer. The obtained organic layer was washed with a saturated sodium chloride solution and then dried over anhydrous magnesium sulfate. After removing the drying agent by filtration, the organic layer was concentrated under a reduced pressure, so as to obtain a product (1.01 g). The obtained product was dissolved in 20 ml of acetic acid without purification, and the obtained solution was stirred while heating at 135° C. After completion of the reaction, the reaction solution was stood to cool. Thereafter, the solvent was concentrated under a reduced pressure. 5 N NaOH and ethyl acetate were added to the residue, so as to separate an organic layer. The obtained organic layer was washed with a saturated sodium chloride solution and then dried over anhydrous magnesium sulfate. After removing the drying agent by filtration, the organic layer was concentrated under a reduced pressure. The residue was then purified by silica gel column chromatography (hexane/ethyl acetate), so as to obtain 371 mg of the subject compound.

$^1$H-NMR (CDCl$_3$) δ (ppm): 2.60 (s, 3H), 3.55-3.65 (m, 2H), 3.88 (s, 3H), 4.95-5.10 (m, 2H), 5.95-6.10 (m, 1H), 6.89 (d, J=8.8 Hz, 1H), 7.43 (d, J=8.8 Hz, 1H).

(5) 1-{1-[2-(6-methoxy-2-methylbenzoxazol-7-yl)ethyl]piperidin-4-yl}-1H-indole-6-carboxamide The subject compound was obtained from 7-allyl-6-methoxy-2-methylbenzoxazole of Example 3, (4), according to the method described in Example 1, (4).

$^1$H-NMR (CDCl$_3$) δ (ppm): 2.06-2.18 (m, 4H), 2.28-2.40 (m, 2H), 2.62 (s, 3H), 2.68-2.77 (m, 2H), 3.06-3.16 (m, 2H), 3.22-3.32 (m, 2H), 3.90 (s, 3H), 4.34-4.47 (m, 1H), 6.58 (dd, J=0.6, 3.2 Hz, 1H), 6.88 (d, J=8.4 Hz, 1H), 7.38-7.46 (m, 3H), 7.67 (d, J=8.4 Hz, 1H), 8.12 (s, 1H).

Example 4

Synthesis of 1-{1-[2-(6-methoxy-2-methylbenzoxazol-5-yl)ethyl]piperidin-4-yl}-1H-indole-6-carboxamide

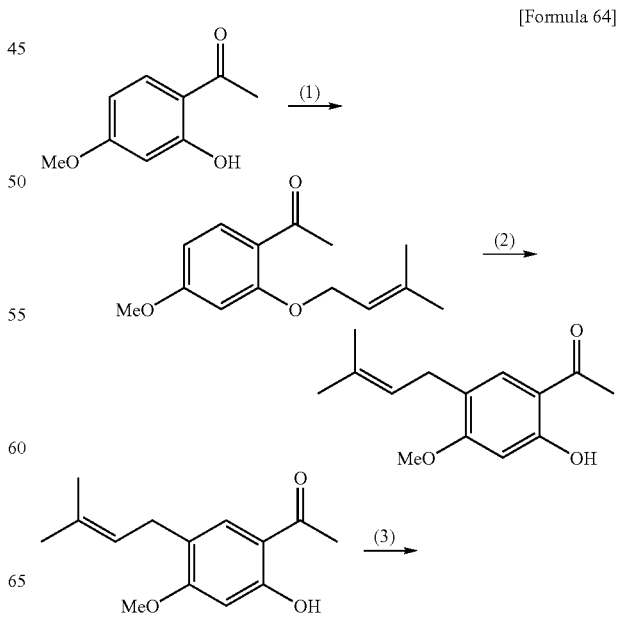

[Formula 64]

-continued

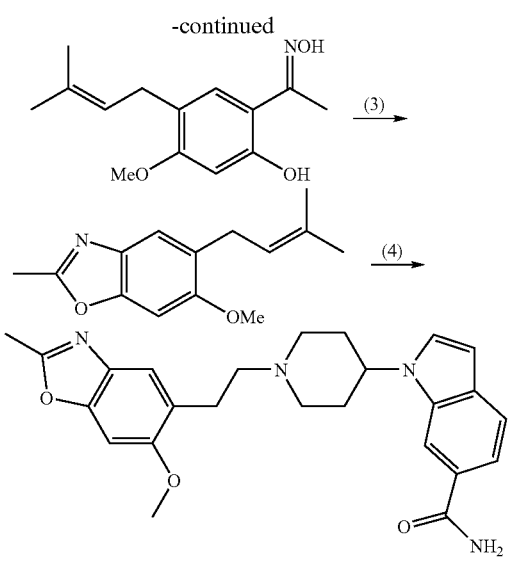

(1) 4'-Methoxy-2'-(3-methyl-2-butenyl)oxyacetophenone 20.7 g of potassium carbonate and 23.2 ml of 1-bromo-3-methyl-2-butene were successively added to 300 ml of acetone containing 25 g of 2'-hydroxy-4'-methoxyacetophenone. The reaction solution was then heated to reflux. Approximately 6 hours later, 4.14 g of potassium carbonate and 4.63 ml of 1-bromo-3-methyl-2-butene were further added thereto, and the obtained mixture was heated to reflux. Approximately 34 hours later, the reaction solution was stood to cool, and then, it was filtered through celite. The filtrate was concentrated under a reduced pressure, and the residue was then purified by silica gel column chromatography (hexane/ethyl acetate), so as to obtain the subject compound. The reaction was further carried out using 2'-hydroxy-4'-methoxyacetophenone (25 g×2 times) under the above described conditions. The total amount of the subject compounds was 98.7 g.

$^1$H-NMR (CDCl$_3$) δ (ppm): 1.76 (d, J=0.8 Hz, 3H), 1.81 (d, J=0.8 Hz, 3H), 2.58 (s, 3H), 3.85 (s, 3H), 4.59 (d, J=6.8 Hz, 2H), 5.47-5.55 (m, 1H), 6.45 (d, J=2.4 Hz, 1H), 6.51 (dd, J=2.4, 8.8 Hz, 1H), 7.84 (d, J=8.8 Hz, 1H).

(2) 2'-Hydroxy-4'-methoxy-5'-(3-methyl-2-butenyl)acetophenone 49.2 g of 4'-methoxy-2'-(3-methyl-2-butenyl)oxyacetophenone was dissolved in 100 ml of N,N-diethylaniline. The reaction solution was heated to reflux under nitrogen atmosphere. 3 hours later, the reaction solution was stood to cool, and then, 5 N hydrochloric acid (300 ml) and t-butylmethyl ether (1,000 ml) were added thereto, so as to separate an organic layer. The obtained organic layer was washed with 5 N hydrochloric acid (300 ml×2) and a saturated sodium chloride solution (500 ml), and then dried over anhydrous magnesium sulfate. After removing the drying agent by filtration, the organic layer was concentrated under a reduced pressure, and the residue was then purified by silica gel column chromatography (hexane/ethyl acetate), so as to obtain the subject compound. The reaction was further carried out using 4'-methoxy-2'-(3-methyl-2-butenyl)oxyacetophenone (49.0 g) under the above described conditions. The total amount of the subject compounds was 74.1 g.

$^1$H-NMR (CDCl$_3$) δ (ppm): 1.71 (d, J=0.8 Hz, 3H), 1.76 (d, J=1.2 Hz, 3H), 2.54 (s, 3H), 3.22 (dd, J=0.4, 7.2 Hz, 2H), 3.86 (s, 3H), 5.21-5.29 (m, 1H), 6.39 (s, 1H), 7.40 (d, J=0.8 Hz, 1H), 12.7 (s, 1H).

(3) 6-Methoxy-2-methyl-5-(3-methyl-2-butenyl)benzoxazole 74.1 g of 2'-hydroxy-4'-methoxy-5'-(3-methyl-2-butenyl) acetophenone was dissolved in 900 ml of ethanol. Thereafter, 56.4 g of hydroxylamine hydrochloride and 69.2 g of sodium acetate dissolved in 315 ml of water were added thereto. The reaction solution was heated to reflux for 4 hours. Thereafter, the reaction solution was stood to cool, and then concentrated under a reduced pressure. A saturated sodium chloride solution (500 ml) and t-butyl methyl ether (1,000 ml) were added to the residue, so as to separate an organic layer. The obtained organic layer was washed with a saturated sodium chloride solution (500 ml×4), and then dried over anhydrous magnesium sulfate. After removing the drying agent by filtration, the organic layer was concentrated under a reduced pressure, so as to obtain 77.4 g of a crude oxime derivative. 77.4 g of the obtained oxime derivative was dissolved in a mixed solvent consisting of 225 ml of acetonitrile and 75 ml of N,N-dimethylacetamide. Thereafter, 31.6 ml of phosphorus oxychloride was added dropwise to the solution for approximately 15 minutes, while cooling on ice. After completion of the addition, the reaction solution was stirred for 5 minutes while cooling on ice, and was then warmed to a room temperature. The reaction solution was then stirred at room temperature for approximately 50 minutes. Thereafter, the reaction solution was added dropwise to a stirred mixed solution consisting of 1,500 ml of t-butyl methyl ether and 1,500 ml of ice water in which 56 g of sodium acetate had been dissolved. The obtained organic layer was washed twice with a mixed solution consisting of 120 ml of a 2 N sodium hydroxide solution and 250 ml of a saturated sodium chloride solution, and then further washed with a saturated sodium chloride solution (500 ml×4 times). Thereafter, the resultant product was dried over anhydrous magnesium sulfate. After removing the drying agent by filtration, the organic layer was concentrated under a reduced pressure, and the residue was then purified by NH silica gel column chromatography (hexane/ethyl acetate). The resultant product was further purified by silica gel column chromatography (hexane/ethyl acetate), so as to obtain 56.2 g of the subject compound.

$^1$H-NMR (CDCl$_3$) δ (ppm): 1.71 (s, 3H), 1.75 (d, J=1.2 Hz, 3H), 2.58 (s, 3H), 3.36 (dd, J=0.8, 7.2 Hz, 2H), 3.87 (s, 3H), 5.28-5.36 (m, 1H), 6.96 (s, 1H), 7.38 (s, 1H).

(4) 1-{1-[2-(6-methoxy-2-methylbenzoxazol-5-yl)ethyl]piperidin-4-yl}-1H-indole-6-carboxamide 37.2 g of the subject compound was obtained from the above described 6-methoxy-2-methyl-5-(3-methyl-2-butenyl)benzoxazole (44.7 g in total for 4 batches) according to the method described in Example 1, (4) (however, when a diol product was obtained, 1 equivalent of methanesulfonamide was added.)

37.2 g of the above described subject compound was recrystallized from 360 ml of methanol, so as to obtain 34.1 g of the subject compound.

$^1$H-NMR (CDCl$_3$) δ (ppm): 2.00-2.24 (m, 4H), 2.24-2.40 (m, 2H), 2.60 (s, 3H), 2.62-2.76 (m, 2H), 2.86-3.02 (m, 2H), 3.14-3.32 (m, 2H), 3.89 (s, 3H), 4.34-4.46 (m, 1H), 6.57 (dd, J=0.8, 2.8 Hz, 1H), 6.99 (s, 1H), 7.36-7.47 (m, 3H), 7.65 (dd, J=0.4, 8.4 Hz, 1H), 8.12 (s, 1H).

Example 5

Synthesis of 1-{1-[2-(2-ethyl-6-methylbenzoxazol-7-yl)ethyl]piperidin-4-yl}-1H-indole-6-carboxamide

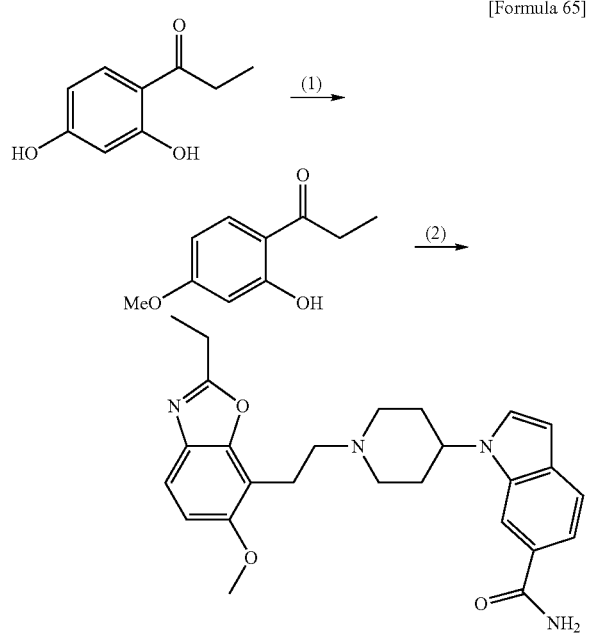

[Formula 65]

(1) 2'-Hydroxy-4'-methoxypropiophenone 6.00 g of 2',4'-dihydroxypropiophenone was dissolved in 70 ml of acetone. Thereafter, 7.09 g of potassium carbonate and 3.03 ml of methyl iodide were successively added to the reaction solution. The reaction solution was then heated to reflux. Approximately 3 hours later, the reaction solution was stood to cool and then filtered. The filtrate was concentrated under a reduced pressure. A saturated sodium chloride solution and ethyl acetate were added to the residue, so as to separate an organic layer. The obtained organic layer was washed with 2 N hydrochloric acid and a saturated sodium chloride solution, and then dried over anhydrous magnesium sulfate. After removing the drying agent by filtration, the organic layer was concentrated under a reduced pressure. The residue was solidified from hexane-ethyl acetate, so as to obtain 5.64 g of the subject compound. $^1$H-NMR (CDCl$_3$) δ (ppm): 1.23 (t, J=7.2 Hz, 3H), 2.95 (q, J=7.2 Hz, 2H), 3.83 (s, 3H), 6.40-6.45 (m, 2H), 7.65 (dd, J=1.6 Hz, 8.0 Hz, 1H), 12.8 (s, 1H).

(2) 1-{1-[2-(2-Ethyl-6-methoxybenzoxazol-7-yl)ethyl]piperidin-4-yl}-1H-indole-6-carboxamide The subject compound was synthesized using, as a raw material, 2'-hydroxy-4'-methoxypropiophenone obtained in Example 5, (1), according to the methods described in Example 4, (1)-(4) (however, allyl bromide was used instead of 1-bromo-3-methyl-2-butene, and two types of isomers obtained by the subsequent Claisen rearrangement (3'-allyl-2'-hydroxy-4'-methoxypropiophenone and 5'-allyl-2'-hydroxy-4'-methoxypropiophenone) were induced into the compound in Example 5 and the compound in Example 6 described later, respectively).

$^1$H-NMR (CDCl$_3$) δ (ppm): 1.45 (t, J=7.6 Hz, 3H), 2.07-2.16 (m, 4H), 2.28-2.37 (m, 2H), 2.68-2.76 (m, 2H), 2.94 (q, J=7.6 Hz, 2H), 3.06-3.14 (m, 2H), 3.22-3.31 (m, 2H), 3.89 (s, 3H), 4.35-4.46 (m, 1H), 6.57 (d, J=2.8 Hz, 1H), 6.87 (d, J=8.4 Hz, 1H), 7.37-7.42 (m, 2H), 7.44 (d, J=8.8 Hz, 1H), 7.63 (d, J=8.4 Hz, 1H), 8.10 (s, 1H).

Example 6

Synthesis of 1-{1-[2-(2-ethyl-6-methoxybenzoxazol-5-yl)ethyl]piperidin-4-yl}-1H-indole-6-carboxamide

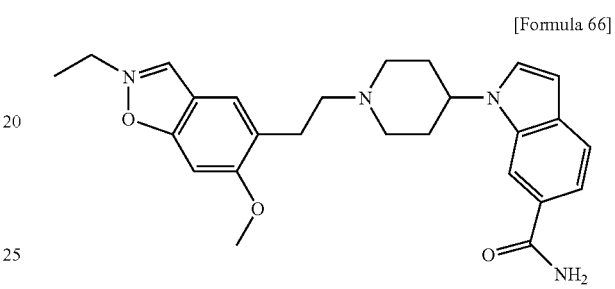

[Formula 66]

The subject compound was synthesized using the above described 5'-allyl-2'-hydroxy-4'-methoxypropiophenone as a raw material according to the synthesis methods described in Example 4, (3)-(4) (refer to the synthesis method of Example 5).

$^1$H-NMR (CDCl$_3$) δ (ppm): 1.43 (t, J=7.6 Hz, 3H), 2.07-2.16 (m, 4H), 2.24-2.34 (m, 2H), 2.62-2.69 (m, 2H), 2.88-2.96 (m, 4H), 3.17-3.26 (m, 2H), 3.88 (s, 3H), 4.32-4.46 (m, 1H), 6.56 (dd, J=0.8, 3.2 Hz, 1H), 6.99 (s, 1H), 7.37-7.42 (m, 2H), 7.44 (s, 1H), 7.63 (d, J=8.4 Hz, 1H), 8.09 (s, 1H).

Example 7

Synthesis of 1-{1-[2-(5-methoxy-2-methylbenzoxazol-4-yl)ethyl]piperidin-4-yl}-1H-indole-6-carboxamide

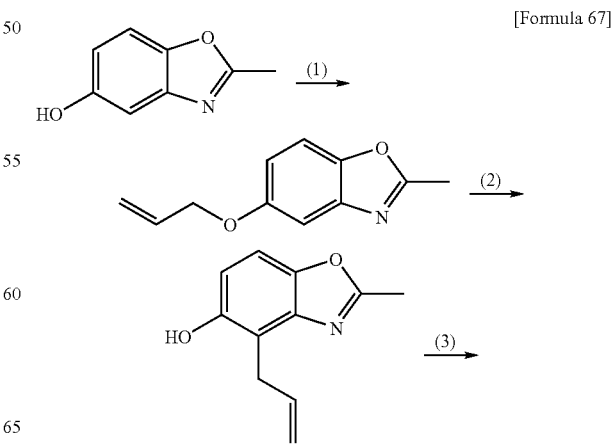

[Formula 67]

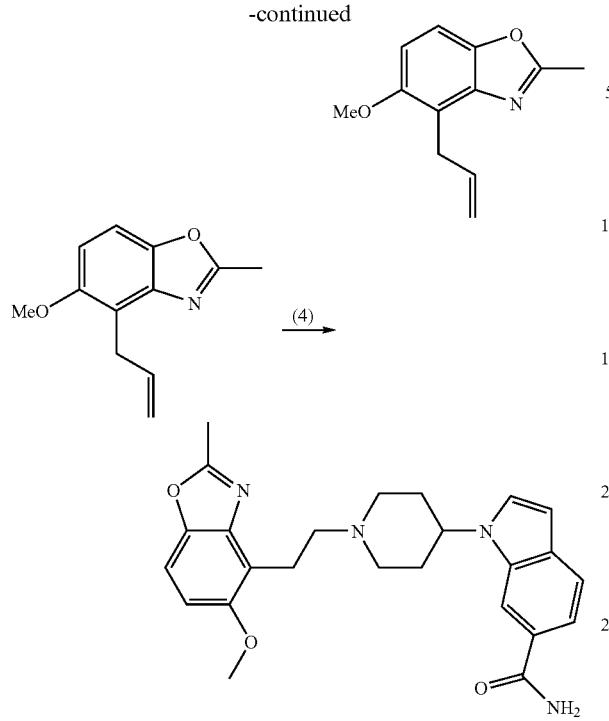

(1) 5-Allyloxy-2-methylbenzoxazole 2.58 g of 5-hydroxy-2-methylbenzoxazole (publication: Synthesis, 1982, 68-69) was dissolved in 15 ml of N,N-dimethylformamide and 15 ml of acetonitrile. Thereafter, 2.39 g of potassium carbonate and 1.61 ml of allyl bromide were successively added to the reaction solution. Approximately 6 hours later, water and ethyl acetate were added to the reaction solution, so as to separate an organic layer. The obtained organic layer was washed with water and a saturated sodium chloride solution, and then dried over anhydrous magnesium sulfate. After removing the drying agent by filtration, the organic layer was concentrated under a reduced pressure, and the residue was then purified by silica gel column chromatography (hexane/ethyl acetate), so as to obtain 2.78 g of the subject compound.

$^1$H-NMR (CDCl$_3$) δ (ppm): 2.61 (s, 3H), 4.53-4.58 (m, 2H), 5.26-5.32 (m, 1H), 5.39-5.46 (m, 1H), 6.01-6.12 (m, 1H), 6.90 (dd, J=2.4, 8.8 Hz, 1H), 7.14 (d, J=2.4 Hz, 1H), 7.33 (dd, J=0.4, 8.8 Hz, 1H).

(2) 4-Allyl-5-hydroxy-2-methylbenzoxazole 2.78 g of 5-allyloxy-2-methylbenzoxazole was stirred while heating at a temperature between 185° C. and 190° C. under nitrogen atmosphere. Approximately 5 hours later, the reaction solution was stood to cool. Thereafter, acetonitrile was added thereto for solidification, so as to obtain 1.44 g of the subject compound.

$^1$H-NMR (CDCl$_3$) δ (ppm): 2.61 (s, 3H), 3.72-3.79 (m, 2H), 5.06 (s, 1H), 5.14-5.22 (m, 2H), 6.01-6.14 (m, 1H), 6.81 (d, J=8.8 Hz, 1H), 7.21 (d, J=8.8 Hz, 1H).

(3) 4-Allyl-5-methoxy-2-methylbenzoxazole 1.44 g of 4-allyl-5-hydroxy-2-methylbenzoxazole was dissolved in 5 ml of N,N-dimethylformamide and 5 ml of acetonitrile. Thereafter, 1.05 g of potassium carbonate and 0.55 ml of methyl iodide were successively added to the reaction solution. Approximately 16 hours later, water and ethyl acetate were added to the reaction solution, so as to separate an organic layer. The obtained organic layer was washed with a saturated sodium chloride solution and then dried over anhydrous magnesium sulfate. After removing the drying agent by filtration, the organic layer was concentrated under a reduced pressure, and the residue was then purified by silica gel column chromatography (hexane/ethyl acetate), so as to obtain 1.26 g of the subject compound.

$^1$H-NMR (CDCl$_3$) δ (ppm): 2.61 (s, 3H), 3.69-3.73 (m, 2H), 3.86 (s, 3H), 4.96-5.05 (m, 2H), 6.02-6.14 (m, 1H), 6.86 (d, J=8.8 Hz, 1H), 7.24 (d, J=8.8 Hz, 1H).

(4) 1-{1-[2-(5-methoxy-2-methylbenzoxazol-4-yl)ethyl]piperidin-4-yl}-1H-indole-6-carboxamide The subject compound was obtained from the above described 4-allyl-5-methoxy-2-methylbenzoxazole according to the method described in Example 1, (4).

$^1$H-NMR (CDCl$_3$) δ (ppm): 2.05-2.20 (m, 4H), 2.28-2.40 (m, 2H), 2.62 (s, 3H), 2.68-2.80 (m, 2H), 3.16-3.33 (m, 4H), 3.88 (s, 3H), 4.32-4.45 (m, 1H), 6.56 (d, J=3.2 Hz, 1H), 6.86 (d, J=8.8 Hz, 1H), 7.22-7.44 (m, 3H), 7.63 (d, J=8.8 Hz, 1H), 8.09 (s, 1H).

Example 8

Synthesis of 1-{1-[2-(5-methoxy-2-methylbenzoxazol-6-yl)ethyl]piperidin-4-yl}-1H-indole-6-carboxamide

[Formula 68]

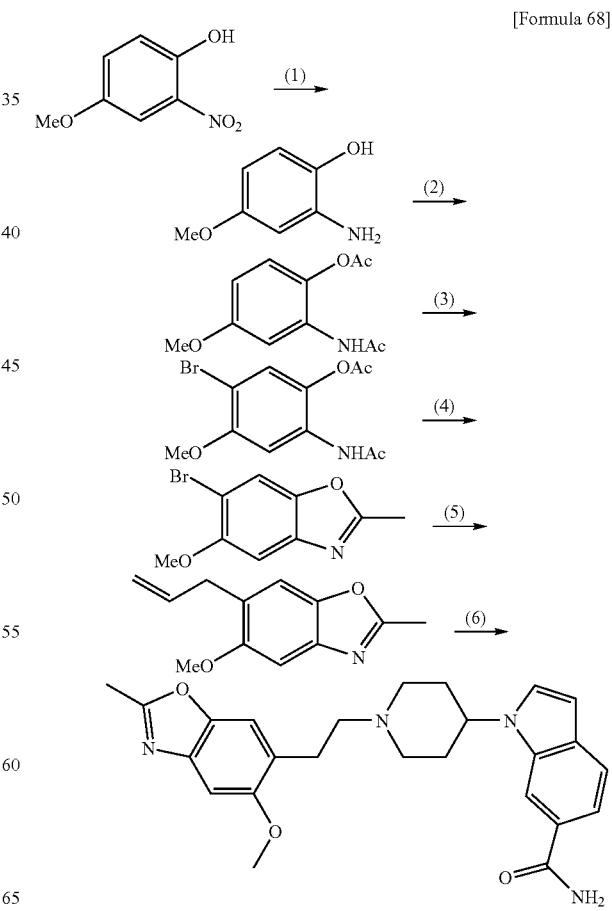

(1) 2-Amino-4-methoxyphenol 10 g of 4-methoxy-2-nitrophenol was dissolved in 120 ml of methanol and 80 ml of ethyl acetate. Thereafter, 800 mg of 10% palladium carbon was added to the reaction solution, followed by reduction under hydrogen atmosphere. After completion of the reaction, the catalyst was removed by filtration, and the residue was then concentration under a reduced pressure. The generated solid was suspended in hexane-t-butylmethyl ether, and the suspension was then filtered, so as to obtain 7.77 g of the subject compound.

$^1$H-NMR (CDCl$_3$) δ (ppm): 3.72 (brs, 5H), 4.33 (brs, 1H), 6.12-6.24 (m, 1H), 6.33 (brs, 1H), 6.58-6.70 (m, 1H).

(2) 2-acetamide-4-methoxyphenyl acetate 2.50 g of 2-amino-4-methoxyphenol and 12.5 ml of triethylamine were dissolved in 50 ml of tetrahydrofuran. The reaction solution was cooled on ice, and then, 3.84 ml of acetyl chloride was added dropwise thereto. Thereafter, the reaction solution was stirred at room temperature. After completion of the reaction, a saturated sodium bicarbonate solution and ethyl acetate were added to the reaction solution, so as to separate an organic layer. The obtained organic layer was washed with a saturated sodium chloride solution and then dried over anhydrous magnesium sulfate. After removing the drying agent by filtration, the organic layer was concentrated under a reduced pressure. The residue was solidified from t-butylmethyl ether-ethyl acetate, so as to obtain 2.30 g of the subject compound.

$^1$H-NMR (CDCl$_3$) δ (ppm): 2.18 (s, 3H), 2.35 (s, 3H), 3.80 (s, 3H), 6.64 (dd, J=2.4 Hz, 8.8 Hz, 1H), 7.01 (d, J=8.8 Hz, 1H), 7.08-7.16 (brs, 1H), 7.84 (d, J=2.4 Hz, 1H).

(3) 2-acetamide-5-bromo-4-methoxyphenyl acetate 2.30 g of 2-acetamide-4-methoxyphenyl acetate was dissolved in 20 ml of N,N-dimethylformamide. The reaction solution was cooled on ice, and then, 1.83 g of N-bromosuccinimide dissolved in 10 ml of N,N-dimethylformamide was added thereto. Thereafter, the temperature of the reaction solution was increased to a room temperature, and it was then stirred for 12 hours. Thereafter, a saturated sodium chloride solution and ethyl acetate were added to the reaction solution, so as to separate an organic layer. The obtained organic layer was washed with a saturated sodium chloride solution and then dried over anhydrous magnesium sulfate. After removing the drying agent by filtration, the organic layer was concentrated under a reduced pressure. The residue was crystallized from hexane-ethyl acetate, so as to obtain 2.70 g of the subject compound.

$^1$H-NMR (CDCl$_3$) δ (ppm): 2.19 (s, 3H), 2.36 (s, 3H), 3.89 (s, 3H), 7.14 (brs, 1H), 7.32 (s, 1H), 7.99 (s, 1H).

(4) 6-bromo-5-methoxy-2-methylbenzoxazole 2.70 g of 2-acetamide-5-bromo-4-methoxyphenyl acetate was dissolved in 60 ml of methanol and 40 ml of tetrahydrofuran. Thereafter, 6.18 g of potassium carbonate was added to the reaction solution, and the obtained mixture was then stirred at room temperature. After completion of the reaction, the reaction solution was adjusted to be pH 2 to 3 with addition of 5 N hydrochloric acid. Thereafter, ethyl acetate was added to the reaction solution, so as to separate an organic layer. The obtained organic layer was washed with a saturated sodium chloride solution and then dried over anhydrous magnesium sulfate. After removing the drying agent by filtration, the organic layer was concentrated under a reduced pressure, so as to obtain 2.14 g of crude 4'-bromo-2'-hydroxy-5'-methoxyacetanilide. 2.14 g of the thus obtained crude 4'-bromo-2'-hydroxy-5'-methoxyacetanilide was dissolved in 40 ml of acetic acid, and the reaction solution was then stirred while heating at 140° C. Approximately 20 hours later, the reaction solution was stood to cool, and then concentrated under a reduced pressure. Thereafter, a saturated sodium bicarbonate aqueous solution and ethyl acetate were added to the reaction solution, so as to separate an organic layer. The obtained organic layer was washed with a saturated sodium chloride solution and then dried over anhydrous magnesium sulfate. After removing the drying agent by filtration, the organic layer was concentrated under a reduced pressure. The residue was suspended in methanol-t-butyl methyl ether, and the suspension was then filtered, so as to obtain 787 mg of the subject compound.

$^1$H-NMR (CDCl$_3$) δ (ppm): 2.61 (s, 3H), 3.93 (s, 3H), 7.16 (s, 1H), 7.67 (s, 1H).

(5) 6-allyl-5-methoxy-2-methylbenzoxazole 400 mg of 6-bromo-5-methoxy-2-methylbenzoxazole was dissolved in 5 ml of toluene. Thereafter, 769 μl of allyl tributyl tin and 57 mg of tetrakis(triphenylphosphine)palladium were successively added to the reaction solution. Thereafter, the reaction solution was heated to reflux under nitrogen atmosphere. Approximately 14 hours later, the reaction solution was stood to cool and then filtered through celite, followed by concentration under a reduced pressure. The residue was purified by silica gel column chromatography (hexane/ethyl acetate), so as to obtain 202 mg of the subject compound.

$^1$H-NMR (CDCl$_3$) δ (ppm): 2.59 (s, 3H), 3.45 (d, J=6.4 Hz, 2H), 3.86 (s, 3H), 5.02-5.10 (m, 2H), 5.94-6.06 (m, 1H), 7.08 (s, 1H), 7.23 (s, 1H).

(6) 1-{1-[2-(5-methoxy-2-methylbenzoxazol-6-yl)ethyl]piperidin-4-yl}-1H-indole-6-carboxamide The subject compound was obtained from the above described 6-allyl-5-methoxy-2-methylbenzoxazole according to the method described in Example 1, (4).

$^1$H-NMR (CDCl$_3$) δ (ppm): 2.06-2.16 (m, 4H), 2.24-2.36 (m, 2H), 2.61 (s, 3H), 2.63-2.71 (m, 2H), 2.90-2.98 (m, 2H), 3.17-3.26 (m, 2H), 3.88 (s, 3H), 4.34-4.46 (m, 1H), 6.57 (dd, J=0.8 Hz, 3.2 Hz, 1H), 7.10 (s, 1H), 7.28 (s, 1H), 7.37-7.42 (m, 2H), 7.63 (dd, J=0.8 Hz, 8.4 Hz, 1H), 8.10 (s, 1H).

Example 9

Synthesis of 1-{1-[2-(8-methoxy-4-methyl-5-oxo-2,3,4,5-tetrahydrobenzo[f][1,4]oxazepin-7-yl)ethyl]piperidin-4-yl}-1H-indole-6-carboxamide

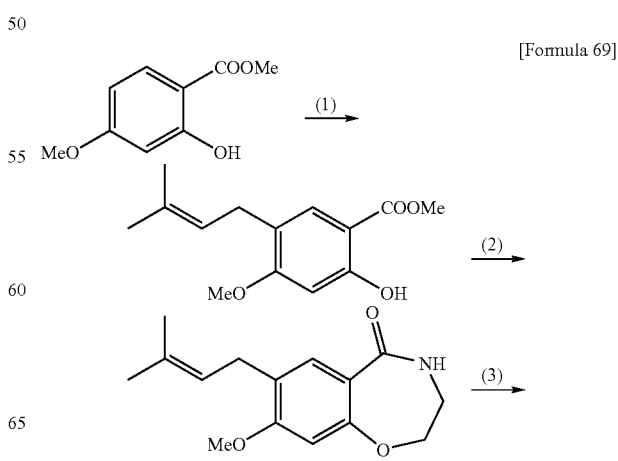

[Formula 69]

-continued

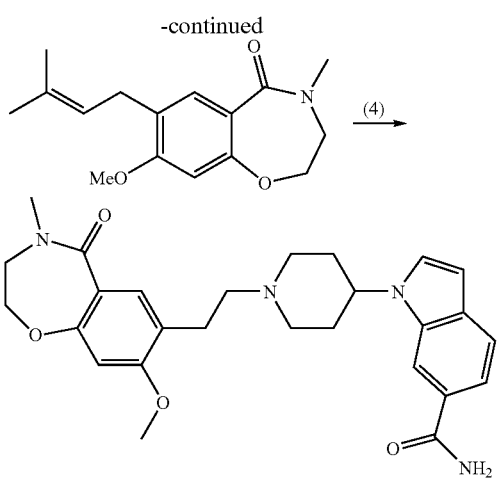

(1) Methyl 2-hydroxy-4-methoxy-5-(3-methyl-2-butenyl)benzoate

The subject compound was obtained from methyl 2-hydroxy-4-methoxybenzoate according to the methods described in Example 4, (1)-(2).

$^1$H-NMR (CDCl$_3$) δ (ppm): 1.70 (s, 3H), 1.74 (d, J=1.2 Hz, 3H), 3.20 (dd, J=0.8, 7.2 Hz, 2H), 3.84 (s, 3H), 3.90 (s, 3H), 5.20-5.28 (m, 1H), 6.41 (s, 1H), 7.51 (t, J=0.8 Hz, 1H), 10.9 (s, 1H).

(2) 8-Methoxy-7-(3-methyl-2-butenyl)-3,4-dihydro-2H-benz[f][1,4]oxazepin-5-one 2.00 g of methyl 2-hydroxy-4-methoxy-5-(3-methyl-2-butenyl)benzoate, 1.29 g of N-(t-butoxycarbonyl)-2-aminoethanol, and 2.31 g of triphephenylphosphine were dissolved in 50 ml of tetrahydrofuran. The obtained mixture was cooled on ice. Thereafter, 1.73 ml of diisopropylazodicarboxylate was added to the reaction solution at the same temperature, and the temperature was then raised to a room temperature. After completion of the reaction, the reaction solution was concentrated. The residue was purified by NH silica gel column chromatography (hexane/ethyl acetate), so as to obtain 1.54 g of methyl 2-(2-t-butoxycarbonylaminoethoxy)-4-methoxy-5-(3-methyl-2-butenyl)benzoate. The obtained product was dissolved in 15 ml of methanol, and the obtained mixture was cooled on ice. Thereafter, 10 ml of a 4 N hydrochloric acid-ethyl acetate solution was added to the reaction solution. After completion of the reaction, the reaction solution was concentrated under a reduced pressure. Ethyl acetate was added to the residue, and the obtained mixture was adjusted to be approximately pH 11 with addition of a 5 N sodium hydroxide aqueous solution and a saturated sodium bicarbonate aqueous solution. The organic layer was dried over anhydrous magnesium sulfate. After removing the drying agent by filtration, the organic layer was concentrated under a reduced pressure. 1.06 g of the obtained residue was dissolved in 20 ml of toluene, and the obtained solution was heated to reflux. After completion of the reaction, the reaction solution was concentrated. The residue was purified by silica gel column chromatography (hexane/ethyl acetate), so as to obtain 601 mg of the subject compound.

$^1$H-NMR (CDCl$_3$) δ (ppm): 1.70 (s, 3H), 1.72 (d, J=1.2 Hz, 3H), 3.26 (d, J=7.2 Hz, 2H), 3.48-3.55 (m, 2H), 3.84 (s, 3H), 4.35-4.41 (m, 2H), 5.25-5.32 (m, 1H), 6.44 (s, 1H), 6.47 (brs, 1H), 7.80 (s, 1H).

(3) 8-Methoxy-4-methyl-7-(3-methyl-2-butenyl)-3,4-dihydro-2H-benz[f][1,4]oxazepin-5-one 601 mg of 8-methoxy-7-(3-methyl-2-butenyl)-3,4-dihydro-2H-benz[f][1,4]oxazepin-5-one was dissolved in 15 ml of N,N-dimethylformamide. Thereafter, 120 mg of sodium hydride was added to the reaction solution. Ten minutes later, 215 μl of methyl iodide was added to the reaction solution, and the obtained mixture was then stirred at room temperature. After completion of the reaction, a saturated ammonium chloride aqueous solution and ethyl acetate were added to the reaction solution, so as to separate an organic layer. The organic layer was washed with a saturated sodium chloride aqueous solution and then dried over anhydrous magnesium sulfate. After removing the drying agent by filtration, the organic layer was concentrated under a reduced pressure. The residue was purified by silica gel column chromatography (hexane/ethyl acetate), so as to obtain 513 mg of the subject compound.

$^1$H-NMR (CDCl$_3$) δ (ppm): 1.69 (s, 3H), 1.72 (d, J=1.2 Hz, 3H), 3.19 (s, 3H), 3.26 (d, J=7.6 Hz, 2H), 3.50-3.60 (m, 2H), 3.82 (s, 3H), 4.32-4.43 (m, 2H), 5.24-5.33 (m, 1H), 6.43 (s, 1H), 7.63 (s, 1H).

(4) 1-{1-[2-(8-Methoxy-4-methyl-5-oxo-2,3,4,5-tetrahydrobenz[f][1,4]oxazepin-7-yl)ethyl]piperidin-4-yl}-1H-indole-6-carboxamide The subject compound was obtained from 8-methoxy-4-methyl-7-(3-methyl-2-butenyl)-3,4-dihydro-2H-benz[f][1,4]oxazepin-5-one according to the method described in Example 4, (4).

$^1$H-NMR (CDCl$_3$) δ (ppm): 2.06-2.35 (m, 6H), 2.60-2.70 (m, 2H), 2.78-2.88 (m, 2H), 3.15-3.26 (m, 2H), 3.20 (s, 3H), 3.53-3.58 (m, 2H), 3.83 (s, 3H), 4.32-4.44 (m, 3H), 6.44 (s, 1H), 6.56 (dd, J=0.4 Hz, 3.2 Hz, 1H), 7.36-7.46 (m, 2H), 7.63 (dd, J=0.4 Hz, 8.0 Hz, 1H), 7.69 (s, 1H), 8.09 (s, 1H).

Example 10

Synthesis of 1-{1-[2-(8-methoxy-4-methyl-5-oxo-2,3,4,5-tetrahydrobenz[f][1,4]oxazepin-7-yl)ethyl]piperidin-4-yl}-N-methyl-1H-indole-6-carboxamide

[Formula 70]

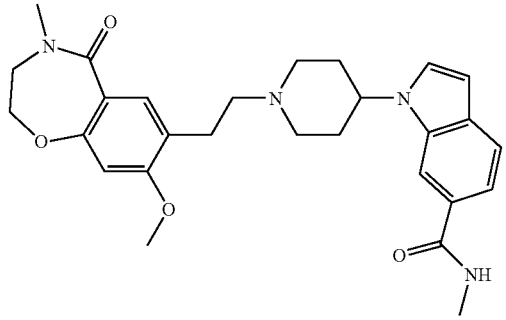

The subject compound was synthesized from N-methyl-1-(piperidin-4-yl)-1H-indole-6-carboxamide according to the method described in Example 9.

$^1$H-NMR (CDCl$_3$) δ (ppm): 2.03-2.37 (m, 6H), 2.55-2.74 (m, 2H), 2.76-2.90 (m, 2H), 3.06 (d, J=4.80 Hz, 3H), 3.12-3.26 (m, 2H), 3.20 (s, 3H), 3.50-3.60 (m, 2H), 3.84 (s, 3H), 4.30-4.43 (m, 3H), 6.28 (brs, 1H), 6.44 (s, 1H), 6.54 (d, J=3.2 Hz, 1H), 7.30-7.42 (m, 2H), 7.61 (d, J=8.0 Hz, 1H), 7.69 (s, 1H), 8.03 (brs, 1H).

Example 11

Synthesis of 1-{1-[2-(5,7-dimethoxy-1-methoxyimi-noindan-4-yl)ethyl]piperidin-4-yl}-1H-indole-6-carboxamide

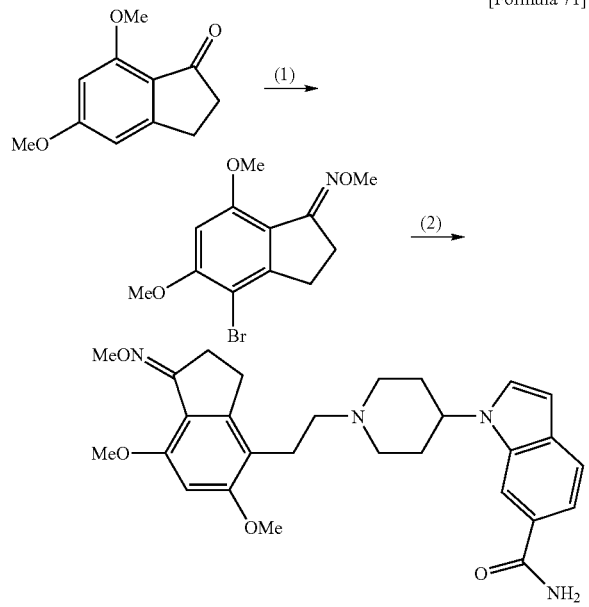

[Formula 71]

(1) 4-Bromo-5,7-dimethoxyindan-1-one O-methyloxime 845 mg of 5,7-dimethoxyindan-1-one was dissolved in 40 ml of dichloromethane. Thereafter, 822 mg of N-bromosuccinimide was added to the reaction solution. After completion of the reaction, chloroform was added to the reaction solution. The organic layer was washed with a saturated sodium chloride solution and then dried over anhydrous magnesium sulfate. After removing the drying agent by filtration, the organic layer was concentrated under a reduced pressure. The residue was suspended in acetone, and the suspension was filtered, so as to obtain 1.03 g of 4-bromo-5,7-dimethoxyindan-1-one. The obtained product was suspended in a mixed solution consisting of 30 ml of methanol, 10 ml of tetrahydrofuran, and 20 ml of chloroform. Thereafter, 952 mg of methoxylamine hydrochloride and 935 mg of sodium acetate were added to the reaction solution, and the obtained mixture was stirred at room temperature. Approximately 4 hours later, 952 mg of methoxylamine hydrochloride and 935 mg of sodium acetate were further added to the reaction solution. After completion of the reaction, the reaction solution was concentrated. A saturated sodium bicarbonate aqueous solution and ethyl acetate were added to the resultant product, so as to separate an organic layer. The organic layer was washed with a saturated sodium bicarbonate aqueous solution and a saturated sodium chloride solution, and then dried over anhydrous magnesium sulfate. After removing the drying agent by filtration, the organic layer was concentrated under a reduced pressure. The residue was suspended in t-butyl methyl ether, and the suspension was filtered, so as to obtain 896 mg of the subject compound.

$^1$H-NMR (CDCl$_3$) δ (ppm): 2.90-3.00 (m, 4H), 3.95 (s, 3H), 3.96 (s, 3H), 4.00 (s, 3H), 6.38 (s, 1H).

(2) 1-{1-[2-(5,7-Dimethoxy-1-methoxyiminoindan-4-yl)ethyl]piperidin-4-yl}-1H-indole-6-carboxamide The subject compound was obtained from 4-bromo-5,7-dimethoxyindan-1-one O-methyloxime according to the methods described in Example 8, (5)-(6).

$^1$H-NMR (CDCl$_3$) δ (ppm): 2.13 (brs, 4H), 2.21-2.36 (m, 2H), 2.46-2.58 (m, 2H), 2.72-2.84 (m, 2H), 2.96 (brs, 4H), 3.16-3.29 (m, 2H), 3.89 (s, 3H), 3.96 (s, 3H), 4.01 (s, 3H), 4.34-4.46 (m, 1H), 6.37 (s, 1H), 6.58 (d, J=2.4 Hz, 1H), 7.36-7.46 (m, 2H), 7.65 (d, J=8.4 Hz, 1H), 8.12 (brs, 1H).

Example 12

Synthesis of 1-{1-[2-(8-methoxy-5-oxo-2,3,4,5-tetrahydrobenzo[b]oxepin-7-yl)ethyl]piperidin-4-yl}-1H-indole-6-carboxamide

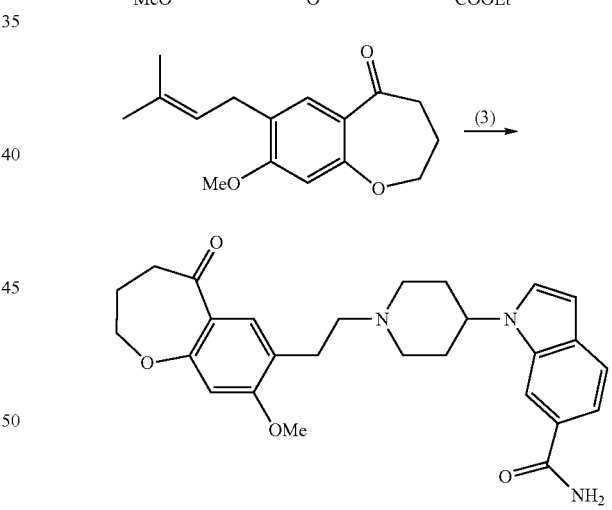

[Formula 72]

(1) Methyl 2-(3-ethoxycarbonylpropoxy)-4-methoxy-5-(3-methyl-2-butenyl)benzoate 3.00 g of methyl 2-hydroxy-4-methoxy-5-(3-methyl-2-butenyl)benzoate was dissolved in 30 ml of N,N-dimethylformamide. Thereafter, 2.16 g of potassium carbonate and 2.23 ml of ethyl 4-bromobutylate were added to the reaction solution, and the obtained mixture was then stirred while heating at 80° C. 829 mg of potassium carbonate and 0.86 ml of ethyl 4-bromobutylate were added thereto at the midpoint of the reaction. After completion of the reaction, ethyl acetate was added to the reaction solution. The obtained organic layer was washed with a saturated ammonium chloride aqueous solution and a saturated sodium chloride solution, and then dried over anhydrous magnesium sulfate. After removing the drying agent by filtration, the organic layer was concentrated under a reduced pressure. The residue was purified by silica gel column chromatography (hexane/ethyl acetate), so as to obtain 2.88 g of the subject compound.

$^1$H-NMR (CDCl$_3$) δ (ppm): 1.25 (t, J=7.2 Hz, 3H), 1.70 (s, 3H), 1.73 (d, J=1.2 Hz, 3H), 2.10-2.20 (m, 2H), 2.61 (t, J=7.2 Hz, 2H), 3.23 (d, J=7.2 Hz, 2H), 3.85 (s, 3H), 3.87 (s, 3H), 4.09 (t, J=6.0 Hz, 2H), 4.13 (q, J=7.2 Hz, 2H), 5.20-5.30 (m, 1H), 6.43 (s, 1H), 7.64 (s, 1H).

(2) 8-Methoxy-7-(3-methyl-2-butenyl)-3,4-dihydro-2H-benz[b]oxepin-5-one 80 ml of a tetrahydrofuran solution containing 18.6 mmol lithium bis(trimethylsilyl)amide was cooled to −75° C. 3.23 g of methyl 2-(3-ethoxycarbonylpropoxy)-4-methoxy-5-(3-methyl-2-butenyl)benzoate was dissolved in 8 ml of tetrahydrofuran, and the obtained solution was added dropwise to the above solution. After completion of the dropping, the reaction solution was warmed to 0° C. After completion of the reaction, a saturated ammonium chloride aqueous solution and ethyl acetate were added to the reaction solution, so as to separate an organic layer. The obtained organic layer was washed with a saturated sodium chloride aqueous solution and then dried over anhydrous magnesium sulfate. After removing the drying agent by filtration, the organic layer was concentrated under a reduced pressure. The residue was purified by silica gel column chromatography (hexane/ethyl acetate), so as to obtain 969 mg of ethyl 8-methoxy-7-(3-methyl-2-butenyl)-5-oxo-2,3,4,5-tetrahydrobenz[b]oxepin-4-carboxylate. Thereafter, 751 mg of the obtained compound was dissolved in 15 ml of tetrahydrofuran. While the reaction solution was stirred under heating at 70° C., 4 ml of a 5 N sodium hydroxide aqueous solution was added thereto in 3 batches. Approximately 2 hours later, tetrahydrofuran as a reaction solution was concentrated under a reduced pressure, and 10 ml of ethanol was then added thereto. Thereafter, 5 ml of 5 N hydrochloric acid was added to this ethanol solution, and the mixture was heated to reflux again. After completion of the reaction, ethyl acetate was added to the reaction solution, and the obtained organic layer was washed with a saturated sodium chloride aqueous solution. The organic layer was then dried over anhydrous magnesium sulfate. After removing the drying agent by filtration, the organic layer was concentrated under a reduced pressure. The residue was purified by silica gel column chromatography (hexane/ethyl acetate), so as to obtain 422 mg of the subject compound.

$^1$H-NMR (CDCl$_3$) δ 1.69 (d, J=0.4 Hz, 3H), 1.72 (d, J=1.2 Hz, 3H), 2.18 (quintet, J=6.8 Hz, 2H), 2.85 (t, J=6.8 Hz, 2H), 3.24 (d, J=6.8 Hz, 2H), 3.85 (s, 3H), 4.22 (t, J=6.8 Hz, 2H), 5.22-5.30 (m, 1H), 6.51 (s, 1H), 7.58 (s, 1H).

(3) 1-{1-[2-(8-methoxy-5-oxo-2,3,4,5-tetrahydrobenz[b]oxepin-7-yl)ethyl]piperidin-4-yl}-1H-indole-6-carboxamide The subject compound was obtained from 8-methoxy-7-(3-methyl-2-butenyl)-3,4-dihydro-2H-benz[b]oxepin-5-one according to the method described in Example 4, (4).

$^1$H-NMR (CDCl$_3$) δ (ppm): 2.12 (brs, 4H), 2.20 (quintet, J=6.8 Hz, 2H), 2.29 (brs, 2H), 2.63 (brs, 2H), 2.74-2.93 (m, 2H), 2.88 (t, J=6.8 Hz, 2H), 3.10-3.30 (m, 2H), 3.87 (s, 3H), 4.24 (t, J=6.8 Hz, 2H), 4.32-4.46 (m, 1H), 6.54 (s, 1H), 6.57 (dd, J=0.8, 3.2 Hz, 1H), 7.36-7.48 (m, 2H), 7.62-7.68 (m, 2H), 8.11 (brs, 1H).

Example 13

Synthesis of 1-{1-[2-(8-methoxy-5-methoxyimino-2,3,4,5-tetrahydrobenzo[b]oxepin-7-yl)ethyl]piperidin-4-yl}-1H-indole-6-carboxamide

[Formula 73]

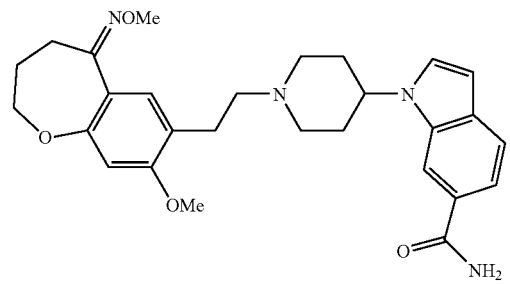

97 mg of 1-(1-(2-(8-methoxy-5-oxo-2,3,4,5-tetrahydrobenzo[b]oxepin-7-yl)ethyl)piperidin-4-yl)-1H-indole-6-carboxamide was dissolved in a mixed solution consisting of 4 ml of methanol, 2 ml of tetrahydrofuran, and 2 ml of chloroform. Thereafter, 105 mg of methoxylamine hydrochloride and 103 mg of sodium acetate were added to the reaction solution, and the obtained mixture was then stirred at room temperature. At the midpoint of the reaction, 1 g of methoxylamine hydrochloride and 1 g of sodium acetate were further added thereto. After completion of the reaction, a 1 N sodium hydroxide aqueous solution, a saturated sodium bicarbonate aqueous solution, and chloroform were added to the reaction solution, so as to separate an organic layer. The obtained organic layer was washed with a saturated sodium bicarbonate aqueous solution and a saturated sodium chloride solution, and then dried over anhydrous magnesium sulfate. After removing the drying agent by filtration, the organic layer was concentrated under a reduced pressure. The residue was solidified from t-butyl methyl ether-ethyl acetate, so as to obtain 70 mg of the subject compound.

$^1$H-NMR (CDCl$_3$) δ (ppm): 1.95-2.05 (m, 2H), 2.05-2.40 (m, 6H), 2.55-2.73 (m, 2H), 2.75-2.90 (m, 2H), 2.86 (t, J=6.8 Hz, 2H), 3.15-3.30 (m, 2H), 3.82 (s, 3H), 3.98 (s, 3H), 4.17 (t, J=6.0 Hz, 2H), 4.32-4.46 (m, 1H), 6.50 (s, 1H), 6.57 (d, J=3.2 Hz, 1H), 7.35 (s, 1H), 7.38-7.46 (m, 2H), 7.65 (d, J=8.4 Hz, 1H), 8.11 (brs, 1H).

Example 14

Synthesis of 1-{1-[2-(5-methoxy-2,2-dimethyl-1-oxoindan-4-yl)ethyl]piperidin-4-yl}-1H-indole-6-carboxamide

[Formula 74]

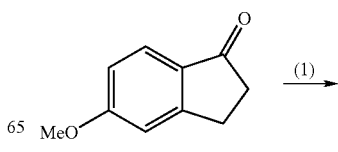

-continued

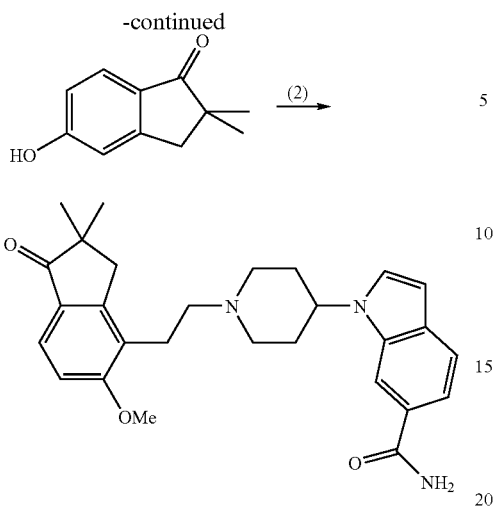

(1) 5-hydroxy-2,2-dimethylindanone 7.78 g of potassium t-butoxide was dissolved in 66.3 ml of t-butanol and 150 ml of toluene. Thereafter, 5.00 g of 5-methoxyindanone dissolved in 170 ml of toluene was added dropwise to the reaction solution at room temperature. Approximately 10 minutes later, 4.79 ml of methyl iodide was added to the reaction solution. After completion of the reaction, a saturated ammonium chloride aqueous solution and ethyl acetate were added to the reaction solution, so as to separate an organic layer. The organic layer was then dried over anhydrous magnesium sulfate. After the organic layer had been filtered through celite, the drying agent was removed by filtration. Thereafter, the organic layer was concentrated under a reduced pressure. The residue was purified by silica gel column chromatography (hexane/ethyl acetate), so as to obtain 2.08 g of 5-methoxy-2,2-dimethylindanone. The obtained product was dissolved in 9 ml of methanesulfonic acid. Then, 2.45 g of methionine was added to the reaction solution, and the obtained mixture was heated to 110° C. After completion of the reaction, a saturated sodium chloride aqueous solution and ethyl acetate were added to the reaction solution, so as to separate an organic layer. The organic layer was then dried over anhydrous magnesium sulfate. After removing the drying agent by filtration, the organic layer was concentrated under a reduced pressure. The residue was purified by silica gel column chromatography (hexane/ethyl acetate), so as to obtain 1.41 g of the subject compound.

$^1$H-NMR (CDCl$_3$) δ (ppm): 1.24 (s, 6H), 2.94 (s, 2H), 6.79-6.90 (m, 3H), 7.68 (dd, J=0.4, 8.0 Hz, 1H).

(2) 1-{1-[2-(5-methoxy-2,2-dimethyl-1-oxoindan-4-yl)ethyl]piperidin-4-yl}-1H-indole-6-carboxamide The subject compound was obtained from 5-hydroxy-2,2,-dimethylindanone according to the methods described in Example 7, (1)-(4).

$^1$H-NMR (CDCl$_3$) δ (ppm): 1.25 (s, 6H), 2.00-2.23 (m, 4H), 2.25-2.40 (m, 2H), 2.50-2.66 (m, 2H), 2.80-3.00 (m, 2H), 2.95 (s, 2H), 3.15-3.33 (m, 2H), 3.94 (s, 3H), 4.33-4.48 (m, 1H), 6.58 (d, J=3.2 Hz, 1H), 6.94 (d, J=8.4 Hz, 1H), 7.36-7.46 (m, 2H), 7.65 (d, J=8.4 Hz, 1H), 7.69 (d, J=8.8 Hz, 1H), 8.12 (s, 1H).

Example 15

Synthesis of 1-{1-[2-(6-methoxy-2-methylbenzoxazol-7-yl)ethyl]piperidin-4-yl})-N-methyl-1H-indole-6-carboxamide

[Formula 75]

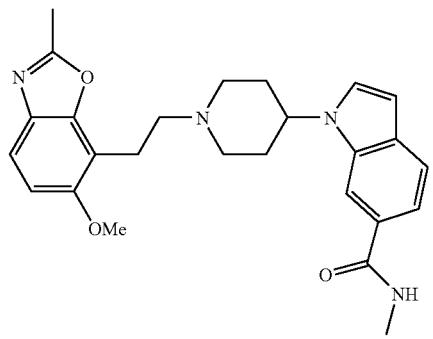

The subject compound was synthesized using N-methyl-1-(piperidin-4-yl)-1H-indole-6-carboxamide according to the method described in Example 3, (5).

$^1$H-NMR (CDCl$_3$) δ (ppm): 2.13 (brs, 4H), 2.33 (brs, 2H), 2.62 (s, 3H), 2.72 (brs, 2H), 3.07 (d, J=4.8 Hz, 3H), 3.02-3.18 (m, 2H), 3.20-3.34 (m, 2H), 3.90 (s, 3H), 4.34-4.48 (m, 1H), 6.24 (brs, 1H), 6.56 (d, J=2.8 Hz, 1H), 6.89 (d, J=8.4 Hz, 1H), 7.32-7.48 (m, 3H), 7.63 (d, J=8.0 Hz, 1H), 8.04 (brs, 1H).

Example 16

Synthesis of 1-{1-[2-(6-methoxy-2-methylbenzoxazol-5-yl)ethyl]piperidin-4-yl}-N-methyl-1H-indole-6-carboxamide

[Formula 76]

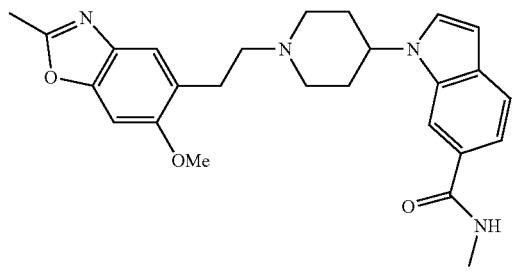

The subject compound was synthesized using N-methyl-1-(piperidin-4-yl)-1H-indole-6-carboxamide according to the method described in Example 4, (4).

$^1$H-NMR (CDCl$_3$) δ (ppm): 2.12 (brs, 4H), 2.30 (brs, 2H), 2.60 (s, 3H), 2.62-2.74 (m, 2H), 2.94 (brs, 2H), 3.06 (d, J=5.2 Hz, 3H), 3.12-3.30 (m, 2H), 3.89 (s, 3H), 4.32-4.45 (m, 1H), 6.24 (brs, 1H), 6.55 (d, J=3.2 Hz, 1H), 6.99 (s, 1H), 7.32-7.42 (m, 2H), 7.43 (s, 1H), 7.62 (d, J=8.4 Hz, 1H), 8.05 (brs, 1H).

Example 17

Synthesis of 1-{1-[2-(6-methoxy-3-methylbenz[d]isoxazol-7-yl)ethyl]piperidin-4-yl}-N-methyl-1H-indole-6-carboxamide

[Formula 77]

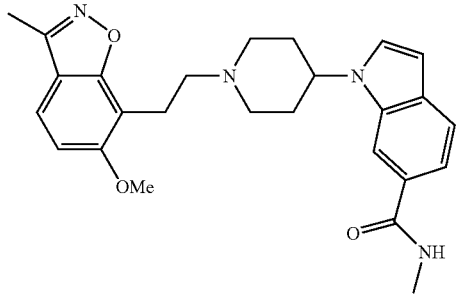

65 mg of 1-(1-(2-(6-methoxy-3-methylbenz[d]isoxazol-7-yl)ethyl)piperidin-4-yl)-1H-indole-6-carboxamide obtained in Example 1 was dissolved in 1 ml of N,N-dimethylformamide, and then, 7.2 mg of 60% sodium hydride was added thereto. The reaction solution was stirred at room temperature for 5 minutes, and 11.2 µl of methyl iodide was then added to the reaction solution. After completion of the reaction, water and ethyl acetate were added to the reaction solution, so as to separate an organic layer. The obtained organic layer was washed with a saturated sodium bicarbonate aqueous solution and then dried over anhydrous magnesium sulfate. After removing the drying agent by filtration, the organic layer was concentrated under a reduced pressure. The residue was purified by NH silica gel column chromatography (hexane/ethyl acetate), so as to obtain 17 mg of the subject compound.

$^1$H-NMR (CDCl$_3$) δ (ppm): 2.11 (brs, 4H), 2.26-2.42 (m, 2H), 2.54 (s, 3H), 2.68-2.82 (m, 2H), 3.06 (d, J=5.2 Hz, 3H), 3.10-3.20 (m, 2H), 3.22-3.32 (m, 2H), 3.95 (s, 3H), 4.32-4.43 (m, 1H), 6.30 (brs, 1H), 6.55 (d, J=3.2 Hz, 1H), 6.95 (d, J=8.8 Hz, 1H), 7.34-7.42 (m, 2H), 7.43 (d, J=8.4 Hz, 1H), 7.62 (d, J=8.4 Hz, 1H), 8.04 (s, 1H).

Example 18

Synthesis of 1-{1-[2-(6-methoxy-3-methylbenz[d]isoxazol-5-yl)ethyl]piperidin-4-yl}-N-methyl-1H-indole-6-carboxamide

[Formula 78]

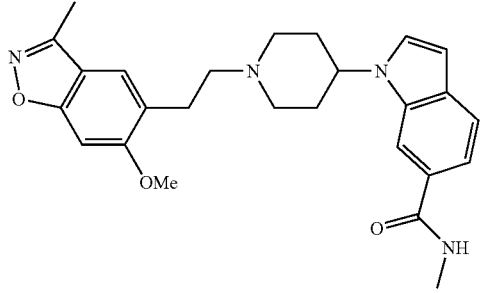

The subject compound was synthesized using 1-(1-(2-(6-methoxy-3-methylbenzo[d]isoxazol-5-yl)ethyl)piperidin-4-yl)-1H-indole-6-carboxamide obtained in Example 2 according to the method described in Example 17.

$^1$H-NMR (CDCl$_3$) δ (ppm): 2.13 (brs, 4H), 2.21-2.39 (m, 2H), 2.54 (s, 3H), 2.60-2.73 (m, 2H), 2.88-3.00 (m, 2H), 3.06 (d, J=5.2 Hz, 3H), 3.15-3.30 (m, 2H), 3.93 (s, 3H), 4.32-4.46 (m, 1H), 6.28 (brs, 1H), 6.56 (d, J=2.8 Hz, 1H), 6.97 (s, 1H), 7.32-7.40 (m, 3H), 7.62 (d, J=8.0 Hz, 1H), 8.08 (s, 1H).

Example 19

Synthesis of 1-{1-[2-(2-methoxy-5-methoxyimino-5,6,7,8-tetrahydronaphthalen-1-yl)ethyl]piperidin-4-yl}-1H-indole-6-carboxamide

[Formula 79]

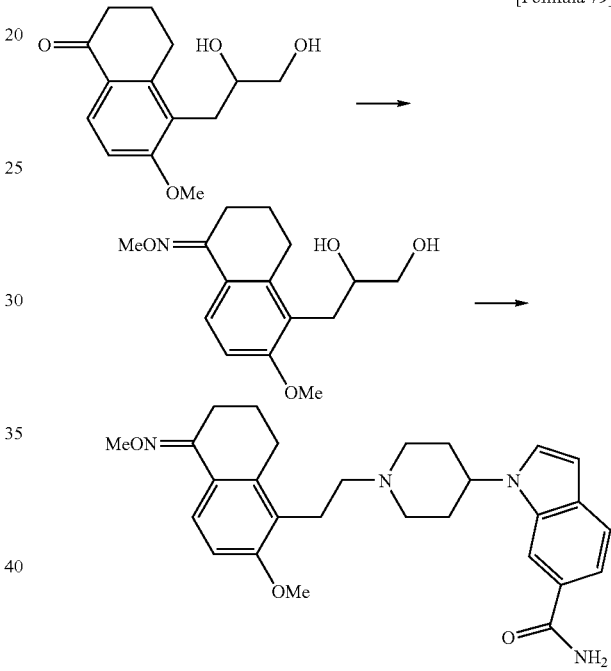

200 mg of 5-(2,3-dihydroxypropyl)-6-methoxy-1-tetralone synthesized from 6-hydroxy-1-tetralone according to the methods described in Example 7, (1)-(4), was dissolved in a mixed solution consisting of 5 ml of methanol and 3 ml of tetrahydrofuran. Thereafter, 401 mg of methoxyamine hydrochloride and 394 mg of sodium acetate were added to the reaction solution, and the obtained mixture was then stirred at room temperature. After completion of the reaction, a saturated sodium bicarbonate aqueous solution and ethyl acetate were added to the reaction solution, so as to separate an organic layer. The obtained organic layer was washed with a saturated sodium bicarbonate aqueous solution and a saturated sodium chloride solution, and then dried over anhydrous magnesium sulfate. After removing the drying agent by filtration, the organic layer was concentrated under a reduced pressure, so as to obtain 183 mg of 5-(2,3-dihydroxypropyl)-6-methoxy-3,4-dihydro-2H-naphthalen-1-one O-methyloxime. The subject compound was obtained from the thus obtained compound according to the method described in Example 1, (4).

$^1$H-NMR (CDCl$_3$) δ (ppm): 1.80-1.90 (m, 2H), 2.15 (brs, 4H), 2.32 (brs, 2H), 2.51 (brs, 2H), 2.65-2.80 (m, 4H), 2.85-

3.02 (m, 2H), 3.15-3.35 (m, 2H), 3.86 (s, 3H), 3.97 (s, 3H), 4.34-4.48 (m, 1H), 6.58 (d, J=3.2 Hz, 1H), 6.77 (d, J=8.8 Hz, 1H), 7.38-7.46 (m, 2H), 7.65 (d, J=8.0 Hz, 1H), 7.90 (d, J=8.8 Hz, 1H), 8.12 (s, 1H).

Example 20

Synthesis of 1-{1-[2-(7-methoxy-2,2-dimethyl-4-oxochroman-8-yl)ethyl]piperidin-4-yl}-N-methyl-1H-indole-6-carboxamide

[Formula 80]

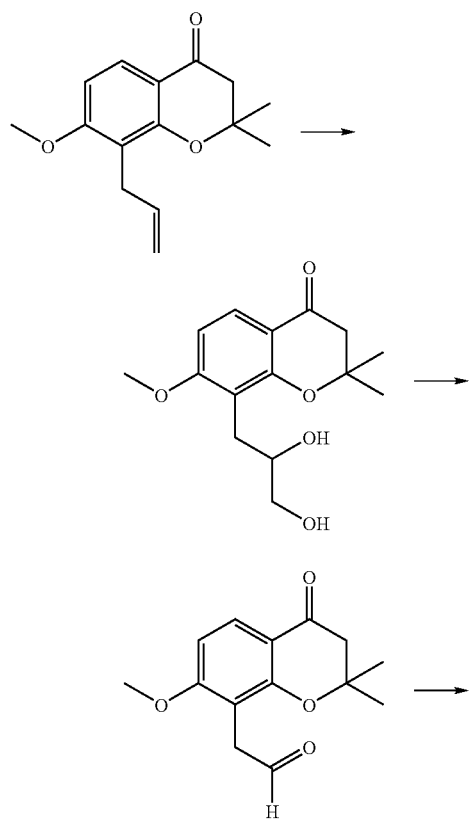

126 mg of 8-allyl-7-methoxy-2,2-dimethyl-4-oxochroman was dissolved in 12 ml of t-butanol-water (1:1) under nitrogen atmosphere. Thereafter, 0.72 g of AD-mix-β was added to the reaction solution, and the obtained mixture was then stirred at room temperature for 24 hours. Thereafter, 0.77 g of sodium sulfite was added to the reaction solution while cooling on ice, and the obtained mixture was stirred at room temperature for 1 hour. The reaction solution was diluted with ethyl acetate, and then washed with a saturated sodium chloride aqueous solution. The organic layer was dried over magnesium sulfate and then filtered. The organic layer was then concentrated under a reduced pressure, so as to obtain 145 mg of 8-(2,3-dihydroxypropyl)-7-methoxy-2,2-dimethyl-4-oxochroman. This compound was used in the following reaction without further purification.

145 mg of 8-(2,3-dihydroxypropyl)-7-methoxy-2,2-dimethyl-4-oxochroman was dissolved in 3 ml of tetrahydrofuran and 4 ml of methanol. Thereafter, 7 ml of water containing 0.22 g of sodium metaperiodate was added to the reaction solution while cooling on ice, and the obtained mixture was then stirred at room temperature for 30 minutes. The reaction solution was diluted with ethyl acetate, and then washed with a saturated sodium chloride aqueous solution. The organic layer was dried over magnesium sulfate and then filtered. The organic layer was then concentrated under a reduced pressure, so as to obtain 120 mg of (7-methoxy-2,2-dimethyl-4-oxochroman-8-yl)acetaldehyde. This compound was used in the following reaction without further purification.

120 mg of N-methyl-1-(piperidin-4-yl)-1H-indole-6-carboxamide and 120 mg of (7-methoxy-2,2-dimethyl-4-oxochroman-8-yl)acetaldehyde were dissolved in 8 ml of methylene chloride. Thereafter, 0.05 ml of acetic acid and 0.15 g of sodium triacetoxyborohydride were added to the reaction solution, and the obtained mixture was then stirred at room temperature for 1 hour. Thereafter, a saturated sodium bicarbonate aqueous solution was added to the reaction solution, followed by extraction with methylene chloride. The extract was dried over magnesium sulfate and then filtered. The filtrate was then concentrated under a reduced pressure. The residue was purified by silica gel column chromatography (methanol-ethyl acetate), so as to obtain 210 mg of the subject compound.

$^1$H-NMR (DMSO-$d_6$) δ (ppm): 1.40 (s, 6H), 1.92-2.10 (m, 4H), 2.22-2.33 (m, 2H), 2.40-2.50 (m, 2H), 2.72 (s, 2H), 2.74-2.83 (m, 2H), 2.82 (d, J=4.4 Hz, 3H), 3.08-3.17 (m, 2H), 3.87 (s, 3H), 4.35-4.47 (m, 1H), 6.50 (d, J=3.2 Hz, 1H), 6.75 (d, J=9.2 Hz, 1H), 7.51-7.59 (m, 2H), 7.62-7.69 (m, 2H), 8.06 (s, 1H), 8.29-8.37 (m, 1H).

Example 22

Synthesis of 1-{1-[2-(7-methoxy-2,2-dimethyl-4-oxochroman-8-yl)ethyl]piperidin-4-yl}-1H-indole-6-carboxamide

[Formula 81]

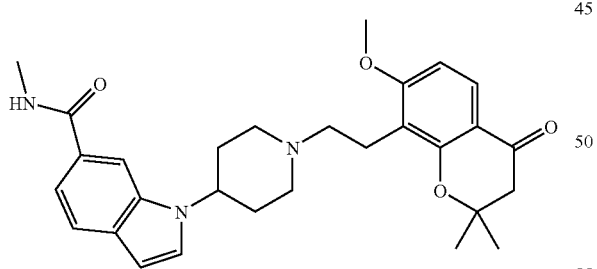

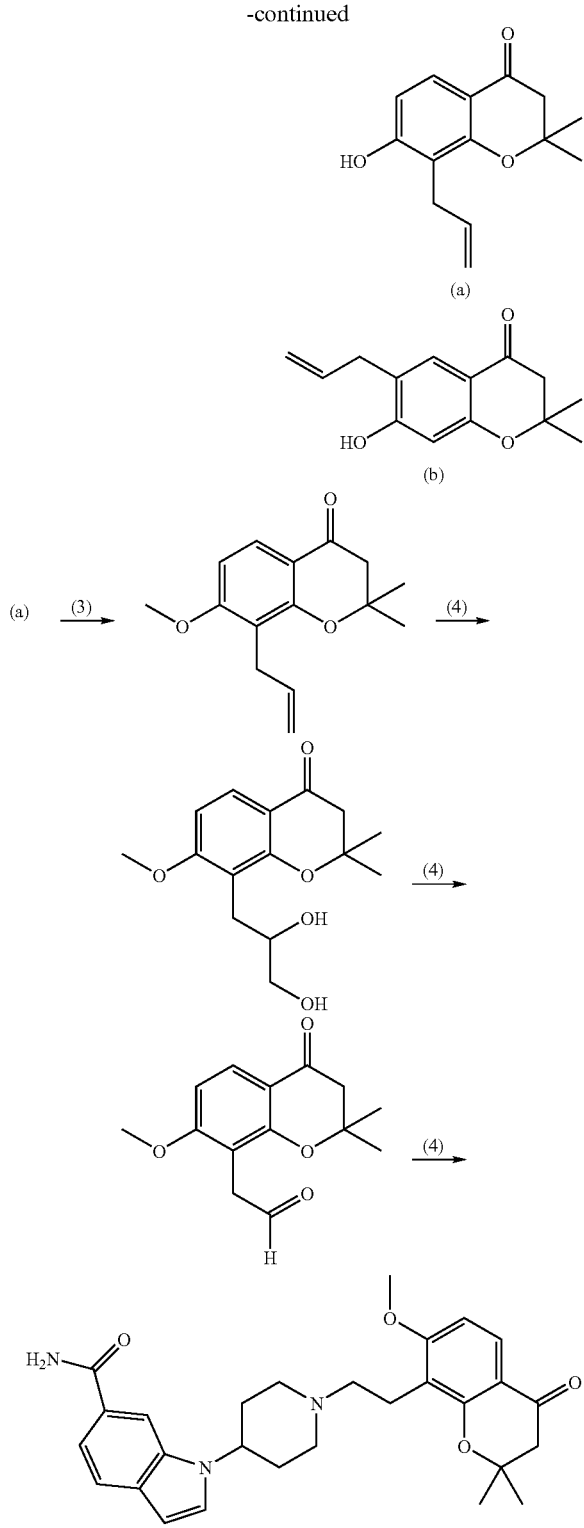

(1) 7-Allyloxy-2,2-dimethyl-4-oxochroman 9.74 g of 7-hydroxy-2,2-dimethyl-4-oxochroman (CAS#: 17771-33-4) was dissolved in 150 ml of N,N-dimethylformamide. Thereafter, 10.5 g of potassium carbonate and 7.36 g of allyl bromide were added to the reaction solution, and the obtained mixture was stirred at room temperature overnight. Thereafter, the reaction solution was diluted with ethyl acetate, and then washed with water and a saturated sodium chloride aqueous solution. The organic layer was dried over magnesium sulfate and then concentrated under a reduced pressure. The residue was then purified by silica gel column chromatography (hexane-ethyl acetate), so as to obtain 11.0 g of the subject compound.

$^1$H-NMR (CDCl$_3$) δ (ppm): 1.45 (s, 6H), 2.67 (s, 2H), 4.53-4.58 (m, 2H), 5.28-5.35 (m, 1H), 5.37-5.46 (m, 1H), 5.98-6.09 (m, 1H), 6.38 (d, J=2.4 Hz, 1H), 6.56 (dd, J=2.4, 8.8 Hz, 1H), 7.80 (d, J=8.8 Hz, 1H).

2) 8-Allyl-7-hydroxy-2,2-dimethyl-4-oxochroman (a) and 6-allyl-7-hydroxy-2,2-dimethyl-4-oxochroman (b)

1.97 g of 7-allyloxy-2,2-dimethyl-4-oxochroman was dissolved in 5 ml of N,N-dimethylaniline under nitrogen atmosphere, and the reaction solution was heated to reflux for 6 hours. Thereafter, the reaction solution was cooled to room temperature. It was then purified by silica gel column chromatography (hexane-ethyl acetate), so as to obtain a mixture consisting of the subject compounds (a) and (b). The mixture was further purified by high performance liquid chromatography (ODS-AM; acetonitrile-water), so as to obtain 1.05 g of the subject compound (a) and 95 mg of the subject compound (b).

Isomer (a)
$^1$H-NMR (CDCl$_3$) δ (ppm): 1.44 (s, 6H), 2.66 (s, 2H), 3.40-3.46 (m, 2H), 5.03-5.17 (m, 2H), 5.55 (s, 1H), 5.86-6.00 (m, 1H), 6.47 (d, J=8.8 Hz, 1H), 7.71 (d, J=8.8 Hz, 1H).

Isomer (b)
$^1$H-NMR (CDCl$_3$) δ (ppm): 1.44 (s, 6H), 2.65 (s, 2H), 3.34-3.37 (m, 2H), 5.14-5.21 (m, 2H), 5.60 (s, 1H), 5.93-6.04 (m, 1H), 6.32 (s, 1H), 7.63 (s, 1H).

(3) 8-Allyl-7-methoxy-2,2-dimethyl-4-oxochroman 567 mg of 8-allyl-7-hydroxy-2,2-dimethyl-4-oxochroman was dissolved in 15 ml of N,N-dimethylformamide. Thereafter, 0.51 g of potassium carbonate and 0.42 g of iodomethane were added to the reaction solution, and the obtained mixture was then stirred at room temperature overnight. The reaction solution was diluted with ethyl acetate, and then washed with a saturated ammonium chloride aqueous solution and a saturated sodium chloride aqueous solution. The organic layer was dried over magnesium sulfate, and then concentrated under a reduced pressure. The residue was purified by silica gel column chromatography (hexane-ethyl acetate), so as to obtain 582 mg of the subject compound.

$^1$H-NMR (CDCl$_3$) δ (ppm): 1.44 (s, 6H), 2.67 (s, 2H), 3.36-3.40 (m, 2H), 3.88 (s, 3H), 4.92-5.04 (m, 2H), 5.84-5.95 (m, 1H), 6.58 (d, J=8.8 Hz, 1H), 7.80 (d, J=8.8 Hz, 1H).

(4) 1-(1-(2-(7-Methoxy-2,2-dimethyl-4-oxochroman-8-yl)ethyl)piperidin-4-yl)-1H-indole-6-carboxamide 150 mg of 8-allyl-7-methoxy-2,2-dimethyl-4-oxochroman was dissolved in 16 ml of t-butanol-water (1:1). Thereafter, 0.85 g of AD-mix-β was added to the reaction solution, and the obtained mixture was then stirred at room temperature overnight. Thereafter, 0.91 g of sodium sulfite was added to the reaction solution while cooling on ice, and the obtained mixture was stirred at room temperature for 1 hour. The reaction solution was diluted with ethyl acetate and then washed with a saturated sodium chloride aqueous solution. The organic layer was dried over magnesium sulfate and then concentrated under reduced pressure, so as to obtain 171 mg of 8-(2,3-dihydroxypropyl)-7-methoxy-2,2-dimethyl-4-oxochroman. This compound was used in the following reaction without further purification.

171 mg of 8-(2,3-dihydroxypropyl)-7-methoxy-2,2-dimethyl-4-oxochroman was dissolved in 4 ml of tetrahydrofuran and 4 ml of methanol. Thereafter, 8 ml of water containing 0.26 g of sodium metaperiodate was added to the reaction solution while cooling on ice, and the obtained mixture was then stirred at room temperature for 30 minutes. The reaction solution was diluted with ethyl acetate and then washed with a saturated sodium chloride aqueous solution. The organic layer was dried over magnesium sulfate and then concentrated under a reduced pressure, so as to obtain 163 mg of (7-methoxy-2,2-dimethyl-4-oxochroman-8-yl)acetaldehyde. This compound was used in the following reaction without further purification.

120 mg of 1-(piperidin-4-yl)-1H-indole-6-carboxamide and 163 mg of (7-methoxy-2,2-dimethyl-4-oxochroman-8-yl)acetaldehyde were dissolved in 10 ml of methylene chloride. Thereafter, 0.06 ml of acetic acid was added to the reaction solution, and the obtained mixture was then stirred at room temperature for 15 minutes. Thereafter, 157 mg of sodium triacetoxyborohydride was added to the reaction solution, and the obtained mixture was then stirred at room temperature for 1 hour. Thereafter, a saturated sodium bicarbonate aqueous solution was added to the reaction solution, followed by extraction with chloroform. The extract was dried over magnesium sulfate and then concentrated under a reduced pressure. The residue was purified by NH silica gel column chromatography (methanol-ethyl acetate), followed by solidification with ethyl acetate, so as to obtain 220 mg of the subject compound.

$^1$H-NMR (DMSO-$d_6$) δ (ppm): 1.40 (s, 6H), 1.93-2.10 (m, 4H), 2.22-2.35 (m, 2H), 2.42-2.50 (m, 2H), 2.72 (s, 2H), 2.74-2.82 (m, 2H), 3.08-3.17 (m, 2H), 3.87 (s, 3H), 4.37-4.48 (m, 1H), 6.50 (d, J=3.2 Hz, 1H), 6.75 (d, J=8.8 Hz, 1H), 7.21 (br.s, 1H), 7.53-7.61 (m, 2H), 7.65 (d, J=8.8 Hz, 1H), 7.67 (d, J=3.2 Hz, 1H), 7.91 (br.s, 1H), 8.13 (s, 1H).

Example 23

Synthesis of 1-{1-[2-(6-methoxy-1-methyl-2-oxo-1,4-dihydro-2H-benz[d][1,3]oxazin-7-yl)ethyl]piperidin-4-yl}-N-methyl-1H-indole-6-carboxamide

[Formula 82]

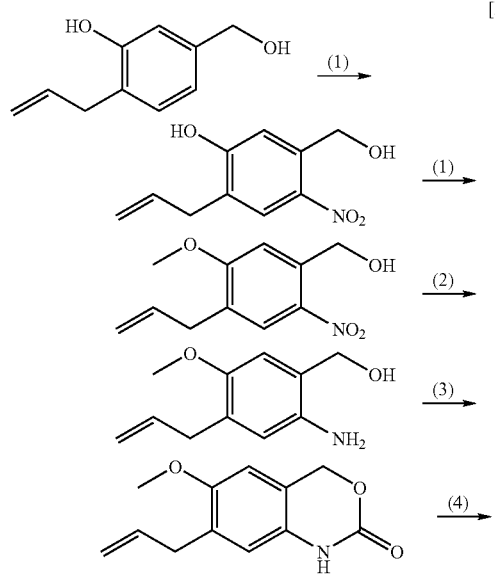

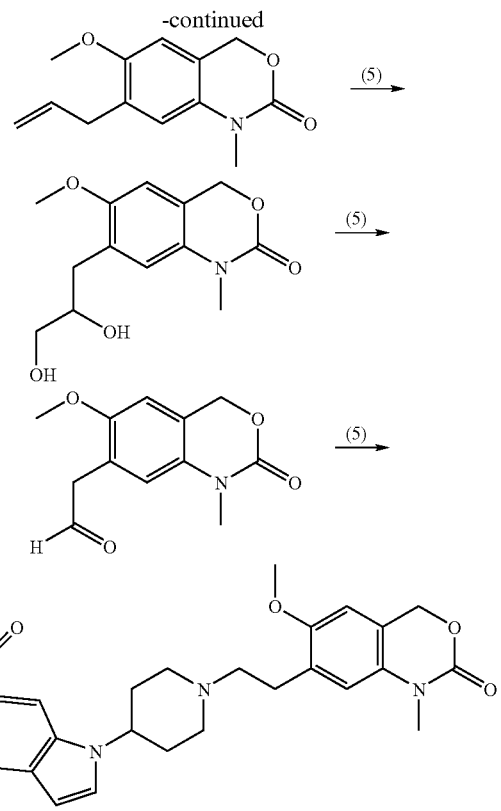

(1) 3-Methoxy-6-nitro-4-(2-propenyl)benzylalcohol 8.40 g of 3-hydroxy-4-(2-propenyl)benzylalcohol (Tetrahedron, 56 (2000), 1873) was dissolved in 70 ml of acetic acid. Thereafter, 4.14 g of concentrated nitric acid and 0.6 ml of fuming nitric acid were added to the reaction solution while cooling on ice, and the obtained mixture was stirred at the same temperature for 20 minutes. Thereafter, the reaction solution was adjusted to be pH 6 with addition of a 5 N sodium hydroxide aqueous solution, while cooling on ice. It was then extracted with ethyl acetate. The extract was washed with a saturated sodium bicarbonate aqueous solution and a saturated sodium chloride aqueous solution. The organic layer was dried over magnesium sulfate and then concentrated under a reduced pressure. The residue was then purified by silica gel column chromatography (hexane-ethyl acetate), so as to obtain 4.68 g of 3-hydroxy-6-nitro-4-(2-propenyl)benzylalcohol.

4.68 g of 3-hydroxy-6-nitro-4-(2-propenyl)benzylalcohol was dissolved in 90 ml of N,N-dimethylformamide. Thereafter, 3.71 g of potassium carbonate and 3.81 g of iodomethane were added to the reaction solution, and the obtained mixture was stirred at room temperature overnight. The reaction solution was extracted with ethyl acetate, and then washed with water and a saturated sodium chloride aqueous solution. The organic layer was dried over magnesium sulfate and then concentrated under a reduced pressure. The residue was then purified by silica gel column chromatography (hexane-ethyl acetate), so as to obtain 3.93 g of the subject compound.

$^1$H-NMR (DMSO-$d_6$) δ (ppm): 3.38 (d, J=6.8 Hz, 2H), 3.94 (s, 3H), 4.87 (d, J=4.8 Hz, 2H), 5.05-5.13 (m, 2H), 5.62 (t, J=4.8 Hz, 1H), 5.89-6.02 (m, 1H), 7.42 (s, 1H), 7.94 (s, 1H).

(2) 2-amino-5-methoxy-4-(2-propenyl)benzylalcohol 24 ml of ethanol-water (5:1) was added to 1.00 g of 3-methoxy-6-nitro-4-(2-propenyl)benzylalcohol, 1.00 g of iron, and 2.00 g of ammonium chloride. The reaction solution was stirred at 90° C. for 1 hour. Thereafter, the reaction solution was cooled to a room temperature, and insoluble matters were then removed by filtration. The filtrate was concentrated under a reduced pressure. The residue was diluted with ethyl acetate and then washed with water and a saturated sodium chloride aqueous solution. The organic layer was dried over magnesium sulfate and then concentrated under a reduced pressure, so as to obtain 793 mg of the subject compound.

$^1$H-NMR (CDCl$_3$) δ (ppm): 3.32 (d, J=6.0 Hz, 2H), 3.76 (s, 3H), 4.64 (s, 2H), 5.00-5.09 (m, 2H), 5.88-6.00 (m, 1H), 6.54 (s, 1H), 6.64 (s, 1H).

(3) 7-allyl-6-methoxy-1,4-dihydrobenz[d][1,3]oxazin-2-one 677 mg of 2-amino-5-methoxy-4-(2-propenyl)benzylalcohol was dissolved in 20 ml of tetrahydrofuran under nitrogen atmosphere. Thereafter, 0.52 g of triphosgene and 1.46 ml of triethylamine were added to the reaction solution while cooling on ice. The obtained mixture was then stirred at room temperature for 30 minutes. Thereafter, while cooling on ice, water and ammonia water were added to the reaction solution until foaming was terminated. The reaction solution was diluted with ethyl acetate and then washed with water and a saturated sodium chloride aqueous solution. The organic layer was dried over magnesium sulfate and then concentrated under a reduced pressure. The residue was purified by silica gel column chromatography (hexane-ethyl acetate) and then reprecipitated from ethyl acetate, so as to obtain 485 mg of the subject compound.

$^1$H-NMR (DMSO-d$_6$) δ (ppm): 3.26 (d, J=6.4 Hz, 2H), 3.73 (s, 3H), 4.99-5.06 (m, 2H), 5.22 (s, 2H), 5.83-5.95 (m, 1H), 6.65 (s, 1H), 6.86 (s, 1H), 9.92 (br.s, 1H).

(4) 7-Allyl-6-methoxy-1-methyl-1,4-dihydrobenz[d][1,3]oxazin-2-one 210 mg of 7-allyl-6-methoxy-1,4-dihydrobenz[d][1,3]oxazin-2-one was dissolved in 6 ml of N,N-dimethylformamide. Thereafter, 46 mg of 60% sodium hydride was added to the reaction solution while cooling on ice. The obtained mixture was then stirred at room temperature for 20 minutes. Thereafter, while cooling on ice, 0.20 g of iodomethane was added to the reaction solution. The obtained mixture was then stirred at room temperature for 2 hours. Thereafter, the reaction solution was diluted with ethyl acetate and then washed with water and a saturated sodium chloride aqueous solution. The organic layer was dried over magnesium sulfate and then concentrated under a reduced pressure. The residue was purified by silica gel column chromatography (hexane-ethyl acetate), so as to obtain 207 mg of the subject compound.

$^1$H-NMR (DMSO-d$_6$) δ (ppm): 3.23 (s, 3H), 3.31-3.36 (m, 2H), 3.76 (s, 3H), 4.99-5.07 (m, 2H), 5.19 (s, 2H), 5.89-6.00 (m, 1H), 6.87 (s, 1H), 6.95 (s, 1H).

(5) 1-{1-[2-(6-Methoxy-1-methyl-2-oxo-1,4-dihydro-2H-benz[d](1,3)-oxazin-7-yl)ethyl]piperidin-4-yl}-N-methyl-1H-indole-6-carboxamide 160 mg of 7-allyl-6-methoxy-1-methyl-1,4-dihydrobenz[d][1,3]oxazin-2-one was dissolved in 20 ml of t-butanol-water (1:1). Thereafter, 0.96 g of AD-mix-β was added to the reaction solution, and the obtained mixture was then stirred at room temperature overnight. Thereafter, 1.03 g of sodium sulfite was added to the reaction solution while cooling on ice, and the obtained mixture was stirred at room temperature for 1 hour. A saturated sodium chloride aqueous solution was added to the reaction solution, followed by extraction with methylene chloride. The extract was dried over magnesium sulfate and then concentrated under a reduced pressure, so as to obtain 280 mg of 7-(2,3-dihydroxypropyl)-6-methoxy-1-methyl-1,4-dihydrobenz[d][1,3]oxazin-2-one. This compound was used in the following reaction without further purification.

280 mg of 7-(2,3-dihydroxypropyl)-6-methoxy-1-methyl-1,4-dihydrobenz[d][1,3]oxazin-2-one was dissolved in 4 ml of tetrahydrofuran and 4 ml of methanol. Thereafter, 8 ml of water containing 0.29 g of sodium metaperiodate was added to the reaction solution while cooling on ice, and the obtained mixture was then stirred at room temperature for 30 minutes. The reaction solution was diluted with ethyl acetate and then washed with a saturated sodium chloride aqueous solution. The organic layer was dried over magnesium sulfate and then concentrated under a reduced pressure. The residue was purified by silica gel column chromatography (ethyl acetate), so as to obtain 167 mg of (6-methoxy-1-methyl-2-oxo-1,4-dihydro-2H-benz[d][1,3]oxazin-7-yl)acetaldehyde.

80 mg of N-methyl-1-(piperidin-4-yl)-1H-indole-6-carboxamide and 83 mg of (6-methoxy-1-methyl-2-oxo-1,4-dihydro-2H-benz[d][1,3]oxazin-7-yl)acetaldehyde were dissolved in 6 ml of methylene chloride. Thereafter, 0.04 ml of acetic acid and 99 mg of sodium triacetoxyborohydride were added to the reaction solution, and the obtained mixture was then stirred at room temperature for 3 hours. Thereafter, a saturated sodium bicarbonate aqueous solution was added to the reaction solution, and then extracted with methylene chloride. The extract was dried over magnesium sulfate and then concentrated under a reduced pressure. The residue was purified by silica gel column chromatography (methanol-ethyl acetate), so as to obtain 141 mg of the subject compound.

$^1$H-NMR (DMSO-d$_6$) δ (ppm): 1.92-2.10 (m, 4H), 2.23-2.32 (m, 2H), 2.51-2.61 (m, 2H), 2.77-2.85 (m, 2H), 2.82 (d, J=4.4 Hz, 3H), 3.08-3.15 (m, 2H), 3.26 (s, 3H), 3.79 (s, 3H), 4.37-4.47 (m, 1H), 5.19 (s, 2H), 6.50 (d, J=3.2 Hz, 1H), 6.94 (s, 1H), 6.99 (s, 1H), 7.52-7.59 (m, 2H), 7.67 (d, J=3.2 Hz, 1H), 8.06 (s, 1H), 8.30-8.37 (m, 1H).

Example 24

Synthesis of 1-{1-[2-(7-methoxy-2,2-dimethyl-4-oxochroman-6-yl)ethyl]piperidin-4-yl}-1H-indole-6-carboxamide

[Formula 83]

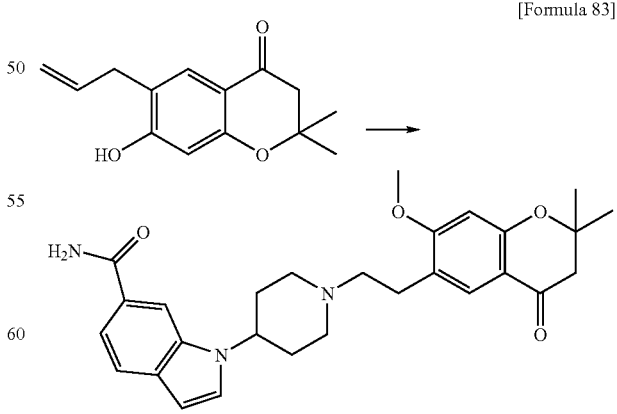

The subject compound was synthesized from 6-allyl-7-hydroxy-2,2-dimethyl-4-oxochroman according to the method described in Example 22, (3) and (4).

¹H-NMR (DMSO-d₆) δ (ppm): 1.39 (s, 6H), 1.92-2.08 (m, 4H), 2.21-2.31 (m, 2H), 2.45-2.56 (m, 2H), 2.65-2.75 (m, 2H), 2.69 (s, 2H), 3.06-3.15 (m, 2H), 3.85 (s, 3H), 4.37-4.47 (m, 1H), 6.50 (d, J=3.2 Hz, 1H), 6.53 (s, 1H), 7.20 (br.s, 1H), 7.50-7.60 (m, 2H), 7.53 (s, 1H), 7.67 (d, J=3.2 Hz, 1H), 7.91 (br.s, 1H), 8.13 (s, 1H).

Example 25

Synthesis of 1-{1-[2-(5-methoxy-1-oxoindan-4-yl)ethyl]piperidin-4-yl}-1H-indole-6-carboxamide

[Formula 84]

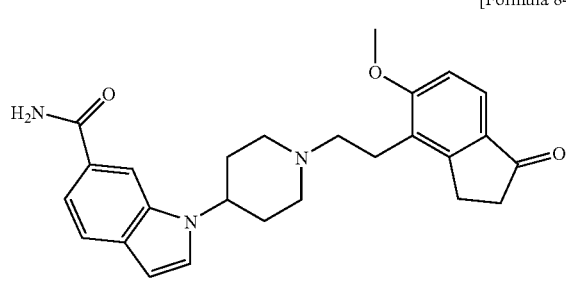

The subject compound was synthesized from 5-hydroxy-1-indanone according to the method described in Example 22.

¹H-NMR (DMSO-d₆) δ (ppm): 1.93-2.10 (m, 4H), 2.24-2.34 (m, 2H), 2.47-2.57 (m, 2H), 2.58-2.65 (m, 2H), 2.80-2.87 (m, 2H), 3.03-3.17 (m, 4H), 3.91 (s, 3H), 4.38-4.47 (m, 1H), 6.51 (d, J=3.2 Hz, 1H), 7.10 (d, J=8.4 Hz, 1H), 7.21 (br.s, 1H), 7.51-7.61 (m, 3H), 7.68 (d, J=3.2 Hz, 1H), 7.91 (br.s, 1H), 8.13 (s, 1H).

Example 26

Synthesis of 1-{1-[2-(6-methoxy-3-oxoindan-5-yl)ethyl]piperidin-4-yl}-1H-indole-6-carboxamide

[Formula 85]

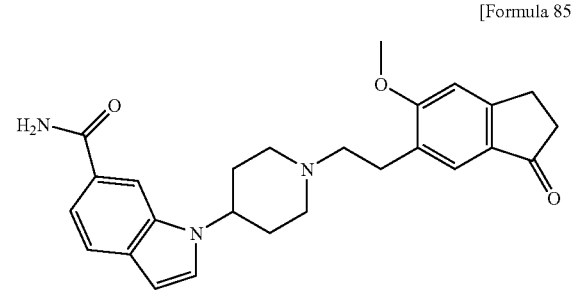

The subject compound was synthesized from 5-hydroxy-1-indanone according to the method described in Example 22.

¹H-NMR (DMSO-d₆) δ (ppm): 1.92-2.07 (m, 4H), 2.21-2.32 (m, 2H), 2.50-2.61 (m, 4H), 2.76-2.84 (m, 2H), 3.02-3.16 (m, 4H), 3.92 (s, 3H), 4.36-4.47 (m, 1H), 6.50 (d, J=2.8 Hz, 1H), 7.13 (s, 1H), 7.21 (br.s, 1H), 7.46 (s, 1H), 7.52-7.61 (m, 2H), 7.64-7.69 (m, 1H), 7.91 (br.s, 1H), 8.13 (s, 1H).

Example 27

Synthesis of 1-{1-[2-(5-methoxy-2-methylbenzothiazol-4-yl)ethyl]piperidin-4-yl}-1H-indole-6-carboxamide

[Formula 86]

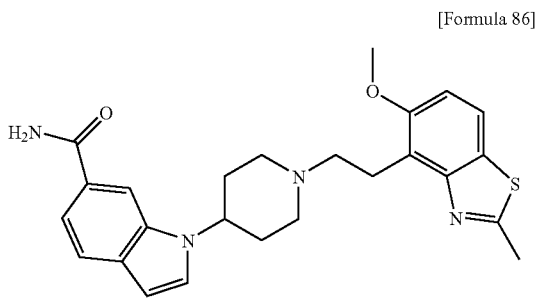

The subject compound was synthesized from 2-methyl-5-benzothiazole according to the method described in Example 22.

¹H-NMR (DMSO-d₆) δ (ppm): 1.94-2.09 (m, 4H), 2.24-2.34 (m, 2H), 2.55-2.63 (m, 2H), 2.78 (s, 3H), 3.13-3.30 (m, 4H), 3.88 (s, 3H), 4.37-4.47 (m, 1H), 6.50 (d, J=3.2 Hz, 1H), 7.16 (d, J=8.8 Hz, 1H), 7.21 (br.s, 1H), 7.53-7.61 (m, 2H), 7.67 (d, J=3.2 Hz, 1H), 7.81 (d, J=8.8 Hz, 1H), 7.91 (br.s, 1H), 8.13 (s, 1H).

Example 28

Synthesis of 1-{1-[2-(5-methoxy-2-methylbenzothiazol-6-yl)ethyl]piperidin-4-yl}-1H-indole-6-carboxamide

[Formula 87]

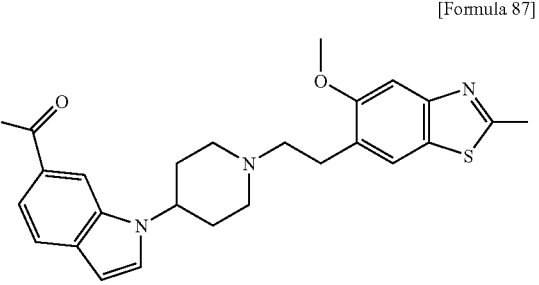

The subject compound was synthesized from 2-methyl-5-benzothiazole according to the method described in Example 22.

¹H-NMR (DMSO-d₆) δ (ppm): 1.93-2.09 (m, 4H), 2.23-2.32 (m, 2H), 2.57-2.63 (m, 2H), 2.76 (s, 3H), 2.84-2.90 (m, 2H), 3.08-3.16 (m, 2H), 3.88 (s, 3H), 4.37-4.48 (m, 1H), 6.50 (d, J=2.8 Hz, 1H), 7.20 (br.s, 1H), 7.47 (s, 1H), 7.53-7.61 (m, 2H), 7.67 (d, J=2.8 Hz, 1H), 7.80 (s, 1H), 7.91 (br.s, 1H), 8.13 (s, 1H).

Example 29

Synthesis of 1-{1-[2-(7-methoxyquinolin-8-yl)ethyl]piperidin-4-yl}-1H-indole-6-carboxamide

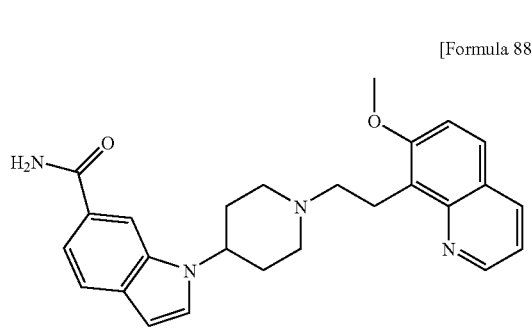

[Formula 88]

The subject compound was synthesized from 7-hydroxyquinoline according to the method described in Example 22.

$^1$H-NMR (DMSO-d$_6$) δ (ppm): 1.95-2.11 (m, 4H), 2.26-2.36 (m, 2H), 2.54-2.63 (m, 2H), 3.17-3.25 (m, 2H), 3.40-3.47 (m, 2H), 3.99 (s, 3H), 4.38-4.48 (m, 1H), 6.51 (d, J=3.2 Hz, 1H), 7.21 (br.s, 1H), 7.37 (dd, J=4.0, 8.0 Hz, 1H), 7.52-7.60 (m, 3H), 7.68 (d, J=3.2 Hz, 1H), 7.88 (d, J=9.2 Hz, 1H), 7.92 (br.s, 1H), 8.14 (s, 1H), 8.27 (dd, J=2.0, 8.0 Hz, 1H), 8.89 (dd, J=2.0, 4.0 Hz, 1H).

Example 30

Synthesis of 1-{1-[2-(6-methoxyquinolin-5-yl)ethyl]piperidin-4-yl}-1H-indole-6-carboxamide

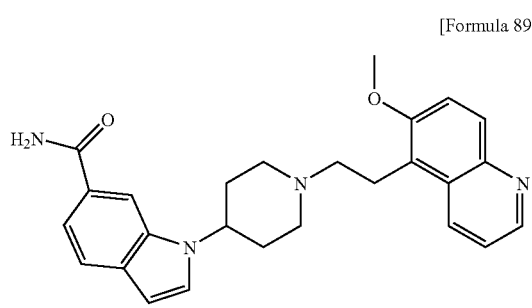

[Formula 89]

The subject compound was synthesized from 6-hydroxyquinoline according to the method described in Example 22.

$^1$H-NMR (DMSO-d$_6$) δ (ppm): 1.96-2.12 (m, 4H), 2.29-2.38 (m, 2H), 2.48-2.58 (m, 2H), 3.17-3.30 (m, 4H), 3.98 (s, 3H), 4.39-4.50 (m, 1H), 6.51 (d, J=3.6 Hz, 1H), 7.21 (br.s, 1H), 7.50-7.62 (m, 3H), 7.66-7.72 (m, 2H), 7.92 (br.s, 1H), 7.95 (d, J=9.2 Hz, 1H), 8.14 (s, 1H), 8.42 (d, J=9.2 Hz, 1H), 8.77-8.79 (m, 1H).

Example 31

Synthesis of 1-{1-[2-(7-methoxy-2,3-dihydrobenz[1,4]dioxin-6-yl)ethyl]piperidin-4-yl}-1H-indole-6-carboxamide

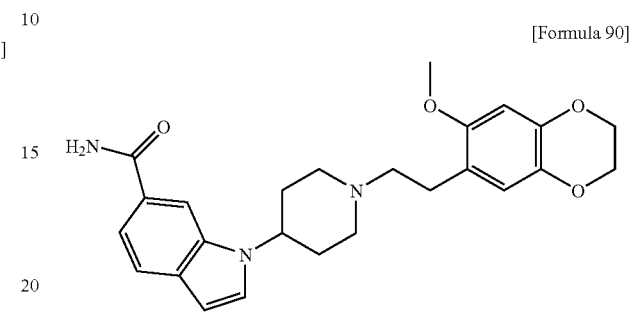

[Formula 90]

The subject compound was synthesized from 6-hydroxy-1,4-benzodioxane (CAS#: 10288-72-9) according to the method described in Example 22.

$^1$H-NMR (DMSO-d$_6$) δ (ppm): 1.92-2.08 (m, 4H), 2.19-2.28 (m, 2H), 2.45-2.54 (m, 2H), 2.61-2.67 (m, 2H), 3.05-3.12 (m, 2H), 3.70 (s, 3H), 4.13-4.22 (m, 4H), 4.36-4.46 (m, 1H), 6.48 (s, 1H), 6.50 (d, J=3.2 Hz, 1H), 6.69 (s, 1H), 7.21 (br.s, 1H), 7.54-7.60 (m, 2H), 7.67 (d, J=3.2 Hz, 1H), 7.91 (br.s, 1H), 8.12 (s, 1H).

Example 32

Synthesis of 1-{1-[2-(6-methoxy-2,3-dihydrobenz[1,4]dioxin-5-yl)ethyl]piperidin-4-yl}-1H-indole-6-carboxamide

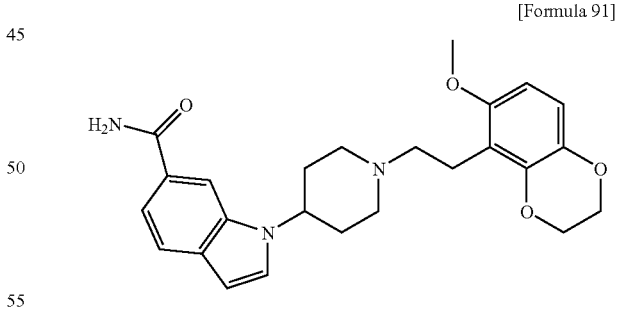

[Formula 91]

The subject compound was synthesized from 6-hydroxy-1,4-benzodioxane (CAS#: 10288-72-9) according to the method described in Example 22.

$^1$H-NMR (DMSO-d$_6$) δ (ppm): 1.92-2.09 (m, 4H), 2.19-2.30 (m, 2H), 2.40-2.48 (m, 2H), 2.71-2.79 (m, 2H), 3.07-3.14 (m, 2H), 3.72 (s, 3H), 4.13-4.19 (m, 2H), 4.23-4.28 (m, 2H), 4.37-4.46 (m, 1H), 6.47 (d, J=8.8 Hz, 1H), 6.50 (d, J=3.2 Hz, 1H), 6.66 (d, J=8.8 Hz, 1H), 7.21 (br.s, 1H), 7.53-7.61 (m, 2H), 7.67 (d, J=3.2 Hz, 1H), 7.91 (br.s, 1H), 8.12 (s, 1H).

Example 33

Synthesis of 1-{1-[2-(6-methoxy-2-methyl-1-oxo-1,2,3,4-tetrahydroisoquinolin-7-yl)ethyl]piperidin-4-yl}-1H-indole-6-carboxamide

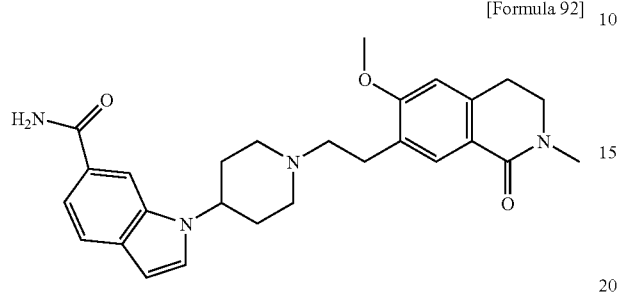

[Formula 92]

The subject compound was synthesized from 6-hydroxy-2-methyl-3,4-dihydro-2H-isoquinolin-1-one (CAS#: 308110-07-8) according to the method described in Example 22.

¹H-NMR (DMSO-d₆) δ (ppm): 1.92-2.08 (m, 4H), 2.21-2.31 (m, 2H), 2.50-2.57 (m, 2H), 2.74-2.81 (m, 2H), 2.94 (t, J=6.4 Hz, 2H), 3.07-3.14 (m, 2H), 3.51 (t, J=6.4 Hz, 2H), 3.85 (s, 3H), 4.37-4.47 (m, 1H), 6.50 (d, J=2.8 Hz, 1H), 6.86 (s, 1H), 7.21 (br.s, 1H), 7.53-7.61 (m, 2H), 7.67 (s, 1H), 7.67 (d, J=2.8 Hz, 1H), 7.91 (br.s, 1H), 8.13 (s, 1H).

Example 34

Synthesis of 1-(1-(2-(6-methoxy-2-methyl-1-oxo-1,2,3,4-tetrahydroisoquinolin-5-yl)ethyl)piperidin-4-yl)-1H-indole-6-carboxamide

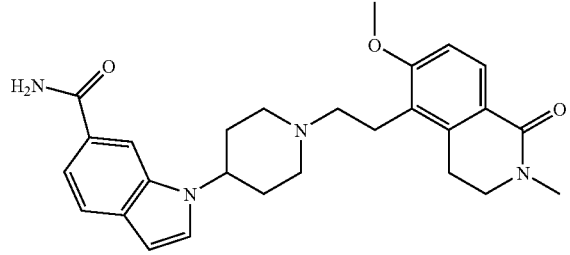

[Formula 93]

The subject compound was synthesized from 6-hydroxy-2-methyl-3,4-dihydro-2H-isoquinolin-1-one (CAS#: 308110-07-8) according to the method described in Example 22.

¹H-NMR (DMSO-d₆) δ (ppm): 1.93-2.09 (m, 4H), 2.23-2.34 (m, 2H), 2.38-2.48 (m, 2H), 2.78-2.87 (m, 2H), 2.94-3.03 (m, 2H), 3.00 (s, 3H), 3.07-3.16 (m, 2H), 3.49-3.56 (m, 2H), 3.85 (s, 3H), 4.37-4.47 (m, 1H), 6.48-6.53 (m, 1H), 6.97 (d, J=8.4 Hz, 1H), 7.21 (br.s, 1H), 7.53-7.61 (m, 2H), 7.68 (d, J=3.2 Hz, 1H), 7.85 (d, J=8.4 Hz, 1H), 7.91 (br.s, 1H), 8.12 (s, 1H).

Example 35

Synthesis of 1-{1-[2-(7-methoxy-4-oxo-4H-chromen-8-yl)ethyl]piperidin-4-yl}-1H-indole-6-carboxamide

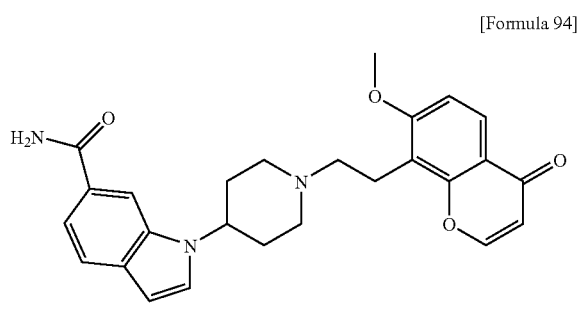

[Formula 94]

The subject compound was synthesized from 7-hydroxy-4H-1-benzopyran-4-one (J. Med. Chem. 34 (1991) 1, 248) according to the method described in Example 22.

¹H-NMR (DMSO-d₆) δ (ppm): 1.95-2.07 (m, 4H), 2.25-2.35 (m, 2H), 2.50-2.58 (m, 2H), 2.99-3.05 (m, 2H), 3.11-3.19 (m, 2H), 3.96 (s, 3H), 4.38-4.48 (m, 1H), 6.27 (d, J=6.0 Hz, 1H), 6.50 (d, J=2.8 Hz, 1H), 7.21 (br.s, 1H), 7.25 (d, J=9.2 Hz, 1H), 7.54-7.60 (m, 2H), 7.66 (d, J=3.2 Hz, 1H), 7.91 (br.s, 1H), 7.94 (d, J=9.2 Hz, 1H), 8.13 (s, 1H), 8.31 (d, J=6.4 Hz, 1H).

Example 36

Synthesis of 1-{1-[2-(7-methoxy-2,3-dimethyl-4-oxo-4H-chromen-8-yl)ethyl]piperidin-4-yl}-1H-indole-6-carboxamide

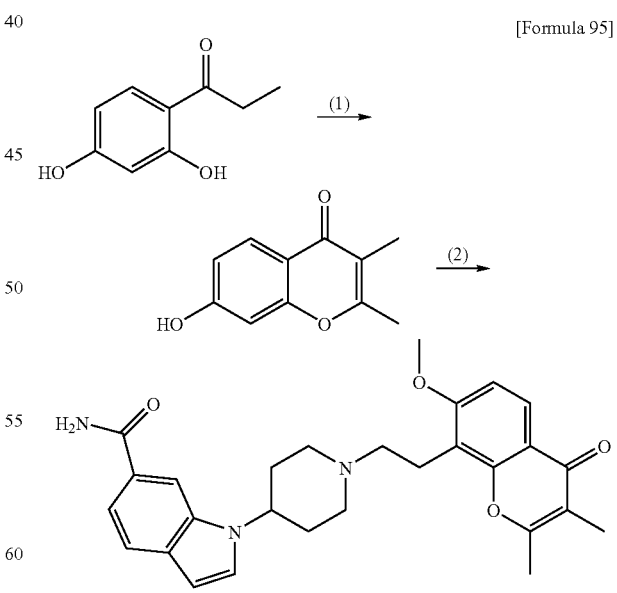

[Formula 95]

(1) 2,3-Dimethyl-7-hydroxy-4H-1-benzopyran-4-one

The subject compound was synthesized from 2',4'-dihydroxypropiophenone in accordance with Bull. Chem. Soc. Jpn., 67, 1972 (1994).

¹H-NMR (DMSO-d₆) δ (ppm): 1.91 (s, 3H), 2.36 (s, 3H), 6.76 (d, J=1.6 Hz, 1H), 6.86 (dd, J=1.6, 8.8 Hz, 1H), 7.84 (d, J=8.8 Hz, 1H), 10.64 (br.s, 1H).

(2) 1-{1-[2-(7-methoxy-2,3-dimethyl-4-oxo-4H-chromen-8-yl)ethyl]piperidin-4-yl}-1H-indole-6-carboxamide The subject compound was synthesized from 2,3-dimethyl-7-hydroxy-4H-1-benzopyran-4-one according to the method described in Example 22.

¹H-NMR (DMSO-d₆) δ (ppm): 1.92-2.07 (m, 4H), 1.94 (s, 3H), 2.27-2.36 (m, 2H), 2.43 (s, 3H), 2.51-2.60 (m, 2H), 2.97-3.05 (m, 2H), 3.13-3.21 (m, 2H), 3.95 (s, 3H), 4.38-4.48 (m, 1H), 6.50 (d, J=3.2 Hz, 1H), 7.19 (d, J=8.8 Hz, 1H), 7.21 (br.s, 1H), 7.53-7.60 (m, 2H), 7.67 (d, J=3.2 Hz, 1H), 7.86-7.94 (m, 1H), 7.91 (d, J=8.8 Hz, 1H), 8.13 (s, 1H).

Example 37

Synthesis of 1-{1-[2-(7-methoxy-3,3-dimethyl-4-oxochroman-8-yl)ethyl]piperidin-4-yl}-1H-indole-6-carboxamide

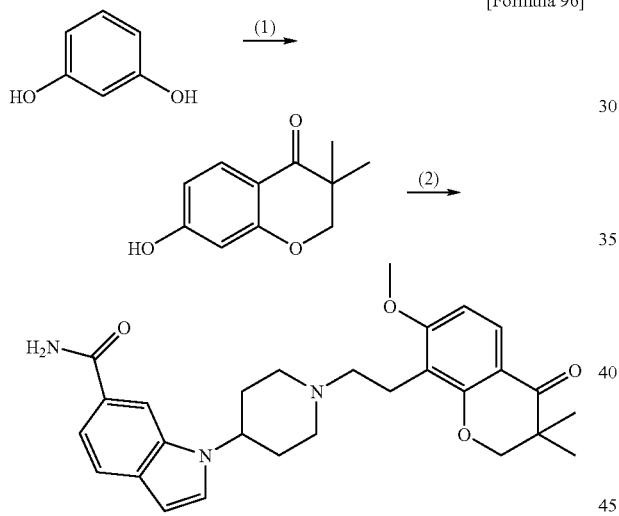

[Formula 96]

(1) 7-Hydroxy-3,3-dimethyl-4-oxochromane

The subject compound was synthesized from resorcinol and 3-chloropivalic acid in accordance with J. Org. Chem. 1994, 59, 1216.

¹H-NMR (DMSO-d₆) δ (ppm): 1.06 (s, 6H), 4.14 (s, 2H), 6.31 (d, J=2.4 Hz, 1H), 6.50 (dd, J=2.4, 8.8 Hz, 1H), 7.61 (d, J=8.8 Hz, 1H), 10.53 (br.s, 1H).

(2) 1-{1-[2-(7-Methoxy-3,3-dimethyl-4-oxochroman-8-yl)ethyl]piperidin-4-yl}-1H-indole-6-carboxamide The subject compound was synthesized from 7-hydroxy-3,3-dimethyl-4-oxochromane according to the method described in Example 22.

¹H-NMR (DMSO-d₆) δ (ppm): 1.09 (s, 6H), 1.92-2.08 (m, 4H), 2.20-2.30 (m, 2H), 2.43-2.52 (m, 2H), 2.76-2.84 (m, 2H), 3.08-3.16 (m, 2H), 3.88 (s, 3H), 4.23 (s, 2H), 4.37-4.46 (m, 1H), 6.50 (d, J=3.2 Hz, 1H), 6.82 (d, J=8.8 Hz, 1H), 7.21 (br.s, 1H), 7.54-7.61 (m, 2H), 7.65 (d, J=3.2 Hz, 1H), 7.69 (d, J=8.8 Hz, 1H), 7.91 (br.s, 1H), 8.12 (s, 1H).

Example 38

Synthesis of 1-{1-[2-(6-methoxy-2-methyl-1-oxo-1,2,3,4-tetrahydroisoquinolin-7-yl)ethyl]piperidin-4-yl}-N-methyl-1H-indole-6-carboxamide

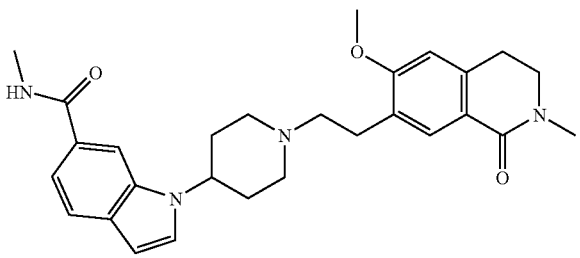

[Formula 97]

The subject compound was synthesized from 6-hydroxy-2-methyl-3,4-dihydro-2H-isoquinolin-1-one (CAS#: 308110-07-8) according to the methods described in Example 22, (1), (2) and (3), and Example 23, (5).

¹H-NMR (DMSO-d₆) δ (ppm): 1.92-2.08 (m, 4H), 2.23-2.31 (m, 2H), 2.49-2.57 (m, 2H), 2.74-2.81 (m, 2H), 2.82 (d, J=4.4 Hz, 3H), 2.94 (t, J=6.4 Hz, 2H), 2.99 (s, 3H), 3.07-3.16 (m, 2H), 3.51 (t, J=6.4 Hz, 2H), 3.86 (s, 3H), 4.36-4.46 (m, 1H), 6.50 (d, J=2.8 Hz, 1H), 6.87 (s, 1H), 7.51-7.58 (m, 2H), 7.66 (d, J=2.8 Hz, 1H), 7.67 (s, 1H), 8.06 (s, 1H), 8.30-8.37 (m, 1H).

Example 39

Synthesis of 1-{1-[2-(6-methoxy-methyl-oxo-1,4-dihydro-2H-benz[d][1,3]oxazin-7-yl)ethyl]piperidin-4-yl}-1H-indole-6-carboxamide

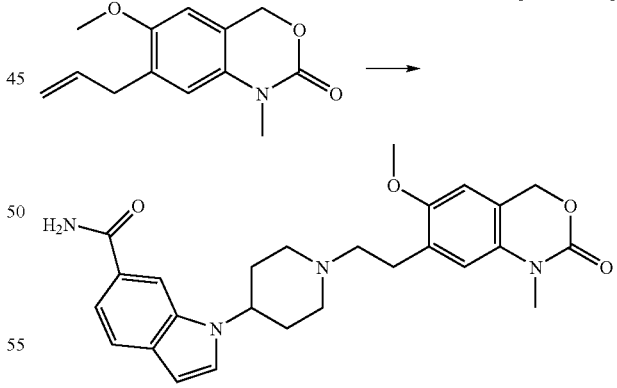

[Formula 98]

The subject compound was synthesized from 7-allyl-6-methoxy-1-methyl-1,4-dihydrobenz[d][1,3]oxazin-2-one according to the method described in Example 20, (4).

¹H-NMR (DMSO-d₆) δ (ppm): 1.93-2.08 (m, 4H), 2.22-2.32 (m, 2H), 2.52-2.61 (m, 2H), 2.76-2.83 (m, 2H), 3.08-3.15 (m, 2H), 3.26 (s, 3H), 3.79 (s, 3H), 4.37-4.47 (m, 1H), 5.19 (s, 2H), 6.50 (d, J=3.2 Hz, 1H), 6.94 (s, 1H), 6.99 (s, 1H), 7.21 (br.s, 1H), 7.54-7.60 (m, 2H), 7.67 (d, J=3.2 Hz, 1H), 7.91 (br.s, 1H), 8.12 (s, 1H).

Example 40

Synthesis of 1-{1-[2-(7-methoxy-2-methoxymethyl-2-methyl-4-oxochroman-8-yl)ethyl]piperidin-4-yl}-1H-indole-6-carboxamide

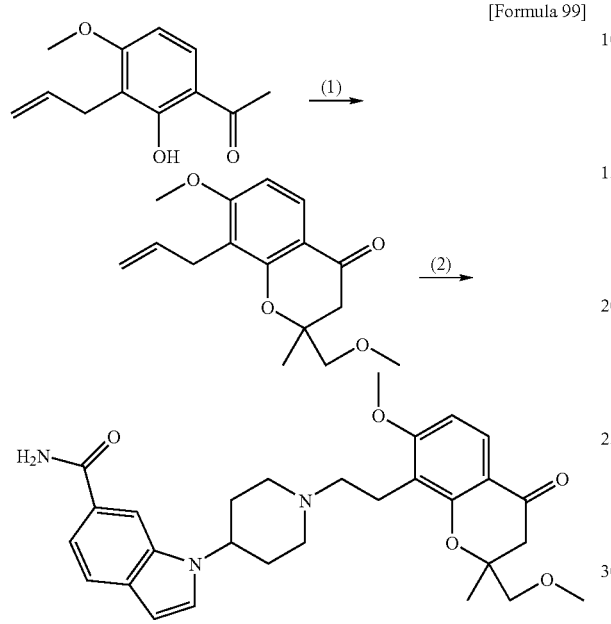

[Formula 99]

(1) 8-Allyl-7-methoxy-2-methoxymethyl-2-methyl-4-oxochromane 445 mg of 3'-allyl-2'-hydroxy-4'-methoxyacetophenone and 0.57 g of methoxyacetone were dissolved in 10 ml of toluene. Thereafter, 0.19 g of pyrrolidine and 0.19 ml of acetic acid were added to the reaction solution. Thereafter, the reaction solution was heated to reflux using Dean-Stark for 1 hour. Thereafter, the reaction solution was cooled to a room temperature. 1.14 g of methoxyacetone, 0.38 g of pyrrolidine, and 0.38 ml of acetic acid were added to the reaction solution, and the obtained mixture was further heated to reflux overnight. The reaction solution was cooled to a room temperature and then concentrated under a reduced pressure. The residue was diluted with ethyl acetate, and then successively washed with 2 N hydrochloric acid, a 1 N sodium hydroxide aqueous solution, water, and a saturated sodium chloride aqueous solution. The organic layer was dried over magnesium sulfate and then concentrated under a reduced pressure. The residue was purified by silica gel column chromatography (hexane-ethyl acetate), so as to obtain 194 mg of the subject compound.

$^1$H-NMR (CDCl$_3$) δ (ppm): 1.36 (s, 3H), 2.53 (d, J=16.0 Hz, 1H), 2.98 (d, J=16.0 Hz, 1H), 3.34-3.40 (m, 2H), 3.41 (s, 3H), 3.43 (d, J=8.8 Hz, 1H), 3.55 (d, J=8.8 Hz, 1H), 3.88 (s, 3H), 4.92-5.03 (m, 2H), 5.84-5.95 (m, 1H), 6.58 (d, J=9.2 Hz, 1H), 7.79 (d, J=9.2 Hz, 1H).

(2) 1-{1-[2-(7-Methoxy-2-methoxymethyl-2-methyl-4-oxochroman-8-yl)ethyl]piperidin-4-yl}-1H-indole-6-carboxamide The subject compound was synthesized from 8-allyl-7-methoxy-2-methoxymethyl-2-methyl-4-oxochromane according to the method described in Example 22, (4).

$^1$H-NMR (DMSO-d$_6$) δ (ppm): 1.33 (s, 3H), 1.92-2.10 (m, 4H), 2.23-2.34 (m, 2H), 2.40-2.52 (m, 2H), 2.61 (d, J=16.8 Hz, 1H), 2.74-2.82 (m, 2H), 2.86 (d, J=16.8 Hz, 1H), 3.07-3.17 (m, 2H), 3.31 (s, 3H), 3.49 (s, 2H), 3.87 (s, 3H), 4.37-4.48 (m, 1H), 6.51 (d, J=3.2 Hz, 1H), 6.75 (d, J=8.8 Hz, 1H), 7.21 (br.s, 1H), 7.53-7.61 (m, 2H), 7.64 (d, J=8.8 Hz, 1H), 7.68 (d, J=3.2 Hz, 1H), 7.91 (br.s, 1H), 8.13 (s, 1H).

Example 41

Synthesis of 1-{1-[2-(7-methoxy-4-oxo-spiro(chroman-2,1'-cyclopentan)-8-yl)ethyl]piperidin-4-yl}-1H-indole-6-carboxamide

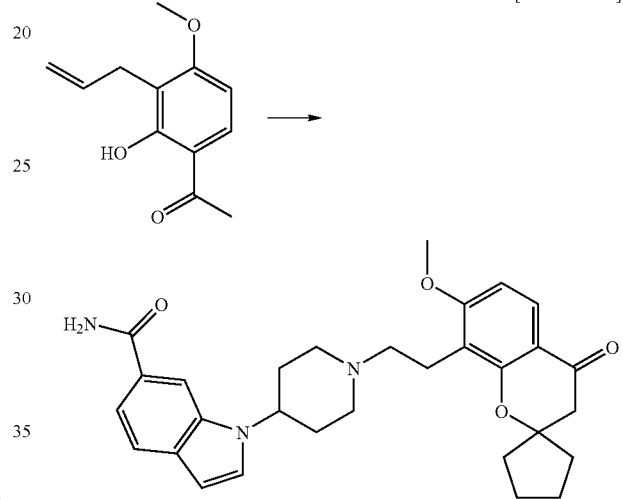

[Formula 100]

The subject compound was synthesized from 3'-allyl-2'-hydroxy-4'-methoxyacetophenone according to the method described in Example 40.

$^1$H-NMR (DMSO-d$_6$) δ (ppm): 1.60-1.90 (m, 6H), 1.90-2.10 (m, 6H), 2.22-2.32 (m, 2H), 2.40-2.48 (m, 2H), 2.73-2.81 (m, 2H), 2.83 (s, 2H), 3.08-3.15 (m, 2H), 3.88 (s, 3H), 4.37-4.48 (m, 1H), 6.51 (d, J=3.2 Hz, 1H), 6.60 (d, J=8.8 Hz, 1H), 7.21 (br.s, 1H), 7.53-7.61 (m, 2H), 7.66 (d, J=8.8 Hz, 1H), 7.68 (d, J=3.2 Hz, 1H), 7.91 (br.s, 1H), 8.14 (s, 1H).

Example 42

Synthesis of 1-{1-[2-(5,7-dimethoxy-2,2-dimethyl-4-oxochroman-8-yl)ethyl]piperidin-4-yl}-1H-indole-6-carboxamide

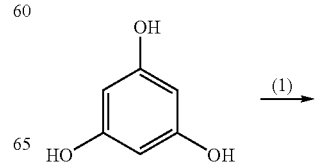

[Formula 101]

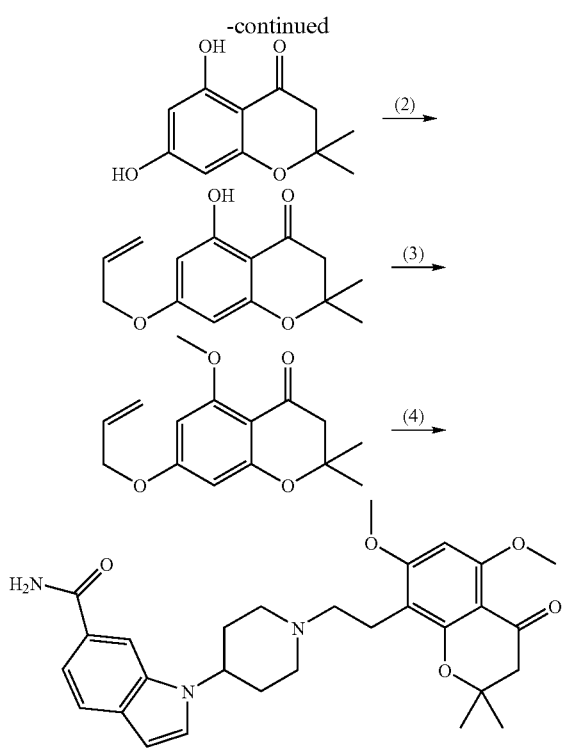

(1) 5,7-Dihydroxy-2,2-dimethyl-4-oxochromane 40 ml of methanesulfonic acid was added to 1.99 g of diphosphorus pentoxide under nitrogen atmosphere. Thereafter, a mixture consisting of 3.15 g of 1,3,5-trihydroxybenzene and 3,3-dimethylacrylic acid was added to the reaction solution at 70° C. The reaction solution was stirred at 70° C. for 30 minutes and then cooled to a room temperature. The reaction solution was added to ice water, followed by extraction with ethyl acetate. The extract was washed with water and a saturated sodium chloride aqueous solution. The organic layer was dried over magnesium sulfate and then concentrated under a reduced pressure. The residue was purified by silica gel column chromatography (hexane/ethyl acetate), so as to obtain 2.81 g of the subject compound.

$^1$H-NMR (CDCl$_3$) δ (ppm): 1.43 (s, 6H), 2.68 (s, 2H), 5.53 (br.s, 1H), 5.87 (d, J=2.4 Hz, 1H), 5.93 (d, J=2.4 Hz, 1H), 12.03 (s, 1H).

(2) 7-Allyloxy-5-hydroxy-2,2-dimethyl-4-oxochromane 2.81 g of 5,7-dihydroxy-2,2-dimethyl-4-oxochromane was dissolved in 60 ml of acetone. Thereafter, 2.05 g of potassium carbonate and 1.80 g of allyl bromide were added to the reaction solution, and the obtained mixture was then stirred at room temperature for 24 hours. Thereafter, 0.20 g of potassium carbonate and 0.18 g of allyl bromide were further added to the reaction solution, and the obtained mixture was then stirred at room temperature for 10 hours. Thereafter, 0.20 g of potassium carbonate and 0.18 g of allyl bromide were further added to the reaction solution, and the obtained mixture was then stirred at room temperature for 14 hours. Thereafter, 0.20 g of potassium carbonate and 0.18 g of allyl bromide were further added to the reaction solution, and the obtained mixture was then stirred at room temperature for 7 hours. The reaction solution was concentrated under a reduced pressure, and the residue was diluted with ethyl acetate. The resultant product was washed with water and a saturated sodium chloride aqueous solution. The organic layer was dried over magnesium sulfate and then concentrated under a reduced pressure. The residue was purified by silica gel column chromatography (hexane/ethyl acetate), so as to obtain 2.90 g of the subject compound.

$^1$H-NMR (CDCl$_3$) δ (ppm): 1.46 (s, 6H), 2.68 (s, 2H), 4.52-4.57 (m, 2H), 5.29-5.35 (m, 1H), 5.37-5.45 (m, 1H), 5.94-6.07 (m, 3H), 11.99 (s, 1H).

(3) 7-Allyloxy-5-methoxy-2,2-dimethyl-4-oxochromane 2.90 g of 7-allyloxy-5-hydroxy-2,2-dimethyl-4-oxochromane was dissolved in 50 ml of N,N-dimethylformamide. Thereafter, 2.42 g of potassium carbonate and 2.32 g of iodomethane were added to the reaction solution, and the obtained mixture was then stirred at room temperature for 3 days. Thereafter, the reaction solution was diluted with ethyl acetate. The resultant product was washed with a saturated sodium chloride aqueous solution. The organic layer was dried over magnesium sulfate and then concentrated under a reduced pressure. The residue was purified by silica gel column chromatography (hexane/ethyl acetate), so as to obtain 2.79 g of the subject compound.

$^1$H-NMR (CDCl$_3$) δ (ppm): 1.43 (s, 6H), 2.64 (s, 2H), 3.87 (s, 3H), 4.54 (d, J=5.6 Hz, 2H), 5.33 (dd, J=1.6, 10.0, 1H), 5.42 (dd, J=1.6, 17.2 Hz, 1H), 5.98-6.10 (m, 1H), 6.03 (d, J=2.0 Hz, 1H), 6.06 (d, J=2.0 Hz, 1H).

(4) 1-{1-[2-(5,7-Dimethoxy-2,2-dimethyl-4-oxochroman-8-yl)ethyl]piperidin-4-yl}-1H-indole-6-carboxamide The subject compound was synthesized from 7-allyloxy-5-methoxy-2,2-dimethyl-4-oxochromane according to the methods described in Example 22, (2), (3) and (4).

$^1$H-NMR (DMSO-d$_6$) δ (ppm): 1.37 (s, 6H), 1.92-2.10 (m, 4H), 2.20-2.31 (m, 2H), 2.35-2.45 (m, 2H), 2.59 (s, 2H), 2.64-2.73 (m, 2H), 3.07-3.16 (m, 2H), 3.81 (s, 3H), 3.89 (s, 3H), 4.37-4.47 (m, 1H), 6.28 (s, 1H), 6.50 (d, J=3.2 Hz, 1H), 7.21 (br.s, 1H), 7.53-7.61 (m, 2H), 7.67 (d, J=3.2 Hz, 1H), 7.91 (br.s, 1H), 8.13 (s, 1H).

Example 43

Synthesis of 1-{1-[2-(7-methoxy-4-oxo-spiro(chroman-2,4'-oxan)-8-yl)ethyl]piperidin-4-yl}-1H-indole-6-carboxamide

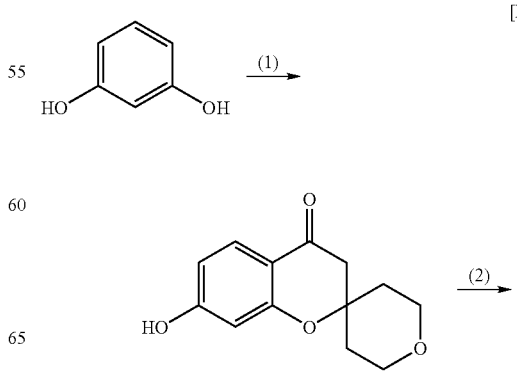

[Formula 102]

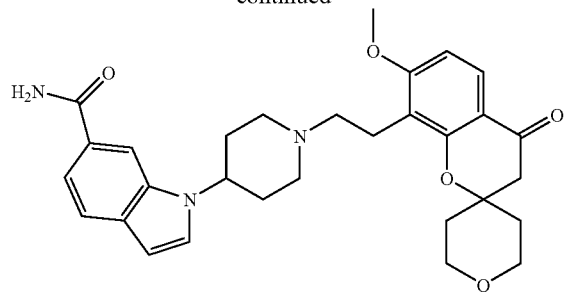

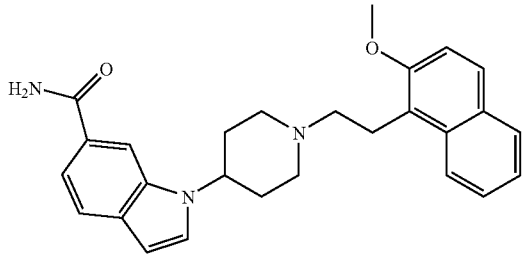

(1) 7-Hydroxy-4-oxo-spiro(chroman-2,4'-oxan)

The subject compound was synthesized from resorcinol and (tetrahydropyran-4-yliden)acetic acid according to the method described in Example 42, (1).

¹H-NMR (CDCl₃) δ (ppm): 1.72-1.82 (m, 2H), 1.94-2.02 (m, 2H), 2.69 (s, 2H), 3.73-3.89 (m, 4H), 6.01 (br.s, 1H), 6.43 (d, J=2.4 Hz, 1H), 6.49 (dd, J=2.4, 8.4 Hz, 1H), 7.79 (d, J=8.4 Hz, 1H).

(2) 1-{1-[2-(7-Methoxy-4-oxo-spiro(chroman-2,4'-oxan)-8-yl)ethyl]piperidin-4-yl}-1H-indole-6-carboxamide The subject compound was synthesized from 7-hydroxy-4-oxo-spiro(chroman-2,4'-oxane) according to the method described in Example 22.

¹H-NMR (DMSO-d₆) δ (ppm): 1.70-1.90 (m, 4H), 1.94-2.12 (m, 4H), 2.27-2.36 (m, 2H), 2.47-2.57 (m, 2H), 2.77 (s, 2H), 2.83-2.92 (m, 2H), 3.10-3.20 (m, 2H), 3.67-3.77 (m, 4H), 3.89 (s, 3H), 4.40-4.50 (m, 1H), 6.51 (d, J=3.2 Hz, 1H), 6.78 (d, J=8.8 Hz, 1H), 7.21 (br.s, 1H), 7.54-7.61 (m, 2H), 7.64-7.71 (m, 2H), 7.91 (br.s, 1H), 8.15 (s, 1H).

Example 44

Synthesis of 1-{1-[2-(2-methoxynaphthalen-1-yl)ethyl]piperidin-4-yl}-1H-indole-6-carboxamide

[Formula 103]

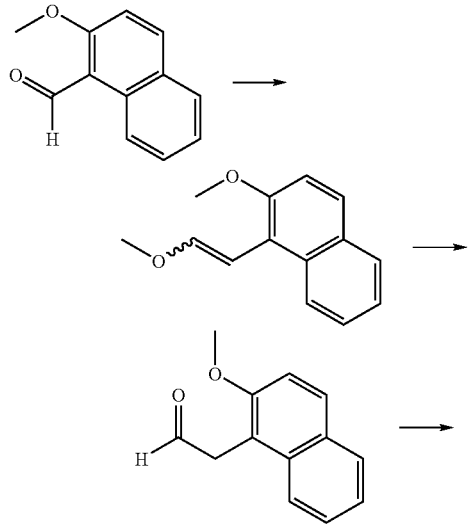

While cooling on ice, 0.61 g of potassium t-butoxide was added to 20 ml of a tetrahydrofuran suspension containing 2.28 g of (methoxymethyl)triphenylphosphonium chloride under nitrogen atmosphere. The obtained mixture was stirred for 5 minutes. Thereafter, 600 mg of 2-methoxy-1-naphthaldehyde was added to the reaction solution while cooling on ice. The obtained mixture was stirred at the same temperature for 20 minutes. The reaction solution was diluted with ethyl acetate, and then washed with water and a saturated sodium chloride aqueous solution. The organic layer was dried over magnesium sulfate and then concentrated under a reduced pressure. The residue was purified by silica gel column chromatography (hexane-ethyl acetate), so as to obtain 667 mg of 2-methoxy-1-(2-methoxyvinyl)naphthalene containing a small amount of triphenylphosphine. This compound was used in the next reaction without further purification.

120 mg of 2-methoxy-1-(2-methoxyvinyl)naphthalene was dissolved in 4 ml of 2 N hydrochloric acid-tetrahydrofuran (1:1). The obtained mixture was then stirred at 70° C. for 2 hours. The reaction solution was cooled to a room temperature and then diluted with ethyl acetate. The resultant product was washed with water and a saturated sodium chloride aqueous solution. The organic layer was dried over magnesium sulfate and then concentrated under a reduced pressure, so as to obtain 115 mg of (2-methoxynaphthalen-1-yl)acetaldehyde. This compound was used in the following reaction without further purification.

70 mg of 1-(piperidin-4-yl)-1H-indole-6-carboxamide and 115 mg of (2-methoxynaphthalen-1-yl)acetaldehyde were dissolved in 2 ml of tetrahydrofuran. Thereafter, 0.03 ml of acetic acid and 91 mg of sodium triacetoxyborohydride were added to the reaction solution, and the obtained mixture was then stirred at room temperature overnight. Thereafter, a saturated sodium bicarbonate aqueous solution was added to the reaction solution, and then extracted with chloroform. The extract was dried over magnesium sulfate and then concentrated under a reduced pressure. The residue was purified by silica gel column chromatography (ethyl acetate-methanol), so as to obtain 72 mg of the subject compound.

¹H-NMR (DMSO-d₆) δ (ppm): 1.98-2.14 (m, 4H), 2.30-2.40 (m, 2H), 2.50-2.60 (m, 2H), 3.18-3.38 (m, 4H), 3.95 (s, 3H), 4.40-4.50 (m, 1H), 6.52 (d, J=3.2 Hz, 1H), 7.22 (br.s, 1H), 7.33-7.40 (m, 1H), 7.45 (d, J=9.2 Hz, 1H), 7.50-7.62 (m, 3H), 7.70 (d, J=3.2 Hz, 1H), 7.82-7.90 (m, 2H), 7.92 (br.s, 1H), 7.97 (d, J=8.4 Hz, 1H), 8.15 (s, 1H).

Example 45

Synthesis of 1-{1-[2-(3-methoxynaphthalen-2-yl)ethyl]piperidin-4-yl}-1H-indole-6-carboxamide

[Formula 104]

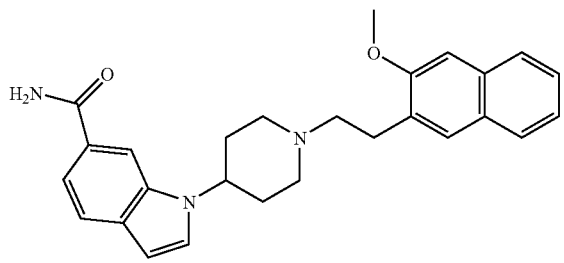

The subject compound was synthesized from 3-methoxy-2-naphthalenecalbaldehyde (CAS#: 56679-88-0) according to the method described in Example 44.

$^1$H-NMR (DMSO-$d_6$) δ (ppm): 1.93-2.10 (m, 4H), 2.25-2.35 (m, 2H), 2.63-2.70 (m, 2H), 2.90-2.96 (m, 2H), 3.11-3.19 (m, 2H), 3.93 (s, 3H), 4.38-4.48 (m, 1H), 6.50 (d, J=3.2 Hz, 1H), 7.21 (br.s, 1H), 7.28-7.35 (m, 2H), 7.37-7.44 (m, 1H), 7.53-7.60 (m, 2H), 7.68 (d, J=3.2 Hz, 1H), 7.72 (s, 1H), 7.75-7.81 (m, 2H), 7.92 (br.s, 1H), 8.14 (s, 1H).

Example 46

Synthesis of 1-{1-[2-(4-hydroxy-7-methoxychroman-8-yl)ethyl]piperidin-4-yl}-1H-indole-6-carboxamide

[Formula 105]

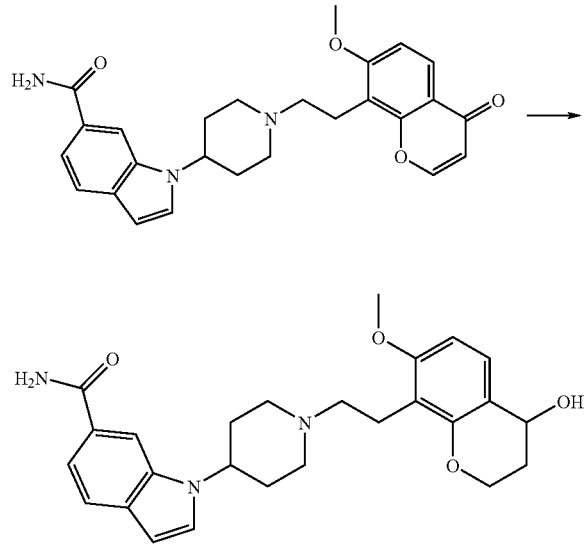

52 mg of 1-(1-(2-(7-methoxy-4-oxo-4H-chromen-8-yl)ethyl)piperidin-4-yl)-1H-indole-6-carboxamide was dissolved in 6 ml of methanol-tetrahydrofuran (1:1). Thereafter, 5 mg of sodium borohydride was added to the reaction solution while cooling on ice. The obtained mixture was then stirred at room temperature for 2 hours. Thereafter, 5 mg of sodium borohydride was added to the reaction solution, and further, 5 mg each of sodium borohydride was added thereto 2 hours and 4 hours later. Thereafter, the reaction solution was stirred at the same temperature overnight. A saturated sodium bicarbonate aqueous solution was added to the reaction solution, followed by extraction with chloroform. The extract was dried over magnesium sulfate and then concentrated under a reduced pressure. The residue was purified by NH silica gel column chromatography (ethyl acetate-methanol), so as to obtain 30 mg of the subject compound.

$^1$H-NMR (DMSO-$d_6$) δ (ppm): 1.80-1.88 (m, 1H), 1.90-2.10 (m, 5H), 2.19-2.28 (m, 2H), 2.36-2.44 (m, 2H), 2.69-2.77 (m, 2H), 3.07-3.15 (m, 2H), 3.76 (s, 3H), 4.16-4.24 (m, 2H), 4.37-4.46 (m, 1H), 4.55-4.60 (m, 1H), 5.17 (d, J=5.2 Hz, 1H), 6.50 (d, J=3.2 Hz, 1H), 6.56 (d, J=8.8 Hz, 1H), 7.11 (d, J=8.8 Hz, 1H), 7.21 (br.s, 1H), 7.54-7.60 (m, 2H), 7.67 (d, J=3.2 Hz, 1H), 7.91 (br.s, 1H), 8.12 (s, 1H).

Example 47

Synthesis of 1-{1-[2-(7-methoxy-4-oxochroman-8-yl)ethyl]piperidin-4-yl}-1H-indole-6-carboxamide

[Formula 106]

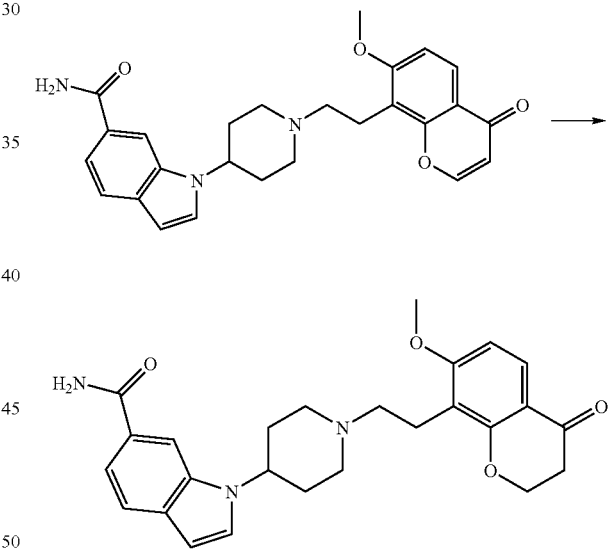

42 mg of 1-(1-(2-(7-methoxy-4-oxo-4H-chromen-8-yl)ethyl)piperidin-4-yl)-1H-indole-6-carboxamide was dissolved in 3 ml of methanol. Thereafter, 15 mg of 10% palladium carbon was added to the reaction solution. The obtained mixture was then stirred at room temperature for 15 hours under hydrogen atmosphere. Thereafter, 15 mg of 10% palladium carbon was further added to the reaction solution. The obtained mixture was then stirred at the same temperature for 4 hours. Thereafter, palladium carbon was removed by filtration, and the filtrate was concentrated under a reduced pressure. The residue was purified by NH silica gel column chromatography (ethyl acetate), so as to obtain 20 mg of the subject compound.

¹H-NMR (DMSO-d₆) δ (ppm): 1.93-2.08 (m, 4H), 2.20-2.30 (m, 2H), 2.42-2.50 (m, 2H), 2.72 (t, J=6.3 Hz, 2H), 2.74-2.82 (m, 2H), 3.08-3.16 (m, 2H), 3.88 (s, 3H), 4.37-4.47 (m, 1H), 4.54 (t, J=6.3 Hz, 2H), 6.50 (d, J=2.8 Hz, 1H), 6.80 (d, J=8.8 Hz, 1H), 7.21 (br.s, 1H), 7.55-7.60(m, 2H), 7.67(d, J=2.8 Hz, 1H), 7.69 (d, J=8.8 Hz, 1H), 7.91 (br.s, 1H), 8.12 (s, 1H).

Example 48

Synthesis of 1-{1-[2-(4-hydroxy-7-methoxy-2,2-dimethylchroman-8-yl)ethyl]piperidin-4-yl}-N-methyl-1H-indole-6-carboxamide

[Formula 107]

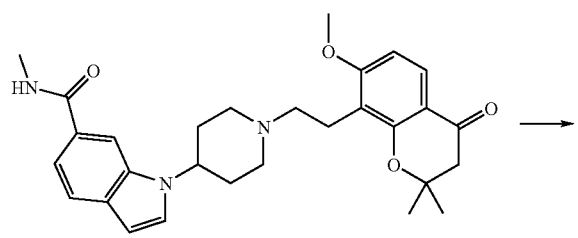

259 mg of 1-(1-(2-(7-methoxy-2,2-dimethyl-4-oxochroman-8-yl)ethyl)piperidin-4-yl)-N-methyl-1H-indole-6-carboxamide was dissolved in 5 ml of methanol. Thereafter, 60 mg of sodium borohydride was added to the reaction solution while cooling on ice. The obtained mixture was then stirred at room temperature overnight. Thereafter, a saturated sodium bicarbonate aqueous solution was added to the reaction solution, followed by extraction with methylene chloride. The extract was dried over magnesium sulfate and then concentrated under a reduced pressure. The residue was purified by NH silica gel column chromatography (ethyl acetate) and then purified by silica gel column chromatography (ethyl acetate-methanol), so as to obtain 216 mg of the subject compound.

¹H-NMR (DMSO-d₆) δ (ppm): 1.24 (s, 3H), 1.37 (s, 3H), 1.92-2.00 (m, 5H), 2.26 (t, J=11.2 Hz, 2H), 2.37-2.46 (m, 2H), 2.68-2.77 (m, 2H), 2.82 (d, J=4.4 Hz, 3H), 3.07-3.16 (m, 2H), 3.75 (s, 3H), 4.36-4.45 (m, 1H), 4.60-4.66 (m, 1H), 5.17 (d, J=6.0 Hz, 1H), 6.50 (d, J=3.2 Hz, 1H), 6.55 (d, J=8.8 Hz, 1H), 7.23 (d, J=8.8 Hz, 1H), 7.51-7.58 (m, 2H), 7.66 (d, J=3.2 Hz, 1H), 8.06 (s, 1H), 8.19-8.36 (m, 1H).

Example 49

Synthesis of 1-{1-[2-(1-hydroxy-5-methoxyindan-4-yl)ethyl]piperidin-4-yl}-1H-indole-6-carboxamide

[Formula 108]

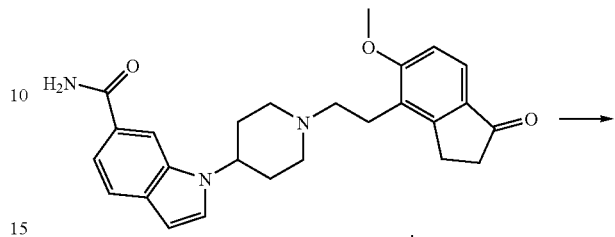

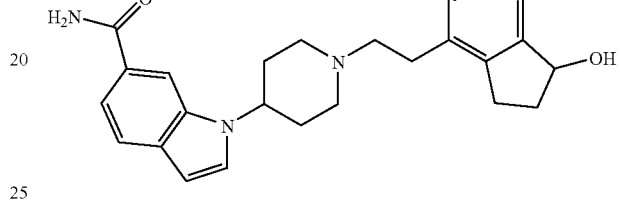

The subject compound was synthesized from 1-(1-(2-(5-methoxy-1-oxoindan-4-yl)ethyl)piperidin-4-yl)-1H-indole-6-carboxamide according to the method described in Example 48.

¹H-NMR (DMSO-d₆) δ (ppm): 1.72-1.83 (m, 1H), 1.90-2.10 (m, 4H), 2.20-2.37 (m, 3H), 2.40-2.50 (m, 2H), 2.62-2.78 (m, 3H), 2.87-2.97 (m, 1H), 3.05-3.16 (m, 2H), 3.77 (s, 3H), 4.36-4.47 (m, 1H), 4.96-5.05 (m, 2H), 6.47-6.53 (m, 1H), 6.82 (d, J=8.0 Hz, 1H), 7.13 (d, J=8.0 Hz, 1H), 7.21 (br.s, 1H), 7.52-7.62 (m, 2H), 7.64-7.70 (m, 1H), 7.91 (br.s, 1H), 8.12 (s, 1H).

Example 50

Synthesis of 1-{1-[2-(3-hydroxy-6-methoxyindan-5-yl)ethyl]piperidin-4-yl}-1H-indole-6-carboxamide

[Formula 109]

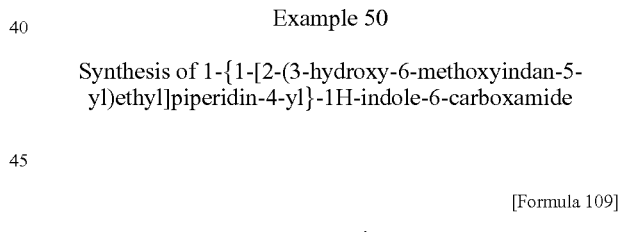

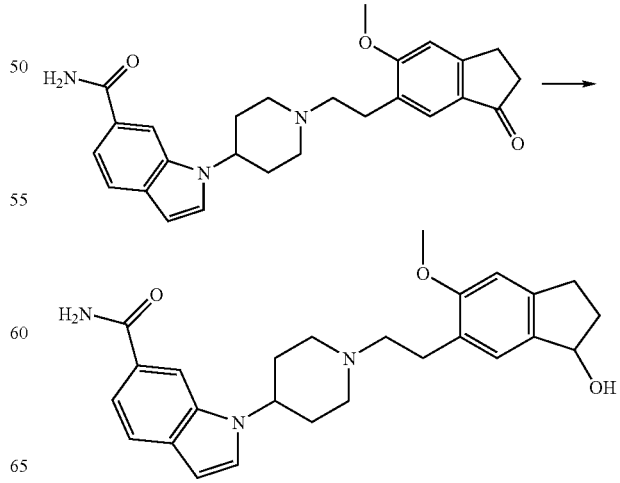

The subject compound was synthesized from 1-(1-(2-(6-methoxy-3-oxoindan-5-yl)ethyl)piperidin-4-yl)-1H-indole-6-carboxamide according to the method described in Example 48.

$^1$H-NMR (DMSO-$d_6$) δ (ppm): 1.72-1.82 (m, 1H), 1.90-2.10 (m, 4H), 2.20-2.36 (m, 3H), 2.44-2.57 (m, 2H), 2.63-2.79 (m, 3H), 2.85-2.94 (m, 1H), 3.07-3.16 (m, 2H), 3.78 (s, 3H), 4.37-4.48 (m, 1H), 4.98 (dd, J=5.6, 12.0 Hz, 1H), 5.03 (d, J=5.6 Hz, 1H), 6.51 (d, J=3.2 Hz, 1H), 6.82 (s, 1H), 7.11 (s, 1H), 7.21 (br.s, 1H), 7.53-7.62 (m, 2H), 7.67 (d, J=3.2 Hz, 1H), 7.92 (br.s, 1H), 8.13 (s, 1H).

Example 51

Synthesis of 1-{1-[2-(6-methoxyquinolin-7-yl)ethyl]piperidin-4-yl}-1H-indole-6-carboxamide

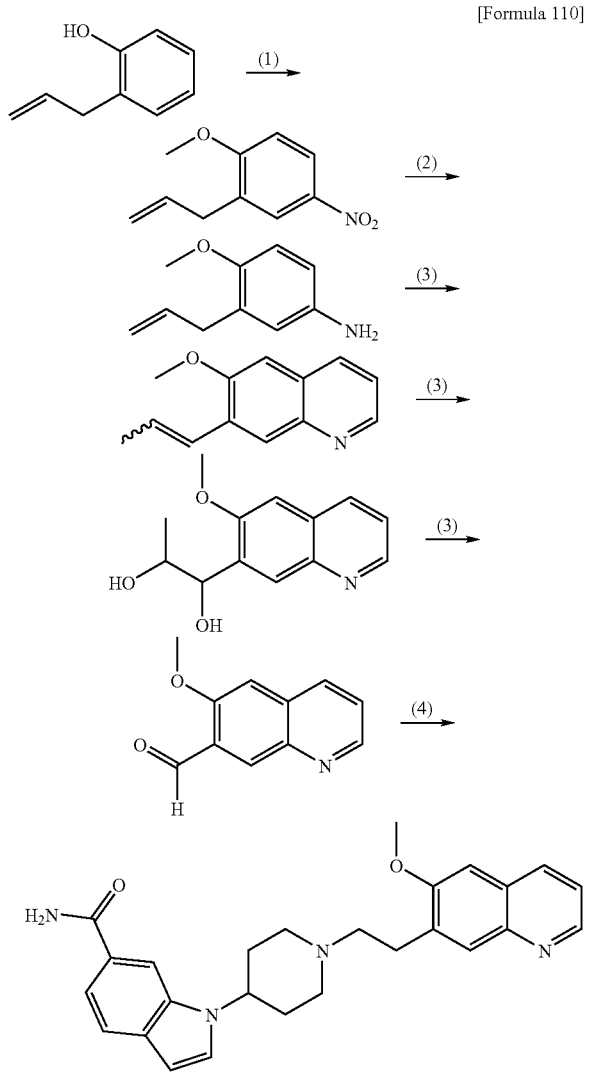

[Formula 110]

(1) 1-Allyl-2-methoxy-5-nitrobenzene

The subject compound was synthesized from 2-allylphenol according to the method described in Example 23, (1).

$^1$H-NMR (CDCl$_3$) δ (ppm): 3.42 (d, J=6.8 Hz, 2H), 3.94 (s, 3H), 5.07-5.17 (m, 2H), 5.91-6.03 (m, 1H), 6.90 (d, J=9.2 Hz, 1H), 8.06 (d, J=2.4 Hz, 1H), 8.15 (dd, J=2.4, 9.2 Hz, 1H).

(2) 3-Allyl-4-methoxyaniline 15.0 g of 1-allyl-2-methoxy-5-nitrobenzene, 33.4 g of ammonium chloride, and 17.5 g of iron were suspended in 270 ml of ethanol and 55 ml of water. The reaction solution was heated to reflux for 1 hour. Thereafter, the reaction solution was cooled to a room temperature, and insoluble matters were then removed by filtration. The filtrate was concentrated under a reduced pressure. The residue was diluted with ethyl acetate and then washed with a saturated sodium bicarbonate aqueous solution and a saturated sodium chloride aqueous solution. The organic layer was dried over magnesium sulfate and then concentrated under a reduced pressure. The residue was purified by silica gel column chromatography (hexane-ethyl acetate), so as to obtain 11.1 g of the subject compound.

$^1$H-NMR (CDCl$_3$) δ (ppm): 3.32 (d, J=6.4 Hz, 2H), 3.39 (br.s, 2H), 3.76 (s, 3H), 5.00-5.10 (m, 2H), 5.91-6.03 (m, 1H), 6.51-6.57 (m, 2H), 6.67-6.73 (m, 1H).

(3) 6-Methoxyquinoline-7-carbaldehyde 6-methoxy-7-(1-propenyl)quinoline with an isomerized double bond was synthesized from 3-allyl-4-methoxyaniline in accordance with Heterocycles, Vol. 54, No. 1, 105 (2001) (wherein isomerization was carried out when 7-allyl-1-methanesulfonyl-6-methoxy-1,2-dihydroquinoline was allowed to react with potassium hydroxide at 80° C. in dimethyl sulfoxide)

1.41 g of AD-mix-α and 93 mg of methanesulfonamide were dissolved in 12 ml of t-butanol-water (1:1). Thereafter, 195 mg of 6-methoxy-7-(1-propenyl)quinoline was added to the reaction solution, and the obtained mixture was then stirred overnight. Thereafter, 2.0 g of sodium sulfite was added to the reaction solution while cooling on ice, and the obtained mixture was stirred at room temperature for 30 minutes. Thereafter, a saturated sodium chloride aqueous solution was added to the reaction solution, followed by extraction of methylene chloride. The extract was then washed with a 2 N potassium hydroxide aqueous solution. The organic layer was dried over magnesium sulfate and then concentrated under a reduced pressure, so as to obtain 236 mg of 1-(6-methoxyquinolin-7-yl)propane-1,2-diol. This compound was used in the following reaction, without further purification.

236 mg of 1-(6-methoxyquinolin-7-yl)propane-1,2-diol was dissolved in 8 ml of tetrahydrofuran and 3 ml of methanol. Thereafter, 4 ml. of water containing 0.43 g of sodium metaperiodate was added to the reaction solution while cooling on ice. The obtained mixture was stirred at room temperature for 1 hour. The reaction solution was diluted with ethyl acetate, and then washed with water and a saturated sodium chloride aqueous solution. The organic layer was dried over magnesium sulfate and then concentrated under a reduced pressure. The residue was purified by silica gel column chromatography (hexane-ethyl acetate), so as to obtain 149 mg of the subject compound.

$^1$H-NMR (CDCl$_3$) δ (ppm): 4.06 (s, 3H), 7.18 (s, 1H), 7.44 (dd, J=4.4, 7.6 Hz, 1H), 8.05-8.11 (m, 1H), 8.57 (s, 1H), 8.84-8.89 (m, 1H), 10.61-10.64 (m, 1H).

(4) 1-{1-[2-(6-Methoxyquinolin-7-yl)ethyl]piperidin-4-yl}-1H-indole-6-carboxamide The subject compound was synthesized from 6-methoxyquinoline-7-carbaldehyde according to the method described in Example 44.

$^1$H-NMR (DMSO-$d_6$) δ (ppm): 1.94-2.10 (m, 4H), 2.27-2.86 (m, 2H), 2.66-2.73 (m, 2H), 2.96-3.02 (m, 2H), 3.12-3.20 (m, 2H), 3.96 (s, 3H), 4.39-4.49 (m, 1H), 6.50 (d, J=3.2 Hz, 1H), 7.21 (br.s, 1H), 7.35 (s, 1H), 7.43 (dd, J=4.4, 8.4 Hz, 1H), 7.53-7.61 (m, 2H), 7.68 (d, J=3.2 Hz, 1H), 7.84 (s, 1H), 7.92 (br.s, 1H), 8.14 (s, 1H), 8.20-8.26 (m, 1H), 8.71 (dd, J=1.2, 4.4 Hz, 1H).

Example 52

Synthesis of 1-{1-[2-(1-acetyl-6-methoxy-1,2,3,4-tetrahydroquinolin-7-yl)ethyl]piperidin-4-yl}-1H-indole-6-carboxamide

[Formula 111]

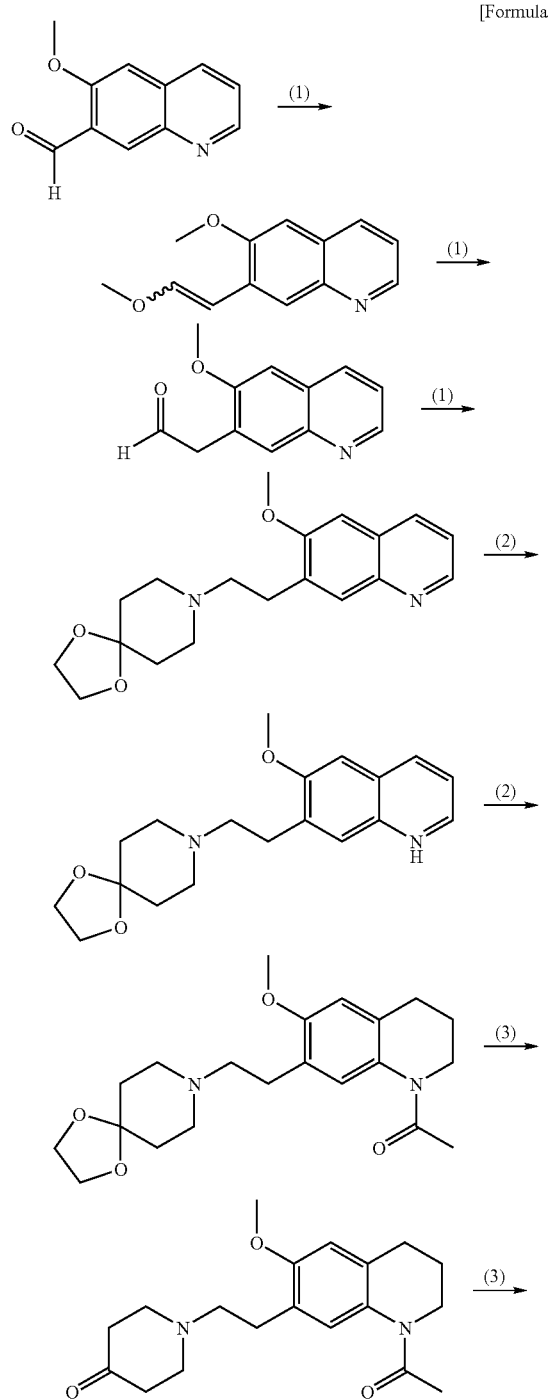

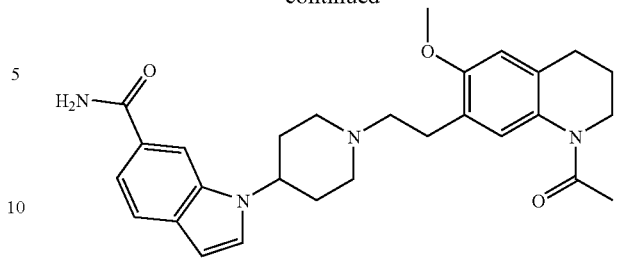

-continued (1) 7-[2-(1,4-Dioxa-8-azaspiro[4.5]decan-8-yl)ethyl]-6-methoxyquinoline While cooling on ice, 0.82 g of potassium t-butoxide was added to 20 ml of a tetrahydrofuran suspension containing 2.50 g of (methoxymethyl)triphenylphosphonium chloride under nitrogen atmosphere. The obtained mixture was then stirred at the same temperature for 10 minutes. Thereafter, 3 ml of a tetrahydrofuran solution containing 545 mg of 6-methoxyquinoline-7-carbaldehyde was added to the reaction solution while cooling on ice, and the obtained mixture was then stirred at the same temperature for 15 minutes. Thereafter, the reaction solution was diluted with ethyl acetate, and then washed with water and a saturated sodium chloride aqueous solution. The organic layer was dried over magnesium sulfate and then concentrated under a reduced pressure. The residue was purified by NH silica gel column chromatography (hexane-ethyl acetate), so as to obtain 1.41 g of 6-methoxy-7-(2-methoxyvinyl)quinoline containing triphenylphosphine oxide. This compound was used in the next reaction without further purification.

1.41 g of 6-methoxy-7-(2-methoxyvinyl)quinoline was dissolved in 40 ml of 2 N hydrochloric acid-tetrahydrofuran (1:1), and the obtained mixture was then stirred at 70° C. for 2 hours. The reaction solution was cooled to a room temperature. It was diluted with ethyl acetate and then washed with a saturated sodium bicarbonate aqueous solution and a saturated sodium chloride aqueous solution. The organic layer was dried over magnesium sulfate and then concentrated under a reduced pressure, so as to obtain 1.45 g of (6-methoxyquinolin-7-yl)acetaldehyde containing triphenylphosphine oxide. This compound was used in the following reaction without further purification.

1.45 g of (6-methoxyquinolin-7-yl)acetaldehyde and 0.63 g of 1,4-dioxa-8-azaspiro[4.5]decane were dissolved in 20 ml of methylene chloride. Thereafter, 0.42 ml of acetic acid and 0.74 g of sodium triacetoxyborohydride were added to the reaction solution, and the obtained mixture was then stirred at room temperature for 3 hours. Thereafter, a saturated sodium bicarbonate aqueous solution was added to the reaction solution, followed by extraction with methylene chloride. The extract was dried over magnesium sulfate and then concentrated under a reduced pressure. The residue was purified by silica gel column chromatography (chloroform-methanol), so as to obtain 445 mg of the subject compound.

$^1$H-NMR (CDCl$_3$) δ (ppm): 1.75-1.86 (m, 4H), 2.59-2.77 (m, 6H), 2.97-3.07 (m, 2H), 3.94 (s, 3H), 3.97 (s, 4H), 7.00 (s, 1H), 7.29 (dd, J=4.4, 8.4 Hz, 1H), 7.84 (s, 1H), 8.01 (dd, J=1.6, 8.4 Hz, 1H), 8.72 (dd, J=1.6, 4.4 Hz, 1H).

(2) 1-acetyl-7-[2-(1,4-dioxa-8-azaspiro[4.5]decan-8-yl)ethyl]-6-methoxy-1,2,3,4-tetrahydroquinoline 445 mg of 7-(2-(1,4-dioxa-8-azaspiro[4.5]decan-8-yl)ethyl)-6-methoxyquinoline was dissolved in 10 ml of methanol. Thereafter, 100 mg of 10% palladium carbon was added to the reaction solution. The obtained mixture was stirred for 6 hours under a 4 kg/cm² of hydrogen atmosphere. Thereafter, palladium carbon was removed by filtration, and the filtrate was concentrated under a reduced pressure. The reaction solution was stirred under the same above conditions for 10 hours 3 times, and then, it was concentrated under a reduced pressure. A saturated sodium bicarbonate aqueous solution was added to the residue, followed by extraction with chloroform. The extract was dried over magnesium sulfate and then concentrated under a reduced pressure, so as to obtain 459 mg of 7-(2-(1,4-dioxa-8-azaspiro[4.5]decan-8-yl)ethyl)-6-methoxy-1,2,3,4-tetrahydroquinoline. This compound was used in the next reaction without further purification.

3 ml of acetic anhydride and 3 ml of pyridine were added to 251 mg of 7-(2-(1,4-dioxa-8-azaspiro[4.5]decan-8-yl)ethyl)-6-methoxy-1,2,3,4-tetrahydroquinoline, and the obtained mixture was then stirred at room temperature for 90 minutes. The reaction solution was concentrated under a reduced pressure. The residue was diluted with ethyl acetate and then washed with water and a saturated sodium chloride aqueous solution. The organic layer was dried over magnesium sulfate and then concentrated under a reduced pressure. The residue was purified by NH silica gel column chromatography (hexane-ethyl acetate) and then by silica gel column chromatography (ethyl acetate-methanol), so as to obtain 162 mg of the subject compound.

¹H-NMR (CDCl₃) δ (ppm): 1.73-1.83 (m, 4H), 1.88-1.97 (m, 2H), 2.18 (br.s, 3H), 2.54-2.73 (m, 8H), 2.75-2.84 (m, 2H), 3.70-3.80 (m, 2H), 3.78 (s, 3H), 3.95 (s, 4H), 6.60 (s, 1H), 6.88 (br.s, 1H).

(3) 1-{1-[2-(1-Acetyl-6-methoxy-1,2,3,4-tetrahydroquinolin-7-yl)ethyl]piperidin-4-yl}-1H-indole-6-carboxamide 162 mg of 1-acetyl-7-(2-(1,4-dioxa-8-azaspiro[4.5]decan-8-yl)ethyl)-6-methoxy-1,2,3,4-tetrahydroquinoline was dissolved in 6 ml of 2 N hydrochloric acid-tetrahydrofuran (1:1), and the reaction solution was then stirred at 70° C. for 10 hours. The reaction solution was cooled to a room temperature, and a saturated sodium bicarbonate aqueous solution was added to the reaction solution, followed by extraction with methylene chloride. The extract was dried over magnesium sulfate and then concentrated under a reduced pressure, so as to obtain 127 mg of 1-(2-(1-acetyl-6-methoxy-1,2,3,4-tetrahydroquinolin-7-yl)ethyl)piperidin-4-one. This compound was used in the following reaction without further purification.

172 mg of 3-amino-4-(2,2-dimethoxyethyl)benzamide and 127 mg of 1-(2-(1-acetyl-6-methoxy-1,2,3,4-tetrahydroquinolin-7-yl)ethyl)piperidin-4-one were dissolved in 5 ml of acetic acid. Thereafter, 0.65 g of sodium sulfate was added to the reaction solution, and the obtained mixture was then stirred at room temperature for 1 hour. Thereafter, 0.16 g of sodium triacetoxyborohydride was added to the reaction solution, and the obtained mixture was then stirred for 1 hour. Thereafter, 5 ml of water was added thereto, and the obtained mixture was then stirred at 100° C. for 2 hours. The reaction solution was cooled to a room temperature, and it was then concentrated under a reduced pressure. A saturated sodium bicarbonate aqueous solution was added to the residue, followed by extraction with chloroform. The extract was dried over magnesium sulfate and then concentrated under a reduced pressure. The residue was purified by silica gel column chromatography (chloroform-methanol) and NH silica gel column chromatography (ethyl acetate-methanol), so as to obtain 146 mg of the subject compound.

¹H-NMR (DMSO-d₆) δ (ppm): 1.78-1.89 (m, 2H), 1.91-2.06 (m, 4H), 2.14 (s, 3H), 2.19-2.30 (m, 2H), 2.47-2.57 (m, 2H), 2.63-2.77 (m, 4H), 3.06-3.13 (m, 2H), 3.63 (t, J=6.4 Hz, 2H), 3.78 (s, 3H), 4.37-4.46 (m, 1H), 6.50 (d, J=2.8 Hz, 1H), 6.78 (br.s, 1H), 7.06-7.26 (m, 2H), 7.53-7.60 (m, 2H), 7.65 (d, J=2.8 Hz, 1H), 7.91 (br.s, 1H), 8.12 (s, 1H).

Example 53

Synthesis of 1-{1-[2-(6-methoxy-1-methyl-1,2,3,4-tetrahydroquinolin-7-yl)ethyl]piperidin-4-yl}-1H-indole-6-carboxamide

[Formula 112]

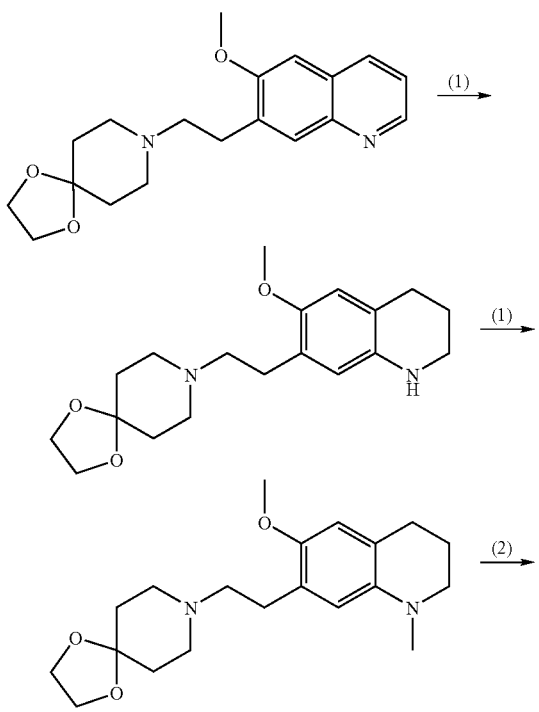

[Formula 113]

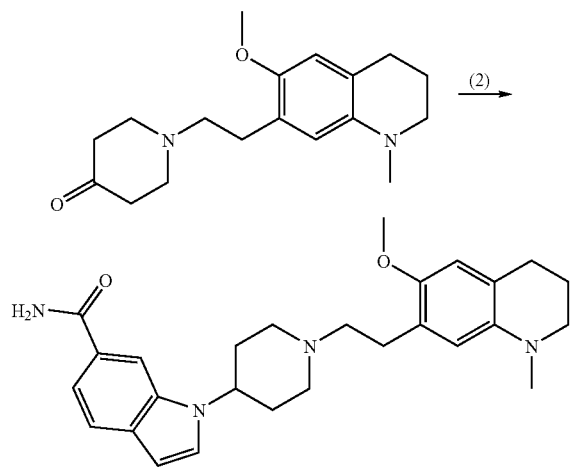

(1) 7-[2-(1,4-dioxa-8-azaspiro[4.5]decan-8-yl)ethyl]-6-methoxy-1-methyl-1,2,3,4-tetrahydroquinoline 445 mg of 7-(2-(1,4-dioxa-8-azaspiro[4.5]decan-8-yl)ethyl)-6-methoxyquinoline was dissolved in 10 ml of methanol. Thereafter, 100 mg of 10% palladium carbon was added to the reaction solution. The obtained mixture was stirred for 6 hours under a 4 kg/cm² of hydrogen atmosphere. Palladium carbon was removed by filtration, followed by concentration under a reduced pressure. The reaction solution was stirred under the same conditions for 10 hours 3 times, followed by concentration under a reduced pressure. A saturated sodium bicarbonate aqueous solution was added to the residue, followed by extraction with chloroform. The extract was dried over magnesium sulfate and then concentrated under a reduced pressure, so as to obtain 459 mg of 7-(2-(1,4-dioxa-8-azaspiro[4.5]decan-8-yl)ethyl)-6-methoxy-1,2,3,4-tetrahydroquinoline. This compound was used in the following reaction without further purification.

196 mg of 7-(2-(1,4-dioxa-8-azaspiro[4.5]decan-8-yl)ethyl)-6-methoxy-1,2,3,4tetrahydroquinoline was dissolved in 5 ml of acetonitrile. Thereafter, 1 ml of 37% formalin, 190 mg of sodium cyanoborohydride, and 0.15 ml acetic acid were added to the reaction solution, and the obtained mixture was then stirred at room temperature for 1 hour. Thereafter, the reaction solution was diluted with ethyl acetate, and then washed with a saturated sodium bicarbonate aqueous solution and a saturated sodium chloride aqueous solution. The organic layer was dried over magnesium sulfate and then concentrated under a reduced pressure. The residue was purified by NH silica gel column chromatography (hexane-ethyl acetate), so as to obtain 100 mg of the subject compound.

¹H-NMR (CDCl₃) δ (ppm): 1.52-1.63 (m, 3H), 1.75-1.88 (m, 3H), 1.94-2.01 (m, 2H), 2.52-2.86 (m, 8H), 2.81 (s, 3H), 3.07-3.12 (m, 2H), 3.72 (s, 3H), 3.97 (s, 4H), 6.48 (s, 1H), 6.51 (s, 1H).

(2) 1-{1-[2-(6-Methoxy-1-methyl-1,2,3,4-tetrahydroquinolin-7-yl)ethyl]piperidin-4-yl}-1H-indole-6-carboxamide 100 mg of 7-(2-(1,4-dioxa-8-azaspiro[4.5]decan-8-yl)ethyl)-6-methoxy-1-methyl-1,2,3,4-tetrahydroquinoline was dissolved in 6 ml of 2 N hydrochloric acid-tetrahydrofuran (1:1). The reaction solution was stirred at 70° C. for 7 hours. The reaction solution was cooled to a room temperature. Thereafter, a saturated sodium bicarbonate aqueous solution was added to the reaction solution, followed by extraction with methylene chloride. The extract was dried over magnesium sulfate and then concentrated under a reduced pressure, so as to obtain 87 mg of 1-(2-(6-methoxy-1-methyl-1,2,3,4-tetrahydroquinolin-7-yl)ethyl)piperidin-4-one. This compound was used in the following reaction without further purification.

129 mg of 3-amino-4-(2,2-dimethoxyethyl)benzamide and 87 mg of 1-(2-(6-methoxy-1-methyl-1,2,3,4-tetrahydroquinolin-7-yl)ethyl)piperidin-4-one were dissolved in 4 ml of acetic acid. Thereafter, 0.49 g of sodium sulfate was added to the reaction solution, and the obtained mixture was then stirred at room temperature for 1 hour. Thereafter, 0.12 g of sodium triacetoxyborohydride was added to the reaction solution, and the obtained mixture was then stirred at room temperature for 1 hour. Thereafter, 4 ml of water was further added to the reaction solution, and the obtained mixture was then stirred at 100° C. for 2 hours. The reaction solution was cooled to a room temperature, followed by concentration under a reduced pressure. A saturated sodium bicarbonate aqueous solution was added to the residue, followed by extraction with chloroform. The extract was dried over magnesium sulfate and then concentrated under a reduced pressure. The residue was purified by silica gel column chromatography (ethyl acetate-methanol) and by NH silica gel column chromatography (ethyl acetate), so as to obtain 70 mg of the subject compound.

¹H-NMR (DMSO-d₆) δ (ppm): 1.83-1.91 (m, 2H), 1.92-2.08 (m, 4H), 2.20-2.29 (m, 2H), 2.47-2.54 (m, 2H), 2.63-2.71 (m, 4H), 2.76 (s, 3H), 3.02-3.13 (m, 4H), 3.68 (s, 3H), 4.37-4.46 (m, 1H), 6.48 (s, 1H), 6.50 (d, J=3.2 Hz, 1H), 6.56 (s, 1H), 7.21 (br.s, 1H), 7.53-7.61 (m, 2H), 7.67 (d, J=3.2 Hz, 1H), 7.91 (br.s, 1H), 8.12 (s, 1H).

Example 54

Synthesis of 1-{1-[2-(1-acetyl-6-methoxy-1,2,3,4-tetrahydroquinolin-5-yl)ethyl]piperidin-4-yl}-1H-indole-6-carboxamide

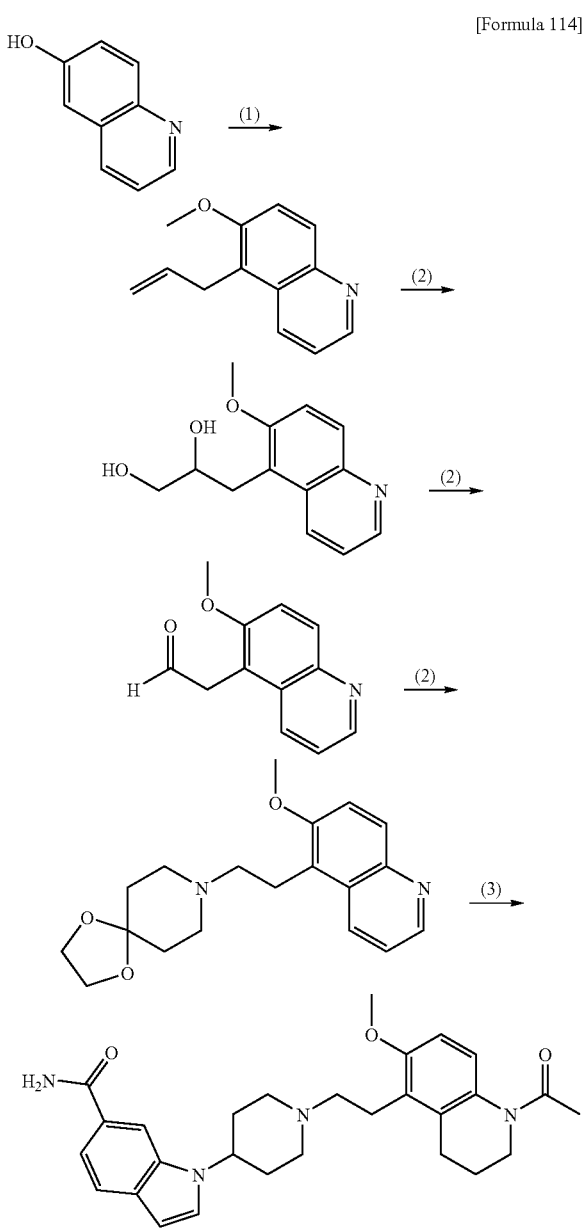

[Formula 114]

(1) 5-Allyl-6-methoxyquinoline

The subject compound was synthesized from 6-hydroxyquinoline according to the methods described in Example 22, (1), (2), and (3).

¹H-NMR (CDCl₃) δ (ppm): 3.80-3.85 (m, 2H), 3.97 (s, 3H), 4.87-4.95 (m, 1H), 4.97-5.02 (m, 1H), 5.95-6.06 (m, 1H), 7.35 (dd, J=4.0, 8.4 Hz, 1H), 7.50 (d, J=9.2 Hz, 1H), 8.01 (d, J=9.2 Hz, 1H), 8.21-8.27 (m, 1H), 8.76 (dd, J=1.6, 4.0 Hz, 1H).

(2)  5-[2-(1,4-Dioxa-8-azaspiro[4.5]decan-8-yl)ethyl]-6-methoxyquinoline 1.24 g of 5-allyl-6-methoxyquinoline was dissolved in 5 ml of t-butanol. Thereafter, 70 ml of a t-butanol-water (1:1) solution containing 10.3 g of AD-mix-α was added to the reaction solution, and the obtained mixture was then stirred at room temperature overnight. Thereafter, 15 g of sodium sulfite was added to the reaction solution, and the obtained mixture was then stirred at room temperature for 30 minutes while cooling on ice. A saturated sodium chloride aqueous solution was added to the reaction solution, followed by extraction with methylene chloride. The extract was dried over magnesium sulfate and then concentrated under a reduced pressure, so as to obtain 1.69 g of 3-(6-methoxyquinolin-5-yl)propane-1,2-diol. This compound was used in the following reaction without further purification.

0.81 g of 3-(6-methoxyquinolin-5-yl)propane-1,2-diol was dissolved in 24 ml of tetrahydrofuran and 8 ml of methanol. Then, 12 ml of water containing 1.49 g of sodium metaperiodate was added to the reaction solution while cooling on ice, and the obtained mixture was then stirred at room temperature for 45 minutes. Thereafter, a saturated sodium chloride aqueous solution was added to the reaction solution, followed by extraction with methylene chloride. The extract was dried over magnesium sulfate and then concentrated under a reduced pressure, so as to obtain 0.72 g of (6-methoxyquinolin-5-yl)acetaldehyde. This compound was directly used in the following reaction without further purification.

0.72 g of (6-methoxyquinolin-5-yl)acetaldehyde and 0.75 g of 1,4-dioxa-8-azaspiro[4.5]decane were dissolved in 30 ml of methylene chloride. Then, 0.50 ml of acetic acid and 0.89 g of sodium triacetoxyborohydride were added to the reaction solution, and the obtained mixture was then stirred at room temperature overnight. Thereafter, a saturated sodium bicarbonate aqueous solution was added to the reaction solution, followed by extraction with methylene chloride. The extract was dried over magnesium sulfate and then concentrated under a reduced pressure. The residue was purified by NH silica gel column chromatography (hexane-ethyl acetate), so as to obtain 1.01 g of the subject compound.

¹H-NMR (CDCl₃) δ (ppm): 1.77-1.87 (m, 4H), 2.53-2.77 (m, 6H), 3.23-3.32 (m, 2H), 3.97 (s, 3H), 3.98 (s, 4H), 7.37 (dd, J=4.0, 8.4 Hz, 1H), 7.47 (d, J=8.8 Hz, 1H), 8.00 (d, J=8.8 Hz, 1H), 8.26-8.34 (m, 1H), 8.76 (dd, J=1.6, 4.0 Hz, 1H).

(3)  1-{1-[2-(1-Acetyl-6-methoxy-1,2,3,4-tetrahydroquinolin-5-yl)ethyl]piperidin-4-yl}-1H-indole-6-carboxamide The subject compound was synthesized from 5-(2-(1,4-dioxa-8-azaspiro[4.5]decan-8-yl)ethyl)-6-methoxyquinoline according to the methods described in Example 52, (2) and (3).

¹H-NMR (DMSO-d₆) δ (ppm): 1.80-1.92 (m, 2H), 1.93-2.14 (m, 4H), 2.24-2.33 (m, 2H), 2.38-2.46 (m, 2H), 2.55-2.73 (m, 2H), 2.77-2.85 (m, 2H), 3.08-3.16 (m, 2H), 3.63 (t, J=6.4 Hz, 2H), 3.80 (s, 3H), 4.37-4.47 (m, 1H), 6.51 (d, J=3.2 Hz, 1H), 6.83 (d, J=8.4 Hz, 1H), 7.06-7.26 (m, 2H), 7.54-7.61 (m, 2H), 7.67 (d, J=3.2 Hz, 1H), 7.91 (br.s, 1H), 8.13 (s, 1H).

Example 55

Synthesis of 1-{1-[2-(6-methoxy-1-methyl-1,2,3,4-tetrahydroquinolin-5-yl)ethyl]piperidin-4-yl}-1H-indole-6-carboxamide

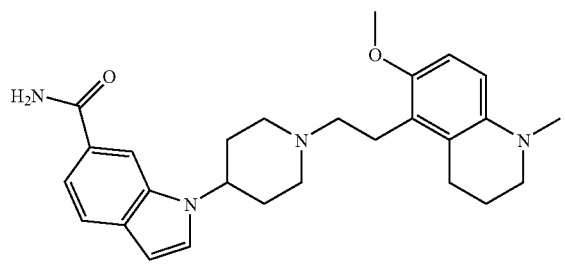

[Formula 115]

The subject compound was synthesized from 5-(2-(1,4-dioxa-8-azaspiro[4.5]decan-8-yl)ethyl)-6-methoxyquinoline according to the methods described in Example 53, (1) and (2).

¹H-NMR (DMSO-d₆) δ (ppm): 1.87-2.10 (m, 6H), 2.23-2.32 (m, 2H), 2.35-2.42 (m, 2H), 2.66-2.78 (m, 4H), 2.75 (s, 3H), 3.00-3.06 (m, 2H), 3.07-3.16 (m, 2H), 3.69 (s, 3H), 4.36-4.47 (m, 1H), 6.46 (d, J=8.8 Hz, 1H), 6.51 (d, J=3.2 Hz, 1H), 6.69 (d, J=8.8 Hz, 1H), 7.21 (br.s, 1H), 7.54-7.61 (m, 2H), 7.68 (d, J=3.2 Hz, 1H), 7.91 (br.s, 1H), 8.12 (s, 1H).

Example 56

Synthesis of 1-{1-[2-(6-methoxy-2-oxo-1,2,3,4-tetrahydroquinolin-7-yl)ethyl]piperidin-4-yl}-1H-indole-6-carboxamide

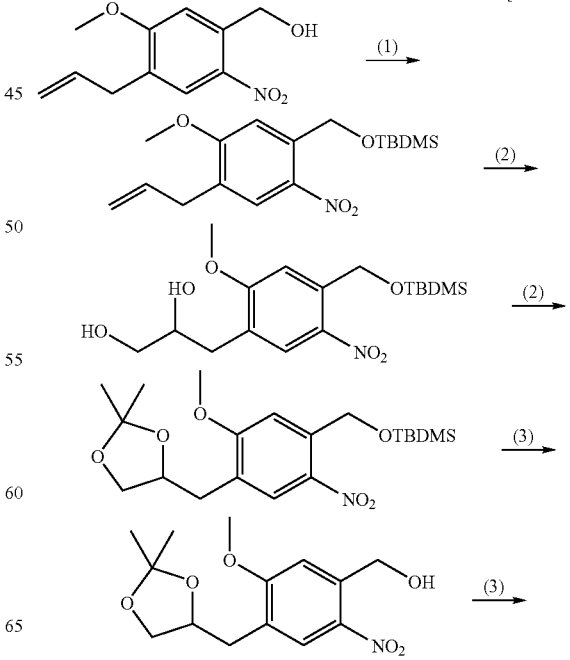

[Formula 116]

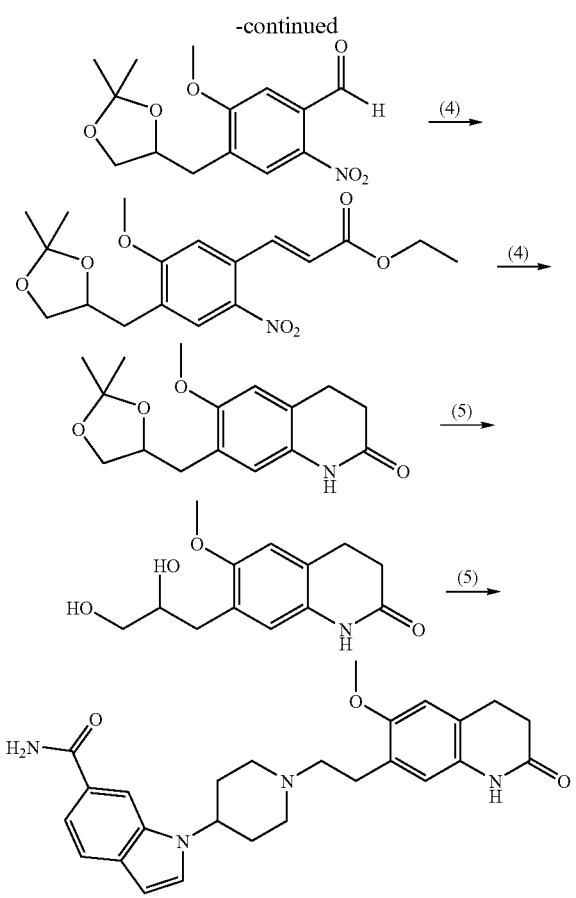

(1) (4-Allyl-5-methoxy-2-nitrobenzyloxy)-t-butyldimethylsilane 229 mg of 4-allyl-5-methoxy-2-nitrobenzyl alcohol was dissolved in 5 ml of N,N-dimethylformamide. Thereafter, 0.17 g of imidazole and 0.23 g of t-butyldimethylsilyl chloride were added to the reaction solution while cooling on ice. The obtained mixture was stirred at room temperature for 2 hours. Thereafter, 34 mg of imidazole and 46 mg of t-butyldimethylsilyl chloride were further added to the reaction solution. The obtained mixture was stirred at room temperature overnight. The reaction solution was diluted with ethyl acetate and then washed with a saturated ammonium chloride aqueous solution and a saturated sodium chloride aqueous solution. The organic layer was dried over magnesium sulfate and then concentrated under a reduced pressure. The residue was purified by silica gel column chromatography (hexane-ethyl acetate), so as to obtain 330 mg of the subject compound.

$^1$H-NMR (CDCl$_3$) δ (ppm): 0.15 (s, 6H), 0.98 (s, 9H), 3.37-3.41 (m, 2H), 3.93 (s, 3H), 5.05-5.14 (m, 2H), 5.12 (s, 2H), 5.89-6.01 (m, 1H), 7.42 (s, 1H), 8.01 (s, 1H).

(2) t-Butyl[4-(2,2-dimethyl-[1,3]dioxolan-4-ylmethyl)-5-methoxy-2-nitrobenzyloxy]dimethylsilane 1.37 g of AD-mix-β was dissolved in 10 ml of t-butanol-water (1:1), and then, 2 ml of a t-butanol solution containing 330 mg of (4-allyl-5-methoxy-2-nitrobenzyloxy)-t-butyldimethylsilane was added to the reaction solution. The obtained mixture was then stirred at room temperature overnight. 1.5 g of sodium sulfite was added to the reaction solution while cooling on ice, and the obtained mixture was stirred at room temperature for 1 hour. A saturated sodium chloride aqueous solution was added to the reaction solution, followed by extraction with methylene chloride. The extract was dried over magnesium sulfate and then concentrated under a reduced pressure, so as to obtain 390 mg of 3-(4-(t-butyldimethylsilyloxy-methyl)-2-methoxy-5-nitrophenyl)propane-1,2-diol. This compound was directly used in the following reaction without further purification.

390 mg of 3-(4-(t-butyldimethylsilyloxy-methyl)-2-methoxy-5-nitrophenyl)propane-1,2-diol was dissolved in 8 ml of acetone. Then, 0.33 g of dimethoxypropane and 26 mg of pyridinium p-toluenesulfonate were added to the reaction solution. The obtained mixture was then stirred at room temperature for 41 hours. Thereafter, the reaction solution was concentrated under a reduced pressure. The residue was diluted with ethyl acetate and then washed with water and a saturated sodium chloride aqueous solution. The organic layer was dried over magnesium sulfate and then concentrated under a reduced pressure. The residue was purified by silica gel column chromatography (hexane-ethyl acetate), so as to obtain 358 mg of the subject compound.

$^1$H-NMR (CDCl$_3$) δ (ppm): 0.15 (s, 6H), 0.99 (s, 9H), 1.34 (s, 3H), 1.43 (s, 3H), 2.87 (dd, J=6.0, 13.6 Hz, 1H), 2.96 (dd, J=6.0, 13.6 Hz, 1H), 3.64 (dd, J=6.8, 8.0 Hz, 1H), 3.92 (s, 3H), 3.99 (dd, J=5.6, 8.0 Hz, 1H), 4.33-4.41 (m, 1H), 5.12 (s, 2H), 7.43 (s, 1H), 8.08 (s, 1H).

(3) 4-[(2,2-Dimethyl-[1,3]dioxolan-4-yl)methyl]-5-methoxy-2-nitrobenzaldehyde 358 mg of t-butyl(4-(2,2-dimethyl-[1,3]dioxolan-4-ylmethyl)-5-methoxy-2-nitrobenzyloxy)dimethylsilane was dissolved in 10 ml of tetrahydrofuran. While cooling on ice, 1 ml of a tetrahydrofuran solution containing 1.0 M tetrabutyl ammonium fluoride was added to the reaction solution, and the obtained mixture was then stirred at room temperature for 3 hours. Thereafter, the reaction solution was diluted with ethyl acetate and then washed with a saturated sodium chloride aqueous solution. The organic layer was dried over magnesium sulfate and then concentrated under a reduced pressure. The residue was purified by silica gel column chromatography (hexane-ethyl acetate), so as to obtain 253 mg of (4-(2,2-dimethyl-[1,3]dioxolan-4-ylmethyl)-5-methoxy-2-nitrophenyl)methanol.

Thereafter, 253 mg of (4-(2,2-dimethyl-[1,3]dioxolan-4-ylmethyl)-5-methoxy-2-nitrophenyl)methanol was dissolved in 10 ml of methylene chloride. Then, 2.5 g of activated manganese dioxide was added to the reaction solution, and the obtained mixture was then stirred at room temperature for 66 hours. Thereafter, the reaction solution was filtered through celite, and the filtrate was concentrated under a reduced pressure, so as to obtain 137 mg of the subject compound.

$^1$H-NMR (CDCl$_3$) δ (ppm): 1.34 (s, 3H), 1.43 (s, 3H), 2.91-3.03 (m, 2H), 3.65 (dd, J=6.0, 8.0 Hz, 1H), 3.98 (s, 3H), 4.06 (dd, J=6.0, 8.0 Hz, 1H), 4.34-4.43 (m, 1H), 7.32 (s, 1H), 8.07 (s, 1H), 10.47 (s, 1H).

(4) 7-[(2,2-Dimethyl-[1,3]dioxolan-4-yl)methyl]-6-methoxy-1,2,3,4-tetrahydroquinolin-2-one 137 mg of 4-((2,2-dimethyl-[1,3]dioxolan-4-yl)methyl)-5-methoxy-2-nitrobenzaldehyde was dissolved in 5 ml of toluene. Thereafter, 204 mg of ethoxycarbonylmethylenetriphenylphospholane was added to the reaction solution, and the obtained mixture was then heated to reflux for 1 hour. The reaction solution was cooled to a room temperature. Thereafter, the reaction solution was concentrated under a reduced pressure. The residue was purified by silica gel column chromatography (hexane-ethyl acetate), so as to obtain 168 mg of 3-(4-((2,2-dimethyl-[1,3]dioxolan-4-yl)methyl)-5-methoxy-2-nitrophenyl)ethyl acrylate.

Thereafter, 168 mg of 3-(4-((2,2-dimethyl-[1,3]dioxolan-4-yl)methyl)-5-methoxy-2-nitrophenyl)ethyl acrylate was dissolved in 5 ml of ethanol. Then, 30 mg of 10% palladium carbon was added to the reaction solution, and the obtained mixture was then stirred under hydrogen atmosphere for 4 hours. Palladium carbon was removed by filtration, and the filtrate was then concentrated under a reduced pressure. The residue was dissolved in 5 ml of ethanol. The reaction solution was stirred at 50° C. for 17 hours. It was then heated to reflux for 30 minutes. The reaction solution was cooled to a room temperature, and it was then concentrated under a reduced pressure. The residue was reprecipitated from diethyl ether-hexane, so as to obtain 110 mg of the subject compound.

$^1$H-NMR (DMSO-$d_6$) δ (ppm): 1.23 (s, 3H), 1.33 (s, 3H), 2.36-2.43 (m, 2H), 2.63-2.77 (m, 2H), 2.80-2.87 (m, 2H), 3.53 (dd, J=6.4, 8.0 Hz, 1H), 3.74 (s, 3H), 3.90 (dd, J=5.6, 8.0 Hz, 1H), 4.15-4.23 (m, 1H), 6.68 (s, 1H), 6.82 (s, 1H), 9.84 (br.s, 1H).

(5)  1-{1-[2-(6-Methoxy-2-oxo-1,2,3,4-tetrahydroquinolin-7-yl)ethyl]piperidin-4-yl}-1H-indole-6-carboxamide 109 mg of 7-((2,2-dimethyl-[1,3]dioxolan-4-yl)methyl)-6-methoxy-1,2,3,4-tetrahydroquinolin-2-one was dissolved in 4 ml of methanol-tetrahydrofuran (1:1). While cooling on ice, 1 ml of 2 N hydrochloric acid was added to the reaction solution, and the obtained mixture was then stirred at room temperature for 3 hours. Thereafter, the reaction solution was concentrated under a reduced pressure, so as to obtain 110 mg of 7-(2,3-dihydroxypropyl)-6-methoxy-1,2,3,4-tetrahydroquinolin-2-one. This compound was directly used in the following reaction without further purification.

110 mg of 7-(2,3-dihydroxypropyl)-6-methoxy-1,2,3,4-tetrahydroquinolin-2-one was dissolved in 2 ml of methanol and 1 ml of tetrahydrofuran. Thereafter, 2 ml of water containing 0.16 g of sodium metaperiodate was added to the reaction solution while cooling on ice. The obtained mixture was stirred at room temperature for 30 minutes. A saturated sodium chloride aqueous solution was added to the reaction solution, followed by extraction with methylene chloride. The extract was dried over magnesium sulfate and then concentrated under a reduced pressure, so as to obtain 87 mg of (6-methoxy-2-oxo-1,2,3,4-tetrahydroquinolin-7-yl)acetaldehyde. This compound was directly used in the following reaction without further purification.

100 mg of 1-(piperidin-4-yl)-1H-indole-6-carboxamide and 87 mg of (6-methoxy-2-oxo-1,2,3,4-tetrahydroquinolin-7-yl)acetaldehyde were suspended in 5 ml of methylene chloride. Thereafter, 0.05 ml of acetic acid and 0.13 g of sodium triacetoxyborohydride were added to the reaction solution, and the obtained mixture was stirred at room temperature overnight. Thereafter, a saturated sodium bicarbonate aqueous solution was added to the reaction solution, followed by extraction with chloroform. The extract was dried over magnesium sulfate and then concentrated under a reduced pressure. The residue was purified by silica gel column chromatography (chloroform-methanol) and by NH silica gel column chromatography (chloroform-methanol), and then reprecipitated from ethyl acetate, so as to obtain 18 mg of the subject compound.

$^1$H-NMR (DMSO-$d_6$) δ (ppm): 1.92-2.10 (m, 4H), 2.20-2.30 (m, 2H), 2.40 (t, J=7.6 Hz, 2H), 2.45-2.55 (m, 2H), 2.65-2.72 (m, 2H), 2.83 (t, J=7.6 Hz, 2H), 3.06-3.12 (m, 2H), 3.75 (s, 3H), 4.37-4.47 (m, 1H), 6.50 (d, J=3.2 Hz, 1H), 6.69 (s, 1H), 6.81 (s, 1H), 7.21 (br.s, 1H), 7.53-7.61 (m, 2H), 7.67 (d, J=3.2 Hz, 1H), 7.91 (br.s, 1H), 8.12 (s, 1H), 9.85 (s, 1H).

Example 57

Synthesis of 1-{1-[2-(6-methoxy-1-methyl-2-oxo-1,2,3,4-tetrahydroquinolin-7-yl)ethyl]piperdin-4-yl}-1H-indole-6-carboxamide

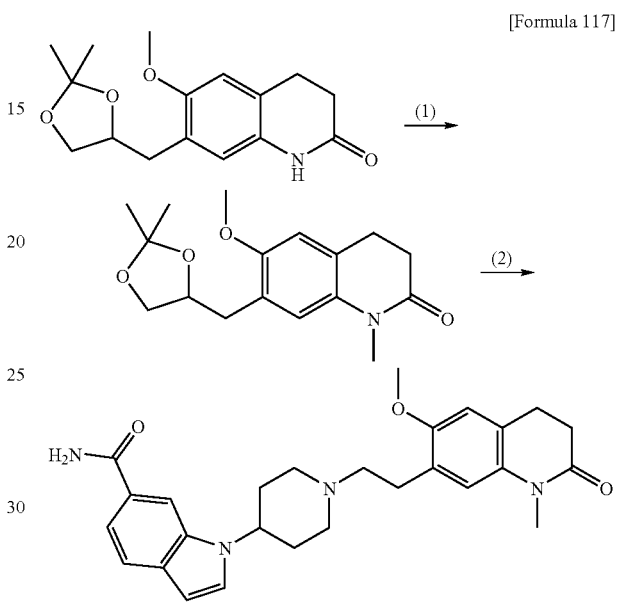

[Formula 117]

(1)  7-[(2,2-Dimethyl-[1,3]dioxolan-4-yl)methyl]-6-methoxy-1-methyl-1,2,3,4-tetrahydroquinolin-2-one 300 mg of 7-((2,2-dimethyl-[1,3]dioxolan-4-yl)methyl)-6-methoxy-1,2,3,4-tetrahydroquinolin-2-one was dissolved in 6 ml of N,N-dimethylformamide. While cooling on ice, 49 mg of 60% sodium hydride was added to the reaction solution, and the obtained mixture was then stirred at room temperature for 30 minutes. Thereafter, 0.29 g of iodomethane was added to the reaction solution while cooling on ice. The obtained mixture was stirred at room temperature for 2 hours. The reaction solution was diluted with ethyl acetate and then washed with a saturated ammonium chloride aqueous solution and a saturated sodium chloride aqueous solution. The organic layer was dried over magnesium sulfate and then concentrated under a reduced pressure. The residue was purified by NH silica gel column chromatography (hexane-ethyl acetate), so as to obtain 310 mg of the subject compound.

$^1$H-NMR (DMSO-$d_6$) δ (ppm): 1.34 (s, 3H), 1.43 (s, 3H), 2.58-2.66 (m, 2H), 2.80-2.89 (m, 3H), 2.94 (dd, J=6.0, 14.0 Hz, 1H), 3.32 (s, 3H), 3.65 (dd, J=6.0, 7.6 Hz, 1H), 3.80 (s, 3H), 3.97 (dd, J=5.6, 7.6 Hz, 1H), 4.32-4.39 (m, 1H), 6.65 (s, 1H), 6.81 (s, 1H).

(2) 1-{1-[2-(6-Methoxy-1-methyl-2-oxo-1,2,3,4-tetrahydroquinolin-7-yl)ethyl]piperidin-4-yl}-1H-indole-6-carboxamide The subject compound was synthesized from 7-((2,2-dimethyl-[1,3]dioxolan-4-yl)methyl)-6-methoxy-1-methyl-1,2,3,4-tetrahydroquinolin-2-one according to the method described in Example 56, (5).

$^1$H-NMR (DMSO-$d_6$) δ (ppm): 1.92-2.09 (m, 4H), 2.22-2.32 (m, 2H), 2.45-2.60 (m, 4H), 2.72-2.86 (m, 4H), 3.08-

3.15 (m, 2H), 3.24 (s, 3H), 3.78 (s, 3H), 4.37-4.48 (m, 1H), 6.50 (d, J=3.2 Hz, 1H), 6.88 (s, 1H), 6.96 (s, 1H), 7.22 (br.s, 1H), 7.53-7.60 (m, 2H), 7.67 (d, J=3.2 Hz, 1H), 7.91 (br.s, 1H), 8.13 (s, 1H).

Example 58

Synthesis of 1-{1-[2-(6-methoxy-1-methyl-2-oxo-1,2,3,4-tetrahydroquinolin-7-yl)ethyl]piperidin-4-yl}-N-methyl-1H-indole-6-carboxamide

[Formula 118]

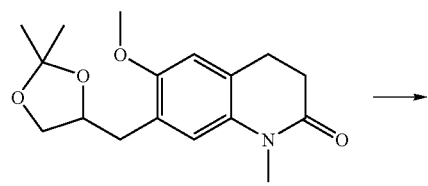

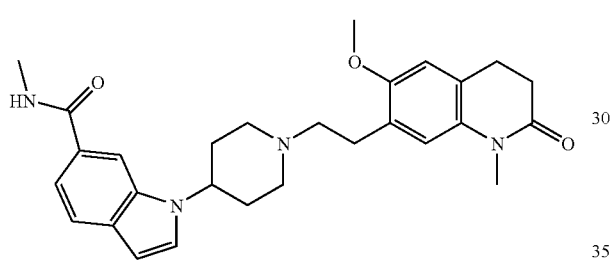

The subject compound was synthesized from 7-((2,2-dimethyl-[1,3]dioxolan-4-yl)methyl)-6-methoxy-1-methyl-1,2,3,4-tetrahydroquinolin-2-one according to the method described in Example 56, (5).

$^1$H-NMR (DMSO-d$_6$) δ (ppm): 1.93-2.10 (m, 4H), 2.22-2.31 (m, 2H), 2.47-2.60 (m, 4H), 2.74-2.85 (m, 4H), 2.82 (d, J=4.4 Hz, 3H), 3.08-3.15 (m, 2H), 3.24 (s, 3H), 3.78 (s, 3H), 4.36-4.46 (m, 1H), 6.50 (d, J=3.2 Hz, 1H), 6.88 (s, 1H), 6.96 (s, 1H), 7.51-7.58 (m, 2H), 7.67 (d, J=3.2 Hz, 1H), 8.05 (s, 1H), 8.30-8.37 (m, 1H).

Example 59

Synthesis of 1-{1-[2-(1-ethyl-6-methoxy-2-oxo-1,2,3,4-tetrahydroquinolin-7-yl)ethyl]piperidin-4-yl}-1H-indole-6-carboxamide

[Formula 119]

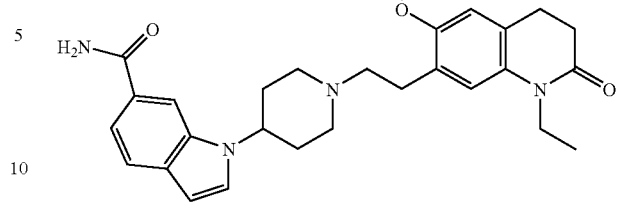

The subject compound was synthesized from 7-((2,2-dimethyl-[1,3]dioxolan-4-yl)methyl)-6-methoxy-1,2,3,4-tetrahydroquinolin-2-one according to the method described in Example 57.

$^1$H-NMR (DMSO-d$_6$) δ (ppm): 1.13 (t, J=7.2, 3H), 1.94-2.07 (m, 4H), 2.21-2.30 (m, 2H), 2.46-2.59 (m, 4H), 2.74-2.83 (m, 4H), 3.08-3.16 (m, 2H), 3.78 (s, 3H), 3.99 (q, J=7.2 Hz, 2H), 4.37-4.47 (m, 1H), 6.50 (d, J=3.2 Hz, 1H), 6.86 (s, 1H), 7.00 (s, 1H), 7.21 (br.s, 1H), 7.54-7.60 (m, 2H), 7.65 (d, J=3.2 Hz, 1H), 7.91 (br.s, 1H), 8.12 (s, 1H).

Example 60

Synthesis of 1-{1-[2-(3-ethyl-6-methoxy-2-oxo-2,3-dihydrobenzoxazol-5-yl)ethyl]piperidin-4-yl}-1H-indole-6-carboxamide

[Formula 120]

(1) 3-Ethyl-6-methoxy-5-(3-methyl-2-butenyl)-3H-benzoxazol-2-one 231 mg of 6-methoxy-2-methyl-5-(3-methyl-2-butenyl)benzoxazole was dissolved in 5 ml of tetrahydrofuran under nitrogen atmosphere. Thereafter, 0.4 ml of a tetrahydrofuran solution containing 0.12 g of sodium borohydride and 0.1 ml of acetic acid was added to the reaction solution over 20 minutes, and the obtained mixture was stirred at room temperature overnight. The reaction solution was concentrated under a reduced pressure. A saturated ammonium chloride aqueous solution was added to the residue, followed by extraction with methylene chloride. The extract was washed with a saturated sodium chloride aqueous solution. The organic layer was dried over magnesium sulfate and then concentrated under a reduced pressure. The residue was purified by silica gel column chromatography (hexane-ethyl acetate), so as to obtain 80 mg of 2-ethylamino-5-methoxy-4-(3-methyl-2-butenyl)phenol containing a product whose structure was unknown. This compound was directly used in the following reaction without further purification.

80 mg of 2-ethylamino-5-methoxy-4-(3-methyl-2-butenyl)phenol was dissolved in 5 ml of tetrahydrofuran under nitrogen atmosphere. Then, 0.11 g of 1,1'-carbonyldiimidazole was added to the reaction solution, and the obtained mixture was then stirred at room temperature for 1 hour. Thereafter, the mixture was further stirred at 50° C. for 1 hour. The reaction solution was concentrated under a reduced pressure. The residue was diluted with ethyl acetate and then washed with a saturated sodium chloride aqueous solution. The organic layer was dried over magnesium sulfate and then concentrated under a reduced pressure. The residue was purified by silica gel column chromatography (hexane-ethyl acetate), so as to obtain 60 mg of the subject compound.

$^1$H-NMR (CDCl$_3$) δ (ppm): 1.35 (t, J=6.8 Hz, 3H), 1.72 (s, 3H), 1.75 (s, 3H), 3.33 (d, J=7.2 Hz, 2H), 3.82 (s, 3H), 3.84 (q, J=6.8 Hz, 2H), 5.23-5.29 (m, 1H), 6.73 (s, 1H), 6.80 (s, 1H).

(2) 1-{1-[2-(3-Ethyl-6-methoxy-2-oxo-2,3-dihydrobenzoxazol-5-yl)ethyl]piperidin-4-yl}-1H-indole-6-carboxamide The subject compound was synthesized from 3-ethyl-6-methoxy-5-(3-methyl-2-butenyl)-3H-benzoxazol-2-one according to the method described in Example 4, (4).

$^1$H-NMR (DMSO-d$_6$) δ (ppm): 1.26 (t, J=7.2, 3H), 1.93-2.08 (m, 4H), 2.24-2.32 (m, 2H), 2.50-2.60 (m, 2H), 2.77-2.84 (m, 2H), 3.08-3.15 (m, 2H), 3.80 (s, 3H), 3.82 (q, J=7.2 Hz, 2H), 4.37-4.47 (m, 1H), 6.50 (d, J=3.2 Hz, 1H), 7.14 (s, 1H), 7.17-7.24 (m, 1H), 7.20 (s, 1H), 7.54-7.60 (m, 2H), 7.66 (d, J=3.2 Hz, 1H), 7.91 (br.s, 1H), 8.13 (s, 1H).

Example 61

Synthesis of 1-{1-[2-(7-methoxy-3-methyl-2-oxo-3,4-dihydro-1,3-benzoxazin-8-yl)ethyl]piperidin-4-yl}-1H-indole-6-carboxamide

[Formula 121]

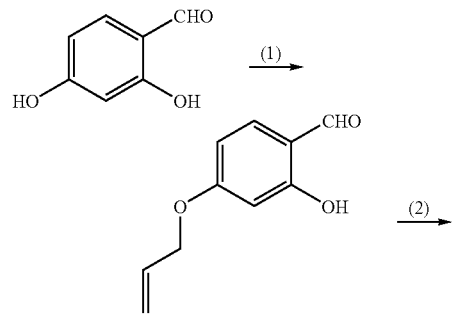

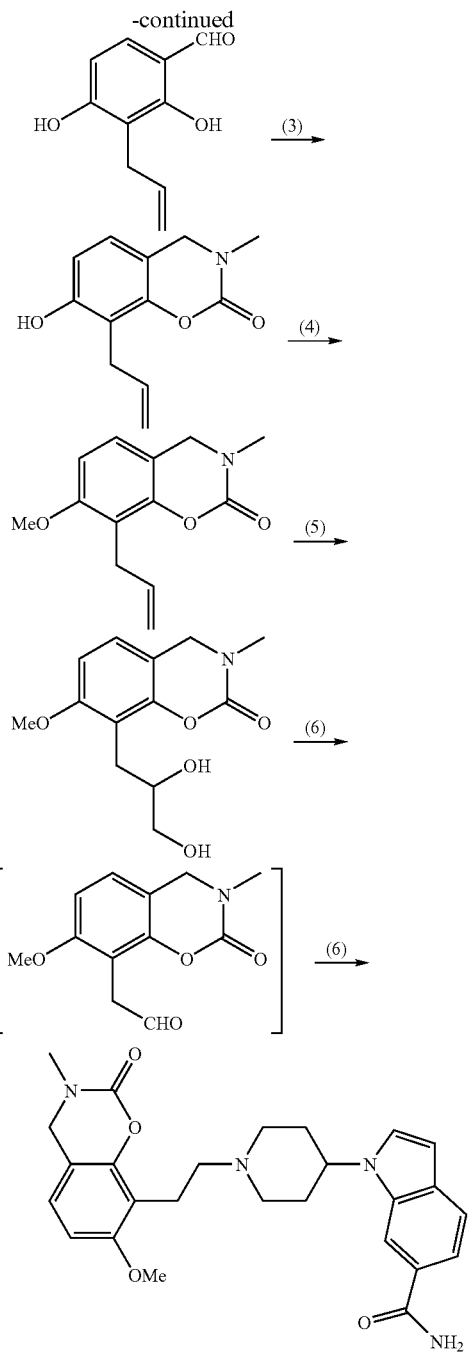

(1) 2-Allyloxy-4-hydroxybenzaldehyde 15.23 g of 2,4-dihydroxybenzaldehyde was dissolved in 200 ml of methyl ethyl ketone. Then, 15.54 g of potassium carbonate, 9.73 ml of allyl bromide, 18.67 g of potassium iodide, and 3.55 g of tetrabutylammonium bromide were successively added to the reaction solution. This reaction solution was heated to reflux under nitrogen atmosphere for 1.5 hours. The precipitate was removed by filtration, and the filtrate was concentrated under a reduced pressure. Ethyl acetate and water were added to the residue, so as to separate an organic layer. The organic layer was washed with a saturated sodium chloride solution and then dried over anhydrous magnesium sulfate. After removing the drying agent by filtration, the organic layer was concentrated under a reduced pressure. The residue was then purified by silica gel column chromatography (hexane/ethyl acetate), so as to obtain 13.72 g of the subject compound.

$^1$H-NMR (CDCl$_3$) δ (ppm): 4.58-4.60 (m, 2H),5.32-5.36 (m, 1H), 5.40-5.46 (m, 1H),5.99-6.08 (m, 1H), 6.44 (d, J=2.4 Hz, 1H), 6.56 (dd, J=2.4, 8.8 Hz, 1H),7.44 (d, J=8.8 Hz, 1H), 9.72 (s, 1H), 11.47 (s, 1H).

(2) 3-Allyl-2,4-dihydroxybenzaldehyde 3.10 g of 2-allyloxy-4-hydroxybenzaldehyde was dissolved in 6 ml of N,N-dimethylaniline, and the reaction solution was heated to reflux under nitrogen atmosphere. Approximately 2.5 hours later, the reaction solution was stood to cool. Thereafter, water and ethyl acetate were added to the reaction solution, so as to separate an organic layer. The obtained organic layer was washed with 5 N hydrochloric acid, water, and a saturated sodium chloride solution, and then dried over anhydrous magnesium sulfate. After removing the drying agent by filtration, the organic layer was concentrated under a reduced pressure. The residue was then purified by silica gel column chromatography (hexane/ethyl acetate), so as to obtain 0.88 g of the subject compound.

$^1$H-NMR (CDCl$_3$) δ (ppm): 3.48-3.50 (m, 2H), 5.15-5.23 (m, 2H), 5.87 (s, 1H), 5.94-6.04 (m, 1H), 6.50 (d, J=8.4 Hz, 1H), 7.35 (d, J=8.4 Hz, 1H), 9.70 (s, 1H), 11.76 (s, 1H).

(3) 8-Allyl-7-hydroxy-3-methyl-3,4-dihydro-2H-1,3-benzoxazin-2-one 0.88 g of 3-allyl-2,4-dihydroxybenzaldehyde was dissolved in 10 ml of methanol. 1.92 ml of a methanol solution containing methylamine (40%) was added to the above solution, and the obtained mixture was then stirred at room temperature for approximately 30 minutes. Thereafter, this reaction solution was cooled on ice, and sodium borohydride was then added thereto little at a time. The reaction solution was stirred at room temperature for 15 minutes. Thereafter, the solvent was removed under a reduced pressure. A saturated sodium bicarbonate aqueous solution was added to the residue, followed by extraction with ethyl acetate twice. The obtained organic layer was washed with a saturated sodium chloride solution and then dried over anhydrous magnesium sulfate. After removing the drying agent by filtration, the organic layer was concentrated under a reduced pressure. 2.40 g of 1,1'-carbonyldiimidazole and 30 ml of anhydrous tetrahydrofuran were added to the residue, and the obtained mixture was then heated to reflux for 2.5 hours. The reaction solution was cooled to a room temperature, and 5 ml of methanol was then added to the reaction solution. The solvent was removed under a reduced pressure. The residue was purified by silica gel column chromatography (hexane/ethyl acetate), so as to obtain 0.66 g of the subject compound.

$^1$H-NMR (CDCl$_3$) δ (ppm): 3.11 (s, 3H), 3.52-3.54 (m, 2H), 4.39 (bs, 2H), 5.11-5.18 (m, 2H), 5.24 (s, 1H), 5.92-6.02 (m, 1H), 6.62 (d, J=8.2 Hz, 1H), 6.85 (d, J=8.2 Hz, 1H).

(4) 8-Allyl-7-methoxy-3-methyl-3,4-dihydro-2H-1,3-benzoxazin-2-one 0.66 g of 8-allyl-7-hydroxy-3-methyl-3,4-dihydro-2H-1, 3-benzoxazin-2-one was dissolved in 6 ml of N,N-dimethylformamide. 0.63 g of potassium carbonate and 0.94 ml of methyl iodide were added to the above solution, and the obtained mixture was then stirred at room temperature overnight under nitrogen atmosphere. Thereafter, water and ethyl acetate were added to the reaction solution, so as to separate an organic layer. The obtained organic layer was washed with a sodium thiosulfate aqueous solution, water, and a saturated sodium chloride solution, and then dried over anhydrous magnesium sulfate. After removing the drying agent by filtration, the organic layer was concentrated under a reduced pressure. The residue was purified by silica gel column chromatography (hexane/ethyl acetate), so as to obtain 0.58 g of the subject compound.

$^1$H-NMR (CDCl$_3$) δ (ppm): 3.11 (s, 3H), 3.46-3.48 (m, 2H),3.83 (s, 3H), 4.40 (bs, 2H), 4.94-5.05 (m, 2H), 5.89-5.99 (m, 1H), 6.64 (d, J=8.6 Hz, 1H), 6.90 (d, J=8.6 Hz, 1H).

(5) 8-(2,3-Dihydroxypropyl)-7-methoxy-3-methyl-3,4-dihydro-2H-1,3-benzoxazin-2-one 12 ml of t-butanol and 10 ml of water were added to and dissolved in 0.58 g of 8-allyl-7-methoxy-3-methyl-3,4-dihydro-2H-1,3-benzoxazin-2-one. 2.48 g of AD-mix-β was added to this solution, and the obtained mixture was stirred at room temperature overnight. After confirming the disappearance of raw material, 2.97 g of sodium sulfite was added to the reaction solution, and the obtained mixture was then stirred for approximately 45 minutes. Thereafter, water and chloroform were added to the reaction solution, so as to separate an organic layer. The obtained organic layer was washed with a saturated sodium chloride solution and then dried over anhydrous magnesium sulfate. After removing the drying agent by filtration, the organic layer was concentrated under a reduced pressure. The residue was purified by silica gel column chromatography (ethyl acetate/methanol), so as to obtain 0.55 g of the subject compound.

$^1$H-NMR (CDCl$_3$) δ (ppm): 2.92-3.02 (m, 2H), 3.11 (s, 3H), 3.50 (dd, J=5.8, 12.0 Hz, 1H), 3.60 (dd, J=3.6, 12.0 Hz, 1H), 3.85 (s, 3H), 3.92-3.96 (m, 1H), 4.40 (s, 2H), 6.66 (d, J=8.4 Hz, 1H), 6.94 (d, J=8.4 Hz, 1H).

(6) 1-{1-[2-(7-Methoxy-3-methyl-2-oxo-3,4-dihydro-1,3-benzoxazin-8-yl)ethyl]piperidin-4-yl}-1H-indole-6-carboxamide 114 mg of 8-(2,3-dihydroxypropyl)-7-methoxy-3-methyl-3,4-dihydro-2H-1,3-benzoxazin-2-one was dissolved in 2 ml of tetrahydrofuran, 2 ml of methanol, and 1.3 ml of water. Thereafter, 182 mg of sodium metaperiodate was added thereto, and the obtained mixture was vigorously stirred. After confirming the disappearance of materials, water and ethyl acetate were added to the reaction solution, so as to separate an organic layer. The obtained organic layer was washed with a saturated sodium chloride solution and then dried over anhydrous magnesium sulfate. After removing the drying agent by filtration, the organic layer was concentrated under a reduced pressure, so as to obtain 135 mg of a crude aldehyde form.

135 mg of the aforementioned crude aldehyde form dissolved in 4 ml of dichloromethane and 40.5 μl of acetic acid were successively added to 86 mg of 1-(piperidin-4-yl)-1H-indole-6-carboxamide, and the obtained mixture was then stirred for 10 minutes. Thereafter, 112 mg of sodium triacetoxyborohydride was added to the reaction solution, and the obtained mixture was then stirred at room temperature overnight. Thereafter, a 10% sodium carbonate aqueous solution and chloroform were added to the reaction solution, so as to separate an organic layer. The obtained organic layer was washed with a saturated sodium chloride solution and then dried over anhydrous magnesium sulfate. After removing the drying agent by filtration, the organic layer was concentrated under a reduced pressure. The residue was purified by NH silica gel column chromatography (ethyl acetate/methanol), so as to obtain 124 mg of the subject compound.

$^1$H-NMR (CDCl$_3$) δ (ppm): 2.04-2.40 (m, 4H), 2.28-2.38 (m, 2H), 2.58-2.66 (m, 2H), 2.95-2.99 (m, 2H), 3.12 (s, 3H), 3.21-3.28 (m, 2H), 3.84 (s, 3H), 4.32-4.40 (m, 2H), 4.40 (s, 2H), 5.56 (bs, 1H), 6.29 (bs, 1H), 6.55 (d, J=3.3 Hz, 1H), 6.64

(d, J=8.4 Hz, 1H), 6.90 (d, J=8.4 Hz, 1H), 7.38 (d, J=3.3 Hz, 1H), 7.45 (br d, 1H), 7.63 (d, J=8.0 Hz, 1H), 8.08 (br s, 1H).
Example 62
Synthesis of 1-{1-[2-(7-methoxy-3-methyl-2,4-dioxo-3,4-dihydro-2H-1,3-benzoxazin-8-yl)ethyl]piperidin-4-yl}-1H-indole-6-carboxamide
[Formula 122]
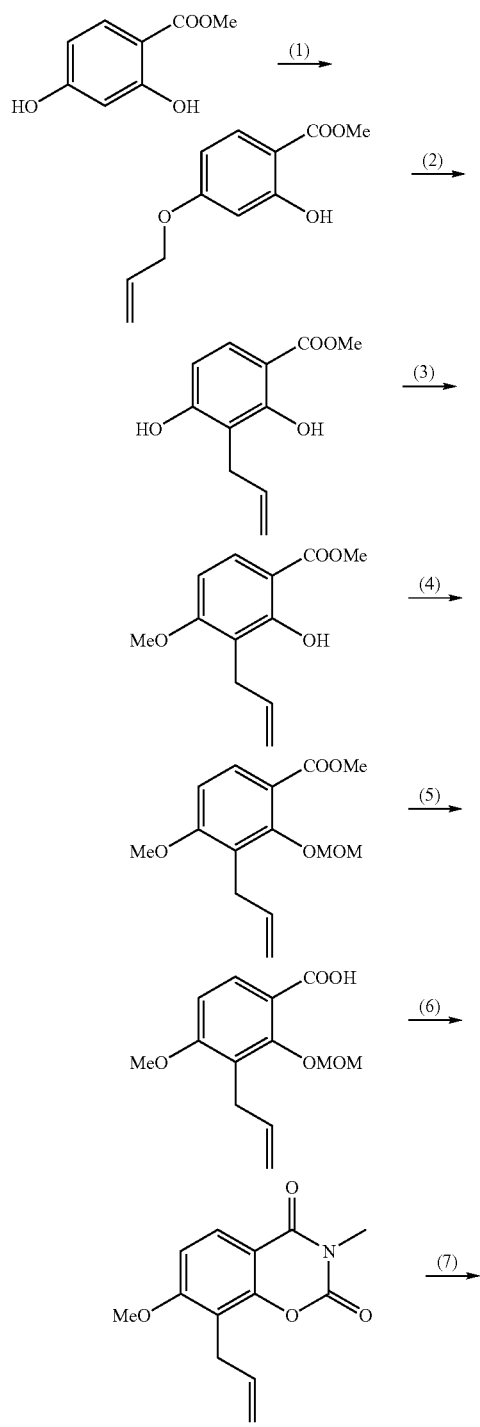
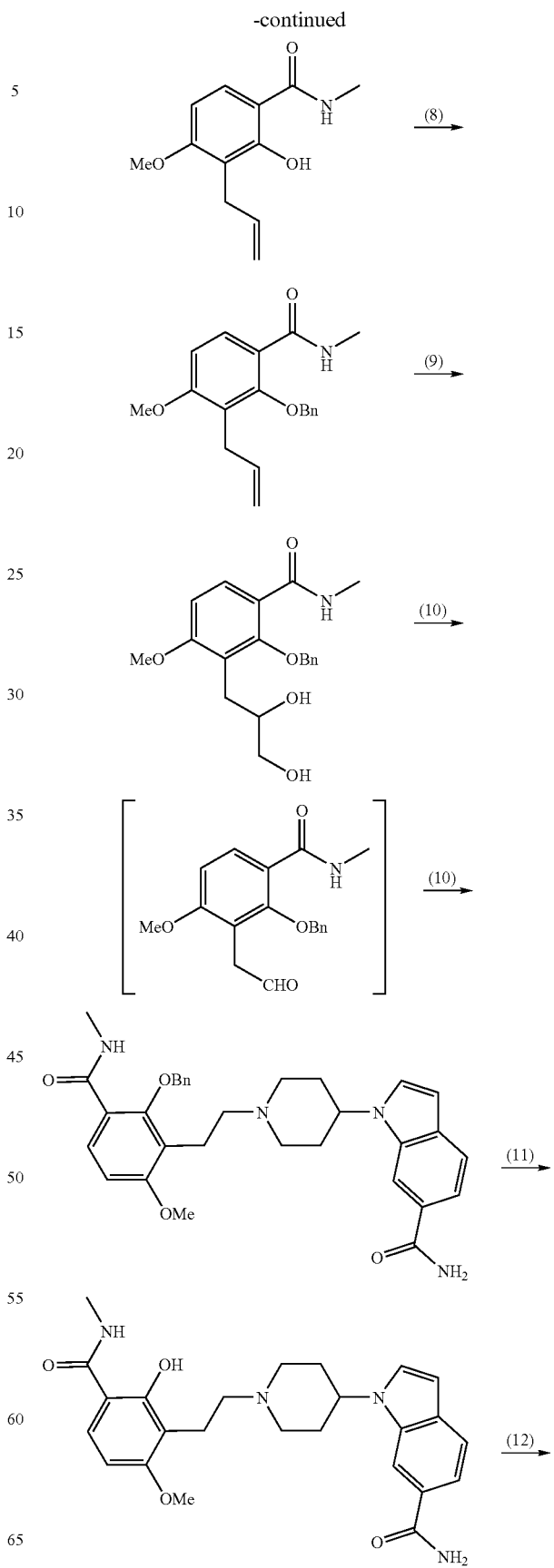

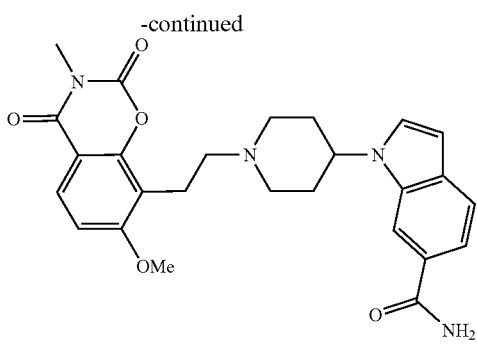

(1) Methyl 4-(allyloxy)-2-hydroxybenzoate 20.05 g of methyl 2,4-dihydroxybenzoate was dissolved in 250 ml of acetone, and then, 17.31 g of potassium carbonate and 12.4 ml of allyl bromide were successively added to the reaction solution. The obtained mixture was stirred at room temperature under nitrogen atmosphere for approximately 2.5 days. Thereafter, the precipitate was removed by filtration, and the filtrate was concentrated under a reduced pressure. The obtained residue was purified by silica gel column chromatography (hexane/ethyl acetate), so as to obtain 20.36 g of the subject compound. A peak that was assumed to be an isomer (methyl4-(allyloxy)-2-hydroxybenzoate) was slightly observed in NMR.

$^1$H-NMR (CDCl$_3$) δ (ppm): 3.91 (s, 3H), 4.54-4.57 (m, 2H), 5.30-5.33 (m, 1H), 5.39-5.45 (m, 1H), 5.99-6.08 (m, 1H), 6.44-6.47 (m, 2H), 7.72-7.75 (m, 1H), 10.96 (s, 1H).

(2) Methyl 3-allyl-2,4-dihydroxybenzoate 9.47 g of methyl 4-(allyloxy)-2-hydroxybenzoate was dissolved in 25 ml of N,N-dimethylaniline, and the obtained mixture was then heated to reflux under nitrogen atmosphere. Approximately 2.5 hours later, the reaction mixture was cooled to a room temperature. Thereafter, water and ethyl acetate were added to the reaction solution, so as to separate an organic layer. The obtained organic layer was washed with 5 N hydrochloric acid, water, and a saturated sodium chloride solution, and then dried over anhydrous magnesium sulfate. After removing the drying agent by filtration, the organic layer was concentrated under a reduced pressure. The obtained residue was purified by silica gel column chromatography (hexane/ethyl acetate), so as to obtain 2.30 g of the subject compound. A peak that was assumed to be an isomer (methyl5-(allyloxy)-2,4-dihydroxybenzoate) was slightly observed in NMR.

$^1$H-NMR (CDCl$_3$) δ (ppm): 3.48-3.50 (m, 2H), 3.91 (s, 3H), 5.11-5.18 (m, 2H), 5.56 (s, 1H), 6.38 (d, J=8.8 Hz, 1H), 7.65 (d, J=8.8 Hz, 1H), 11.27 (s, 1H).

(3) Methyl 3-allyl-2-hydroxy-4-methoxybenzoate 2.30 g of methyl 3-allyl-2,4-dihydroxybenzoate was dissolved in 30 ml of acetone, and then, 1.83 g of potassium carbonate and 0.76 ml of methyl iodide were added to the above solution. The obtained mixture was then stirred at room temperature under nitrogen atmosphere overnight. Thereafter, a 5% sodium hydrogen sulfate aqueous solution, water, and ethyl acetate were added to the reaction solution, so as to separate an organic layer. The obtained organic layer was washed with a sodium thiosulfate aqueous solution, water, and a saturated sodium chloride solution, and then dried over anhydrous magnesium sulfate. After removing the drying agent by filtration, the organic layer was concentrated under a reduced pressure. The obtained residue was purified by silica gel column chromatography (hexane/ethyl acetate), so as to obtain 1.83 g of the subject compound. A peak that was assumed to be an isomer (methyl 5-(allyloxy)-2-hydroxy-4-methoxybenzoate) was slightly observed in NMR.

$^1$H-NMR (CDCl$_3$) δ (ppm): 3.41-3.43 (m, 2H), 3.86 (s, 3H), 3.91 (s, 3H), 4.93-5.02 (m, 2H), 5.90-6.00 (m, 1H), 6.45 (d, J=8.8 Hz, 1H), 7.73 (d, J=8.8 Hz, 1H), 11.05 (s, 1H).

(4) Methyl 3-allyl-4-methoxy-2-(methoxymethoxy)benzoate

Sodium hydride (60%) was washed with n-hexane and then suspended in 2 ml of anhydrous tetrahydrofuran. This suspension was cooled on ice and then stirred under nitrogen atmosphere. 2.30 g of methyl 3-allyl-2-hydroxy-4-methoxybenzoate dissolved in 8 ml of anhydrous tetrahydrofuran was added to the above suspension. The reaction solution was stirred at room temperature for approximately 1 hour. Thereafter, 1.25 ml of chloromethyl methyl ether was added to the reaction solution, and the obtained mixture was further stirred overnight. Thereafter, a 10% sodium carbonate aqueous solution and ethyl acetate were added to the reaction solution, so as to separate an organic layer. The obtained organic layer was washed with a saturated sodium chloride solution and then dried over anhydrous magnesium sulfate. After removing the drying agent by filtration, the organic layer was concentrated under a reduced pressure. The residue was purified by silica gel column chromatography (hexane/ethyl acetate), so as to obtain 1.32 g of the subject compound.

$^1$H-NMR (CDCl$_3$) δ (ppm): 3.49-3.51 (m, 2H), 3.58 (s, 3H), 3.86 (s, 6H), 4.94-5.00 (m, 2H), 5.04 (s, 2H), 5.90-6.00 (m, 1H), 6.68 (d, J=8.8 Hz, 1H), 7.79 (d, J=8.8 Hz, 1H).

(5) 3-Allyl-4-methoxy-2-(methoxymethoxy)benzoic acid 1.32 g of methyl 3-allyl-4-methoxy-2-(methoxymethoxy)benzoate was dissolved in 12 ml of methanol, and the obtained mixture was then stirred while cooling on ice. Thereafter, 2.97 ml of a 5 N sodium hydroxide aqueous solution was added to the reaction mixture, and the obtained mixture was then stirred at room temperature overnight. The reaction solution was cooled on ice, and ethyl acetate was added thereto. Then, the obtained mixture was adjusted to be approximately pH 5 with addition of a 5% sodium hydrogen sulfate aqueous solution. An organic layer was separated, and a water layer was extracted with ethyl acetate. The obtained organic layers were gathered. The combined organic layer was washed with water and a saturated sodium chloride solution, and then dried over anhydrous magnesium sulfate. After removing the drying agent by filtration, the organic layer was concentrated under a reduced pressure, so as to obtain 1.19 g of the subject compound. This compound was used in the following reaction without further purification.

$^1$H-NMR (CDCl$_3$) δ (ppm): 3.44-3.46 (m, 2H), 3.59 (s, 3H), 3.89 (s, 3H), 4.95-5.03 (m, 2H), 5.13 (s, 2H), 5.92-6.01 (m, 1H), 6.79 (d, J=8.8 Hz, 1H), 8.02 (d, J=8.8 Hz, 1H), 10.8 (bs, 1H).

(6) 8-Allyl-7-methoxy-3-methyl-2H-1,3-benzoxazin-2,4(3H)-dione 1.20 g of 3-allyl-4-methoxy-2-(methoxymethoxy)benzoic acid was dissolved in 15 ml of anhydrous tetrahydrofuran, and 0.84 g of 1,1'-carbonyldiimidazole was then added thereto. The obtained mixture was stirred at room temperature under nitrogen atmosphere for 25 minutes. Thereafter, 11.8 ml of methylamine (a 2.0 M tetrahydrofuran solution) was added to the reaction solution, and the obtained mixture was then stirred at room temperature for approximately 5 hours. Thereafter, the reaction mixture was cooled on ice, and 2.5 ml of concentrated hydrochloric acid was added thereto.

The obtained mixture was stirred at room temperature for 15 minutes. The reaction solution was extracted with ethyl acetate. The organic layer was washed with water 3 times and then washed with a saturated sodium bicarbonate aqueous solution and a saturated sodium chloride solution. The resultant product was then dried over anhydrous magnesium sulfate. After removing the drying agent by filtration, the organic layer was concentrated under a reduced pressure. 20 ml of anhydrous tetrahydrofuran was added to the obtained residue, and then, 1.53 g of 1,1'-carbonyldiimidazole was added thereto. The reaction mixture was heated to reflux under nitrogen atmosphere for approximately 2 hours. The reaction solution was cooled to a room temperature, and the solvent was then removed under a reduced pressure. Ethyl acetate and water were added to the residue, so as to separate an organic layer. The obtained organic layer was washed with water twice and then with a saturated sodium chloride solution. The resultant product was then dried over anhydrous magnesium sulfate. After removing the drying agent by filtration, the organic layer was concentrated under a reduced pressure. The residue was reprecipitated from ethyl acetate-n-hexane, so as to obtain 0.97 g of the subject compound.

$^1$H-NMR (CDCl$_3$) δ (ppm): 3.45 (s, 3H), 3.52-3.54 (m, 2H), 3.94 (s, 3H), 4.97-5.06 (m, 2H), 5.85-5.95 (m, 1H), 6.90 (d, J=8.8 Hz, 1H), 7.96 (d, J=8.8 Hz, 1H).

(7) 3-Allyl-2-hydroxy-4-methoxy-N-methylbenzamide 3.94 g of AD-mix-β was added to a mixture consisting of 0.97 g of 8-allyl-7-methoxy-3-methyl-2H-1,3-benzoxazin-2,4(3H)-dione, 30 ml of tert-butanol, and 20 ml of water. The obtained mixture was stirred at room temperature overnight. Thereafter, 4.73 g of sodium sulfite was added to the reaction solution, and the obtained mixture was stirred for 50 minutes. The reaction solution was adjusted to be approximately pH 5 with addition of 1 N hydrochloric acid, and the reaction mixture was then extracted with ethyl acetate. The obtained organic layer was washed with a saturated sodium chloride solution and then dried over anhydrous magnesium sulfate. After removing the drying agent by filtration, the organic layer was concentrated under a reduced pressure. 8 ml of methanol and 4 ml of tetrahydrofuran were added to the obtained residue, and then, 1.44 ml of a 5 N sodium hydroxide aqueous solution was added thereto. The reaction mixture was then stirred for 10 minutes. The reaction solution was cooled on ice, and then 1 N hydrochloric acid was added thereto, so as to adjust pH to be approximately 6. Ethyl acetate was added to the reaction solution for extraction. The obtained organic layer was washed with a saturated sodium chloride solution and then dried over anhydrous magnesium sulfate. After removing the drying agent by filtration, the organic layer was concentrated under a reduced pressure, so as to obtain 0.81 g of the subject compound. It was observed as a mixture of two conformers in NMR. The ratio was approximately 2:1. The following measurement results are indicated with the number of hydrogen atoms such that the sum of conformers becomes a single molecule.

$^1$H-NMR (CDCl$_3$) δ (ppm): 2.99 (s, 2H), 3.02 (s, 1H), 3.42-3.44 (m, 2H), 3.85 (s, 3H), 4.94-5.04 (m, 2H), 5.93-6.02 (m, 1H), 6.14 (br s, 1H), 6.41 (d, J=8.8 Hz, 1H), 7.21 (d, J=8.8 Hz, 0.33H), 7.21 (d, J=8.8 Hz, 0.67H), 12.69 (br s, 1H).

(8) 3-Allyl-2-(benzyloxy)-4-methoxy-N-methylbenzamide 0.15 g of sodium hydride was washed with n-hexane, and it was then suspended in 0.5 ml of anhydrous tetrahydrofuran. The suspension was cooled on ice and then stirred under nitrogen atmosphere. Thereafter, 0.81 g of 3-allyl-2-hydroxy-4-methoxy-N-methylbenzamide dissolved in 5 ml of anhydrous tetrahydrofuran was added to the above suspension.

The reaction mixture was stirred at room temperature for 30 minutes. The reaction mixture was then cooled on ice, and 520 μl of benzyl bromide was added thereto. The obtained mixture was stirred at room temperature for 40 minutes. Thereafter, 3 ml of N,N-dimethylformamide was added to the reaction solution, and the obtained mixture was further stirred for 1 hour. Ice was added to the reaction mixture, followed by extraction with ethyl acetate. The organic layer was washed with water 3 times and then with a saturated sodium chloride solution. Then, the resultant product was dried over anhydrous magnesium sulfate. After removing the drying agent by filtration, the organic layer was concentrated under a reduced pressure. The residue was reprecipitated from ethyl acetate-n-hexane, so as to obtain 0.49 g of the subject compound. It was observed as a mixture of two conformers in NMR. The ratio was approximately 1:1. The following measurement results are indicated with the number of hydrogen atoms such that the sum of conformers becomes a single molecule.

$^1$H-NMR (CDCl$_3$) δ (ppm): 2.84 (s, 1.5H), 2.85 (s, 1.5H), 3.51-3.53 (m, 2H), 3.88 (s, 3H), 4.84 (s, 2H), 4.97-5.02 (m, 2H), 5.98-6.07 (m, 1H), 6.81 (d, J=8.8 Hz, 1H), 7.38-7.45 (m, 5H), 7.63 (br d, 1H), 8.01 (d, J=8.8 Hz, 1H).

(9) 2-Benzyloxy-3-(2,3-dihydroxypropyl)-4-methoxy-N-methylbenzamide 1.57 g of AD-mix-β was added to a mixture consisting of 0.49 g of 3-allyl-2-(benzyloxy)-4-methoxy-N-methylbenzamide, 14 ml of tert-butanol, and 12 ml of water. The obtained mixture was stirred at room temperature overnight. Thereafter, 1.88 g of sodium sulfite was added to the reaction solution, and the obtained mixture was then stirred at room temperature for 1 hour. The reaction solution was extracted with ethyl acetate twice. The obtained organic layer was washed with a saturated sodium chloride solution and then dried over anhydrous magnesium sulfate. After removing the drying agent by filtration, the organic layer was concentrated under a reduced pressure. The residue was purified by silica gel column chromatography (hexane/ethyl acetate), so as to obtain 0.47 g of the subject compound.

$^1$H-NMR (CDCl$_3$) δ (ppm): 2.90 (d, J=4.8 Hz, 3H), 2.93 (dd, J=6.0, 13.6 Hz, 1H), 3.01 (dd, J=3.0, 13.6 Hz, 1H), 3.47 (dd, J=5.2, 11.6 Hz, 1H), 3.59 (dd, J=3.6, 11.6 Hz, 1H), 3.91 (s, 3H), 3.94-4.00 (m, 1H), 4.84 (d, J=10.6 Hz, 1H), 4.89 (d, J=10.6 Hz, 1H), 6.83 (d, J=8.8 Hz, 1H), 7.39-7.47 (m, 5H), 8.01 (d, J=8.8 Hz, 1H).

(10) 1-{1-[2-(2-(benzyloxy)-6-methoxy-3-((methylamine)carbonyl)phenyl)ethyl]piperidin-4-yl}-1H-indole-6-carboxamide 0.47 g of 2-benzyloxy-3-(2,3-dihydroxypropyl)-4-methoxy-N-methylbenzamide was dissolved in 6 ml of tetrahydrofuran, 6 ml of methanol, and 4 ml of water. Thereafter, 0.57 g of sodium metaperiodate was added thereto, and the obtained mixture was vigorously stirred. After confirming the disappearance of raw material, water and ethyl acetate were added to the reaction solution, so as to separate an organic layer. A water layer was extracted with ethyl acetate, and it was gathered with the above organic layer. The obtained layer was washed with a saturated sodium chloride solution and then dried over anhydrous magnesium sulfate. After removing the drying agent by filtration, the organic layer was concentrated under a reduced pressure, so as to obtain 0.49 g of a crude aldehyde form.

0.27 g of 1-(piperidin-4-yl)-1H-indole-6-carboxamide was dissolved in 20 ml of dichloromethane. Thereafter, 0.49 g of the aforementioned crude aldehyde form and 129 μl of acetic acid were successively added to the above reaction solution. The obtained mixture was then stirred for 20 minutes. Thereafter, 0.36 g of sodium triacetoxyborohydride was added to the reaction solution, and the obtained mixture was then stirred at room temperature overnight. Thereafter, a 10% sodium carbonate aqueous solution and chloroform were added to the reaction solution, so as to separate an organic layer. The obtained organic layer was washed with a saturated sodium chloride solution and then dried over anhydrous magnesium sulfate. After removing the drying agent by filtration, the organic layer was concentrated under a reduced pressure. The residue was purified by NH silica gel column chromatography (ethyl acetate/methanol), so as to obtain 0.49 g of the subject compound.

$^1$H-NMR (CDCl$_3$) δ (ppm): 2.04-2.52 (m, 4H), 2.25-2.51 (m, 2H), 2.60-2.64 (m, 2H), 2.87 (d, J=4.8 Hz, 3H), 2.97-2.99 (m, 2H), 3.18 (br d, 2H), 3.90 (s, 3H), 4.35-4.42 (m, 1H), 4.88 (s, 2H), 5.59 (br s, 1H), 6.15 (br s, 1H), 6.57-6.58 (m, 1H), 6.80 (d, J=8.8 Hz, 1H), 7.30-7.46 (m, 7H), 7.56 (br d, 1H), 7.65 (d, J=8.4 Hz, 1H), 7.99 (d, J=8.8 Hz, 1H), 8.12 (s, 1H).

(11) 1-{1-[2-(2-Hydroxy-6-methoxy-3-((methylamino)carbonyl)phenyl)ethyl]piperidin-4-yl}-1H-indole-6-carboxamide 15 ml of methanol and 10 ml of tetrahydrofuran were added to and dissolved in 486 mg of 1-(1-(2-(2-(benzyloxy)-6-methoxy-3-((methylamino)carbonyl)phenyl)ethyl)piperidin-4-yl)-1H-indole-6-carboxamide. Thereafter, 74 mg of 10% Pd—C (containing water) was added thereto, and the obtained mixture was then stirred at room temperature under hydrogen atmosphere overnight. Thereafter, Pd—C was removed by filtration, and the solvent was removed under a reduced pressure, so as to obtain 408 mg of the subject compound.

$^1$H-NMR (DMSO-d$_6$) δ (ppm): 1.94-2.08 (m, 4H), 2.23-2.30 (m, 2H), 2.43-2.47 (m, 2H), 2.76-2.80 (m, 5H), 3.12 (br d, 2H), 3.83 (s, 3H), 4.38-4.46 (m, 1H), 6.49 (d, J=2.8 Hz, 1H), 6.56 (br d, 1H), 7.20 (s, 1H), 7.53-7.58 (m, 2H), 7.66-7.69 (m, 2H), 7.90 (s, 1H), 8.11 (s, 1H), 8.17 (br s, 1H).

(12) 1-{1-[2-(7-Methoxy-3-methyl-2,4-dioxo-3,4-dihydro-2H-1,3-benzoxazin-8-yl)ethyl]piperidin-4-yl}-1H-indole-6-carboxamide 30 ml of anhydrous tetrahydrofuran was added to 408 mg of 1-(1-(2-(2-hydroxy-6-methoxy-3-((methylamino)carbonyl)phenyl)ethyl)piperidin-4-yl)-1H-indole-6-carboxamide. Thereafter, 294 mg of 1,1'-carbonyldiimidazole was added thereto. The obtained mixture was then heated to reflux under nitrogen atmosphere for 5 minutes. Thereafter, 5 ml of N,N-dimethylformamide was added to the reaction solution, and the obtained mixture was then heated to reflux under nitrogen atmosphere for 45 minutes. The reaction solution was cooled to a room temperature, and the solvent was then removed under a reduced pressure. Thereafter, 294 mg of 1,1'-carbonyldiimidazole was added to the residue. The reaction mixture was heated to reflux under nitrogen atmosphere for 30 minutes. The reaction solution was cooled to a room temperature, and the solvent was then removed under a reduced pressure. Water was added to the residue, and the precipitate was collected by filtration. The precipitate was washed with diethyl ether. It was then suspended in ethanol, and the solvent was removed under a reduced pressure. Ethyl acetate was added to the residue, followed by filtration, so as to obtain 451 mg of the subject compound.

$^1$H-NMR (DMSO-d$_6$) δ (ppm): 1.94-2.07 (m, 4H), 2.25-2.33 (m, 2H), 2.50-2.55 (m, 2H), 2.89-2.92 (m, 2H), 3.14 (br d, 2H), 3.27 (s, 3H), 3.96 (s, 3H), 4.39-4.47 (m, 1H), 6.50 (d, J=3.4 Hz, 1H), 7.14 (d, J=8.8 Hz, 1H), 7.21 (s, 1H), 7.54-7.60 (m, 2H), 7.66 (d, J=3.4 Hz, 1H), 7.87 (d, J=8.8 Hz, 1H), 7.91 (s, 1H), 8.13 (s, 1H).

Example 63

Synthesis of 1-{1-[2-(2-methoxy-5-oxo-5,6,7,8-tetrahydronaphthalen-1-yl)ethyl]piperidin-4-yl}-1H-indole-6-carboxamide

[Formula 123]

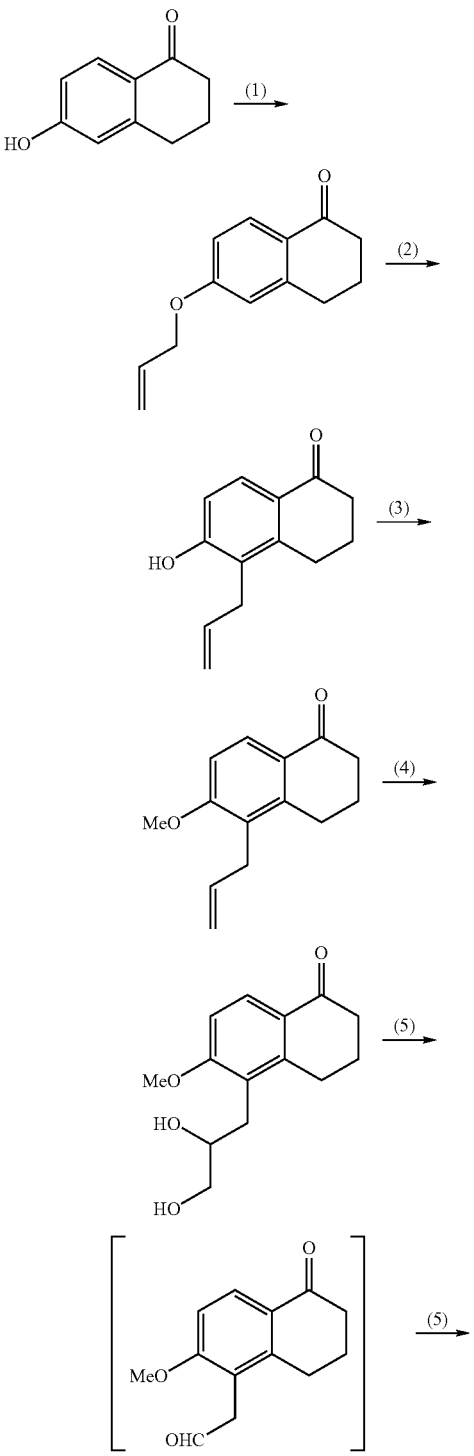

-continued

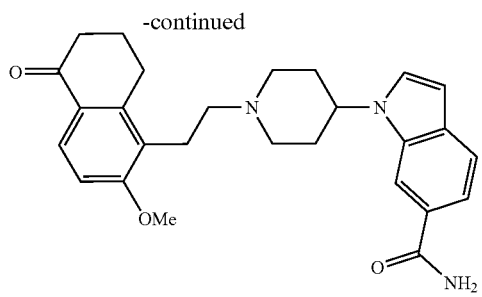

(1) 6-(Allyloxy)-3,4-dihydronaphthalen-1(2H)-one 3.30 ml of allyl bromide was added to a mixture consisting of 5.62 g of 6-hydroxy-3,4-dihydroxynaphthalen-1(2H)-one, 5.27 g of potassium carbonate, and 60 ml of acetone. The obtained mixture was heated to reflux under nitrogen atmosphere overnight. The reaction solution was cooled to a room temperature, and the precipitate was removed by filtration. The solvent was removed under a reduced pressure. The residue was purified by silica gel column chromatography (hexane/ethyl acetate), so as to obtain 6.35 g of the subject compound.

$^1$H-NMR (CDCl$_3$) δ (ppm): 2.08-2.15 (m, 2H), 2.59-2.62 (m, 2H), 2.92 (t, J=6.0 Hz, 2H), 4.58-4.60 (m, 2H), 5.30-5.34 (m, 1H), 5.40-5.45 (m, 1H), 6.00-6.10 (m, 1H), 6.72 (d, J=2.6 Hz, 1H), 6.84 (dd, J=2.4, 8.8 Hz, 1H), 8.00 (d, J=8.8 Hz, 1H).

(2) 5-Allyl-6-hydroxy-3,4-dihydronaphthalen-1(2H)-one 1.13 g of 6-(allyloxy)-3,4-dihydronaphthalen-1(2H)-one was dissolved in 8 ml of N,N-dimethylaniline. The obtained mixture was heated to reflux under nitrogen atmosphere for 5 hours. In the same manner, 5.21 g of 6-(allyloxy)-3,4-dihydronaphthalen-1(2H)-one was dissolved in 40 ml of N,N-dimethylaniline, and the obtained mixture was heated to reflux under nitrogen atmosphere for 7 hours. The obtained reaction solutions were cooled to a room temperature. The two reaction solutions were mixed, and then, water and ethyl acetate were added thereto, so as to separate an organic layer. The obtained organic layer was washed with 5 N hydrochloric acid, water, and a saturated sodium chloride solution, and then dried over anhydrous magnesium sulfate. After removing the drying agent by filtration, the organic layer was concentrated under a reduced pressure. Ethyl acetate and t-butylmethyl ether were added to the residue, followed by filtration, so as to obtain 3.52 g of the subject compound.

$^1$H-NMR (CDCl$_3$) δ (ppm): 2.07-2.14 (m, 2H), 2.57-2.61 (m, 2H), 2.89 (t, J=6.0 Hz, 2H), 3.45-3.47 (m, 2H), 4.97-5.02 (m, 1H), 5.07-5.11 (m, 1H), 5.65 (s, 1H), 5.91-6.01 (m, 1H), 6.78 (d, J=8.8 Hz, 1H), 7.95 (d, J=8.8 Hz, 1H).

(3) 5-Allyl-6-methoxy-3,4-dihydronaphthalen-1(2H)-one

901 µl of methyl iodide was added to a mixture consisting of 1.46 g of 5-allyl-6-hydroxy-3,4-dihydronaphthalen-1 (2H)-one, 1.20 g of potassium carbonate, and 15 ml of N,N-dimethylformamide. The obtained mixture was stirred at room temperature under nitrogen atmosphere overnight. Thereafter, water and ethyl acetate were added to the reaction solution, so as to separate an organic layer. The obtained organic layer was washed with water (5 times) and a saturated sodium chloride solution, and then dried over anhydrous magnesium sulfate. After removing the drying agent by filtration, the organic layer was concentrated under a reduced pressure. The residue was purified by silica gel column chromatography (hexane/ethyl acetate), so as to obtain 1.51 g of the subject compound.

$^1$H-NMR (CDCl$_3$) δ (ppm): 2.06-2.13 (m, 2H), 2.57-2.61 (m, 2H), 2.89 (t, J=6.0 Hz, 2H), 3.43-3.46 (m, 2H), 3.88 (s, 3H), 4.87-4.93 (m, 1H), 4.97-5.00 (m, 1H), 5.85-5.94 (m, 1H), 6.86 (d, J=8.8 Hz, 1H), 8.03 (d, J=8.8 Hz, 1H).

(4) 5-(2,3-Dihydroxypropyl)-6-methoxy-3,4-dihydronaphthalen-1(2H)-one 6.99 g of AD-mix-β, 15 ml of tert-butanol, and 20 ml of water were blended. 1.51 g of 5-allyl-6-methoxy-3,4-dihydronaphthalen-1(2H)-one was dissolved in 14 ml of tert-butanol, and the obtained solution was added to the above mixture. The obtained mixture was then stirred at room temperature overnight. Thereafter, 8.38 g of sodium sulfite was added thereto, and the obtained mixture was stirred for approximately 1 hour, followed by extraction with ethyl acetate. The obtained organic layer was washed with a saturated sodium chloride solution and then dried over anhydrous magnesium sulfate. After removing the drying agent by filtration, the organic layer was concentrated under a reduced pressure. Ethyl acetate and hexane were added to the residue, followed by filtration, so as to obtain 1.51 g of the subject compound.

$^1$H-NMR (CDCl$_3$) δ (ppm): 2.09-2.15 (m, 2H), 2.59-2.62 (m, 2H), 2.91-3.05 (m, 4H), 3.52 (dd, J=6.0, 11.2 Hz, 1H), 3.66 (dd, J=3.4, 11.2 Hz, 1H), 3.89-3.97 (m, 1H), 3.92 (s, 3H), 6.88 (d, J=8.8 Hz, 1H), 8.06 (d, J=8.8 Hz, 1H).

(5) 1-{1-[2-(2-Methoxy-5-oxo-5,6,7,8-tetrahydronaphthalen-1-yl)ethyl]piperidin-4-yl}-1H-indole-6-carboxamide 0.13 g of 5-(2,3-dihydroxypropyl)-6-methoxy-3,4-dihydronaphthalen-1(2H)-one was dissolved in a mixed solution consisting of 2 ml of tetrahydrofuran, 2 ml of methanol and 1.3 ml of water. Thereafter, 224 mg of sodium metaperiodate was added thereto, and the obtained mixture was vigorously stirred for 30 minutes. After confirming the disappearance of the raw material, water and ethyl acetate were added to the reaction solution, so as to separate an organic layer. A water layer was extracted with ethyl acetate, and the obtained water layer was mixed with the aforementioned organic layer. The obtained layer was washed with a saturated sodium chloride solution and then dried over anhydrous magnesium sulfate. After removing the drying agent by filtration, the organic layer was concentrated under a reduced pressure, so as to obtain 129 mg of a crude aldehyde form.

105 mg of 1-(piperidin-4-yl)-1H-indole-6-carboxamide was dissolved in 4 ml of dichloromethane. Thereafter, 129 mg of the aforementioned crude aldehyde form and 49.4 µl of acetic acid were successively added to the reaction solution, and the obtained mixture was then stirred for 15 minutes. Thereafter, 137 mg of sodium triacetoxyborohydride was added to the reaction solution, and the obtained mixture was then stirred at room temperature overnight. Thereafter, a 10% sodium carbonate aqueous solution and chloroform were added to the reaction solution, so as to separate an organic layer. The obtained organic layer was washed with a saturated sodium chloride solution and then dried over anhydrous magnesium sulfate, followed by filtration. The organic layer was concentrated under a reduced pressure and dried. Ethyl acetate and tert-butylmethyl ether were added to the residue, followed by filtration, so as to obtain 142 mg of the subject compound.

$^1$H-NMR (CDCl$_3$) δ (ppm): 2.05-2.16 (m, 6H), 2.32 (br s, 2H), 2.50-2.55 (m, 2H), 2.60-2.63 (m, 2H), 2.92-2.98 (m, 4H), 2.25 (br d, 2H), 3.91 (s, 3H), 4.38-4.45 (m, 1H), 5.62 (br s, 1H), 6.17 (br s, 1H), 6.58-6.59 (m, 1H), 6.86 (d, J=8.8 Hz, 1H), 7.39-7.43 (m, 2H), 7.65 (d, J=8.0 Hz, 1H), 8.04 (d, J=8.8 Hz, 1H), 8.13 (s, 1H).

183
Example 64

Synthesis of 1-{1-[2-(2-methoxy-6,6-dimethyl-5-oxo-5,6,7,8-tetrahydronaphthalen-1-yl)ethyl]piperidin-4-yl}-1H-indole-6-carboxamide

[Formula 124]

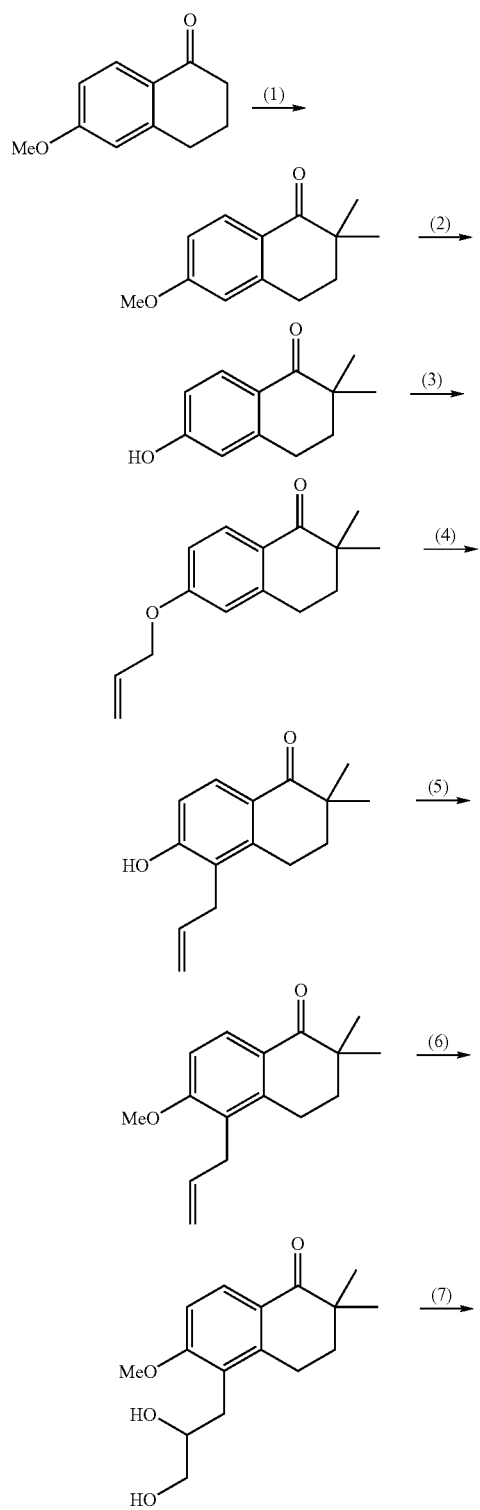

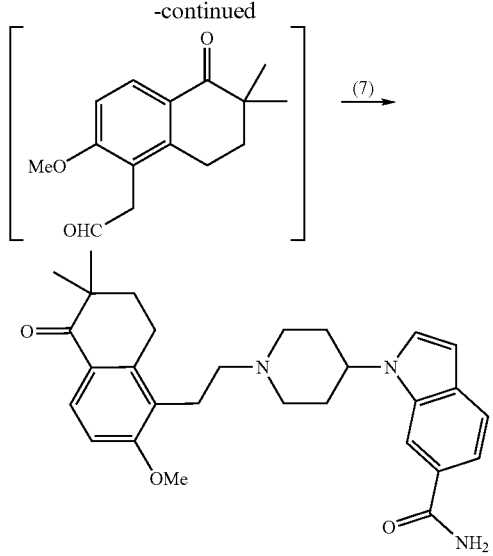

(1) 6-Methoxy-2,2-dimethyl-3,4-dihydronaphthalen-1(2H)-one

A mixture consisting of 7.12 g of potassium tert-butoxide, 20 ml of tert-butanol, and 50 ml of toluene was cooled on ice and then stirred under nitrogen atmosphere. 5.02 g of 6-hydroxy-2,2-dimethyl-3,4-dinaphthalen-1(2H)-one dissolved in 100 ml of toluene was added to the above mixture. Ten minutes later, 3.99 ml of methyl iodide was added to the reaction solution, and the obtained mixture was stirred at room temperature overnight. Thereafter, water and ethyl acetate were added to the reaction solution, so as to separate an organic layer. The obtained organic layer was successively washed with water (5 times), a 10% sodium carbonate aqueous solution, and a saturated sodium chloride solution. The resultant product was then dried over anhydrous sodium sulfate. After removing the drying agent by filtration, the organic layer was concentrated under a reduced pressure. The residue was purified by silica gel column chromatography (hexane/ethyl acetate), so as to obtain 3.69 g of the subject compound.

$^1$H-NMR (CDCl$_3$) δ (ppm): 1.21 (s, 6H), 1.96 (t, J=6.4 Hz, 2H), 2.95 (d, J=6.4 Hz, 2H), 3.85 (s, 3H), 6.66-6.67 (m, 1H), 6.83 (dd, J=2.8, 8.8 Hz, 1H), 8.02 (d, J=8.8 Hz, 1H).

(2) 6-Hydroxy-3,4-dihydronaphthalen-1(2H)-one 3.69 g of 6-methoxy-2,2-dimethyl-3,4-dihydronaphthalen-1(2H)-one was dissolved in 70 ml of anhydrous methylene chloride. The obtained solution was cooled in a dry ice-acetone bath. Thereafter, 36 ml of boron tribromide (a 1.0 M methylene chloride solution) was added thereto, and the obtained mixture was stirred at room temperature overnight. Thereafter, the reaction solution was again cooled in a dry ice-acetone bath. 36 ml of boron tribromide (a 1.0 M methylene chloride solution) was added thereto, and the obtained mixture was stirred at room temperature overnight. Thereafter, the reaction solution was poured into ice, and chloroform was then added thereto. An insoluble precipitate was removed by filtration. The organic layer was separated and then dried over anhydrous sodium sulfate. The obtained solution was passed through a glass filter filled with silica gel, and the solvent was removed under a reduced pressure. The residue was purified by silica gel column chromatography (hexane/ethyl acetate), so as to obtain 1.52 g of the subject compound.

¹H-NMR (CDCl₃) δ (ppm): 1.20 (s, 6H), 1.94-1.97 (m, 2H), 2.92 (t, J=6.4 Hz, 2H), 5.57 (s, 1H), 6.62-6.63 (m, 1H), 6.74 (dd. J=2.8, 8.4 Hz, 1H), 7.97 (d, J=8.4 Hz, 1H).

(3) 6-(Allyloxy)-2,2-dimethyl-3,4-dihydronaphthalen-1 (2H)-one

830 μl of allyl bromide was added to a mixture consisting of 1.52 g of 6-hydroxy-3,4-dihydronaphthalen-1(2H)-one, 1.22 g of potassium carbonate, and 15 ml of N,N-dimethylformamide. The obtained mixture was stirred at room temperature under nitrogen atmosphere overnight. Water and ethyl acetate were added to the reaction solution, so as to obtain an organic layer. The obtained organic layer was successively washed with water (4 times) and a saturated sodium chloride solution, and then dried over anhydrous sodium sulfate. After removing the drying agent by filtration, the organic layer was concentrated under a reduced pressure. The residue was purified by silica gel column chromatography (hexane/ethyl acetate), so as to obtain 1.69 g of the subject compound.

¹H-NMR (CDCl₃) δ (ppm): 1.20 (s, 6H), 1.96 (t, J=6.4 Hz, 2H), 2.94 (t, J=6.4 Hz, 2H), 4.58-4.60 (m, 2H), 5.30-5.33 (m, 1H), 5.40-5.45 (m, 1H), 6.00-6.10 (m, 1H), 6.68 (d, J=2.4 Hz, 1H), 6.84 (dd, J=2.4, 8.4 Hz, 1H), 8.01 (d, J=8.4 Hz, 1H).

(4) 5-Allyl-6-hydroxy-2,2-dimethyl-3,4-dihydronaphthalen-1(2H)-one 1.69 g of 6-(allyloxy)-2,2-dimethyl-3,4-dihydronaphthalen-1(2H)-one was dissolved in 10 ml of N,N-dimethylaniline, and the obtained mixture was heated to reflux under nitrogen atmosphere for 7 hours. The reaction solution was cooled to a room temperature. Water and ethyl acetate were added to the reaction solution, so as to obtain an organic layer. The obtained organic layer was successively washed with 5 N hydrochloric acid (3 times), water (4 times), and a saturated sodium chloride solution. The resultant product was then dried over anhydrous sodium sulfate. After removing the drying agent by filtration, the organic layer was concentrated under a reduced pressure. Hexane was added to the residue, and the precipitate was then collected by filtration, so as to obtain 1.06 g of the subject compound.

¹H-NMR (CDCl₃) δ (ppm): 1.19 (s, 6H), 1.95 (t, J=6.4 Hz, 2H), 2.89 (t, J=6.4 Hz, 2H), 3.44-3.47 (m, 2H), 4.97-5.03 (m, 1H), 5.07-5.10 (m, 1H), 5.92-6.01 (m, 1H), 6.78 (d, J=8.6 Hz, 1H), 7.94 (d, J=8.6 Hz, 1H).

(5) 5-Allyl-6-methoxy-2,2-dimethyl-3,4-dihydronaphthalen-1(2H)-one

575 μl of methyl iodide was added to a mixture consisting of 1.06 g of 5-allyl-6-hydroxy-2,2-dimethyl-3,4-dihydronaphthalen-1(2H)-one, 0.77 g of potassium carbonate, and 10 ml of N,N-dimethylformamide. The obtained mixture was stirred at room temperature under nitrogen atmosphere overnight. Water and ethyl acetate were added to the reaction solution, so as to obtain an organic layer. The obtained organic layer was washed with water (5 times) and a saturated sodium chloride solution, and then dried over anhydrous sodium sulfate. After removing the drying agent by filtration, the organic layer was concentrated under a reduced pressure. The residue was purified by silica gel column chromatography (hexane/ethyl acetate), so as to obtain 1.09 g of the subject compound.

¹H-NMR (CDCl₃) δ (ppm): 1.19 (s, 6H), 1.94 (t, J=6.4 Hz, 2H), 2.89 (t, J=6.4 Hz, 2H), 3.42-3.45 (m, 2H), 3.88 (s, 3H), 4.87-4.93 (m, 1H), 4.96-5.00 (m, 1H), 5.85-5.95 (m, 1H), 6.87 (d, J=9.0 Hz, 1H), 8.03 (d, J=9.0 Hz, 1H).

(6) 5-(2,3-Dihydroxypropyl)-6-methoxy-2,2-dimethyl-3,4-dihydronaphthalen-1(2H)-one 4.47 g of AD-mix-β was added to a mixture consisting of 1.09 g of 5-allyl-6-methoxy-2,2-dimethyl-3,4-dihydronaphthalen-1(2H)-one, 17 ml of tert-butanol, and 17 ml of water. The obtained mixture was stirred at room temperature overnight. Thereafter, 5.37 g of sodium sulfite was added to the reaction solution, and the obtained mixture was stirred for 35 minutes, followed by extraction with ethyl acetate. The obtained organic layer was washed with a saturated sodium chloride solution and then dried over anhydrous sodium sulfate. After removing the drying agent by filtration, the reaction solution was concentrated under a reduced pressure. The residue was purified by silica gel column chromatography (ethyl acetate/methanol), so as to obtain 1.25 g of the subject compound.

¹H-NMR (CDCl₃) δ (ppm): 1.19 (s, 3H), 1.19 (s, 3H), 1.97 (t, J=6.7 Hz, 2H), 2.14 (br s, 1H), 2.37 (br s, 1H), 2.90-3.05 (m, 4H), 3.51-3.55 (m, 1H), 3.65-3.69 (m, 1H), 3.89-3.96 (m, 1H), 3.91 (s, 3H), 6.89 (d, J=8.8 Hz, 1H), 8.05 (d, J=8.8 Hz, 1H).

(7) 1-{1-[2-(2-Methoxy-6,6-dimethyl-5-oxo-5,6,7,8-tetrahydronaphthalen-1-yl)ethyl]piperidin-4-yl}-1H-indole-6-carboxamide 0.13 g of 5-(2,3-dihydroxypropyl)-6-methoxy-2,2-dimethyl-3,4-dihydronaphthalen-1(2H)-one was dissolved in a mixed solution consisting of 2 ml of tetrahydrofuran, 2 ml of methanol, and 1.3 ml of water. Thereafter, 197 mg of sodium metaperiodate was added thereto, and the obtained mixture was vigorously stirred for 30 minutes. After confirming the disappearance of the raw material, water and ethyl acetate were added to the reaction solution, so as to separate an organic layer. A water layer was extracted with ethyl acetate, and the obtained water layer was mixed with the aforementioned organic layer. The obtained layer was washed with a saturated sodium chloride solution and then dried over anhydrous magnesium sulfate. After removing the drying agent by filtration, the organic layer was concentrated under a reduced pressure, so as to obtain 117 mg of a crude aldehyde form.

93 mg of 1-(piperidin-4-yl)-1H-indole-6-carboxamide was dissolved in 4 ml of dichloromethane. Thereafter, 117 mg of the aforementioned crude aldehyde form and 43.8 μl of acetic acid were successively added to the reaction solution, and the obtained mixture was then stirred for 10 minutes. Thereafter, 122 mg of sodium triacetoxyborohydride was added to the reaction solution, and the obtained mixture was then stirred at room temperature for 50 minutes. Thereafter, a 10% sodium carbonate aqueous solution and chloroform were added to the reaction solution, so as to separate an organic layer. The obtained organic layer was washed with a saturated sodium chloride solution and then dried over anhydrous magnesium sulfate. After removing the drying agent by filtration, the organic layer was concentrated under a reduced pressure. Ethyl acetate and tert-butylmethyl ether were added to the residue, followed by filtration, so as to obtain 153 mg of the subject compound.

¹H-NMR (DMSO-d₆) δ (ppm): 1.11 (s, 6H), 1.92-2.08 (m, 6H), 2.29-2.33 (m, 2H), 2043-2.47 (m, 2H), 2.83-2.87 (m, 2H), 2.94-2.97 (m, 2H), 3.14 (br d, 2H), 3.88 (s, 3H), 4.39-4.47 (m, 1H), 6.51 (d, J=2.8 Hz, 1H), 7.03 (d, J=8.8 Hz, 1H), 7.22 (s, 1H), 7.55-7.61 (m, 2H), 7.67 (d, J=3.6 Hz, 1H), 7.84 (d, J=8.8 Hz, 1H), 7.92 (s, 1H), 8.13 (s, 1H).

Example 65

Synthesis of {1-[1-(3,4-dihydro-7-methoxy-1(2H)-naphthalenon-8-yl)ethylpiperidin-4-yl]-(1H)-indole-6-yl}carboxamide

[Formula 125]

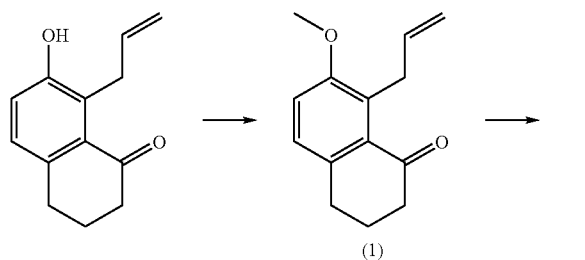

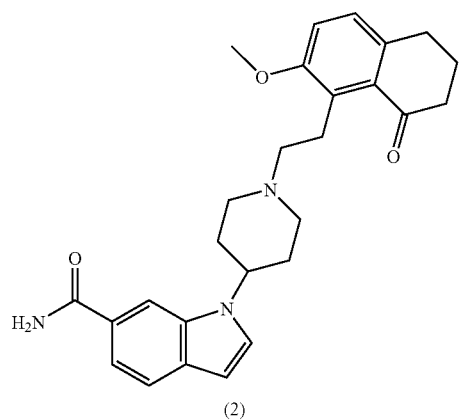

(1) 3,4-Dihydro-7-methoxy-8-(2-propenyl)-1(2H)-naphthalenone 160 mg of 3,4-dihydro-7-hydroxy-8-(2-propenyl)-1(2H)-naphthalenone (CAS No. 122076-30-6), 140 mg of iodomethane, and 400 mg of potassium carbonate were dissolved in 15 ml of acetone. The reaction solution was then stirred at 70° C. for 1.5 hours. The mixture was filtered and then washed with acetone. The organic layer was then concentrated under a reduced pressure. The residue was purified by silica gel column chromatography, so that 140 mg of the subject compound was obtained from an ethyl acetate-hexane eluate (1:10).

$^1$H-NMR (CDCl$_3$) δ (ppm) 2.05 (ddd, J=6.0, 6.4, 7.2 Hz, 2H), 2.63 (dd, J=6.4, 7.2 Hz, 2H), 2.88 (dd, J=6.0, 6.4 Hz, 2H), 3.83 (s, 3H), 3.85-3.88 (m, 2H), 4.91-5.05 (m, 2H), 5.97-6.08 (m, 1H), 7.01 (d, J=8.4 Hz, 1H), 7.10 (d, J=8.4 Hz, 1H).

(2) {1-[1-(3,4-Dihydro-7-methoxy-1(2H)-naphthalenon-8-yl)ethylpiperidin-4-yl]-(1H)-indole-6-yl}carboxamide 130 mg of 3,4-dihydro-7-methoxy-8-(2-propenyl)-1(2H)-naphthalenone was dissolved in 6 ml of tetrahydrofuran and 3 ml of water. Then, 0.2 ml of a 3.3% osmium tetroxide aqueous solution was added thereto at room temperature, and the obtained mixture was then stirred for 15 minutes. Thereafter, 600 mg of sodium perchlorate was added thereto, and the obtained mixture was then stirred at room temperature for 4 hours. The mixture was divided into ethyl acetate and water, and the ethyl acetate layer was separated. The ethyl acetate layer was washed with a 5% sodium thiosulfate solution, water, and a saturated sodium chloride solution. The resultant product was then dried over magnesium sulfate. The mixture was filtered, and the organic layer was concentrated under a reduced pressure. The residue was passed through a silica gel short column, so as to obtain 110 mg of the corresponding crude aldehyde product.

A mixture consisting of 110 mg of the obtained aldehyde, 90 mg of 1-(piperidin-4-yl-1H-indole-6-yl)carboxamide, and 100 mg of acetic acid, was dissolved in 5 ml of tetrahydrofuran, and the obtained mixture was then stirred at room temperature for 15 minutes. Thereafter, 200 mg of sodium triacetoxyborohydride was added to the reaction solution, and the obtained mixture was then stirred for 1.5 hours. Thereafter, a 10% potassium carbonate solution was added to the reaction solution, followed by extraction with ethyl acetate. The ethyl acetate layer was washed with a saturated sodium chloride solution and then dried over magnesium sulfate, followed by filtration. The layer was then concentrated under a reduced pressure. The residue was purified by silica gel flash chromatography, so that 38 mg of the subject compound was obtained in the form of a light yellow solid from a methylene chloride-methanol (10:1) eluate.

$^1$H-NMR (CDCl$_3$) δ (ppm) 2.10-2.26 (m, 6H), 2.41-2.57 (m, 2H), 2.63 (dd, J=6.4, 7.2 Hz, 2H), 2.62-2.78 (m, 2H), 2.85 (dd, J=6.0, 6.4 Hz, 2H), 3.28-3.44 (m, 4H), 3.83 (s, 3H), 4.36-4.46 (m, 1H), 6.57 (d, J=3.6 Hz, 1H), 7.01 (d, J=8.4 Hz, 1H), 7.12 (d, J=8.4 Hz, 1H), 7.41 (d, J=3.6 Hz, 1H), 7.46 (dd, J=1.2, 8.8 Hz, 1H), 7.64 (d, J=8.8 Hz, 1H), 8.11 (brs, 1H).

Example 66

Synthesis of 1-{1-[2-(7-methoxy-2,2-dimethyl-4-oxochroman-8-yl)ethyl]piperidin-4-yl}-N-methyl-1H-indole-6-carboxamide fumarate

[Formula 126]

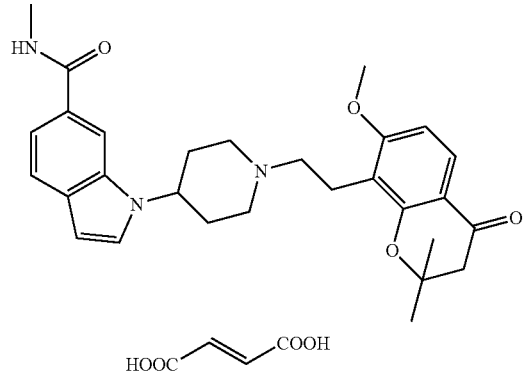

1-{1-[2-(7-Methoxy-2,2-dimethyl-4-oxochroman-8-yl)ethyl]piperidin-4-yl}-N-methyl-1H-indole-6-carboxamide (1.00 g) and fumaric acid (0.249 g) were dissolved in a mixed solvent consisting of acetone (5 ml) and water (15 ml) at 60° C. Thereafter, the obtained mixture was left at room temperature for 1 hour. The deposited solid was collected by filtration, and the obtained product was then washed with a mixed solvent consisting of acetone (2.5 ml) and water (7.5 ml), so as to obtain the subject compound (1.09 g).

$^1$H-NMR (DMSO-$d_6$) δ (ppm): 1.40 (s, 6H), 1.94-2.11 (m, 4H), 2.27-2.37 (m, 2H), 2.45-2.56 (m, 2H), 2.72 (s, 2H), 2.75-2.84 (m, 5H), 3.12-3.20 (m, 2H), 3.87 (s, 3H), 4.38-4.47 (m, 1H), 6.48-6.51 (m, 1H), 6.60 (s, 1.5H), 6.75 (d, J=9.6 Hz, 1H), 7.50-7.58 (m, 2H), 7.63-7.67 (m, 2H), 8.05 (br s, 1H), 8.29-8.35 (m, 1H).

Example 67

Synthesis of 1-{1-[2-(7-methoxy-2,2-dimethyl-4-oxochroman-8-yl)ethyl]piperidin-4-yl}-N-methyl-1H-indole-6-carboxamide L-(+)-tartrate

[Formula 127]

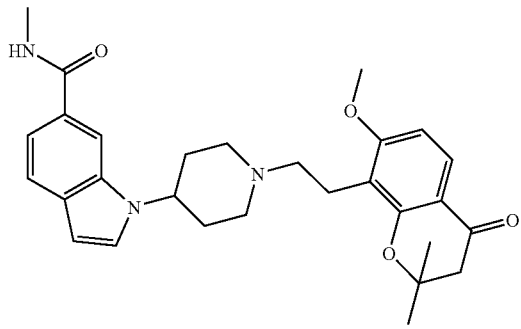

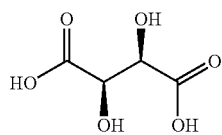

1-{1-[2-(7-Methoxy-2,2-dimethyl-4-oxochroman-8-yl)ethyl]piperidin-4-yl}-N-methyl-1H-indole-6-carboxamide (100 mg) was dissolved in a mixed solvent consisting of tetrahydrofuran (1 ml) and diethyl ether (25 ml). Thereafter, a mixed solvent consisting of tetrahydrofuran (1 ml) and diethyl ether (25 ml) containing L-(+)-tartaric acid (31 mg) was added to the reaction solution at room temperature. The deposited solid was collected by filtration, and the obtained product was then washed with diethyl ether, so as to obtain the subject compound (110 mg).

$^1$H-NMR (DMSO-$d_6$) δ (ppm): 1.40 (s, 6H), 1.97-2.14 (m, 4H), 2.40-2.60 (m, 4H), 2.72 (s, 2H), 2.78-2.84 (m, 5H), 3.20-3.30 (m, 2H), 3.87 (s, 3H), 4.20 (s, 2H), 4.43-4.53 (m, 1H), 6.50 (d, J=3.2 Hz, 1H), 6.75 (d, J=8.4 Hz, 1H), 7.50-7.58 (m, 2H), 7.63-7.67 (m, 2H), 8.05 (br s, 1H), 8.28-8.34 (m, 1H).

Example 68

Synthesis of 1-{1-[2-(7-methoxy-2,2-dimethyl-4-oxochroman-8-yl)ethyl]piperidin-4-yl}-N-methyl-1H-indole-6-carboxamide maleate

[Formula 128]

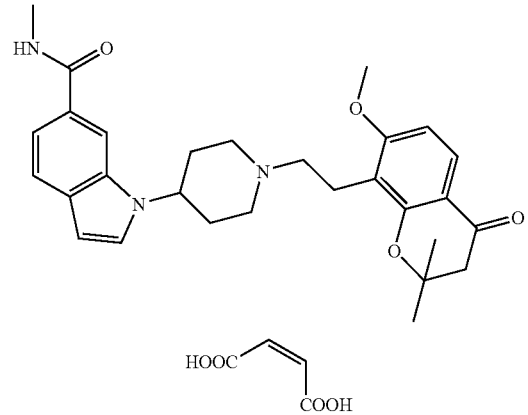

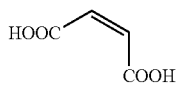

1-{1-[2-(7-Methoxy-2,2-dimethyl-4-oxochroman-8-yl)ethyl]piperidin-4-yl}-N-methyl-1H-indole-6-carboxamide (105 mg) was dissolved in tetrahydrofuran (10 ml). Thereafter, a tetrahydrofuran solution (10 ml) containing maleic acid (25 mg) was added to the reaction solution at room temperature. Thereafter, t-butyl methyl ether was added thereto at room temperature, and the obtained mixture was then concentrated under a reduced pressure. Diethyl ether was added to the residue for solidification. This suspension was stirred for 10 minutes while cooling on ice, and a solid was then collected by filtration. The solid was washed with diethyl ether, so as to obtain the subject compound (117 mg).

$^1$H-NMR (DMSO-$d_6$) δ (ppm): 1.44 (s, 6H), 2.17-2.32 (m, 4H), 2.45-2.55 (m, 4H), 2.76 (s, 2H), 2.83 (d, J=7.2 Hz, 3H), 2.94-3.05 (m, 2H), 3.25-3.40 (m, 2H), 3.91 (s, 3H), 4.74-4.85 (m, 1H), 6.02 (s, 1.5H), 6.54-6.59 (m, 1H), 6.82 (d, J=8.0 Hz, 1H), 7.50-7.62 (m, 3H), 7.73 (d, J=8.0 Hz, 1H), 8.09 (s, 1H), 8.28-8.35 (m, 1H).

Example 69

Synthesis of 1-{1-[2-(7-methoxy-2,2-dimethyl-4-oxochroman-8-yl)ethyl]piperidin-4-yl}-N-methyl-1H-indole-6-carboxamide fumarate 1-{1-[2-(7-methoxy-2,2-dimethyl-4-oxochroman-8-yl)ethyl]piperidin-4-yl}-N-methyl-1H-indole-6-carboxamide fumarate (2.05 g) was dissolved in a mixed solvent consisting of n-propanol (6 ml) and water (18 ml) at 60° C. Thereafter, the reaction solution was left at room temperature and then at 0° C. The deposited crystal was collected by filtration. The collected crystal was dried at room temperature under a reduced pressure for 30 minutes, so as to obtain the subject compound (2.02 g).

Example 70

Synthesis of 1-{1-[2-(7-methoxy-2,2-dimethyl-4-oxochroman-8-yl)ethyl]piperidin-4-yl}-N-methyl-1H-indole-6-carboxamide fumarate (A-type Crystal)

1-{1-[2-(7-methoxy-2,2-dimethyl-4-oxochroman-8-yl)ethyl]piperidin-4-yl}-N-methyl-1H-indole-6-carboxamide (1.00 g) and fumaric acid (0.249 g) were dissolved in a mixed solvent consisting of acetone (5 ml) and water (15 ml) at 60° C. Thereafter, the reaction solution was left at room temperature for 1 hour. The deposited solid was collected by filtration. The collected crystal was washed with a mixed solvent consisting of acetone (2.5 ml) and water (7.5 ml), so as to obtain the subject compound (1.09 g).

[X-ray Powder Diffractometry of A-type Crystal]

The crystal (Crystal form A) obtained by the above described crystallization method was crushed in an agate mortar. The obtained sample was placed on the platform of X-ray powder diffractometer, and analysis was carried out under the following conditions (FIG. 1).

Measurement Conditions

TABLE 8

| | |
|---|---|
| Sample holder | Glass or copper |
| Target | Copper |
| Detector | Scintillation counter |
| Tube voltage | 40 kV |
| Tube current | 200 mA |
| Slit | DS1/2°, RS0.3 mm, SS1/2° |
| Scanning speed | 2°/min |
| Sampling interval | 0.02° |
| Scanning range | From 5° to 40° |
| Goniometer | Vertical goniometer |

Example 71

Synthesis of 1-{1-[2-(7-methoxy-2,2-dimethyl-4-oxochroman-8-yl)ethyl]piperidin-4-yl}-N-methyl-1H-indole-6-carboxamide fumarate (B-type Crystal)

1-{1-[2-(7-Methoxy-2,2-dimethyl-4-oxochroman-8-yl)ethyl]piperidin-4-yl}-N-methyl-1H-indole-6-carboxamide fumarate (2.05 g) was dissolved in a mixed solvent consisting of n-propanol (6 ml) and water (18 ml) at 60° C. Thereafter, the reaction solution was left at room temperature and then at 0° C. The deposited crystal was collected by filtration. The collected crystal was dried at room temperature under a reduced pressure for 30 minutes, so as to obtain the subject compound (2.02 g).

[Powder X-ray Diffractometry of B-type Crystal]

The crystal (Crystal form B) obtained by the above described crystallization method was crushed in an agate mortar. The obtained sample was placed on a sample plate for powder X-ray diffractometry, and analysis was carried out under the following conditions (FIG. 2).

Measurement conditions

TABLE 9

| | |
|---|---|
| Sample holder | Glass or copper |
| Target | Copper |
| Detector | Scintillation counter |
| Tube voltage | 40 kV |
| Tube current | 200 mA |

TABLE 9-continued

| | |
|---|---|
| Slit | DS1/2°, RS0.3 mm, SS1/2° |
| Scanning speed | 2°/min |
| Sampling interval | 0.01° |
| Scanning range | From 5° to 40° |
| Goniometer | Vertical goniometer |

Example 72

Synthesis of 1-{1-[2-(7-methoxy-2,2-dimethyl-4-oxochroman-8-yl)ethyl]piperidin-4-yl}-N-methyl-1H-indole-6-carboxamide fumarate (Crystal Form C)

1-{1-[2-(7-Methoxy-2,2-dimethyl-4-oxochroman-8-yl)ethyl]piperidin-4-yl}-N-methyl-1H-indole-6-carboxamide fumarate (100 mg) was weighed and placed in a round bottom flask. The compound was once dissolved in a mixed solvent consisting of water (1 ml) and methanol (0.6 ml) while heating. The reaction solution was then left at room temperature. The deposited crystal was collected by filtration. The collected crystal was dried at 60° C., so as to obtain the subject compound (68 mg).

[Powder X-ray Diffractometry of C-type Crystal]

The crystal (C-type crystal) obtained by the above described crystallization method was crushed in an agate mortar. The obtained sample was placed on a sample plate for powder X-ray diffractometry, and analysis was carried out under the following conditions (FIG. 3).

Measurement Conditions

TABLE 10

| | |
|---|---|
| Sample holder | Glass or copper |
| Target | Copper |
| Detector | Scintillation counter |
| Tube voltage | 40 kV |
| Tube current | 200 mA |
| Slit | DS1/2°, RS0.3 mm, SS1/2° |
| Scanning speed | 2°/min |
| Sampling interval | 0.01° |
| Scanning range | From 5° to 40° |
| Goniometer | Vertical goniometer |

Example 73

Synthesis of 1-{1-[2-(7-methoxy-2,2-dimethyl-4-oxochroman-8-yl)ethyl]piperidin-4-yl}-N-methyl-1H-indole-6-carboxamide fumarate (D-type Crystal)

1-{1-[2-(7-methoxy-2,2-dimethyl-4-oxochroman-8-yl)ethyl]piperidin-4-yl}-N-methyl-1H-indole-6-carboxamide fumarate (100 mg) was weighed and placed in a round bottom flask. The compound was once dissolved in 2-propanol (1 ml) while heating. The reaction solution was then left at room temperature. The deposited crystal was collected by filtration. The collected crystal was dried at 60° C., so as to obtain the subject compound (80 mg).

[Powder X-ray Diffractometry of D-type Crystal]

The crystal (D-type crystal) obtained by the above described crystallization method was crushed in an agate mortar. The obtained sample was placed on a sample plate for powder X-ray diffractometry, and analysis was carried out under the following conditions (FIG. 4).

Measurement Conditions

TABLE 11

| Sample holder | Glass or copper |
|---|---|
| Target | Copper |
| Detector | Scintillation counter |
| Tube voltage | 40 kV |
| Tube current | 200 mA |
| Slit | DSI/2°, RS0.3 mm, SSI/2° |
| Scanning speed | 2°/min |
| Sampling interval | 0.01° |
| Scanning range | From 5° to 40° |
| Goniometer | Vertical goniometer |

Formulation Examples

Formulation examples of the compound of the present invention will be described below. However, formulation of the compound of the present invention is not limited to such formulation examples.

Formulation Example 1

| Compound in Example 20 | 45 (parts) |
|---|---|
| Heavy magnesium oxide | 15 |
| Lactose | 75 |

The above compounds were uniformly mixed, so as to obtain a powder or fine granule powder with a size of 350 μm or less. This powder was encapsulated in a capsule container, so as to produce a capsule.

Formulation Example 2

| Compound in Example 24 (1-{1-[2-(7-methoxy-2,2-dimethyl-4-oxochroman-6-yl)ethyl]piperidin-4-yl}-1H-indole-6-carboxamide) | 45 (parts) |
|---|---|
| Starch | 15 |
| Lactose | 16 |
| Crystalline cellulose | 21 |
| Polyvinyl alcohol | 3 |
| Distilled water | 30 |

The above compounds were uniformly mixed. The obtained mixture was granulated by crushing and then dried. Thereafter, the resultant product was separated by sieving, so as to produce a granule with a size between 1410 and 177 μm.

Formulation Example 3

A granule was produced by the same method as in Formulation example 2. Thereafter, 4 parts of calcium stearate were added to 96 parts of the above granule, followed by compression molding, so as to produce a tablet with a diameter of 10 mm.

Formulation Example 4

10 parts of crystalline cellulose and 3 parts of calcium stearate were added to 90 parts of the granule obtained by the method described in Formulation example 2. The obtained mixture was subjected to compression molding, so as to obtain a table with a diameter of 8 mm. Thereafter, a suspension containing syrup gelatin and precipitated calcium carbonate was added to the tablet, so as to produce a sugarcoated tablet.

Formulation Example 5

| Compound in Example 22 (1-{1-[2-(7-methoxy-2,2-dimethyl-4-oxochroman-8-yl)ethyl]piperidin-4-yl}-1H-indole-6-carboxamide) | 0.6 parts |
|---|---|
| Nonionic surfactant | 2.4 |
| Normal saline solution | 97 |

The above components were mixed while heating, and the obtained mixture was then placed in an ampule. It was then sterilized, so as to produce an injection.

Formulation Example 6

The compound in Example 20, (1-{1-[2-(7-methoxy-2,2-dimethyl-4-oxochroman-8-yl)ethyl]piperidin-4-yl}-N-methyl-1H-indole-6-carboxamide, lactose, corn starch, and low substituted hydroxypropylcellulose were mixed. Thereafter, using hydroxypropylcellulose dissolved in an appropriate amount of purified water, wet granulation was carried out. The thus granulated product was dried and then sized. Thereafter, low substituted hydroxypropylcellulose and magnesium stearate were added to the obtained granule, and these components were then blended, followed by tablet making. The obtained tablet was coated with an aqueous solution containing a coating base (Opadry yellow). The amounts of materials used per tablet are shown in table below.

TABLE 12

| Material used | 1 mg tablet | 10 mg tablet | 60 mg tablet |
|---|---|---|---|
| Compound 1 of the present invention | 1 mg | 10 mg | 60 mg |
| Lactose | 122 mg | 113 mg | 63 mg |
| Corn starch | 20 mg | 20 mg | 20 mg |
| Low substituted hydroxypropylcellulose | 20 mg | 20 mg | 20 mg |
| Hydroxypropylcellulose | 6 mg | 6 mg | 6 mg |
| Purified water | Appropriate amount | Appropriate amount | Appropriate amount |
| Low substituted hydroxypropylcellulose | 10 mg | 10 mg | 10 mg |
| Crystalline cellulose | 20 mg | 20 mg | 20 mg |
| Magnesium stearate | 1 mg | 1 mg | 1 mg |
| Opadry yellow (note) | 8 mg | 8 mg | 8 mg |
| Total | 208 mg | 208 mg | 208 mg |

(Note) A premixed material formed by mixing 56% hydroxypropylmethylcellulose 2910, 28% talc, 10% Macrogol 6000, 4% titanium oxide, and 2% yellow iron sesquioxide.

INDUSTRIAL APPLICABILITY

The compound represented by general formula (I) of the present invention has an effect to bind to a 5-HT1A receptor and also has an antagonistic effect against to the receptor. Thus, it is useful as an agent for treating or preventing lower urinary tract symptoms, and particularly, increased urinary frequency, urinary incontinence, or the like. ///

Figure 1:
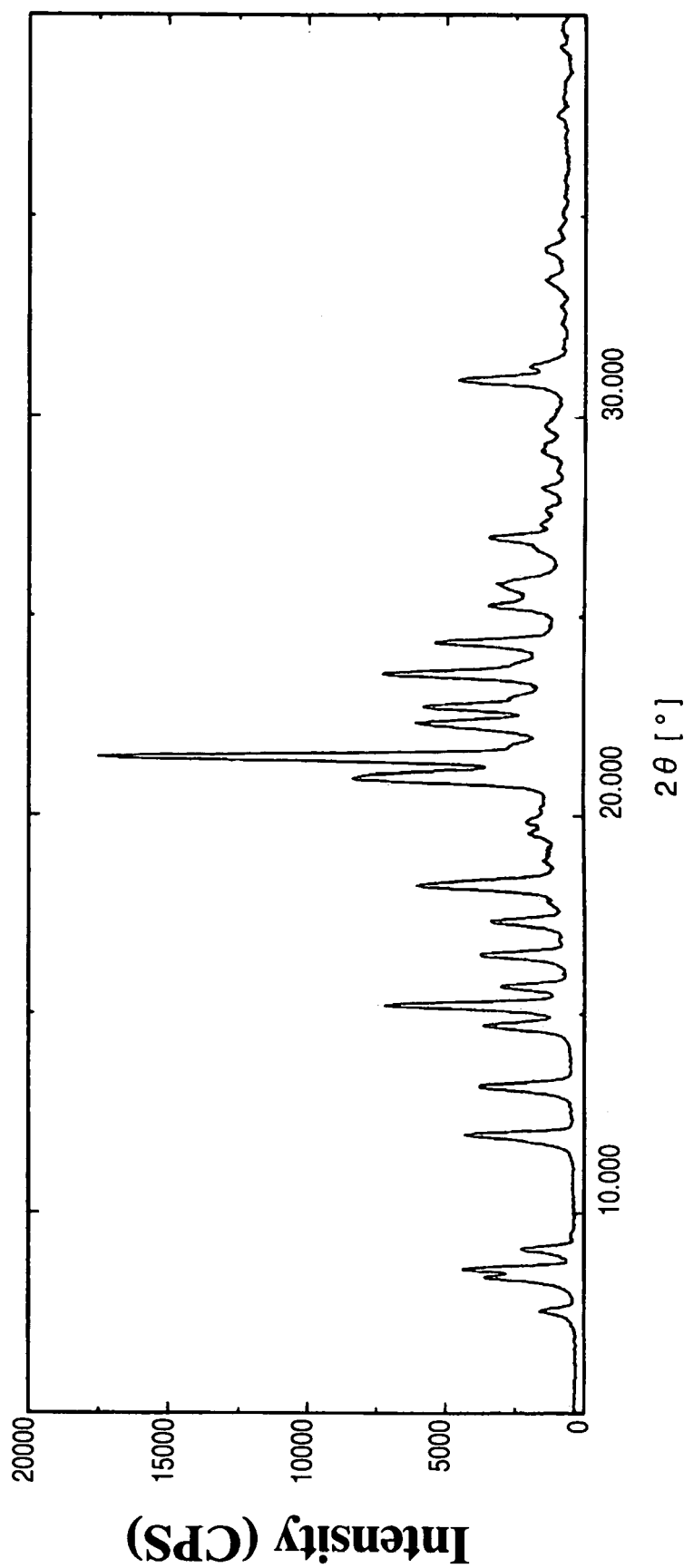
[FIG. 1] shows a powder X-ray diffraction pattern of the A-type crystal obtained in Example 70. The horizontal axis indicates a diffraction angle (2θ), and the vertical axis indicates peak strength.
Figure 2:
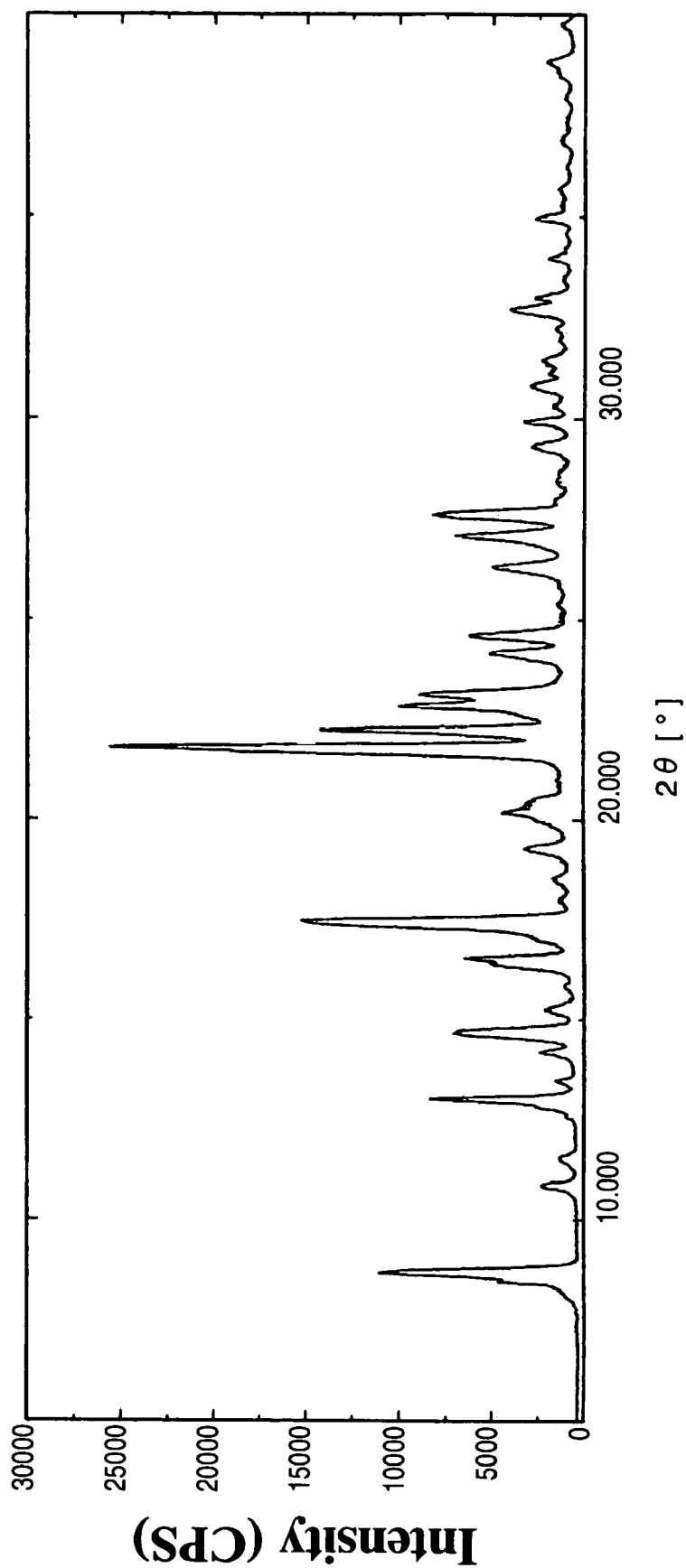
[FIG. 2] shows a powder X-ray diffraction pattern of the B-type crystal obtained in Example 71. The horizontal axis indicates a diffraction angle (2θ), and the vertical axis indicates peak strength.
Figure 3:
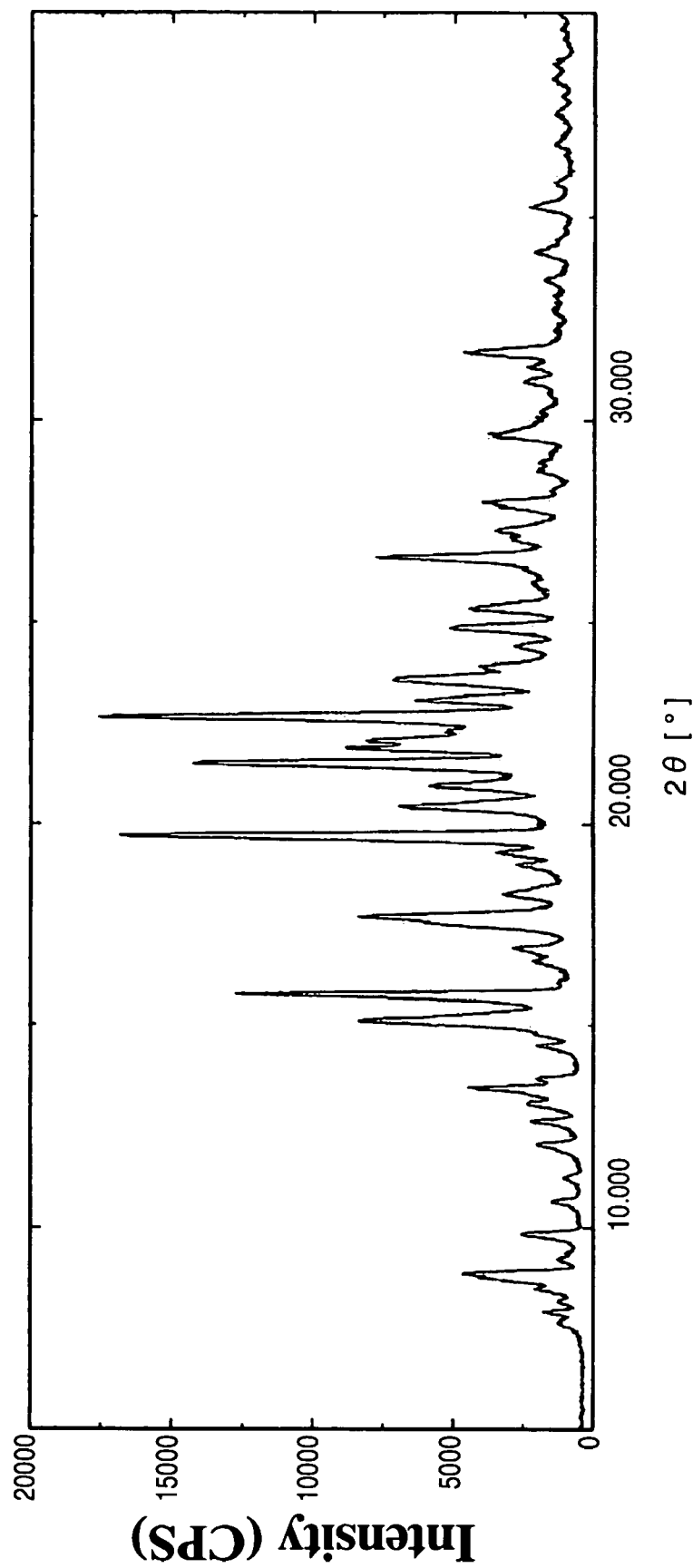
[FIG. 3] shows a powder X-ray diffraction pattern of the C-type crystal obtained in Example 71. The horizontal axis indicates a diffraction angle (2θ), and the vertical axis indicates peak strength.
Figure 4:
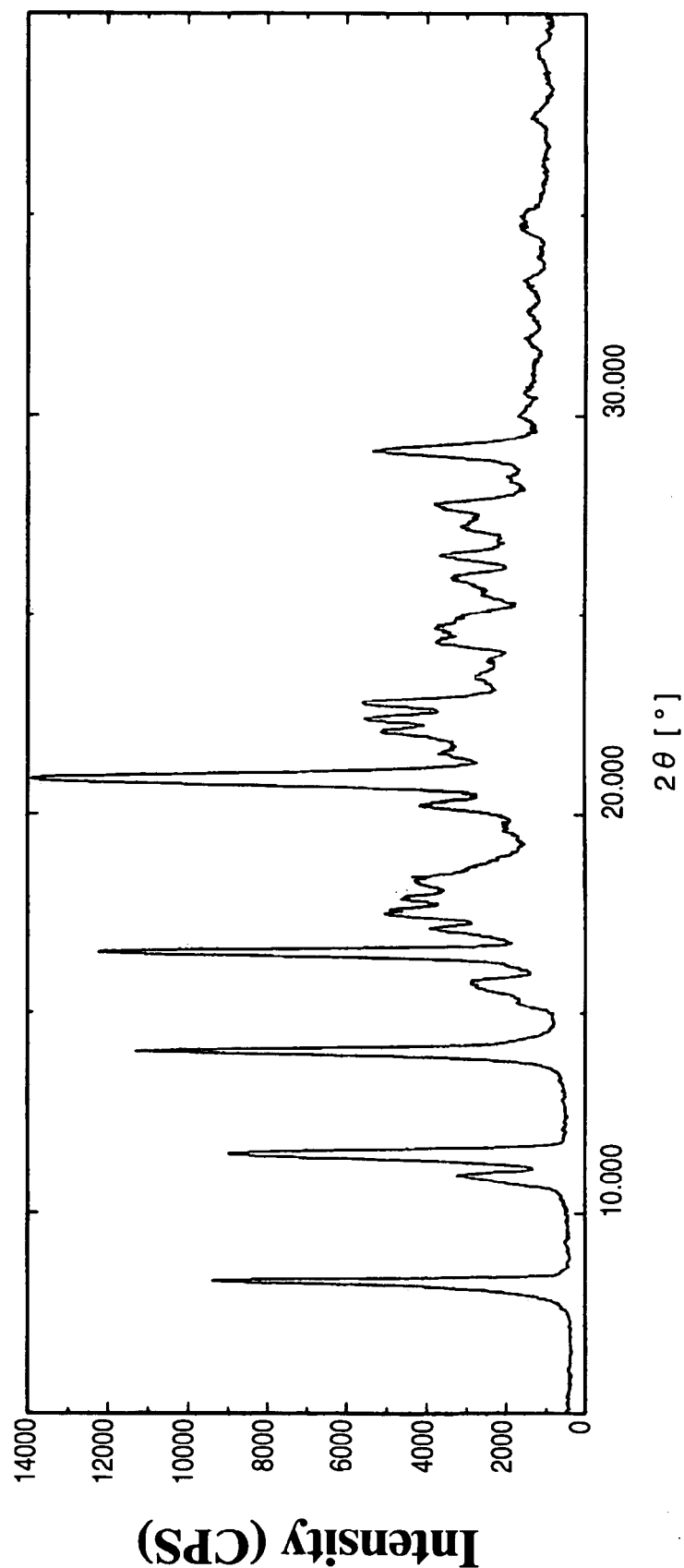
[FIG. 4] shows a powder X-ray diffraction pattern of the D-type crystal obtained in Example 72. The horizontal axis indicates a diffraction angle (2θ), and the vertical axis indicates peak strength.

The invention claimed is:

1. A compound represented by the following formula (I) or a pharmacologically acceptable salt thereof:

[Formula 1]

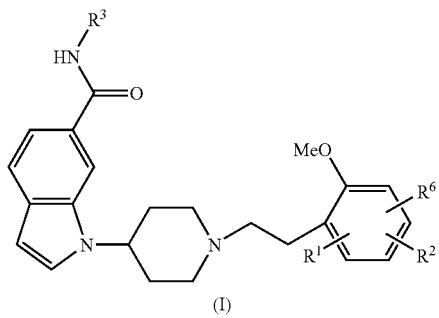

(I)

wherein $R^1$ and $R^2$ are substituents adjacent to each other, and together with two carbon atoms to each of which they attach, form:
(1) a 5- to 7-membered non-aromatic carbocyclic group,
(2) a 5- to 7-membered non-aromatic heterocyclyl group,
(3) a 6-membered aromatic carbocyclic group, or
(4) a 5- or 6-membered aromatic heterocyclyl group,
which may be substituted by 1 to 4 substituents selected from the following substituent group B1;

$R^3$ represents a hydrogen atom or a methyl group; and $R^6$ represents a substituent selected from the following substituent group A1, Substituent group A1: (1) a hydrogen atom, (2) a halogen atom, (3) a cyano group, (4) a hydroxyl group, (5) a nitro group, (6) a carboxyl group, (7) a C3-C8 cycloalkyl group, (8) a C2-C6 alkenyl group, (9) a C2-C6 alkynyl group, (10) a C1-C6 alkylthio group, (11) a C1-C6 alkoxycarbonyl group, (12) a C1-C6 alkylsulfonyl group, (13) a C1-C6 alkyl group (wherein said C1-C6 alkyl group may be substituted by 1 to 3 substituents selected from the group consisting of a halogen atom, a hydroxyl group, and a C1-C6 alkoxy group), (14) a C1-C6 alkoxy group (wherein said C1-C6 alkoxy group may be substituted by 1 to 3 halogen atoms), (15) an amino group (wherein said amino group may be substituted by a substituent selected from the group consisting of a C1-C6 alkyl group, a formyl group, a C1-C6 alkanoyl group, and a C1-C6 alkylsulfonyl group), and (16) a carbamoyl group (wherein said carbamoyl group may be substituted by one or two C1-C6 alkyl groups);

Substituent group B1: (1) a hydrogen atom, (2) a halogen atom, (3) a cyano group, (4) a hydroxyl group, (5) a nitro group, (6) an oxo group, (7) a carboxyl group, (8) a C3-C8 cycloalkyl group, (9) a C2-C6 alkenyl group, (10) a C2-C6 alkynyl group, (11) a C1-C6 alkylthio group, (12) a C1-C6 alkoxycarbonyl group, (13) a C1-C6 alkylsulfonyl group, (14) a C1-C6 alkyl group (wherein said C1-C6 alkyl group may be substituted by a halogen atom, a hydroxyl group, or a C1-C6 alkoxy group), (15) a C1-C6 alkoxy group (wherein said C1-C6 alkoxy group may be substituted by 1 to 3 halogen atoms), (16) an amino group (wherein said amino group may be substituted by a substituent selected from the group consisting of a C1-C6 alkyl group, a formyl group, a C1-C6 alkanoyl group, and a C1-C6 alkylsulfonyl group), (17) a carbamoyl group (wherein said carbamoyl group may be substituted by one or two C1-C6 alkyl groups), (18) a C1-C6 alkoxyimino group, (19) a C5-C6 cycloalkyl group formed by two C1-C3 alkyl groups attaching to the same carbon atom, and (20) a tetrahydropyranyl group formed by two C1-C3 alkyl group attaching to the same carbon atom, together with an oxygen atom and said carbon atom.

2. The compound according to claim 1 or a pharmacologically acceptable salt thereof, wherein $R^1$ and $R^2$ are substituents adjacent to each other, and together with two carbon atoms to each of which they attach, forms a group represented by the following formula:

[Formula 2]

1)

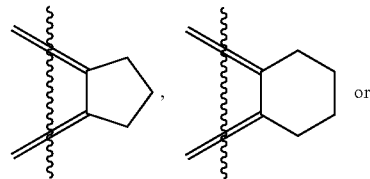

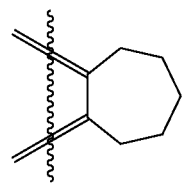

2)

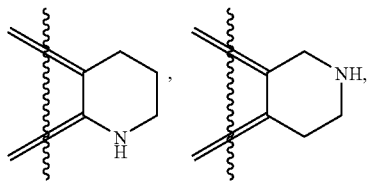

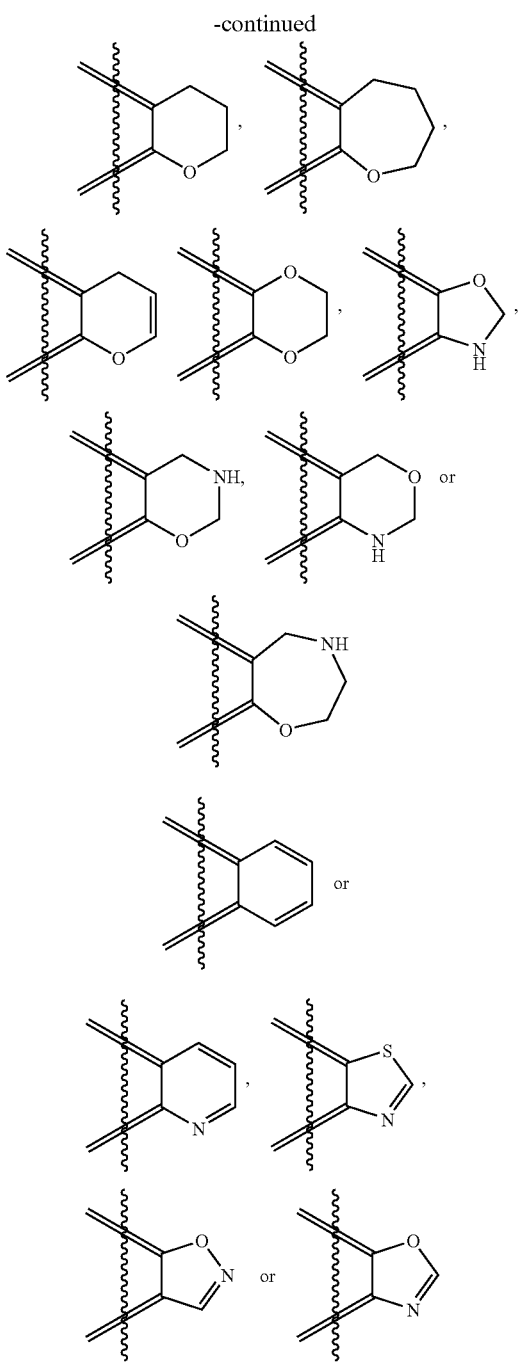

wherein a hydrogen atom on each cyclic group may be substituted by 1 to 4 substituents selected from the following substituent group B 1, Substituent group B1: (1) a hydrogen atom, (2) a halogen atom, (3) a cyano group, (4) a hydroxyl group, (5) a nitro group, (6) an oxo group, (7) a carboxyl group, (8) a C3-C8 cycloalkyl group, (9) a C2-C6 alkenyl group, (10) a C2-C6 alkynyl group, (11) a C1-C6 alkylthio group, (12) a C1-C6 alkoxycarbonyl group, (13) a C1-C6 alkylsulfonyl group, (14) a C1-C6 alkyl group (wherein said C1-C6 alkyl group may be substituted by a halogen atom, a hydroxyl group, or a C1-C6 alkoxy group), (15) a C1-C6 alkoxy group (wherein said C1-C6 alkoxy group may be substituted by 1 to 3 halogen atoms), (16) an amino group (wherein said amino group may be substituted by a substituent selected from the group consisting of a C1-C6 alkyl group, a formyl group, a C1-C6 alkanoyl group, and a C1-C6 alkylsulfonyl group), (17) a carbamoyl group (wherein said carbamoyl group may be substituted by one or two C1-C6 alkyl groups), (18) a C1-C6 alkoxyimino group, (19) a C5-C6 cycloalkyl group formed by two C1-C3 alkyl groups attaching to the same carbon atom, and (20) a tetrahydropyranyl group formed by two C1-C3 alkyl group attaching to the same carbon atom, together with an oxygen atom and said carbon atom.

3. The compound according to claim 1 or a pharmacologically acceptable salt thereof, which is represented by formula (I-a-1), formula (I-a-2), formula (I-a-3), or formula (I-a-4):

[Formula 3]

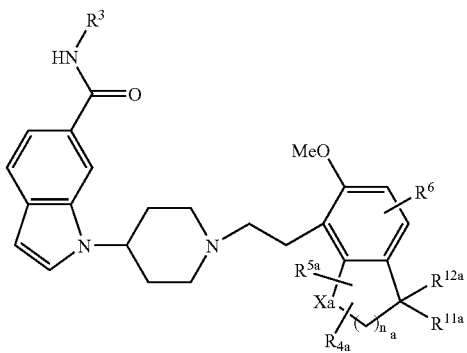

(I-a-1)

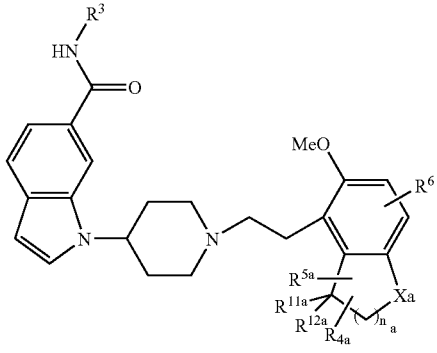

(I-a-2)

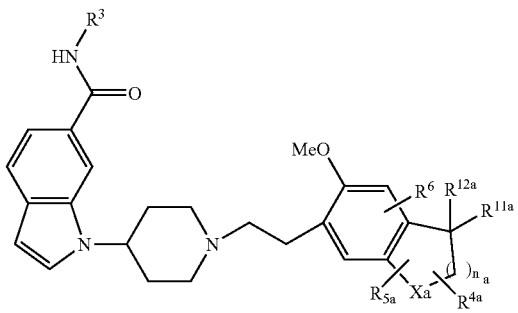

(I-a-3)

-continued

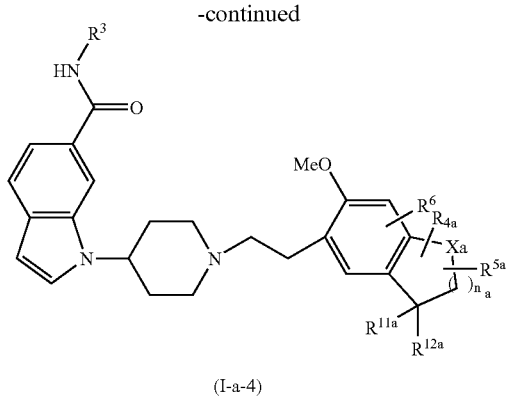

(I-a-4)

wherein $R^3$ represents a hydrogen atom or methyl group; $R^{4a}$ and $R^{5a}$ represent substituents selected from the following substituent group B1; $R^6$ represents a substituent selected from the following substituent group A1; $R^{11a}$ represents a hydroxyl group, $R^{12a}$ represents a hydrogen atom or C1-C6 alkyl group, or $R^{11a}$ and $R^{12a}$ represent a carbonyl group or the formula C=N—OR$^{8c}$ (wherein $R^{8c}$ represents a C1-C6 alkyl group), together with carbon atoms to which $R^{11a}$ and $R^{12a}$ attach; $X_a$ represents a methylene group or oxygen atom; and $n_a$ represents an integer between 1 and 3, Substituent group A1: (1) a hydrogen atom, (2) a halogen atom, (3) a cyano group, (4) a hydroxyl group, (5) a nitro group, (6) a carboxyl group, (7) a C3-C8 cycloalkyl group, (8) a C2-C6 alkenyl group, (9) a C2-C6 alkynyl group, (10) a C1-C6 alkylthio group, (11) a C1-C6 alkoxycarbonyl group, (12) a C1-C6 alkylsulfonyl group, (13) a C1-C6 alkyl group (wherein said C1-C6 alkyl group may be substituted by 1 to 3 substituents selected from the group consisting of a halogen atom, a hydroxyl group, and a C1-C6 alkoxy group), (14) a C1-C6 alkoxy group (wherein said C1-C6 alkoxy group may be substituted by 1 to 3 halogen atoms), (15) an amino group (wherein said amino group may be substituted by a substituent selected from the group consisting of a C1-C6 alkyl group, a formyl group, a C1-C6 alkanoyl group, and a C1-C6 alkylsulfonyl group), and (16) a carbamoyl group (wherein said carbamoyl group may be substituted by one or two C1-C6 alkyl groups);

Substituent group B1: (1) a hydrogen atom, (2) a halogen atom, (3) a cyano group, (4) a hydroxyl group, (5) a nitro group, (6) an oxo group, (7) a carboxyl group, (8) a C3-C8 cycloalkyl group, (9) a C2-C6 alkenyl group, (10) a C2-C6 alkynyl group, (11) a C1-C6 alkylthio group, (12) a C1-C6 alkoxycarbonyl group, (13) a C1-C6 alkylsulfonyl group, (14) a C1-C6 alkyl group (wherein said C1-C6 alkyl group may be substituted by a halogen atom, a hydroxyl group, or a C1-C6 alkoxy group), (15) a C1-C6 alkoxy group (wherein said C1-C6 alkoxy group may be substituted by 1 to 3 halogen atoms), (16) an amino group (wherein said amino group may be substituted by a substituent selected from the group consisting of a C1-C6 alkyl group, a formyl group, a C1-C6 alkanoyl group, and a C1-C6 alkylsulfonyl group), (17) a carbamoyl group (wherein said carbamoyl group may be substituted by one or two C1-C6 alkyl groups), (18) a C1-C6 alkoxyimino group, (19) a C5-C6 cycloalkyl group formed by two C1-C3 alkyl groups attaching to the same carbon atom, and (20) a tetrahydropyranyl group formed by two C1-C3 alkyl group attaching to the same carbon atom, together with an oxygen atom and said carbon atom.

4. The compound according to claim 3 or a pharmacologically acceptable salt thereof, wherein $R^{11a}$ and $R^{12a}$ form a carbonyl group, together with carbon atoms to which $R^{11a}$ and $R^{12a}$ attach.

5. The compound according to claim 3 or 4 or a pharmacologically acceptable salt thereof, wherein $R^{4a}$ and $R^{5a}$ are substituents selected from the following substituent group B2, and $R^6$ represents a substituent selected from the following substituent group A2, Substituent group A2: (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) C1-C6 alkoxy C1-C6 alkyl group;

Substituent group B2: (1) a hydrogen atom, (2) a C1-C6 alkyl group, (3) a halogen atom, (4) a hydroxyl group, (5) a C1-C6 alkoxy group, (6) a C1-C6 alkoxy C1-C6 alkyl group, (7) a C5-C6 cycloalkyl group formed by two C1-C3 alkyl groups attaching to the same carbon atom, and (8) a tetrahydropyranyl group formed by two C1-C3 alkyl group attaching to the same carbon atom, together with an oxygen atom and said carbon atom.

6. The compound according to claim 3 or a pharmacologically acceptable salt thereof, wherein $R^{4a}$ and $R^{5a}$ represent substituents selected from the following substituent group B5, and $R^6$ represents a substituent selected from the following substituent group A4, Substituent group A4: (1) a hydrogen atom, and (2) a C1-C6 alkoxy group; Substituent group B5: (1) a hydrogen atom, (2) a C1-C6 alkyl group, (3) a C1-C6 alkoxy C1-C6 alkyl group, (4) a C5-C6 cycloalkyl group formed by two C1-C3 alkyl groups attaching to the same carbon atom, and (5) a tetrahydropyranyl group formed by two C1-C3 alkyl group attaching to the same carbon atom, together with an oxygen atom and said carbon atom.

7. The compound according to claim 3 or a pharmacologically acceptable salt thereof, wherein $X_a$ represents an oxygen atom.

8. The compound according to claim 1 or a pharmacologically acceptable salt thereof, which is represented by formula (I-b-1), formula (I-b-2), formula (I-b-3), or formula (I-b-4):

[Formula 4]

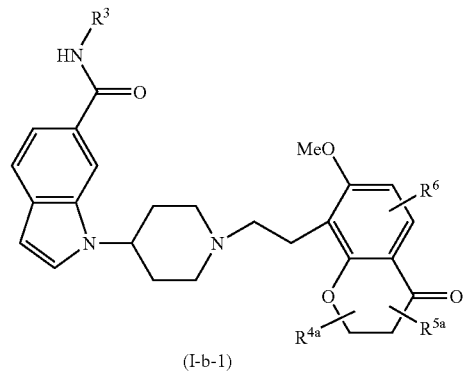

(I-b-1)

-continued

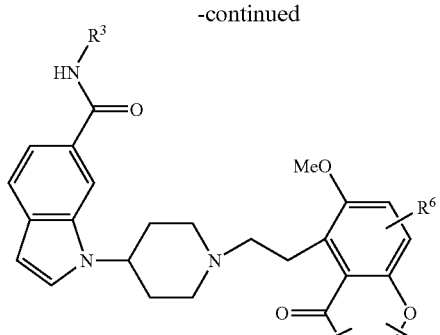

(I-b-2)

[Formula 5]

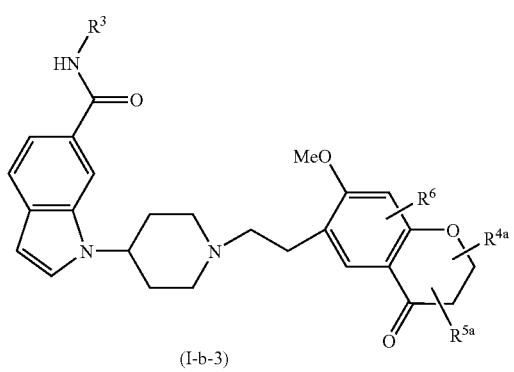

(I-b-3)

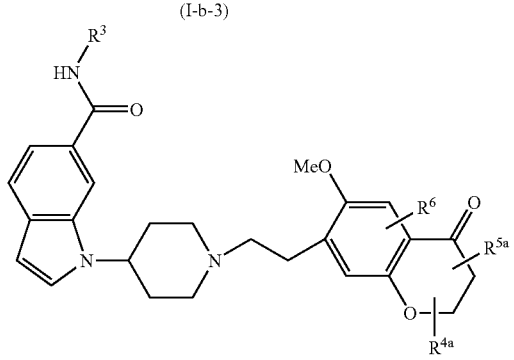

(I-b-4)

wherein $R^{4a}$ and $R^{5a}$ represent substituents selected from the following substituent group B5, and $R^6$ represents a substituent selected from the following substituent group A4, Substituent group A4: (1) a hydrogen atom, and (2) a C1-C6 alkoxy group; Substituent group B5: (1) a hydrogen atom, (2) a C1-C6 alkyl group, (3) a C1-C6 alkoxy C1-C6 alkyl group, (4) a C5-C6 cycloalkyl group formed by two C1-C3 alkyl groups attaching to the same carbon atom, and (5) a tetrahydropyranyl group formed by two C1-C3 alkyl group attaching to the same carbon atom, together with an oxygen atom and said carbon atom.

9. The compound according to claim 3 or a pharmacologically acceptable salt thereof, wherein $R^{11a}$ represents a hydroxyl group, and $R^{12a}$ represents a hydrogen atom or C1-C6 alkyl group.

10. The compound according to claim 9 or a pharmacologically acceptable salt thereof, wherein $R^{4a}$ and $R^{5a}$ are substituents selected from the following substituent group B2, and $R^6$ represents a substituent selected from the following substituent group A2, Substituent group A2: (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) C1-C6 alkoxy C1-C6 alkyl group;

Substituent group B2: (1) a hydrogen atom, (2) a C1-C6 alkyl group, (3) a halogen atom, (4) a hydroxyl group, (5) a C1-C6 alkoxy group, (6) a C1-C6 alkoxy C1-C6 alkyl group, (7) a C5-C6 cycloalkyl group formed by two C1-C3 alkyl groups attaching to the same carbon atom, and (8) a tetrahydropyranyl group formed by two C1-C3 alkyl group attaching to the same carbon atom, together with an oxygen atom and said carbon atom.

11. The compound according to claim 9 or 10 or a pharmacologically acceptable salt thereof, wherein $X_a$ represents an oxygen atom.

12. The compound according to claim 3 or a pharmacologically acceptable salt thereof, wherein $R^{11a}$ and $R^{12a}$ together form the formula $=N-OR^{8c}$ (wherein $R^{8c}$ represents a C1-C6 alkyl group).

13. The compound according to claim 12 or a pharmacologically acceptable salt thereof, wherein $R^{4a}$ and $R^{5a}$ are substituents selected from the following substituent group B3, and $R^6$ represents a substituent selected from the following substituent group A2, Substituent group A2: (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) C1-C6 alkoxy C1-C6 alkyl group;

Substituent group B3: (1) a hydrogen atom, (2) a C1-C6 alkyl group, (3) a halogen atom, (4) a hydroxyl group, (5) a C1-C6 alkoxy group, and (6) a C1-C6 alkoxy C1-C6 alkyl group.

14. The compound according to claim 12 or 13 or a pharmacologically acceptable salt thereof, wherein $X_a$ represents an oxygen atom.

15. The compound according to claim 1 or a pharmacologically acceptable salt thereof, which is represented by formula (I-c-1) or formula (I-c-2):

[Formula 6]

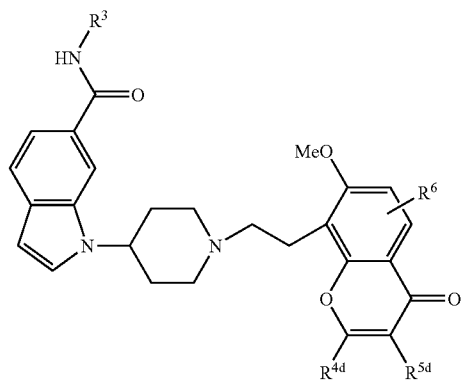

(I-c-1)

-continued

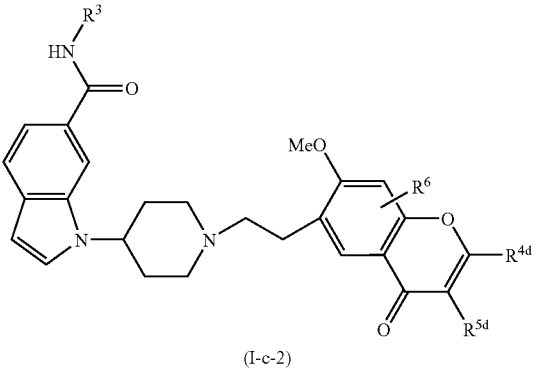

(I-c-2)

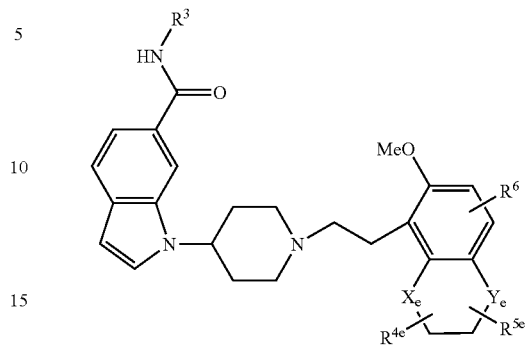

(I-d-1)

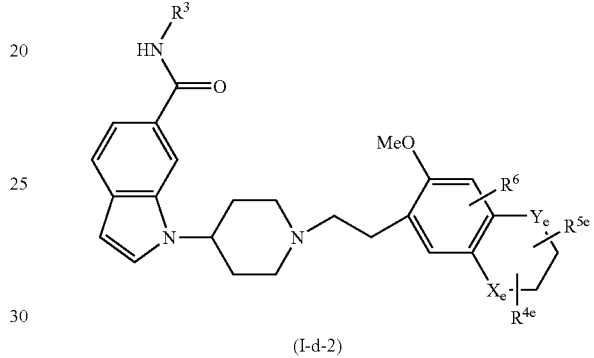

(I-d-2)

wherein $R^3$ represents a hydrogen atom or methyl group; and $R^{4d}$, $R^{5d}$, and $R^6$ represent substituents selected from the following substituent group A1, Substituent group A1: (1) a hydrogen atom, (2) a halogen atom, (3) a cyano group, (4) a hydroxyl group, (5) a nitro group, (6) a carboxyl group, (7) a C3-C8 cycloalkyl group, (8) a C2-C6 alkenyl group, (9) a C2-C6 alkynyl group, (10) a C1-C6 alkylthio group, (11) a C1-C6 alkoxycarbonyl group, (12) a C1-C6 alkylsulfonyl group, (13) a C1-C6 alkyl group (wherein said C1-C6 alkyl group may be substituted by 1 to 3 substituents selected from the group consisting of a halogen atom, a hydroxyl group, and a C1-C6 alkoxy group), (14) a C1-C6 alkoxy group (wherein said C1-C6 alkoxy group may be substituted by 1 to 3 halogen atoms), (15) an amino group (wherein said amino group may be substituted by a substituent selected from the group consisting of a C1-C6 alkyl group, a formyl group, a C1-C6 alkanoyl group, and a C1-C6 alkylsulfonyl group), and (16) a carbamoyl group (wherein said carbamoyl group may be substituted by one or two C1-C6 alkyl groups).

16. The compound according to claim 15 or a pharmacologically acceptable salt thereof, wherein $R^{4d}$ and $R^{5d}$ are substituents selected from the following substituent group B4, and $R^6$ represents a substituent selected from the following substituent group A2, Substituent group A2: (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) C1-C6 alkoxy C1-C6 alkyl group;

Substituent group B4: (1) a hydrogen atom, (2) a C1-C6 alkyl group, (3) a C1-C6 alkoxy group, and (4) a C1-C6 alkoxy C1-C6 alkyl group.

17. The compound according to claim 1 or a pharmacologically acceptable salt thereof, which is represented by formula (I-d-1) or formula (I-d-2):

wherein $R^3$ represents a hydrogen atom or methyl group; $R^{4e}$ and $R^{5e}$ represent substituents selected from the following substituent group A1; $R^6$ represents a substituent selected from the following substituent group A1; and each of $X_e$ and $Y_e$ represents (1) an oxygen atom, (2) a methylene group, (3) —$CONR^{7e}$— (wherein $R^{7e}$ represents (1) a hydrogen atom, or (2) a C1-C6 alkyl group), (4) —$NR^{7e}Co$— (wherein $R^{7e}$ has the same above meaning), (5) —$NR^{8e}$— (wherein $R^{8e}$ represents (1) a C1-C6 alkyl group, or (2) a C1-C6 acyl group), or (6) a single bond, Substituent group A1: (1) a hydrogen atom, (2) a halogen atom, (3) a cyano group, (4) a hydroxyl group, (5) a nitro group, (6) a carboxyl group, (7) a C3-C8 cycloalkyl group, (8) a C2-C6 alkenyl group, (9) a C2-C6 alkynyl group, (10) a C1-C6 alkylthio group, (11) a C1-C6 alkoxycarbonyl group, (12) a C1-C6 alkylsulfonyl group, (13) a C1-C6 alkyl group (wherein said C1-C6 alkyl group may be substituted by 1 to 3 substituents selected from the group consisting of a halogen atom, a hydroxyl group, and a C1-C6 alkoxy group), (14) a C1-C6 alkoxy group (wherein said C1-C6 alkoxy group may be substituted by 1 to 3 halogen atoms), (15) an amino group (wherein said amino group may be substituted by a substituent selected from the group consisting of a C1-C6 alkyl group, a formyl group, a C1-C6 alkanoyl group, and a C1-C6 alkylsulfonyl group), and (16) a carbamoyl group (wherein said carbamoyl group may be substituted by one or two C1-C6 alkyl groups).

18. The compound according to claim 17 or a pharmacologically acceptable salt thereof, wherein $R^{4e}$ and $R^{5e}$ are substituents selected from the following substituent group B3, and $R^6$ represents a substituent selected from the following substituent group A2, Substituent group A2: (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) C1-C6 alkoxy C1-C6 alkyl group;

Substituent group B3: (1) a hydrogen atom, (2) a C1-C6 alkyl group, (3) a halogen atom, (4) a hydroxyl group, (5) a C1-C6 alkoxy group, and (6) a C1-C6 alkoxy C1-C6 alkyl group.

19. The compound according to claim 1 or a pharmacologically acceptable salt thereof, which is represented by formula (I-e-1) or formula (I-e-2):

[Formula 8]

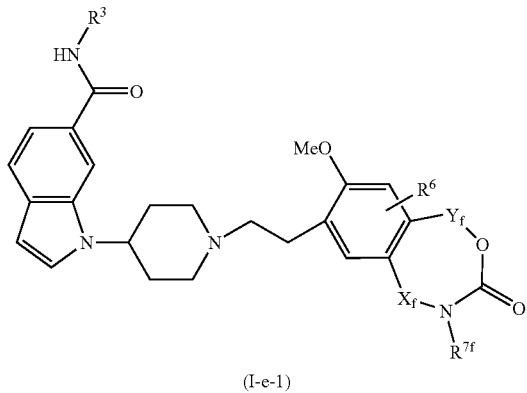

(I-e-1)

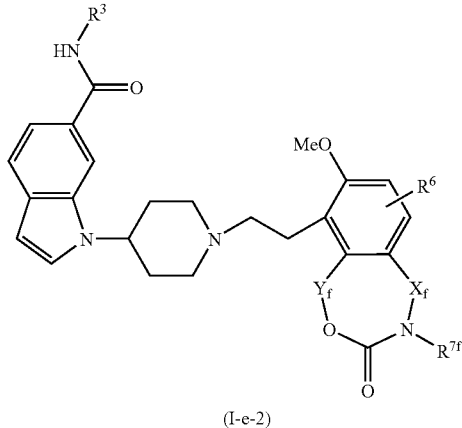

(I-e-2)

wherein $R^3$ represents a hydrogen atom or methyl group; $R^6$ represents a substituent selected from the following substituent group A1; $R^{7f}$ represents (1) hydrogen atom, (2) a C1-C6 alkyl group, (3) a C3-C8 cycloalkyl group, (4) a C2-C6 alkenyl group, (5) a C2-C6 alkynyl group, or (6) a C1-C6 alkoxy C1-C6 alkyl group; and each of $X_f$ and $Y_f$ represents (1) a single bond, (2) a methylene group which may have a substituent selected from the following substituent group A1, or (3) a carbonyl group, Substituent group A1: (1) a hydrogen atom, (2) a halogen atom, (3) a cyano group, (4) a hydroxyl group, (5) a nitro group, (6) a carboxyl group, (7) a C3-C8 cycloalkyl group, (8) a C2-C6 alkenyl group, (9) a C2-C6 alkynyl group, (10) a C1-C6 alkylthio group, (11) a C1-C6 alkoxycarbonyl group, (12) a C1-C6 alkylsulfonyl group, (13) a C1-C6 alkyl group (wherein said C1-C6 alkyl group may be substituted by 1 to 3 substituents selected from the group consisting of a halogen atom, a hydroxyl group, and a C1-C6 alkoxy group), (14) a C1-C6 alkoxy group (wherein said C1-C6 alkoxy group may be substituted by 1 to 3 halogen atoms), (15) an amino group (wherein said amino group may be substituted by a substituent selected from the group consisting of a C1-C6 alkyl group, a formyl group, a C1-C6 alkanoyl group, and a C1-C6 alkylsulfonyl group), and (16) a carbamoyl group (wherein said carbamoyl group may be substituted by one or two C1-C6 alkyl groups).

20. The compound according to claim 19 or a pharmacologically acceptable salt thereof, wherein $R^6$ represents a substituent selected from the following substituent group A2; $R^{7f}$ represents a substituent selected from the following substituent group B4; and each of $X_f$ and $Y_f$ represents (1) a single bond, (2) a methylene group which may have a substituent selected from the following substituent group B4, or (3) a carbonyl group, Substituent group A2: (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) C 1-C6 alkoxy C1-C6 alkyl group;

Substituent group B4: (1) a hydrogen atom, (2) a C1-C6 alkyl group, and (3) C1-C6 alkoxy group (4) a C1-C6 alkoxy C1-C6 alkyl group.

21. The compound according to claim 1 or a pharmacologically acceptable salt thereof, which is represented by formula (I-f-1), formula (I-f-2), formula (I-f-3), formula (I-f-4), formula (I-g-1), formula (I-g-2), formula (I-h-1), formula (I-h-2), formula (I-h-3), or formula (I-h-4):

[Formula 9]

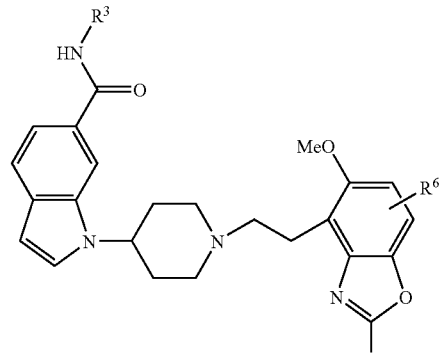

(I-f-2)

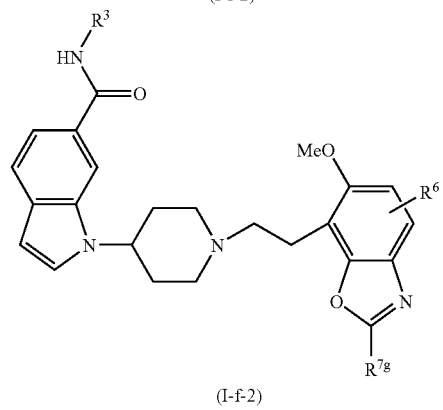

(I-f-2)

-continued
[Formula 10]
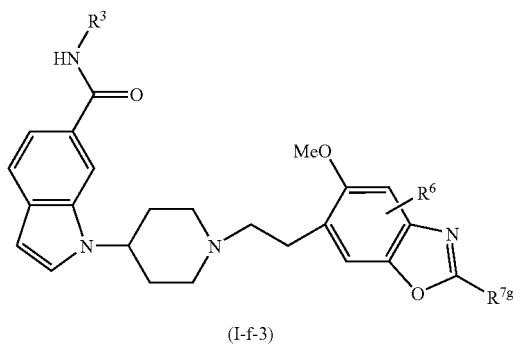
(I-f-3)
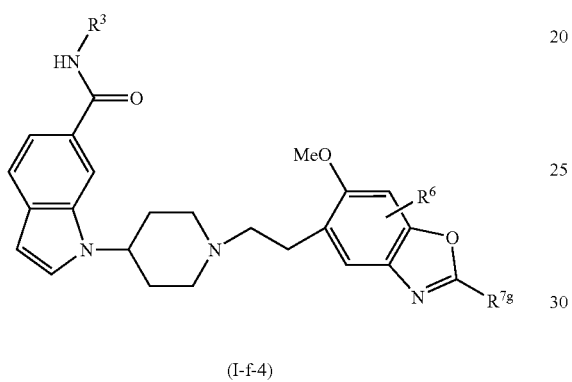
(I-f-4)
[Formula 11]
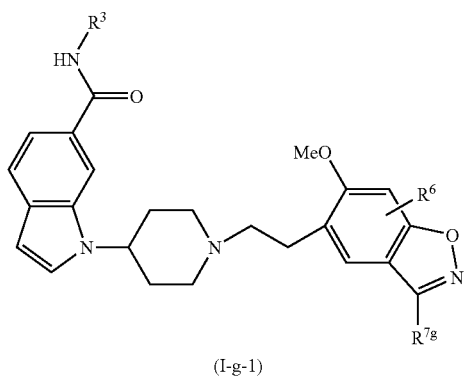
(I-g-1)
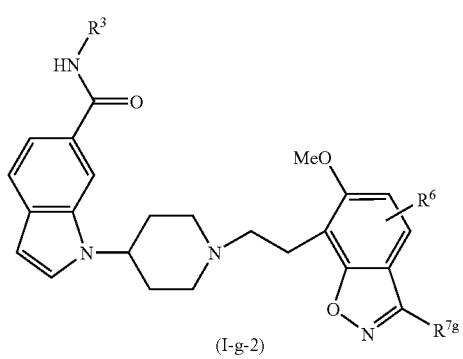
(I-g-2)
-continued
[Formula 12]
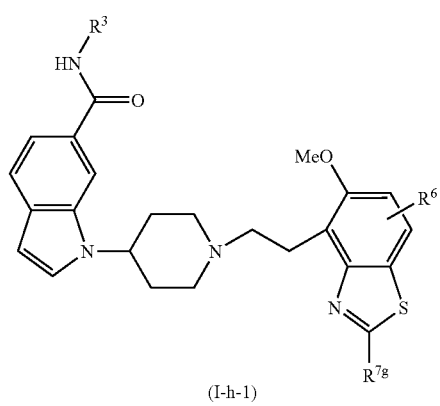
(I-h-1)
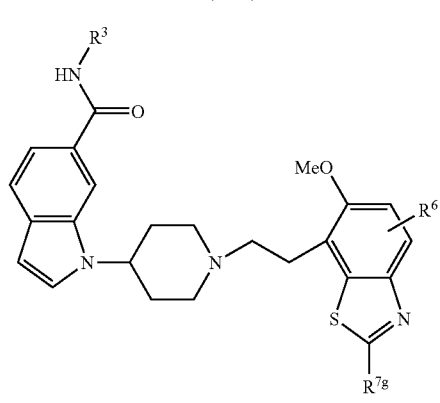
(I-h-2)
[Formula 13]
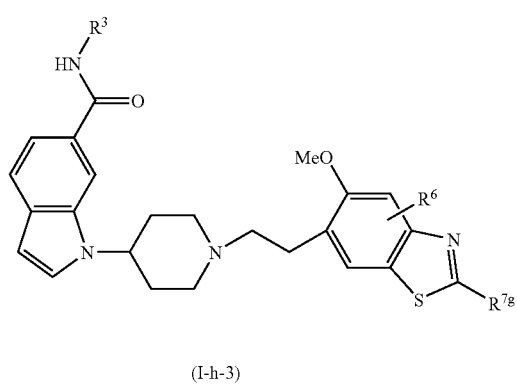
(I-h-3)
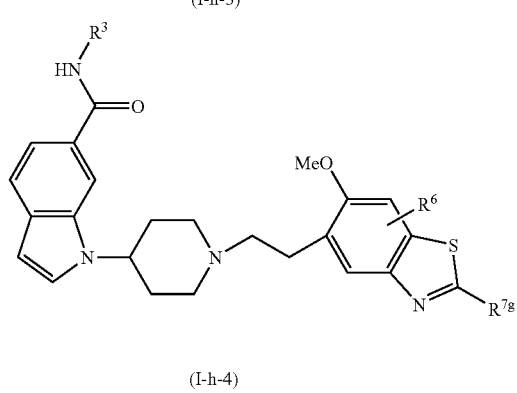
(I-h-4)

wherein R³ represents a hydrogen atom or methyl group; and R⁶ and R⁷ᵍ represent substituents selected from the following substituent group A1 (however, a case where R⁷ᵍ represents a hydroxyl group is excluded), Substituent group A1: (1) a hydrogen atom, (2) a halogen atom, (3) a cyano group, (4) a hydroxyl group, (5) a nitro group, (6) a carboxyl group, (7) a C3-C8 cycloalkyl group, (8) a C2-C6 alkenyl group, (9) a C2-C6 alkynyl group, (10) a C1-C6 alkylthio group, (11) a C1-C6 alkoxycarbonyl group, (12) a C1-C6 alkylsulfonyl group, (13) a C1-C6 alkyl group (wherein said C1-C6 alkyl group may be substituted by 1 to 3 substituents selected from the group consisting of a halogen atom, a hydroxyl group, and a C1-C6 alkoxy group), (14) a C1-C6 alkoxy group (wherein said C1-C6 alkoxy group may be substituted by 1 to 3 halogen atoms), (15) an amino group (wherein said amino group may be substituted by a substituent selected from the group consisting of a C1-C6 alkyl group, a formyl group, a C1-C6 alkanoyl group, and a C1-C6 alkylsulfonyl group), and (16) a carbamoyl group (wherein said carbamoyl group may be substituted by one or two C1-C6 alkyl groups).

22. The compound according to claim 21 or a pharmacologically acceptable salt thereof, wherein R⁶ represents a substituent selected from the following substituent group A2, and R⁷ᵍ represents a substituent selected from the following substituent group B7, Substituent group A2: (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) C1-C6 alkoxy C1-C6 alkyl group;

Substituent group B7: (1) a hydrogen atom, (2) a C1-C6 alkyl group, (3) a halogen atom, (4) a cyano group, and (5) a C1-C6 alkoxy C1-C6 alkyl group.

23. The compound according to claim 21 or 22 or a pharmacologically acceptable salt thereof, wherein R⁶ represents a substituent selected from the following substituent group A4, and R⁷ᵍ represents a substituent selected from the following substituent group B6, Substituent group A4: (1) a hydrogen atom, and (2) a C1-C6 alkoxy group;

Substituent group B6: (1) a hydrogen atom, and (2) a C1-C6 alkyl group.

24. The compound according to claim 1 or a pharmacologically acceptable salt thereof, which is represented by formula (I-i-1) or formula (I-i-2):

[Formula 14]

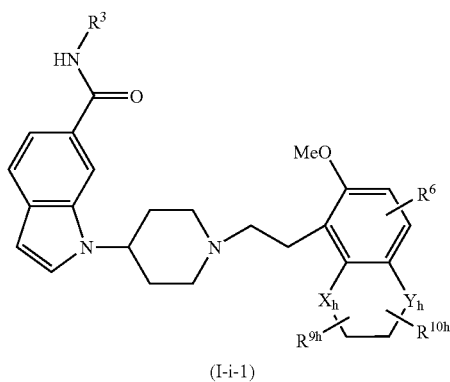

(I-i-1)

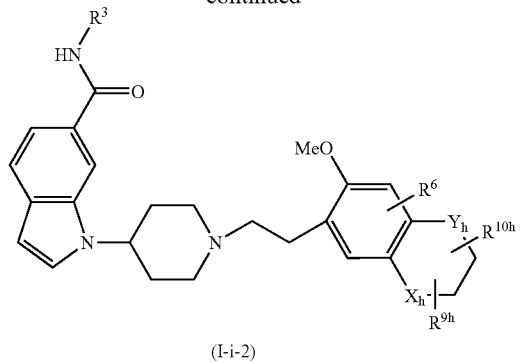

(I-i-2)

wherein R³ represents a hydrogen atom or methyl group; and R⁶, R⁹ʰ, and R¹⁰ʰ represent substituents selected from the following substituent group A1; and Xₕ and Yₕ represent (1) a methine group or (2) a nitrogen atom, Substituent group A1: (1) a hydrogen atom, (2) a halogen atom, (3) a cyano group, (4) a hydroxyl group, (5) a nitro group, (6) a carboxyl group, (7) a C3-C8 cycloalkyl group, (8) a C2-C6 alkenyl group, (9) a C2-C6 alkynyl group, (10) a C1-C6 alkylthio group, (11) a C1-C6 alkoxycarbonyl group, (12) a C1-C6 alkylsulfonyl group, (13) a C1-C6 alkyl group (wherein said C1-C6 alkyl group may be substituted by 1 to 3 substituents selected from the group consisting of a halogen atom, a hydroxyl group, and a C1-C6 alkoxy group), (14) a C1-C6 alkoxy group (wherein said C1-C6 alkoxy group may be substituted by 1 to 3 halogen atoms), (15) an amino group (wherein said amino group may be substituted by a substituent selected from the group consisting of a C1-C6 alkyl group, a formyl group, a C1-C6 alkanoyl group, and a C1-C6 alkylsulfonyl group), and (16) a carbamoyl group (wherein said carbamoyl group may be substituted by one or two C1-C6 alkyl groups).

25. The compound according to claim 24 or a pharmacologically acceptable salt thereof, wherein R⁹ʰ, R¹⁰ʰ, and R⁶ represent substituents selected from the following substituent group A2; and Xₕ and Yₕ represent (1) a methine group or (2) a nitrogen atom, Substituent group A2: (1) a hydrogen atom, (2) a C1-C6 alkyl group, (3) a halogen atom, (4) a cyano group, (5) a C1-C6 alkoxy group, (6) an amino group wherein a nitrogen atom may be substituted by a C1-C6 alkyl group, and (7) C1-C6 alkoxy C1-C6 alkyl group.

26. The compound according to claim 1 selected from the following group or a pharmacologically acceptable salt thereof:

1) 1-{1-[2-(7-Methoxy-2,2-dimethyl-4-oxochroman-8-yl)ethyl]piperidin-4-yl}-N-methyl-1H-indole-6-carboxamide, 2) 1-{1-[2-(7-Methoxy-2,2-dimethyl-4-oxochroman-8-yl)ethyl]piperidin-4-yl}-1H-indole-6-carboxamide, 3) 1-{1-[2-(7-Methoxy-2,2-dimethyl-4-oxochroman-6-yl)ethyl]piperidin-4-yl}-1H-indole-6-carboxamide, 4) 1-{1-[2-(6-Methoxy-3-oxoindan-5-yl)ethyl]piperidin-4-yl}-1H-indole-6-carboxamide, 5) 1-{1-[2-(6-Methoxy-2-methylbenzoxazol-5-yl)ethyl]piperidin-4-yl}-1H-indole-6-carboxamide, 6) 1-{1-[2-(6-Methoxy-2-methylbenzoxazol-7-yl)ethyl]piperidin-4-yl}-1H-indole-6-carboxamide, 7) 1-{1-[2-(6-Methoxy-3-methylbenzo[d]isoxazol-5-yl)ethyl]piperidin-4-yl}-1H-indole-6-carboxamide, 8) 1-{1-[2-(6-Methoxy-3-methylbenzo[d]isoxazol-7-yl)ethyl]piperidin-4-yl}-1H-indole-6-carboxamide, 9) 1-{1-[2-(5-Methoxy-1-oxoindan-4-yl)ethyl]piperidin-4-yl}-1H-indole-6-carboxamide, and 10) 1-{1-[2-(7-Methoxy-2,3-dihydrobenzo[1,4]dioxin-6-yl)ethyl]piperidin-4-yl}-1H-indole-6-carboxamide.

27. The compound according to claim 1 selected from the following group or a pharmacologically acceptable salt thereof:

1) 1-{1-[2-(7-Methoxy-2,2-dimethyl-4-oxochroman-8-yl)ethyl]piperidin-4-yl}-N-methyl-1H-indole-6-carboxamide, 2) 1-{1-[2-(7-Methoxy-2,2-dimethyl-4-oxochroman-8-yl)ethyl]piperidin-4-yl}-1H-indole-6-carboxamide, and 3) 1-{1-[2-(7-Methoxy-2,2-dimethyl-4-oxochroman-6-yl)ethyl]piperidin-4-yl}-1H-indole-6-carboxamide.

28. A pharmaceutical composition comprising, as an active ingredient, a compound represented by the following formula (I) or a pharmacologically acceptable salt thereof:

[Formula 15]

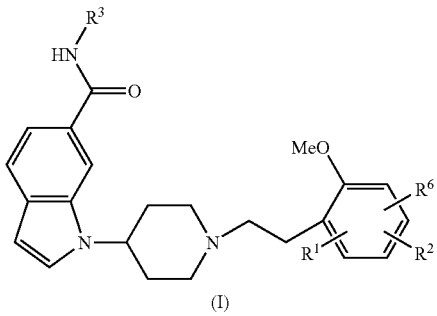

(I)

wherein R¹ and R² are substituents adjacent to each other, and together with two carbon atoms to each of which they attach, form:

(1) a 5- to 7-membered non-aromatic carbocyclic group,
(2) a 5- to 7-membered non-aromatic heterocyclyl group,
(3) a 6-membered aromatic carbocyclic group, or
(4) a 5- or 6-membered aromatic heterocyclyl group, which may be substituted by 1 to 4 substituents selected from the following substituent group B1;

R³ represents a hydrogen atom or methyl group; and

R⁶ represents a substituent selected from the following substituent group A1,

Substituent group A1: (1) a hydrogen atom, (2) a halogen atom, (3) a cyano group, (4) a hydroxyl group, (5) a nitro group, (6) a carboxyl group, (7) a C3-C8 cycloalkyl group, (8) a C2-C6 alkenyl group, (9) a C2-C6 alkynyl group, (10) a C1-C6 alkylthio group, (11) a C1-C6 alkoxycarbonyl group, (12) a C1-C6 alkylsulfonyl group, (13) a C1-C6 alkyl group (wherein said C1-C6 alkyl group may be substituted by 1 to 3 substituents selected from the group consisting of a halogen atom, a hydroxyl group, and a C1-C6 alkoxy group), (14) a C1-C6 alkoxy group (wherein said C1-C6 alkoxy group may be substituted by 1 to 3 halogen atoms), (15) an amino group (wherein said amino group may be substituted by a substituent selected from the group consisting of a C1-C6 alkyl group, a formyl group, a C1-C6 alkanoyl group, and a C1-C6 alkylsulfonyl group), and (16) a carbamoyl group (wherein said carbamoyl group may be substituted by one or two C1-C6 alkyl groups);

Substituent group B1: (1) a hydrogen atom, (2) a halogen atom, (3) a cyano group, (4) a hydroxyl group, (5) a nitro group, (6) an oxo group, (7) a carboxyl group, (8) a C3-C8 cycloalkyl group, (9) a C2-C6 alkenyl group, (10) a C2-C6 alkynyl group, (11) a C1-C6 alkylthio group, (12) a C1-C6 alkoxycarbonyl group, (13) a C1-C6 alkylsulfonyl group, (14) a C1-C6 alkyl group (wherein said C1-C6 alkyl group may be substituted by a halogen atom, a hydroxyl group, or a C1-C6 alkoxy group), (15) a C1-C6 alkoxy group (wherein said C1-C6 alkoxy group may be substituted by 1 to 3 halogen atoms), (16) an amino group (wherein said amino group may be substituted by a substituent selected from the group consisting of a C1-C6 alkyl group, a formyl group, a C1-C6 alkanoyl group, and a C1-C6 alkylsulfonyl group), (17) a carbamoyl group (wherein said carbamoyl group may be substituted by one or two C1-C6 alkyl groups), (18) a C1-C6 alkoxyimino group, (19) a C5-C6 cycloalkyl group formed by two C1-C3 alkyl groups attaching to the same carbon atom, and (20) a tetrahydropyranyl group formed by two C1-C3 alkyl group attaching to the same carbon atom, together with an oxygen atom and said carbon atom.

29. The pharmaceutical composition according to claim 28 characterized in that it is an agent for treating or preventing increased urinary frequency or urinary incontinence.

* * * * *